(12) United States Patent
Ochiai

(10) Patent No.: US 9,822,354 B2
(45) Date of Patent: Nov. 21, 2017

(54) POLYNUCLEOTIDE ENCODING ACYL-COA SYNTHETASE HOMOLOG AND USE THEREOF

(71) Applicant: SUNTORY HOLDINGS LIMITED, Osaka (JP)

(72) Inventor: Misa Ochiai, Osaka (JP)

(73) Assignee: SUNTORY HOLDINGS LIMITED, Osaka (JP)

( * ) Notice: Subject to any disclaimer, the term of this patent is extended or adjusted under 35 U.S.C. 154(b) by 22 days.

(21) Appl. No.: 15/041,665

(22) Filed: Feb. 11, 2016

(65) Prior Publication Data
US 2016/0230166 A1 Aug. 11, 2016

Related U.S. Application Data

(62) Division of application No. 13/574,026, filed as application No. PCT/JP2011/052035 on Feb. 1, 2011, now Pat. No. 9,289,007.

(30) Foreign Application Priority Data

Feb. 1, 2010 (JP) .................... 2010-019967

(51) Int. Cl.
| | |
|---|---|
| C12N 15/52 | (2006.01) |
| C12N 9/00 | (2006.01) |
| A61K 8/36 | (2006.01) |
| A61K 8/60 | (2006.01) |
| A61Q 1/02 | (2006.01) |
| A61Q 1/06 | (2006.01) |
| A61Q 5/00 | (2006.01) |
| A61Q 5/12 | (2006.01) |
| A61Q 11/00 | (2006.01) |
| A61Q 19/00 | (2006.01) |
| A61Q 19/08 | (2006.01) |
| C12N 15/82 | (2006.01) |
| C12P 7/64 | (2006.01) |
| A23L 33/115 | (2016.01) |
| A61K 38/00 | (2006.01) |

(52) U.S. Cl.
CPC ............ *C12N 9/93* (2013.01); *A23L 33/115* (2016.08); *A61K 8/361* (2013.01); *A61K 8/606* (2013.01); *A61Q 1/02* (2013.01); *A61Q 1/06* (2013.01); *A61Q 5/006* (2013.01); *A61Q 5/12* (2013.01); *A61Q 11/00* (2013.01); *A61Q 19/00* (2013.01); *A61Q 19/08* (2013.01); *C12N 15/8247* (2013.01); *C12P 7/6409* (2013.01); *C12P 7/6427* (2013.01); *C12P 7/6463* (2013.01); *C12P 7/6472* (2013.01); *A61K 38/00* (2013.01); *C12Y 602/01001* (2013.01); *C12Y 602/01003* (2013.01)

(58) Field of Classification Search
CPC .................................................... C12N 9/93
See application file for complete search history.

(56) References Cited

U.S. PATENT DOCUMENTS

| | | |
|---|---|---|
| 7,183,458 B1 | 2/2007 | Heinz et al. |
| 7,927,845 B2 | 4/2011 | Ochiai |
| 8,541,208 B1 | 9/2013 | Plesch et al. |
| 9,289,007 B2 | 3/2016 | Ochiai |
| 2003/0037357 A1 | 2/2003 | Shockey et al. |
| 2003/0097676 A1 | 5/2003 | Shockey et al. |
| 2004/0010817 A1 | 1/2004 | Shockey et al. |
| 2007/0220634 A1 | 9/2007 | Metz |
| 2007/0244192 A1 | 10/2007 | Metz |
| 2007/0245431 A1 | 10/2007 | Metz et al. |
| 2007/0270494 A1 | 11/2007 | Metz et al. |

FOREIGN PATENT DOCUMENTS

| | | |
|---|---|---|
| CN | 1969640 | 5/2007 |
| EP | 2 096 177 | 9/2009 |
| EP | 2 199 304 | 6/2010 |
| JP | 2009-529890 A | 8/2009 |
| RU | 2 268 939 | 1/2006 |
| RU | 2007106971 | 11/2008 |
| WO | 02/09295 A2 | 1/2002 |
| WO | 2006/037947 | 4/2006 |
| WO | 2006/069610 | 7/2006 |
| WO | 2010/115156 | 10/2010 |

OTHER PUBLICATIONS

International Search Report for PCT/JP2011/052035, dated Apr. 26, 2011.
Office Action issued with respect to Russian Patent App. No. 2012137109/10(Jun. 2, 2005), dated Dec. 3, 2013.
Office Action issued with respect to Russian Patent App. No. 2012137109/10(Jun. 2, 2005), dated Apr. 28, 2014, along with an English language translation.
Black et al., "Yeast Acyl-CoA Synthetases at the Crossroads of Fatty Acid Metabolism and Regulation" *Biochimica et Biophysica Acta*, vol. 1771, No. 3, p. 286-298, 2007.
Hortmann et al., "Inhibitory Effect of Undecanoic Acid on the Biosynthesis of Long-chain Fatty Acids in *Mortierella isabellina*" Appl. Microbiol. Biotechnol., vol. 20, No. 2, p. 139-145, 1984.
Sakuradani et al., "Cloning and Elucidation of Properties of Fatty Acid Elongase Gene of an Arachidonic Acid-producing Filamentous Fungus, *Mortierella alpina* 1S-4" 2009 Nendo Japan Society for Bioscience, Biotechnology, and Agrochemistry Kansai Shibu Koenkai Koen Yoshishu, Oct. 30, 2009, p. 107 (E14p), along with an English language translation.
Pei et al., "Mouse Very Long-chain Acyl-CoA Synthetase 3/Fatty Acid Transport Protein 3 Catalyzes Fatty Acid Activation but Not Fatty Acid Transport in MA-10 Cells" *The Journal of Biological Chemistry*, vol. 279, No. 52, p. 54454-54462, 2004.

(Continued)

*Primary Examiner* — Rebecca Prouty
(74) *Attorney, Agent, or Firm* — Greenblum & Bernstein, P.L.C.

(57) ABSTRACT

The present invention relates to an acyl-CoA synthetase homolog protein from microorganisms of the genus *Mortierella*, a polynucleotide encoding the protein, and so on. The invention provides polynucleotides comprising an acyl-CoA synthetase homolog protein gene from, e.g., *Mortierella alpina*, expression vectors comprising these polynucleotides and transformants thereof, a method for producing lipids or fatty acids using the transformants, food products containing the lipids or fatty acids produced by the method, etc.

16 Claims, 55 Drawing Sheets

(56) References Cited

OTHER PUBLICATIONS

Pei et al., "The Second Member of the Human and Murine "Bubblegum" Family Is a Testis- and Brainstem-specific Acyl-CoA Synthetase" *The Journal of Biological Chemistry*, vol. 281, No. 10, p. 6632-6641, 2006.

Watkins et al., "Evidence for 26 Distinct Acyl-coenzyme A Synthetase Genes in the Human Genome" *Journal of Lipid Research*, vol. 48, No. 12, p. 2736-2750, 2007.

DiRusso et al., "Functional Domains of the Fatty Acid Transport Proteins: Studies Using Protein Chimeras" *Biochimica et Biophysica Acta*, vol. 1781, No. 3, p. 135-143, 2008.

Shimizu et al., "Metabolic Engineering of Oleaginous Fungus, *Mortierella alpina*" *Bioscience & Industry*, Jul. 1, 2001, vol. 59, No. 7, p. 451-454, along with an English language translation.

Soupene et al., "Mammalian Long-Chain Acyl-CoA Synthetases" *Experimental Biology and Medicine*, vol. 233, No. 5, p. 507-521, 2008.

Database EMBL [Online] EBI; Sep. 26, 2005, XP002727427, accession No. EIE80757.

Database UniParc [Online], XP002741551, Database accession No. UPI00025EDD2A, time-stamped Jun. 30, 2015.

Extended European Search Report issued in EP Patent Application No. 15153586.1, dated Jul. 22, 2015.

Office Action issued in AU Patent Appl. No. 2014202244, dated Aug. 13, 2015.

Extended European Search Report issued in EP Patent Application No. 14157739.5, dated Aug. 1, 2014.

Seiki Takeno et al., *Journal of Bioscience and Bioengineering*, 100 (6), pp. 617-622 (2005).

Chinese Office Action of 201180007631.0 dated Feb. 13, 2014 with English translation.

U.S. Appl. No. 15/041,599, filed Feb. 11, 2016.

Office Action issued in Chinese Patent App. No. 201410512727.8, dated May 24, 2017, along with an English language translation.

Figure 1

```
   1  GCTCTTTTTGTTCTGTTCTTTGCCACCCCACTCTGCTGTGCCTCTCCACTCCCCCTGCCCGTCGAACGTTCTTCTGTCACTTTGCACAGCAGTATCTCC

101  TCTGATCTCGCTTGRTTATATTCCCTCTAATCTCGTTTGGTTATATTCCCTCTGATCTCGGTCGGTTATATTCTTCAGATATGGATGCTGTCCCTGCAGT
                                                                                       M  D  A  V  P  A  V

201  TGCTGCTGCGGCCATCCCCGCAGCCATGTATGTCGGCTCCAAGCTTGCAATCCCCCGTGATGTCAAGTTAGCTAAAGGCCTAGTCAGTGCCAAGCTAGGT
       A  A  A  A  I  P  A  A  M  Y  V  G  S  K  L  A  I  P  R  D  V  K  L  A  K  G  L  V  S  A  K  L  G

301  TACAGGTCCTACGAGAAGAACGACTCGATCAATATCTCTTATCGTTTTGAAGAGACCTGTAAGAAGCACCCTCATCGCGAAGCTTTGGTGTTTGAAGGCA
       Y  R  S  Y  E  K  N  D  S  I  N  I  S  Y  R  F  E  E  T  C  K  K  H  P  H  R  E  A  L  V  F  E  G  K

401  AATCGTACACCTTCCAGGACATCCAGCGAGAATCGAATAGGGTGGGACACTGGCTGTTGTCCAAAGGCGTCAAGCGAGGAGAGATCGTGTCGCTCTTCAT
       S  Y  T  F  Q  D  I  Q  R  E  S  N  R  V  G  H  W  L  L  S  K  G  V  K  R  G  E  I  V  S  L  F  M

501  GCAAAATAAGCCAGAGTTTCTCTTCTTCTGGCTTGGACTCAACAAGATCGGCGCTACGGGAGCATTCATCAACACGAACCTCTCGGGCAAACCTCTGACG
       Q  N  K  P  E  F  L  F  F  W  L  G  L  N  K  I  G  A  T  G  A  F  I  N  T  N  L  S  G  K  P  L  T

601  CACTCATTGCGTACCGCGACAGCATCCATTCTGATTATGGATGCGGAACTGCCGACGCCCATTTATAGTGTCCTCGATGAAGTCCTTGAGATGGGATATC
       H  S  L  R  T  A  T  A  S  I  L  I  M  D  A  E  L  P  T  P  I  Y  S  V  L  D  E  V  L  E  M  G  Y  Q

701  AGATATATTCCTACGGAGGATCCCAGCAACACGCCTTTGCTACACAAGTTGAACTTTCTCAAATCTCGGATGCGGCCTTGCCCAAGAGTCTGCGAAGGAA
       I  Y  S  Y  G  G  S  Q  Q  H  A  F  A  T  Q  V  E  L  S  Q  I  S  D  A  A  L  P  K  S  L  R  R  K

801  AACCACTGCAAATGATATTGCCATGTTGATTTACACCTCCGGAACGACGGGTTTGCCCAAAGCTGGACGGTTCTCCCATGCTCGAGCCAACGTTGCCGCA
       T  T  A  N  D  I  A  M  L  I  Y  T  S  G  T  T  G  L  P  K  A  G  R  F  S  H  A  R  A  N  V  A  A

901  CTTTTCTGGACGTCTTTCTACCACTTCAGCGAAAAAGACCGCCTGTACATCGCCTTGCCTCTTTACCACAGTGCTGGAGCTGTCCTTGGAATATGTGTGG
       L  F  W  T  S  F  Y  H  F  S  E  K  D  R  L  Y  I  A  L  P  L  Y  H  S  A  G  A  V  L  G  I  C  V  A

1001  CCTGGGTCACCGGTGCTACGGTGGTCCTGGCGCGCAAGTTTTCAACTACTTCCTTCTGGGACGAATGCAGGGCCAACAAGGTCACCGTGATCCAGTATAT
       W  V  T  G  A  T  V  V  L  A  R  K  F  S  T  T  S  F  W  D  E  C  R  A  N  K  V  T  V  I  Q  Y  I

1101  TGGAGAAATCTGCCGATACTTACTGAATGCTCCTCCTTCTCCCTTGGACAAGACACACACGATCCGAATGGCGCATGGCAACGGCATGCGTCCGGATGTA
       G  E  I  C  R  Y  L  L  N  A  P  P  S  P  L  D  K  T  H  T  I  R  M  A  H  G  N  G  M  R  P  D  V

1201  TGGAACAGATTCAGAGATCGTTTCGGCATCCCTTTGATCGGAGAATGGTATGCAAGCACTGAGGGCACCGGAATCTTGACAAACTATAACACAGGACCCA
       W  N  R  F  R  D  R  F  G  I  P  L  I  G  E  W  Y  A  S  T  E  G  T  G  I  L  T  N  Y  N  T  G  P  N

1301  ATGGCGGCTGGTGCGATAGGATACAGAGGCTCCTTGGCCAGAACTGTCGATAAGGGTCTGAAGATTGCGAAGTTCGACATCCAAACCGAGGAACTTATTCG
       G  A  G  A  I  G  Y  R  G  S  L  A  R  T  V  D  K  G  L  K  I  A  K  F  D  I  Q  T  E  E  L  I  R

1401  TGACAAAAATGGTCGATGCATTGAGTGTGTCGCAGATGAGCCCGGCGAGCTCTTGACAATGATTGATTCAAGTGATCCCACTCGCGGCTTTCCAAGGGTAC
       D  K  N  G  R  C  I  E  C  V  A  D  E  P  G  E  L  L  T  M  I  D  S  S  D  P  T  R  A  F  Q  G  Y

1501  CATAAAAATGCAGGTGCAAACTCCAAGAAAGTCGTCCAGGATGCATTCAGTGTTGGGGACCAATACTTTCGTACTGGTGACATCCTTCGTCGCGACGCTG
       H  K  N  A  G  A  N  S  K  K  V  V  Q  D  A  F  S  V  G  D  Q  Y  F  R  T  G  D  I  L  R  R  D  A  D

1601  ATGGCTATTTCTATTTTGGCGATCGTGTTGGAGATACTTTCCGCTGGAAATCTGAAAACGTGTCAACTGCGGAGGTTTCTGAGGTGCTCTCAGCATACCC
       G  Y  F  Y  F  G  D  R  V  G  D  T  F  R  W  K  S  E  N  V  S  T  A  E  V  S  E  V  L  S  A  Y  P

1701  GGACTGCATCGAGGTCAACGTTTATGGCGTTCAAGTCCCTGGACACGACGGCCGCGCAGGCATGGCTGCCATTGTCTCCAAGGACACCATGAACTGGGAT
       D  C  I  E  V  N  V  Y  G  V  Q  V  P  G  H  D  G  R  A  G  M  A  A  I  V  S  K  D  T  M  N  W  D

1801  AGTTTCGCCAAGTTTGCACTCAAAAATCTGCCCAAGTACTCTGTGCCGATTTTCATCCGCAAGGTCCCAGAGATGGAGATTACGGGAACGTTCAAGCAAC
       S  F  A  K  F  A  L  K  N  L  P  K  Y  S  V  P  I  F  I  R  K  V  P  E  M  E  I  T  G  T  F  K  Q  R

1901  GAAAGGTTGAACTGGTGAACGAGGGCATGGACCCGAGCAAGATCAAAGACGAAATGCTGTGGTTGGATGGGCACTCCTACCGGCCCTTCAAAGAGGCGGA
       K  V  E  L  V  N  E  G  M  D  P  S  K  I  K  D  E  M  L  W  L  D  G  H  S  Y  R  P  F  K  E  A  E

2001  GCATACTAGAGTCGTCAGCGGCAAAGCCAGGCTTTGACGAATAAAATTATTTCGTTTTGTCCGTTGAAAAAAAAAAA
       H  T  R  V  V  S  G  K  A  R  L
```

Figure 2A

```
            1                                                                                                  100
genome  ATGCATGCTGTCCGTGCAGTTGCTGCTGCGGCCATCGCGGCAGGCATGTATGTCGGCTCGAAGCTTGCAATGCCGGTGATGTGAAGTTAGGTAAAGGCG
   CDS  ATGCATGCTGTCCGTGCAGTTGCTGCTGCGGCCATCGCGGCAGGCATGTATGTCGGCTCGAAGCTTGCAATGCCGGTGATGTGAAGTTAGGTAAAGGCG 101                                                                                                200
genome  TAGTCAGTGCCAAGCCTAGGTTACAGGTGCTAGGAGAAGAAGGACTCGATGAATATCTCTTATCGTTTTGAAGAGACCTGTAAGAAGCACCCTCATCGCGA
   CDS  TAGTCAGTGCCAAGCTTAGGTTACAGGTGCTAGGAGAAGAACGACTCGATGAATATCTCTTATCGTTTTGAAGAGACTGTAAGAAGCACCCTCATCGCGA 201                                                                                                300
genome  AGCTTTGCTGTTTGAAGGCAAATCGTACAGCCTTCCAGGACATCCAGGCAGGTAACAAGAAAAACAATTGTCCAAAGTGACAGTCGAACGCATGCCGAAATT
   CDS  AGCTTTGCTGTTTGAAGGCAAATCGTAGACCTTCCAGCAGATCGAGCCAG 301                                                                                                400
genome  TTTACTCAAGATAAATTGGATCATCGCACCACACCCCTCCGTCGATTTCACTAACCCTTGACTTGGAATGTAGAATCGAATAGGGTGGGACACTGGGTG
   CDS                                                                                AATCGAATAGGGTGGGACACTGGCTG 401                                                                                                500
genome  TGTCCAAACGCGGTCAAGCGAGGAGAGATCGTGTCGGTCTTCATGCAAAATAAGCGAGAGTTTCTCTTCTTCTCGGCTTGGACTCAAGAAGATCGGCGGTAC
   CDS  TGTCCAAAGGCCGTCAAGCGAGGAGAGATCGTGTCGGTCTTCATGCAAAATAAGCGAGAGTTTCTCTTGTCTCGGCTTGGACTCAACAAGATCGGCGGTAC 501                                                                                                600
genome  GGGAGCATTCATGAACACGAACCTCTCGGCAAACCTGTCGACGCACTCATTGGGTACGCGACAGGATCGATTCTGATTATGGATGCGGAACTGCCGACG
   CDS  GGGAGCATTCATCAACACGAACCTCTCGGCAAACCTGTCGACGGACTCATTGGGTACGCGACAGCATGGATTCTGATTATGGATGCGGAACTGCCGACG 601                                                                                                700
genome  GGCATTATAGTGTCCTCGATGAACTCCTTCAGATGGGATATCAGATATATTCCTACGGAGGATCGGAGCAACAGGCCTTGCTACAACAAGTTGAAGTTT
   CDS  GGCATTATAGTGTCCTCGATGAAGTCCTTCAGATGGGATATCAGATATATTCCTACGGAGGATCGGAGCAACAGGCGTTGCTACAACAAGTTGAACTTT 701                                                                                                800
genome  CTCAAATCTCGGATGCGGGCGTTGCCCAAGAGTCTGGAAGGAAAAACGACTGCAAATGATATTGCGATGTTGATTTACACGCTCGGGAACGACGGGTTTGCC
   CDS  GTCAAATCTCGGATGCGGCCTTGCCCAACAGTCTGCGAAGGAAAACGACTGCAAATGATATTGCCATGTTGATTTACACGTCGGGAACGACGGGTTTGCC 801                                                                                                900
genome  CAAAGCTGGACGGTTCTCGGATGCTCGAGGCAACGGTAGGATTATACCCCCCCTCCTCCCCCCCCCCCTTTTTTTTGCATTTGCTGTGAAGTTATTAGCTG
   CDS  CAAAGCTGGACGGCTTCTCGGATGCTCGACGGAACG 901                                                                                                1000
genome  TTCCACTAGCATATTGACTCATATTCACGTTCCTTTTACACGTCGGGATCCAGTGCCGGCACTTTCTGACGGTCTTCTACCACTCAGCGGAAAAAGAC
   CDS                                                                    TGCCGGCACTTTTCTGGACGTCTTCTACCACTCAGCGGAAAACAG 1001                                                                                               1100
genome  GGCCTGTAGATCGCCGTTGCCTCTTTACCAGAGTGCTGGAGCTGTCCTTGGAATATGTGGCCTGGGTGACCGGTGCTAGGGTGGTCCTGGGGCGCAAGT
   CDS  GGCCTGTAGATCGCCTTGCCTGTTTACCAGAGTGCTGGAGCTGTCCTTGGAATATGTGGCCTGGTCACCGGTGCTAGGGTGGTCCTGGGGCGCAAGT 1101                                                                                               1200
genome  TTTCAAGTACTTCCTTCTGGACGAATGCAGGGCCAACAAGGTGACGCTGATCGACTATATTGGAGAAATCTCGGCGATAGTACTGAATGGTCCTGCCTTC
   CDS  TTTCAACTACTTCCTTCTGGACGAATGCAGGGCGAACAAGGTGACGCTGATCCACTATATTGGAGAAATCTCGGCGATAGTACTGAATGGTCGGTCCTTC 1201                                                                                               1300
genome  TCCCTTGGACAAGACACAGACGGATCCGAATGCGGCATGGCAACGGCATGCGTCGGATGTATGGAAGAGATTCAGAGATCGTTCGGCATCGCTTTGATC
   CDS  TCCCTTGGACAAGACACAGACGGATCCGAATGCGGCATGGCAACGGCATGCGTCGGATGTATGGAAGAGATTCAGAGATCGTTCGGCATCGCTTTGATC 1301                                                                                               1400
genome  GGAGAATCGTATCCAAGCACTGAGGCCACGGAATCTTGACAAACTATAACACAGGACCCAATGGCGCTGCTGCGATAGGATACGAGGCTCCTTCGCCA
   CDS  GGAGAATCGTATCCAAGCACTGAGGCCACGGAATCTTGACAAACTATAACACAGGACCCAATGGCGCTCCTGCGATAGGATACGAGGCTCCTTGGCCA
```

```
   1 ATCCGCCCATCCGCTCTCTTGCCACTGATCTCAAAGCGTGATCCAAAGGTCATTCTTAGGCAGCACTCACGCAGCTACTTAGAACTCTACCCACATATCC

101 CTTATTGATACAATGGCTCCCGTCGCTGCACTCGCCGCCGCTCTGGCGGCAGGATACTATCTCAATGGCAAGTACCAAATCACTAAGGACTTGGCGCTTG
                                                                  M  A  S  T  K  S  L  R  T  W  R  L

201 TTCGCGTTGGTGTCCATGCACGCAAAAGACTTGAGGGCTTGGTCGAGAATCGGGACTGCAGTCTTTACAACAGGTTCGAGGAACAATGCCAGATCCGGCC
      F  A  L  V  S  M  H  A  K  D  L  R  P  W  S  R  I  G  T  A  V  F  T  T  G  S  R  N  N  A  R  S  G  L

301 TTTCTCTGTTGCCCTTGTTTTTGAGAACACGTCTTACACCTGGAGAGACTTGGAGCTGGCGTCCAACAGGATGGCCCATTGGTTTGTTGCTCAAGGAATC
       S  L  L  P  L  F  L  R  T  R  L  T  P  G  E  T  W  S  W  R  P  T  G  W  P  I  G  L  L  L  K  E  S

401 CAAAAAAAGGAGCGTGTGGCGATGATGATGCATAACTCGCCTCTGTTCATTATCACCTGGCTGGCAATGCTCAAGATCATGGTTGTAGCTGCTTTTATC
        K  K  K  E  R  V  A  M  M  M  H  N  S  P  L  F  I  I  T  W  L  A  M  L  K  I  M  V  V  P  A  F  I

501 AATAACCAGATTGCAGGACCTGTTCTGGTTCATTCTCTTAAAGTGGCCGACGCCAAGTTTCTCTTGTTCGATTACGAGTTGGCACCTGTCATCCAAAAGT
        N  N  Q  I  A  G  P  V  L  V  H  S  L  K  V  A  D  A  K  F  L  L  F  D  Y  E  L  A  P  V  I  Q  K  S

601 CGCTCAATGAGATCAAGGACATGGGTTACAATCTCTACACTGTCACACCCAAGGATCAAGTTCTAGGTCAACTTTACGCCAATCTGCCCGAGGCTGCTCG
        L  N  E  I  K  D  M  G  Y  N  L  Y  T  V  T  P  K  D  Q  V  L  G  Q  L  Y  A  N  L  P  E  A  A  R

701 TCAGGTGTTGGATGAGGCTCCTTCATTCTTTGGTTATGTCGAATGGCAGAACCTCAGTACCGAAGGTTTCTCGAACGAGAGTCGTCAGGAGGTGGTGATC
        Q  V  L  D  E  A  P  S  F  F  G  Y  V  E  W  Q  N  L  S  T  E  G  F  S  N  E  S  R  Q  E  V  V  I

801 TCCGACCCCGCAGCCTTGATTTACACCAGCGGGGACCACGGGATTCCCCAAGGCTGCTATCATGGACCATGGACGTTGCAAGTTGGCTTCGATCTCTTATG
         S  D  P  A  A  L  I  Y  T  S  G  T  T  G  F  P  K  A  A  I  M  D  H  G  R  C  N  L  A  S  I  S  Y  G

901 GCACTCTATGCGGCATCAAACCAGAGAACAAGGTTTACATCACATTGCCGCTCTATCATTCTGCTGGAGCCATCATTGGTCTGGGCCAGAGCTTCACCAG
        T  L  C  G  I  K  P  E  N  K  V  Y  I  T  L  P  L  Y  H  S  A  G  A  I  I  G  L  G  Q  S  F  T  S

1001 CGGATGCACCATTGTGCTGGCGCGAAAGTTCTCCGTGACAAAGTTTTGGCGTGATTGCGTTGAGTACGACGTAACTCATTTTCAGTACATTGGCGAACTC
        G  C  T  I  V  L  A  R  K  F  S  V  T  K  F  W  R  D  C  V  E  Y  D  V  T  H  F  Q  Y  I  G  E  L

1101 TGCCGCTACCTTCTAAATGCCCCCGAAAGTCCACTGGACAAAAGGCATAAGGTTCGGATGGCGTTTGGCAACGGAATGCGCCCGGATGTTTGGGCAAAGT
         C  R  Y  L  L  N  A  P  E  S  P  L  D  K  R  H  K  V  R  M  A  F  G  N  G  M  R  P  D  V  W  A  K  F

1201 TTCAGGAACGATTCAATATCCCCATTATTGTTGAGTACTACGCCATGAGCGAAGGAACATCGTCGCTTTTGAATGTGGCCAGGAACAAGCGGGACCAAGG
        Q  E  R  F  N  I  P  I  I  V  E  Y  Y  A  M  S  E  G  T  S  S  L  L  N  V  A  R  N  K  R  D  Q  G

1301 TGCGGTGGGATTCCGTGGCCCCGTCGTGAGGGCCTTGACGGCCTCCCGTTCAACTGGTCAAGGTGGACTTTGACACGGAGGAGCTGATCCGCGATAAGAAG
        A  V  G  F  R  G  P  V  V  R  A  L  T  P  P  V  Q  L  V  K  V  D  F  D  T  E  E  L  I  R  D  K  K

1401 ACGGGACTTTGCGTCCTATGCCAGCCTGGTGAGATTGGAGAACTGGTCACGCTAGCCGACAACAAGACGACTGGGCGCACGCTATGCTGGGTATTTCAATC
         T  G  L  C  V  L  C  Q  P  G  E  I  G  E  L  V  T  L  A  D  N  K  T  T  G  A  R  Y  A  G  Y  F  N  Q

1501 AGCCAGAGGTTTCGAAGGCAAGGCTGGTCCAGAACGTGGTAGTGAAGGACGACATCTACTTCCGGACGGGTGACCTCTTGTACTCCAAGGACCAGTACTG
        P  E  V  S  K  A  R  L  V  Q  N  V  V  K  D  D  I  Y  F  R  T  G  D  L  L  Y  S  K  D  Q  Y  W

1601 GTACTTTGCTGATCGCGCAGGAGACACGTACCGGTGGAAAGGAGAGAACGTGTCGACAGCCGAGATTGCAGACACTATCGGCCGTGTTGAGGGCGTGGCT
        Y  F  A  D  R  A  G  D  T  Y  R  W  K  G  E  N  V  S  T  A  E  I  A  D  T  I  G  R  V  E  G  V  A

1701 AGTTGTACTGTTTATGGCGTATCGGTCCCGGGCATGGATGGACGCGCGGGCATGGCTGCTTTGGTGCTCAAGAACTCGATTGTGCAGATGGCAGGTGGAA
        S  C  T  V  Y  G  V  S  V  P  G  M  D  G  R  A  G  M  A  A  L  V  L  K  N  S  I  V  Q  M  A  G  G  S

1801 GCCAGGCAAAGTTCCATGTGGATGAGGCTGCCGTGAACGCGTTTTTGCGTGACTTGAGCAAGGATCTGGTCAAAAAACTGCCGGCGTATGCGATTCCTCG
         Q  A  K  F  H  V  D  E  A  A  L  N  A  F  L  R  D  L  S  K  D  V  V  K  K  L  P  A  Y  A  I  P  R

1901 GTTCTTGCGCATTGCAGAGCAGGAACTGGAGACGACGGGCACGTTCAAGAACAAGAAGGTGGAGCTGAAGAAGGAAGGGTTCGACCTGGGTAAGGTCAAG
         F  L  R  I  A  E  Q  E  L  E  T  T  G  T  F  K  N  K  K  V  E  L  K  K  E  G  F  D  L  G  K  V  K
```

Figure 3B

2001  GAGCGGCTGTACTGGTGGACACCCAAGGGTGAATATGCCCCTTTTGGCGTGGCGGAGAACGAGCAGATCCTCGCAGGACGCGCTCGTCTTTGAGCGATGT
       E  R  L  Y  W  W  T  P  K  G  E  Y  A  P  F  G  V  A  E  N  E  Q  I  L  A  G  R  A  R  L

2101  TTGTCAATGAAGTCATCGGCATCATCATCATCATCAAAAAAAAAAAAAAAAAAAA

Figure 4A

```
            1                                                                                                  100
genome   ATGGCAAGTACGAAATCACTAAGGACTTGGGGCTTGTTCGCGTTGGTGTGCATGCACGCAAAAGGTATGAACGATGCACTTGGGGGACGCATCTGTCTCA
CDS      ATGGCAAGTACGAAATCACTAAGGACTTGGGGCTTGTTCGCGTTGGTGTGCATGCACGCAAA----------------------------------------

101                                                                                                200
genome   ATGTGATTTGCTTGTTCNNNNNNNNNNNNNNNNNNNNNNNNNNNNNNNNNNNNNNNNNNNNNNNNNNNNNNNNNNNNNNNNNNNNNNNNNNNNNNNNNNNN
CDS      ----------------------------------------------------------------------------------------------------

201                                                                                                300
genome   NNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNN
CDS      ----------------------------------------------------------------------------------------------------

301                                                                                                400
genome   NNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNN
CDS      ----------------------------------------------------------------------------------------------------

401                                                                                                500
genome   NNNNNNNNNNNNNNNNNNNNNNNNNNNNNNNNNNNNNNNNNNNNNNNNNNNNNNNNNNNNNNNNNNNNNNNNNCGTCTACTTTTTTTTTTTTTTTTTTTTGAGAGAGAAAGGT
CDS      ----------------------------------------------------------------------------------------------------

501                                                                                                600
genome   CGAATGTGGGGACCGAACCTATTTTTTTTCCGTGCCTTTTAGGTTTGTTGCTTCAGCGTTCTTTTGAGCTGATATCTTTTCGCCACTCTTGCATACCTTA
CDS      ---------------------------------------------------------------------------------------------------G 601                                                                                                700
genome   GAGTTGAGGGCTGGTCGAGAATCGGGAGTGCAGTCTTAGAAGAGGTCGAGGAACAATGGCAGATCGGCCTTCTCTGTTGCGGTTGTTTGAGAA
CDS      GAGTTGAGGGCTGGTCGAGAATCGGGAGTGCAGTCTTACAACAGGTTGGAGGAACAATGGCAGATCGGCCTTCTCTGTTGCGGTTGTTTGAGAA 701                                                                                                800
genome   GAGGTCTTAGAGCTGGAGAGAGTTGGAGCTGGGTATGTGCAGTAGGATTTTTTTGGACGCCTGATGCTGCATTCTGTGATAGAGGACATACATTTAAATAAT
CDS      GAGGTCTTAGAGCTGGAGAGAGTTGGAGCTGG--------------------------------------------------------------------

801                                                                                                900
genome   TGATATCATTTCGTCTGTCGACCTGTCTGTCTATCGATATACAGGCTGCAAGAGGATGGTAAGTTGGCAACTGCATACAAGTACTTCGTGCTCTTTATCA
CDS      ----------------------------------------------GCTCCAACAGGATGG---------------------------------------

901                                                                                               1000
genome   TGCGTTACTCACGCTTCATTGCCTCAATGTTTCCTTTGAACTAGGCCCATGGTTTGTTGCTCAAGGAATCCAAAAAAAGGAGCGTGTGGGCATGATGA
CDS      ------------------------------------------------CCGATGGTTTGTTGCTCAAGGAATCCAAAAAAAGGAGCGTGTGGGCATGATGA 1001                                                                                              1100
genome   TGCATAACTCGCCTCTGTTCATTATCACCTGGCTGGCAATGCTCAAGATCATGGTCTACCTGCTTTTATCAATAACCAGATCCAGGACCTGTTCTGCT
CDS      TGCATAACTCGCCTCTGTTCATTATCACCTGGCTGGCAATGCTCAAGATCATGGTCTACCTGCTTTTATCAATAACCAGATCCAGGACCTGTTCTGCT 1101                                                                                              1200
genome   TCATTCTCTTAAAGTGGCCGACGCCAAGTTCTCTTGTCGATTAGGACTTGGCACCTGTCATCCAAAAGTCGCTCAATGACGATCAAGGACATGGTTAC
CDS      TCATTCTCTTAAAGTGGCCGACGCCAAGTTCTCTTGTCGATTAGGACTTGGCACCTGTCATCCAAAAGTCGCTCAATGACGATCAAGGACATGGTTAC 1201                                                                                              1300
genome   AATCTCTACACTGTCACACCGAAGGATCAAGTTCTAGGTCAACTTTAGGCCAATCTGCCGGAGGCTGCTCGTCAGGTCTTGCATGAGGCTCGTTCATTCT
CDS      AATCTCTACACTGTCACACCGAAGGATCAAGTTCTAGCTCAACTTTAGGCCAATCTGCGGGAGGCTGCTCGTCAGGTCTTGCATGAGGCTCGTTCATTCT 1301                                                                                              1400
genome   TTGGTTATGTCGAATGGCAGAAGGTCAGTAGCGAAGGTTTCTGGAACGAGAGTCGTCAGGAGCTGGTCATCTGCACCCGCAGCGTTGATTTACACCAG
CDS      TTGGTTATGTCGAATGGCAGAAGGTCAGTACCGAAGGTTTCTGGAACGAGAGTCGTCAGGAGTGGTCATCTGCAGCGCCAGCGTTGATTTACACCAG
```

```
   1 GCCTACTTTGCGCTCGGCTCATCGACCCAAAGGCAGCAATGGAAACGGATGCTCTTACCATCGCTTTGACCATCGCCATCGCCATCGTGCTGGCTTTGGT
                                      M  E  T  D  A  L  T  I  A  L  T  I  A  I  A  I  V  L  A  L  V

101 CAAATTCAACGAAAAAGAGCCTGACCTGCATCCGCTCCTGCTCGGGCAGCAATCGTCTGTCACGCCCATTCGGAACGAGGGCGAGTCCGTTATCCATAGA
      K  F  N  E  K  E  P  D  L  H  P  L  L  L  G  Q  Q  S  S  V  T  P  I  R  N  E  G  E  S  V  I  H  R

201 TCCAAAACGGTGCCACACGGGACACTGCTGACGAAGCGCCCGAGCGAGAAAATCAAGACTCTGCACGATGTCTGGCAGACTGGAGCAGCTGTCAACCCAG
      S  K  T  V  P  H  G  T  L  L  T  K  R  P  S  E  K  I  K  T  L  H  D  V  W  Q  T  G  A  A  V  N  P  A

301 CCGGCCGATCGTTGATGTTTATGCTGCAGAACCAGTTTGCGTTTATCGAGGCCACGTATGAGCAAGTCAATAGGAGGATTGGCGGCTTCGGAACAGGTTT
       G  R  S  L  M  F  M  L  Q  N  Q  F  A  F  I  E  A  T  Y  E  Q  V  N  R  R  I  G  G  F  G  T  G  F

401 CGTGAAGGCAACAGGGCTAAAGCCCAAGACGGACACACCAGTAGGAATCTTTATGCCCTACTCTCAAGAATCGTTCGTTGCCCAGCAGGCATTCTATCGA
      V  K  A  T  G  L  K  P  K  T  D  T  P  V  G  I  F  M  P  Y  S  Q  E  S  F  V  A  Q  Q  A  F  Y  R

501 TACAGCTTTGTTGCTGTCCCCATCCATGATCTGAGGAACAAGGACCTCTTGGTGGAGGTAGTAGACCAGACCAAGCTCAAGGCCATCATAGTCTCACAAA
      Y  S  F  V  A  V  P  I  H  D  L  R  N  N  D  L  L  V  E  V  V  D  Q  T  K  L  K  A  I  I  V  S  Q  K

601 AGGTGCTCCCGTTATTGCTGCAATCTCTGAAGGAGTGTCCAACCATCAAGACAATCATCATGCAGGAATCTACATCTCACAGGAGCAGCTGGAAATGGC
       V  L  P  L  L  L  Q  S  L  K  E  C  P  T  I  K  T  I  I  M  A  G  I  Y  I  S  Q  E  Q  L  E  M  A

701 AGCACAGCATGGAGTAAAGCTGCTCAAATTCGCGGCAGTGGAATATGAGGGATCCTCGACTCTGATGGAGCCTGTTCAGCCTGATCCGGAGGATGTTGCC
      A  Q  H  G  V  K  L  L  K  F  A  A  V  E  Y  E  G  S  S  T  L  M  E  P  V  Q  P  D  P  E  D  V  A

801 ATGATCAACTATAACACAAAGTCGTCTTCGCTCTCGAAAGGCGTCATGCTTACCCATGCCAACCTGATCGCGGCGATGACTGCCTTCACGGAGTCACTTC
      M  I  N  Y  N  T  K  S  S  S  L  S  K  G  V  M  L  T  H  A  N  L  I  A  A  M  T  A  F  T  E  S  L  P

901 CGGCAAAAAAGCGTTTCTCCAGCAAAGATCGTCTTCTCTCTCATTTTTCCAATGGAGATGTCATCTCTGTCTTCATGTCGAGCGCCATCATCCTGATGGG
       A  K  K  R  F  S  S  K  D  R  L  L  S  H  F  S  N  G  D  V  I  S  V  F  M  S  S  A  I  I  L  M  G

1001 AGGTTGTTTGGTCTTTCCATCTGGTTTGATGAAGAACGTTTTGCATGATTCCCAAGCTTCTGCACCAACGATCTTTGCAAGCACACCGATCATCCTGGAA
       G  S  L  V  F  P  S  G  L  M  K  N  V  L  H  D  S  Q  A  S  A  P  T  I  F  A  S  T  P  I  I  L  E

1101 AAGATTCACGAAGCACTTCAGTTGACGTATGGGCAAGGCTCCATGTTCAGGCGCGGCTTTGCTGCCAAATTGGCCATAGTTCAAGCTGGACGAATCACTA
       K  I  H  E  A  L  Q  L  T  Y  G  Q  G  S  M  F  R  R  G  F  A  A  K  L  A  I  L  Q  A  G  R  I  T  T

1201 CAACAAGCCTATGGGACTTGATTGACTGGGCGAGGTCCGCAGCAAACTTGGTGGAAAGGTTCGAATGGTTGTAACAACACATCCTACCAAACCTGAGAC
       T  S  L  W  D  L  I  G  L  G  E  V  R  S  K  L  G  G  K  V  R  M  V  V  T  T  H  P  T  K  P  E  T

1301 GCTGGATTATATCAGAGCGGCGATGGGCATCCATGTCATTACCACTTACGGCAGGACAGAGACGTCGGGCATTGTGACAGCCCGCAACATGCTGGATTAT
       L  D  Y  I  R  A  A  M  G  I  H  V  I  T  T  Y  G  R  T  E  T  S  G  I  V  T  A  R  N  M  L  D  Y

1401 GCCAACGCACCTCATTTAGGACCAGCCAGTGGGTTGCAACGAGGTTAAGCTTGTGGACGATGTTGCAGCTGGCTTTACAAGTGCAGACGAGCCCAAGCCAC
       A  N  A  P  H  L  G  P  P  V  G  C  N  E  V  K  L  V  D  D  V  A  A  G  F  T  S  A  D  E  P  N  P  R

1501 GAGGCGAGATCCTTATCCGAGGCCCCAATGTGATGAAAGGTTATTACAAGAAGCCGGGTGCCACTTCAACGGCTATCGATGAGGAAGGGTGGTTCCATTC
       G  E  I  L  I  R  G  P  N  V  M  K  G  Y  Y  K  K  P  G  A  T  S  T  A  I  D  E  E  G  W  F  H  S

1601 AGGAGAGCTGGGCACATTCCACTCCAACGGCACTTTAGACGTGTTGGGCAAGAAGAAGAAGACGAAGTCTGCAGTTGGATCACCGTCATGAAAGGAGATG
       G  E  L  G  T  F  H  S  N  G  T  L  D  V  L  G  K  K  K  K  T  K  S  A  V  G  S  P  S

1701 CTGCATGTGCTACAGAATATAAAAAGGGAGAAGATACGTTCGGTAACCACATCAAAAAAAAAAAAAAAAAAAA
```

```
           1401                                                                                    1500
genome     CATCCTGATGGGAGGTTCTTTGGTGTTTCCATCTGGTTTGATGAAGAAGGTTTTCGATGATTCCGAAGCTTCTGCAGGAAGATCTTTGCAAGGTACAAG
   CDS     CATCCTGATGGGAGGTTCTTTGGTGTTTCCATCTGGTTTGATGAAGAAGGTTTTCGATGATTCCGAAGCTTCTGCAGGAAGATCTTTGCAAG-------

1501                                                                                    1600
genome     ATGTTCCAGTGTGATCTGTGGATTGTCTCGTTATTCATGTGCAAGATACTTACGGGCGCTGTTCCATTTATTTTTGACCCCTCCTAGAGAGCCATCATCG
   CDS     --------------------------------------------------------------------------------GAGACCCATCATCG 1601                                                                                    1700
genome     TGGAAAAGATTCAGGAAGCACTTCAGTTGACGTATGGCCAAGGCTCCATGTTCAGGGCGCGGCTTTGCTGCCAAATTGGCCATAGTTGAAGCTGCAGGAAT
   CDS     TGGAAAAGATTCAGGAAGCACTTCAGTTGACGTATGGCCAAGGCTCCATGTTCAGGGCGCGGCTTTGGTGCCAAATTGGCCATAGTTGAAGCTGGAGGAAT 1701                                                                                    1800
genome     GACTAGAAGAAGCCTATGGGACTTGATTGGACTGGGCGAGGTCGGCAGGAAACTTGGTGGAAAGGTTGGAATGCTTGTAACAAGAGGTAAGTCTCCTTTT
   CDS     GACTAGAACAAGCCTATGGGACTTGATTGGACTGGGCGAGGTCGGCAGGAAACTTGGTGGAAAGGTTGGAATGCTTGTAACAAGAG-------------

1801                                                                                    1900
genome     TTACCATGCGGGCTTACGTACTTGCAGCATGATATTCGAAGATACTAACAGTCTTTTCATGACGCTCCTGTAGATGCTACCAAACGTGAGACGCTGGATT
   CDS     -----------------------------------------------------------------------ATGCTACCAAACGTGAGACGCTGGATT 1901                                                                                    2000
genome     ATATCAGAGCGGCGATGGGCATCCATGTCATTACCACTTACGGCAGGACAGAGACGTCGGGCATTGTGACAGCCCGCAACATGCTGGATTATGCGAACGG
   CDS     ATATCAGAGCGGCGATGGGCATCCATGTCATTACCACTTACGGCAGGACAGAGACGTCGGGCATTGTGACAGCCCGCAACATGCTGGATTATGCGAACGG 2001                                                                                    2100
genome     ACCTCATTTAGGACCACGAGTGGTTGCAACGAGGTTAAGCTTGTGGACGATGTTCGAGCTGGCTTTACAAGTGCAGAGGAGCGCAACCGACGAGGCGAG
   CDS     ACGTCATTTAGGACCACGAGTGGTTGCAACGAGGTTAAGCTTGTGGACGATGTTCGAGCTGGCTTTACAAGTGCAGAGGAGCGCAACCGACGAGGCGAG 2101                                                                                    2200
genome     GTAAGGAGTGCATATCTCTTGCTGCTTCATGGGCGATAAAAAGGCTCAAATGCCGTTGATTCTACTCTAACAGCGTTATTTTATTGTTCAACAATATTTT
   CDS     ---------------------------------------------------------------------------------------------------

2201                                                                                    2300
genome     GTGCCTAGATCCTTATCGAGGCCGCAATGTGATGAAAGGTTATTACAAGAAGCCGGGTGCCACTTCAAGCGGCTATGGATGAGGAAGGTTGCTTCATT
   CDS     ----------ATCCTTATCGAGGCCGCAATGTGATGAAAGGTTATTACAAGAAGCCGGGTGCCACTTCAAGCGGCTATGGATGAGGAAGGTTGCTTCATT 2301                                                              2391
genome     AGGAGAGCTGGGCACATTCGACTCGAAGGGCACTTTAGACGTGTTGGCCAAGAAGAAGAAGACGAAGTCTGCAGTTGGATCACCGTCGATGA
   CDS     AGGAGAGCTGGGCACATTCGACTCGAAGGGCACTTTAGACGTGTTGGCCAAGAAGAAGAAGACGAAGTCTGCAGTTGGATCACCGTCGATGA
```

Figure 7A

```
   1  CACACGCTCACGTTCGCTCTCACCCGACCCACTCCCCACTCTCGCTCTCATTCTCTCCCTTGTCCTTCCCTTGTCCCTTTCAAGGTCTAACAGCATCAAC

101  ATCAGCATCAGCATCAAGCTTCTCATTCCTCCCTCGTCTAAATCTCTGAAAGAGTTCGCTTTGCAATTCAGCAATGTCCCTCGACCAGAACGCCCAGTCC
                                                                         M  S  L  D  Q  N  A  Q  S

201  GTTGAGCTCCCAGGCACCCGGCAACCAGGCCAGACAGGCATCTATCGCCGCAAAGGCTTCGAGAATGCCCTTCTCGCCGTCCCACCCAGCAGACCGCACA
       V  E  L  P  G  T  R  Q  P  G  Q  T  G  I  Y  R  R  K  G  F  E  N  A  L  L  A  V  P  P  S  R  P  H  I

301  TCAAGACCATCTACGATGCCTTCCAGCACGGACTGAAGCTTAATCCCAACGGAGCTGCCCTGGGCAGCCGAGTGTACGACCCGGTGACGGACACCTTTGG
        K  T  I  Y  D  A  F  Q  H  G  L  K  L  N  P  N  G  A  A  L  G  S  R  V  Y  D  P  V  T  D  T  F  G

401  AGGCTATGTCTGGCAGACGTATGCACAGGTGAACGACCGCATCACTCGCTTGGGCAGTGGATTGGTCAAAATTCATAAGGACGTCCATGGTCTTGCCACC
       G  Y  V  W  Q  T  Y  A  Q  V  N  D  R  I  T  R  F  G  S  G  L  V  K  I  H  K  D  V  H  G  L  A  T

501  GTGGGCCAGAAGTGGTCTCTCGGAATCTGGGCCATCAACCGACCCGAGTGGACCATCGCGTCCGAGGCTTGCTCGGCCTACAACCTGGTCTCCGTGGGTC
       V  G  Q  K  W  S  L  G  I  W  A  I  N  R  P  E  W  T  I  A  S  E  A  C  S  A  Y  N  L  V  S  V  G  L

601  TTTACGATACTTTGGGACCGGAGGCTGTGACTTATGGCATTAATCACGCTGAGTGCTCTATTGTCGTAACAAGTGTGGATCATATCGCGACGCTGCTGAA
        Y  D  T  L  G  P  E  A  V  T  Y  G  I  N  H  A  E  C  S  I  V  V  T  S  V  D  H  I  A  T  L  L  N

701  CGAATCTTCCAAGATGCCTGGGCTCAAAATCATCATCAGCATGGATGACCTCGATACTGGGAGAGCAGGCCCAGGACTGGCTCCCACCGGCACCATCCTC
        E  S  S  K  M  P  G  L  K  I  I  I  S  M  D  D  L  D  T  G  R  A  G  P  G  L  A  P  T  G  T  I  L

801  AGGACTTACGCTCAGGACAAAGGGGTAGTACTTTATGATTGGTCTGAGGTTGAAGCCGTGGGTATTCAGCATGGACGAAAGCATACGCCACCAACCTCCT
       R  T  Y  A  Q  D  K  G  V  L  L  Y  D  W  S  E  V  E  A  V  G  I  Q  H  G  R  K  H  T  P  P  T  S  S

901  CCGACGCATATACGATCTGCTATACCAGCGGGACAACAGGCTTGCCAAAAGGTGCCATTTTGACCCATGGAAACTTGATCGCCCTTTTGGCCTCCAGTGA
        D  A  Y  T  I  C  Y  T  S  G  T  T  G  L  P  K  G  A  I  L  T  H  G  N  L  I  A  L  L  A  S  S  D

1001  TGTGGCCACACCAGTGCTGGCTGACGATTGCCTCATCAGTTTCTTGCCCGTGCCTCACGTCTTTGGTCGGGTCATGGAGCTCTTCGCGATGGCCGCAGGA
        V  A  T  P  V  L  A  D  D  C  L  I  S  F  L  P  H  V  F  G  R  V  M  E  L  F  A  M  A  A  G

1101  GGAAAGATTGGCTACAGCACGGGGAGATCCTTTGCGTCTCTTGGAGGACGTCTCGCACCTAAAGCCCTCCATCTTCCCGGCTGTGCCCAGACTGCTGAACC
       G  K  I  G  Y  S  T  G  D  P  L  R  L  L  E  D  V  S  H  L  K  P  S  I  F  P  A  V  P  R  L  L  N  R

1201  GCGTGTATGCCAAGGTGTATGCGGCAACTGTTGGAGCGCCTGGACTCACAGGGGCACTGGCGCGACGAGGATTGGCCACCAAGCTCACCAATTTGAGAGA
        V  Y  A  K  V  Y  A  A  T  V  G  A  P  G  L  T  G  A  L  A  R  R  G  L  A  T  K  L  T  N  L  R  E

1301  GGGCAAAGGTTTCCACCACCCATTGTGGGACCGAATCCTCTTCTCAAAGGTCAAGCAAGGGCTCGGCGGCAATGTGAGACTGATGTTGACTGCCTCCGCT
       G  K  G  F  H  H  P  L  W  D  R  I  L  F  S  K  V  K  Q  A  L  G  G  N  V  R  L  M  L  T  A  S  A

1401  CCCATCTGGGCGGAGATCTTGGAATTCGTCCGTGTCGCTTTCTGCTGCGAGGTCGTGGAGGCATATGGACAGACTGAGGGCGGTGGAGCGGCCACAAACA
        P  I  S  A  E  I  L  E  F  V  R  V  A  F  C  C  E  V  V  E  A  Y  G  Q  T  E  G  G  A  A  T  N  T

1501  CCGTGATTGGCGAGACCGAGGCTGGACACGTCGGTCCTCCTCAAGCTTGTTGCGAGATCAAACTGGTGGATGTACCCGAGCTGAACTACTTTGCGACCGA
        V  I  G  E  T  E  A  G  H  V  G  P  P  Q  A  C  C  E  I  K  L  V  D  V  P  E  L  N  Y  F  A  T  D

1601  TAAACCATTCCCTCGTGGTGAGATTTGTGTCCGTGGACCCGGTGTCATTCCTGGTTATCTCAAGGATGAGGCCAAGACCAAGGAGACCATTGATGAGGAG
        K  P  F  P  R  G  E  I  C  V  R  G  P  G  V  I  P  G  Y  L  K  D  E  A  K  T  K  E  T  I  D  E  E

1701  GGCTGGCTGCACTCGGGCGATATCGCCATCATGAGTGGCAAAGGCACCGTTACCATCATTGACAGGAAGAAGAACGTGTTCAAGCTGAGCCAAGGAGAAT
       G  W  L  H  S  G  D  I  A  I  M  S  G  K  G  T  V  T  I  I  D  R  K  K  N  V  F  K  L  S  Q  G  E  Y

1801  ACATCGCGGCAGAGAACATTGAAGGGCGTTTCCTCTCCAAGGTTCCATTCATCCAACAAATTCTGGTGCACGGGGACTCGACCGAGAGCTGTTTGGTGGC
        I  A  A  E  N  I  E  G  R  F  L  S  K  V  P  F  I  Q  Q  I  L  V  H  G  D  S  T  E  S  C  L  V  A

1901  CATCTTGATCCCAGAGCCTGAGGCCTTCATCCCCTTTGTGAACAAAGTGCTGGAGAACGTCAATCTTCAACCTGGAGATCTTGCAGGCTACAGGAAGATC
        I  L  I  P  E  P  E  A  F  I  P  F  V  N  K  V  L  E  N  V  N  L  Q  P  G  D  L  A  A  Y  R  K  I
```

Figure 7B

```
2001   GTTAACAACCCAAAGCTGCGCCAGGCTGTCCTCAAAGAGCTGATCAAGGCTGGCAAGGATGCTGGATTGAAAGGCTTTGAGATTCCAAAGGCGATCCTCC
        V  N  N  P  K  L  R  Q  A  V  L  K  E  L  I  K  A  G  K  D  A  G  L  K  G  F  E  I  P  K  A  I  L  L·

2101   TCGAATCTGAGGCATTCACGGTCGAAAACGACAAGATGACCCCGACTTTCAAGATCAAAAGACACCCTGTCGTCCAGGCTTACCGCGAGCAACTGACAGC
        · E  S  E  A  F  T  V  E  N  D  K  M  T  P  T  F  K  I  K  R  H  P  V  V  Q  A  Y  R  E  Q  L  T  A·

2201   GCTCTACAACGAAATCCATCAAAAGGAATCCAAGCTGTAAAAAGAAACCCTTAGAACCTGCGGTGCTCGCAGCAATTAAAAAAAAAAGAGAGATATTACT
        · L  Y  N  E  I  H  Q  K  E  S  K  L  *

2301   CTCACAGCTAAAAAAAAAAAAAAAAAAAAAAAAAAA
```

```
              2801
genome
   CDS
```

Figure 9A

```
  1  TTTTTTTTTTTTTCTTTTCTCTCCAACCGTTTGACCCCCACGGCTCGGCTCGTACTCAAGCCTCACGTCCAGACTCTCGTCCTCTAGCCTGCTGCATTCA

101  CGATTCACATTCCTCCTCGACTCCAGCATCGCTACTCCCTCGTGCTACTTTCACCATGACCACCCAATTGTACTCCATCGAAGTGGCAGGCAGCCCAGAG
                                                      M  T  T  Q  L  Y  S  I  E  V  A  G  S  P  E

201  ATTCCGGGCGAGGGCAAACCTCGGCGCAGCGTTCTCAGCCCAGACAAAGTCGTCCAGAGGTATCAGTCTTTCAAGGGGCACGGCTCCATCACCACTCTAT
     I  P  G  E  G  K  P  R  R  S  V  L  S  P  D  K  L  V  Q  S  Y  Q  S  F  K  G  D  G  S  I  T  T  L  Y

301  ATGAGAACTTTTTGGAGGGCATCCAGCGCTCAGAGGGAGGAGAGTTTCTGGACACCGCCCCATCGTCGATAATGTAGCTCAGCCGTACGAATGGCTAAG
      E  N  F  L  E  G  I  Q  R  S  E  G  G  E  F  L  G  H  R  P  I  V  D  N  V  A  Q  P  Y  E  W  L  S

401  CTACACGCGCGTTCAGGAACGTGTCGCCAACTTTGGCGCTGGTCTCATCCAGCTGGGCCTGAAAGTGGACTCGAACTTTGGCATCTTTTCCATCAACAGG
      Y  T  R  V  Q  E  R  V  A  N  F  G  A  G  L  I  Q  L  G  L  K  V  D  S  N  F  G  I  F  S  I  N  R

501  CCCGAATGGACAATGAGTGAGCTGGCAGGCTACATGTACAACTTTACATCTGTGCCGCTTTACGACACTCTGGGCGTCTCGGCCATCGAATACATCGTTA
      P  E  W  T  M  S  E  L  A  G  Y  M  Y  N  F  T  S  V  P  L  Y  D  T  L  G  V  S  A  I  E  Y  I  V  N

601  ATCAGACCGAGATGGAGACCATCATCGCGTCGGCTGATAAAGCCTCGATCCTGTTAAACATGAAATCAACTCTGCCGACACTCAAGAACATTGTCGTTAT
      Q  T  E  M  E  T  I  I  A  S  A  D  K  A  S  I  L  L  N  M  K  S  T  L  P  T  L  K  N  I  V  V  M

701  GGGCTCGCTCGAAGACGCGCTCGTTGTCGAGGGTAGGGAAATGGATATCCACATCGTTGCGTGGAGTGACGTCGAACGCGATGGCTTCAACAACCCCGCG
      G  S  L  E  D  A  L  V  V  E  G  R  E  M  D  I  H  I  V  A  W  S  D  V  E  R  D  G  F  N  N  P  A

801  CCAGCCAACCCTCCAACACCGGACGACGTCGCCACCATCTGCTACACGTCAGGAACAACCGGGACACCAAAGGGGGCAATCCTGACCCACAAAAACTTTG
      P  A  N  P  P  T  P  D  D  V  A  T  I  C  Y  T  S  G  T  T  G  T  P  K  G  A  I  L  T  H  K  N  F  V

901  TGGCTGGCCTTGCCTCGTTCCATATGATGGCAAAGCACCAAAAGTTTTTCATCCCCTCGAGCGTTGACACTCACATATCTTACCTGCCGCCTGGCACATGT
      A  G  L  A  S  F  H  M  M  A  K  H  Q  K  F  F  I  P  S  S  V  D  T  H  I  S  Y  L  P  L  A  H  V

1001 GTTCGAGCGTTTGTCTCAGGCTGTTATGATTTCTGGCGCAGCTCGGATTGGGTATTACCAAGGAGACACTTTGAAGCTACTCGATGATGTGGCGATCTTG
      F  E  R  L  S  Q  A  V  M  I  S  G  A  A  R  I  G  Y  Y  Q  G  D  T  L  K  L  L  D  D  V  A  I  L

1101 CAGCCCACCATCTTTGTGTCCGTTCCACGACTCTTTAACAGGATTTACGACAAGGTTCTAGCAGGTGTGAAAGCCAAGGGCGGTCTCGCCAGCTTTCTTAT
      Q  P  T  I  F  V  S  V  P  R  L  F  N  R  I  Y  D  K  V  L  A  G  V  K  A  K  G  G  L  A  A  F  L  F

1201 TCAACGCGCTTTTGAAACCAAGAAGGCTAATTTGAAACGCGGTATCCTGGAGCACGCCATCTGGGATCGACTGGTATTTGGTGCAATTCGTGCGCGACT
      N  R  A  F  E  T  K  K  A  N  L  K  R  G  I  L  E  H  A  I  W  D  R  L  V  F  G  A  I  R  A  R  L

1301 CGGTGGCAAAGTTAAGCATATTGTCTCAGGATCAGCCCCTATAGCCCCGGACGTCATGGATTTCCTTCGCATTTGCTTCAGTGCCGACGTTTATGAAGGG
      G  G  K  V  K  H  I  V  S  G  S  A  P  I  A  P  D  V  M  D  F  L  R  I  C  F  S  A  D  V  Y  E  G

1401 TATGGACAGACGGAGCAGGCTGCTGGTTTGTGTATGAGCTACAGAGGTGACTTGACCTCGGGTCAAGTGGGACCCCCTCAGCTGTGCGTCGAAGTGAAGC
      Y  G  Q  T  E  Q  A  A  G  L  C  M  S  Y  R  G  D  L  T  S  G  Q  V  G  P  P  Q  L  C  V  E  V  K  L

1501 TCAGAGACGTTCGGGACATGCACTACACAAGCCAGGACAAGCCTCGCCGTCGCGGGGAGATCATGCTTCGAGGCCATTCAGTTTTCAAAGGCTATTACAA
      R  D  V  P  D  M  H  Y  T  S  Q  D  K  P  R  P  R  G  E  I  M  L  R  G  H  S  V  F  K  G  Y  Y  K

1601 GGCTCCAAAGCAAACAGAGGAGACACTGGACGCACAGGGATGGGCAAGCACTGGAGACGTTGGTGAATGGGACGAGCGTGGCCGCTTGGTGGTGATCGAC
      A  P  K  Q  T  E  E  T  L  D  A  Q  G  W  A  S  T  G  D  V  G  E  W  D  E  R  G  R  L  V  V  I  D

1701 CGTGTCAAAAACATTTTCAAGTTGGCTCAAGGCGAATACATTGCACCTGAAAAGATCGAAGCCGTCCTGGCCAAACACTACCTTGTCGCCCAGGTCTTTG
      R  V  K  N  I  F  K  L  A  Q  G  E  Y  I  A  P  E  K  I  E  A  V  L  A  K  H  Y  L  V  A  Q  V  F  V

1801 TCTACGGAGACTCCTTCCAAGCGACATTGGTGGGAGTTGTCGTGCCCGATGCGGAGACGCTAAAGCCTTGGGCCGATGACCATGGCCTTGGAGGCAAGAG
      Y  G  D  S  F  Q  A  T  L  V  G  V  V  V  P  D  A  E  T  L  K  P  W  A  D  D  H  G  L  G  G  K  S
```

Figure 9B

```
1901   CTATGAAGAACTATGCGCTCATCCCGCTGTCAAAGAAACTTTGCTGAAGGAGCTCAAAGAGTTTGGTCGTGAAAATGATCTGAAGGGCTTTGAGATATTG
        · Y  E  E  L  C  A  H  P  A  V  K  E  T  L  L  K  E  L  K  E  F  G  R  E  N  D  L  K  G  F  E  I  L

2001   AAGAACATTCATGTAACGGCGGAGCAATTCTCAATTGAGAATGATCTTTTGACACCCACATTCAAGCTGAAGAGACACACCGCGAAAGAGAAGTACATCG
         K  N  I  H  V  T  A  E  Q  F  S  I  E  N  D  L  L  T  P  T  F  K  L  K  R  H  T  A  K  E  K  Y  I  A ·

2101   CCGAGATTGAGCTGATGTATAACGGGATCCACTGAAAGAGTCTAGCCAAAGCAGATCTTTTTATTACTGTCGTTAAAAAAACTACTCGTAACCATCAAAA
          E  I  E  L  M  Y  N  G  I  H  *

2201   AAAAAAAAAAAAAAAA
```

Figure 10A

```
           1                                                                                                  100
genome     ATGACCACCCAATTCTACTCCATCGAAGTGGCAGGCAGCCCAGAGATTCCGGGCGAGGGCAAACCTGGGCGGAGCCTTCTCAGCCCAGACAAACTCGTCC
CDS        ATGACCACCCAATTCTACTCCATCGAAGTGGCAGGCAGCCCAGAGATTCCGGGCGAGGGCAAACCTGGGCGGAGCCTTCTCAGCCCAGACAAACTCGTCC 101                                                                                                200
genome     AGAGCTATCAGTCTTTCAAGGGCGAGGGCTCCATCACCACTCTATATGAGAACTTTTTGGAGGGCATCGAGGCGTCAGGTACTGACACCCCACATGGTCA
CDS        AGAGCTATCAGTCTTTCAAGGGCGAGGGCTCCATCACCACTCTATATGAGAACTTTTTGGAGGGCATCGAGGCGTCAG---------------------

201                                                                                                300
genome     GCGAGACTTGTCCACATGACACCAGCGTTTCTCTATTAACGTTATCCCTTGGCGCCTTTGGCTTTGTTGTGGTTAACGATGTGCCTAATCATAGAGGGAG
CDS        ---------------------------------------------------------------------------------------------AGGGAG 301                                                                                                400
genome     GAGAGTTTCTGGACACCGCCCCATCGTCGATAATGTAGCTCAGCCCTACGAATGCCTAAGCTACACCGGCGTTCAGGAACGTGTCGGCAACTTTGGCGC
CDS        GAGAGTTTCTGGACACCGCCCCATCGTCGATAATGTAGCTCAGCCCTACGAATGCCTAAGCTACACCGGCGCTTCAGGAACGTGTCGGCAACTTTGGCGC 401                                                                                                500
genome     TGGTCTCATCGAGCTGGGCCTGAAAAGTCGAGTCGAAGTTTGGCATCTTTTGCATCAAGAGGCCGAATGGGTGAGTGCAGTGGGAGGATCCTTTTTCTTT
CDS        TGGTCTCATCGAGCTGGCCTGAAAAGTCGAGTCGAAACTTTGGCATCTTTTGCATCAAGAGGCCGAATGG-----------------------------

501                                                                                                600
genome     TATGAAATGGGCCCGTGCGAGTCTAGATTCGATGATGGCTGCGGTTGGACCCGGCCTCGGCCCCCAACCAAACACGTGTGGGAAACCCCAACCGACTCTA
CDS        ----------------------------------------------------------------------------------------------------

601                                                                                                700
genome     ATAGAACTCCGTTCCTCTGATTTGGCGACGAACATACTATTACCTGTAGAGAATGAGTGAGCTGGCAGGCTACATGTAGAACTTTACATCTGTGCCGCTT
CDS        ------------------------------------------------ACAATGAGTGAGCTGGCAGGCTACATGTAGAACTTTACATCTGTGCCGCTT 701                                                                                                800
genome     TACGACACTCTGGGCGTCTCGGCGATCGAATACATCGTTAATCAGACCGAGATGGAGACCATCATCGCGTCGGCTGATAAAGCGTCGATCCTGTTAAAGA
CDS        TACGACACTCTGGGCCGTCTCGGCCATGAATACATCGTTAATCAGACGGAGATGGAGACCATCATCGCGTCGGCTGATAAAGCGTCGATCCTGTTAAAGA 801                                                                                                900
genome     TGAAATCAACTCTGCCGACACTCAAGAACATTGTCGTTATGGGCTCGCTCGAAGACGCGCTCGTTGTCGAGGGTAGGGAAATGGATATCGACATCGTTGC
CDS        TGAAATCAACTCTGCCGACACTCAAGAACATTGTCGTTATGGGCTCGCTCGAAGACGCGCTCGTTGTCGAGGGTAGGGAAATGGATATCGACATCGTTGC 901                                                                                               1000
genome     GTCGAGTCGACGTCGAACGCGATGGCTTCAAGAACGCCGGCGCCAGGCAACCGTCCAACACCGGACGACGTCGGCCACCATCTGCTACACGTCAGGAACAACC
CDS        GTCGAGTCGACGTCGAACGCGATGGCTTCAAGAACGCCGGCGCCAGGCAAGCCTCCAACACCGGACGACGTCGGCCACCATCTGCTACACGTCAGGAACAACC 1001                                                                                              1100
genome     GGGACACCGAAAGTAACGTTAAGATGTCGATATGAGAATATCTCTAAAATGTGGCATGCAGCTTGAATGAGAATTCACTCCTTCATAGACACTTGTTGTCC
CDS        GGGACACCGAAAG---------------------------------------------------------------------------------------

1101                                                                                              1200
genome     TTTCTCAAGTCACTCACCTCTCTTGATTTATCCTACGTGTATGTGTATGTAGGGGCCGAATCGTGACCGACAAAAACTTTGTGGCTGGCTTGCCTCGTT
CDS        ----------------------------------------------------GGCCGAATCGTGACCGACAAAAACTTTGTGGCTGGCTTGCCTCGTT 1201                                                                                              1300
genome     GGATATGATGGCAAAGCACCAAAAGTTTTGATCGCGTCGAGCGGTTGACACTCAGATATCTTAGCTGCCCTGGCACATGTGTTCGAGCGTTTGTCTCAG
CDS        GGATATGATGGCAAAGCACCAAAAGTTTTGATCGGCTCGAGCGGTTGACAGTCAGATATCTTAGCTGCCGTGGCACATGTGTTCGAGCGTTTGTCTCAG 1301                                                                                              1400
genome     GCTGTTATGATTTCTGGCGGAGCTCGGATTGGCTATTACGAAGGAGACACTTTGAAGCTACTCGATGATGTGGCGATCTTGCAGCCGCACCATCTTTGTGT
CDS        GCTGTTATGATTTCTGGCGGAGCTCGGATTGGCTATTACGAAGGAGACACTTTGAAGCTACTCGATGATGTGGGGATCTTGCAGCCGCACCATCTTTGTGT
```

```
   1  TTTCCTCACCTTCCCTCCGCTGCCCTCTGCTGCACACTCCTCTGGCTTATACCATCCAGCCCTCTAGCCCGCCACTTCGCCGCCAACCTCATCCGACTC

101  ACACCGCAATGGCTACTCAAATGTACTCGGTGGTCGTCCCCAACAGCCCCGACATTCCGGGCGAAGGCAAGCCCCGCCGTAGTGTGCTTTGTCCAGACAA
                 M  A  T  Q  M  Y  S  V  V  V  P  N  S  P  D  I  P  G  E  G  K  P  R  R  S  V  L  C  P  D  K

201  GCTCCTGGAGAACTACCCCTCAGTGAAAGCAGGCTCAACGATCACGACCCTGTACGAGAACTTCCAAGAAGGTGTTCTCCGTTCAGGCGGCGCCCATTTT
       L  L  E  N  Y  P  S  V  K  A  G  S  T  I  T  T  L  Y  E  N  F  Q  E  G  V  L  R  S  G  G  A  H  F

301  TTGGGCCATCGTCCCATTGTGAATGGCCAGCCTCAGGCTTACAAGTGGCAGTCGTATGTCGATGTCAGCAAGCGTGTTACGCACTTCGGCGCTGGCCTGG
       L  G  H  R  P  I  V  N  G  Q  P  Q  A  Y  K  W  Q  S  Y  V  D  V  S  K  R  V  T  H  F  G  A  G  L  A

401  CTCATCTCGGCTTGTCTCCAAAGCAAAACTTTGGAATTTTCTCTATCAACCGGCCTGAGTGGACCATGAGTGAGCTTGCTGGCTATATGCACAACTACAC
        H  L  G  L  S  P  K  Q  N  F  G  I  F  S  I  N  R  P  E  W  T  M  S  E  L  A  G  Y  M  H  N  Y  T

501  CAGCGTCCCCCTCTATGATACATTGGGAGTCGCCGCGATCGAGTATATCGTTAACCAGACTGAGATGCAGATCATCATTGCTTCGTCCGACAAAGCTTCT
        S  V  P  L  Y  D  T  L  G  V  A  A  I  E  Y  I  V  N  Q  T  E  M  Q  I  I  I  A  S  S  D  K  A  S

601  ATCATCCTCCACATGAAATCAGCACTTCCAACCGTTCAGACGATTGTCGTCATGGGGGAATTTACTGACGGTCTCGTCGCAGAGGGTAAGGAGCTCAACA
        I  I  L  H  M  K  S  A  L  P  T  V  Q  T  I  V  V  M  G  E  F  T  D  A  L  V  A  E  G  K  E  L  N  I

701  TCAACATTGTATCCTGGACCGATGTCGAAAAGAGCGGTCTTGAGCGGCCTGTCGAAGCCGTGCACCCCACAGCCGAGGATATCGCTACCATCTGTTACAC
        N  I  V  S  W  T  D  V  E  K  S  G  L  E  R  P  V  E  A  V  H  P  T  A  E  D  I  A  T  I  C  Y  T

801  ATCTGGAACCACTGGAACGCCAAAAGGTGCTATCTTGACCCACAAGAACTTTGTTGCCACTATCGGCTTCATTCCACATGATGGCAAAGCATGGCAGGTTC
        S  G  T  T  G  T  P  K  G  A  I  L  T  H  K  N  F  V  A  T  I  A  S  F  H  M  M  A  K  H  G  R  F

901  TTCATTCCCTCGCCTGCCGACACACATGTATCCTACCTGCCCCTTGCCCACGTCTTTGAGCGCCTTTGCCAGGCTGTTATGATCTCGGGCGCTGCGCGTA
       F  I  P  S  P  A  D  T  H  V  S  Y  L  P  L  A  H  V  F  E  R  L  C  Q  A  V  M  I  S  G  A  A  R  I

1001  TTGGTTACTACCAAGGAGATACGCTGAAGCTGCTGGACGATGTTGCCGTCCTGCATGCCACCATTTTTGCCTCCGTCCCTGTGTCTCTTTAACCGTATCTA
        G  Y  Y  Q  G  D  T  L  K  L  L  D  D  V  A  V  L  H  P  T  I  F  A  S  V  P  R  L  F  N  R  I  Y

1101  CGACAAGGTGCTTGCTGGCGTCAAGGCCAAGGGTGGTATCGCCGCCTTCTTGTTTAACCGCGCATATAATTCCAAGAAGGCCAACTTGCGAAAGGGCGTA
        D  K  V  L  A  G  V  K  A  K  G  G  I  A  A  F  L  F  N  R  A  Y  N  S  K  K  A  N  L  R  K  G  V

1201  CTTGAGCATCCGCTCTGGGACAAGCTGGTGTTTGGAGCGATTCGCGCGGCGCTTGGGTGGCAAGGTTAAGCACATCGTGTCAGGATCTGCCCCCATCTCTG
       L  E  H  P  L  W  D  K  L  V  F  G  A  I  R  A  R  L  G  G  K  V  K  H  I  V  S  G  S  A  P  I  S  P

1301  CTGATGTGATGGATTTCCTCCGCATCTGCTTCAGGGCTGATGTGTATGAGGGATATGGCCAGACGGAACAGGCAGCCGGATTAAGTATGAGCTATCGCGG
        D  V  M  D  F  L  R  I  C  F  S  A  D  V  Y  E  G  Y  G  Q  T  E  Q  A  A  G  L  S  M  S  Y  R  G

1401  TGATTTGACTCCAGGACAGGTTGGCCCCACCTCAACTGTGCACAGAGGTCAAGTTGAAGGACATGCCTAGTATGAACTATAGCAGCGCGGACAAGCCTTTC
        D  L  T  P  G  Q  V  G  P  P  Q  L  C  T  E  V  K  L  K  D  I  P  S  M  N  Y  S  S  A  D  K  P  F

1501  CCCCGTGGAGAAATCATGCTTCGCGGAAACTCTGTGTTCAAGGGCTATTACAAAGCACCAAAGCAGACTGAAGAAACATTGGATGCTGACGGTTGGTCCA
        P  R  G  E  I  M  L  R  G  N  S  V  F  K  G  Y  Y  K  A  P  K  Q  T  E  E  T  L  D  A  D  G  W  S  S

1601  GTACCGGAGACGTTGGACAGTGGGATGCCCAAGGCCGTCTGGTGGTCATTGATCGCGTCAAGAACATCTTCAAGTTGGCGCAAGGAGAATATATTGCGCC
        T  G  D  V  G  Q  W  D  A  Q  G  R  L  V  V  I  D  R  V  K  N  I  F  K  L  A  Q  G  E  Y  I  A  P

1701  TGAAAAGATCGAGGCTGTCCTGGCCAAGCACTTCCTCGTTGCCCAGATTTTTGTCTATGGGCACTCGGTCGAGGCCACCATTGTCGCGGTGGTTGTCCCT
        E  K  I  E  A  V  L  A  K  H  F  L  V  A  Q  I  F  V  Y  G  H  S  L  Q  A  T  I  V  A  V  V  P

1801  GATGCTGAGACGCTCAAGTTGTGGGCTAAAGAAAACAAGCTGGGTGACAAGTCTTACGAGGAGCTGTGCGCTCTCCCTCAGCTTCGCACAACCCTCCAAA
        D  A  E  T  L  K  L  W  A  K  E  N  K  L  G  D  K  S  Y  E  E  L  C  A  L  P  Q  L  R  T  T  L  Q  K

1901  AGGAGTTGGCTACTTTTGGCAAAGAATCGGATCTGAAGGGCTTTGAGATTCCTAAGAACATTCATGTTATCTCCGAGCAGTTTTCAATTGAGAACGATCT
        E  L  A  T  F  G  K  E  S  D  L  K  G  F  E  I  P  K  N  I  H  V  I  S  E  Q  F  S  I  E  N  D  L
```

Figure 11B

2001 TTTGACCCCCACCTTCAAGCTGAAGAGACATGCTGCCAAAGAGAAGTATAACGCCGAAATCGACCGCATGTATGCAGAAATCGCTTAATATAAATAATGG
       L  T  P  T  F  K  L  K  R  H  A  A  K  E  K  Y  N  A  E  I  D  R  M  Y  A  E  I  A

2101 TTGTACTCAATATAAAAAAAAAA

```
            1401                                                                            1500
genome      TGGAGCGATTCGCGCCGGCTTGGGTGCCAAGGTTAAGGACATCGTGTCAGGATCTGCGCCCATCTCTCCTGATGTGATGGATTTGCTCGGCATCTGCTTG
CDS         TGGAGCGATTCGCGCCGGCTTGGGTGCCAAGGTTAAGGACATCGTGTCAGGATCTGCGCCCATCTCTCCTGATGTGATGGATTTGCTCGGCATCTGCTTG 1501                                                                            1600
genome      AGCGCTGATGTGTATGAGGGATATGGCCAGACGGAACNNNNNNNNNNNNNNNNNNNNNNNNNNNNNNNNNNNNNNNNNNNNNNNNNNNNNNNNNNNNNNN
CDS         AGCGCTGATGTGTATGAGGGATATGGCCAGACGGAACAGGCAGCCGGATTAAGTATGAGCTATCGCGGTGATTTGACTCCAGGACAGGTTGGCCCACCTC 1601                                                                            1700
genome      NNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNN
CDS         AACTGTGCACAGAGGTCAAGTTGAAGGACATCCCTAGTATGAACTATAGCAGCGCGGACAAGCCTTTCCCCCGTGGAGAAATCATGCTTCGCGGAAACTC 1701                                                                            1800
genome      NNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNN
CDS         TGTGTTCAAGGGCTATTACAAAGCACCAAAGCAGACTGAAGAAACATTGGATGCTGACGGTTGGTCC--------------------------------

1801                                                                            1900
genome      NNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNN
CDS         ----------------------------------------------------------------------------------------------------

1901                                                                            2000
genome      NNNNNNNNNNNNNNNNNNNNNNNNNNNNNNNNNNNNNNNNNNNTTACCCCACGACTTTCTTTTGTCTCGGCCTGTTCCGCAATGATAGTACGGGAGACGGTTGGACA
CDS         ------------------------------------------------------------------------------------AGTACGGGAGACGGTTGGACA 2001                                                                            2100
genome      GTGGGATGCGCAAGGCGGTCTGGTGGTCATTGATCGCGTCAAGAACATCTCAAGTTGGCGCAAGGAGAATATATTGCGGCTGAAAAGATCGAGGCTGTC
CDS         GTGGGATGCGCAAGGCGGTCTGGTGGTCATTGATCGCGTCAAGAACATCTCAAGTTGGCGCAAGGAGAATATATTGCGGCTGAAAAGATCGAGGCTGTC 2101                                                                            2200
genome      GTCGGCAAGCACTTCCTCGTTGCCCAGATTTTTGTCTATGGGCACTGGCTCCAGGCACCATTGTCGCGGTGGTTGTCCCTGATGCTGAGACGGTCAAGT
CDS         GTCGGCAAGCACTTCCTCGTTGCCCAGATTTTTGTCTATGGGCACTGGCTCCAGGCACCATTGTCGCGGTGGTTGTCCCTGATGCTGAGACGGTCAAGT 2201                                                                            2300
genome      TGTGGGCTAAAGAAAACAAGCTGGCTGACAAGTCTTAGGAGGAGCTGTGCGCTCTCCCTCAGCTTCGGACAAAGGCTCCAAAAGGAGTTGGCTACTTTTGG
CDS         TGTGGGCTAAAGAAAACAAGCTGGCTGACAAGTCTTAGGAGGAGCTGTGCGCTCTCCCTCAGCTTCGGACAAAGGCTCCAAAAGGAGTTGGCTACTTTTGG 2301                                                                            2400
genome      CAAAGAATCGGATCTGAAGGGCTTTGAGATTCCTAAGAACATTGATGTTATCTCGGAGGAGTTTTCAATTGAGAACGATCTTTTGGTGAGTGTGCTTCCG
CDS         CAAAGAATCGGATCTGAAGGGCTTTGAGATTCCTAAGAACATTGATGTTATCTCGGAGGAGTTTTCAATTGAGAACGATCTTTTG-----------------

2401                                                                            2500
genome      AGTATGAACCACTGTGTCGTATGTACGTTCGCATTCTGAAAGCTAACTCTCCGTACCCTTCTACTTCAATTGTGAATTCTCCTCTTGTCGCATACAGACG
CDS         ------------------------------------------------------------------------------------------------ACG 2501                         2581
genome      CGCACCTTCAAGCTGAAGAGACATGCTGCCAAAGAGAAGTATAACGCCGAAATCGACCGCATGTATGCAGAAATCGCCTAA
CDS         CGCACCTTCAAGCTGAAGAGACATGCTGCCAAAGAGAAGTATAACGCCGAAATCGACCGCATGTATGCAGAAATCGCCTAA
```

Figure 13

```
   1 GGCACGAGGCTCTACTCTCCATTGCCCACTCACTCATTGCCCCTCTGTCCATCACCGGCATTGCTCGTTCGCGCCTTCCGCCACTCCACTCTTTCTTTCA

101 TTCCTTCTTTACAACGGCCATCTCCCCCTCGCTCTGCGCTTCTCCCATCCACGCTAACAATGCACATTCTGAATGCCACAAGACCATTCTCCAGGCTGTC
                                                   M  H  I  L  N  A  T  R  P  F  S  R  L  S

201 TCCAACGGTAAGGAGACCTTGGCTAGGACTCGGGCCAGACGCGGCCTTATGCTATCGCGCAGACCGAGGCCAGTCCTAGGCTGTCATATGTCCGAGGCACC
      P  T  V  R  R  P  W  L  G  L  G  Q  T  R  P  Y  A  I  A  Q  T  E  A  S  P  R  L  S  Y  V  R  G  T

301 ACCGTCGGCACCCAGCTATGCGAGGATCCCATCGGTGCGTACTGGGACAGGGTCGTCAATCGTCACGGTGACGGCCTCGGACTTGTCGTCAAGCACGAGC
      T  V  G  T  Q  L  C  E  D  P  I  G  A  Y  W  D  R  V  V  N  R  H  G  D  R  L  G  L  V  V  K  H  E  Q

401 AGGACCTGCACTGGACCTTCCGTCAGTTTGGCGGGCAGGTTGATAGCCTCTGCCGTGGGCTCTATGAGTCTGGCTTGCGAAAGGGTGATCGACTCGCTGT
      D  L  H  W  T  F  R  Q  F  G  G  Q  V  D  S  L  C  R  G  L  Y  E  S  G  L  R  K  G  D  R  L  A  V

501 CTGGATGCCGAACAACAGCGCGTGGGCCACGCTCCAGTATGCTACTGCCAAGTCTGGCATCATTCTGGTAACTCTCAACCCTGCGTACCGGAGGCAAGAG
      W  M  P  N  N  S  A  W  A  T  L  Q  Y  A  T  A  K  S  G  I  I  L  V  T  L  N  P  A  Y  R  R  Q  E

601 CTACTGCAGACATTGTCTTTGGTCGAGTGCAAGTCATTGGTCTATGTGCCAAGTCTAAAGACTTCGAATTATAGCGAGATGTTGCTCGACCTCCTACCAG
      L  L  Q  T  L  S  L  V  E  C  K  S  L  V  Y  V  P  S  L  K  T  S  N  Y  S  E  M  L  L  D  L  L  P  E

701 AACTCCAGTACCAGTCGCCAAATCAGCTCTTGACCGAGAAGCTACCCTCACTTCGTCAAGTCATCGTGTTTGACAATGGCTCGCAAGTCCCAGAGACAGC
      L  Q  Y  Q  S  P  N  Q  L  L  T  E  K  L  P  S  L  R  Q  V  I  V  F  D  N  G  S  Q  V  P  E  T  A

801 AAAATTGAAGGGATTGACAAAGTATCAGGATTTGTTGATCAAGAATCCCTCGACCGCTGTCGACGGAGGTCTTGAAAAGGAACGGCTCGCTATCGACAAC
      K  L  K  G  L  T  K  Y  Q  D  L  L  I  K  N  P  S  T  A  V  D  G  A  L  E  K  E  R  L  A  I  D  N

901 AGGGATATCATCAATCTCCAGTTTACTAGCGGAACTACAGGCCTTCCCAAGGGCGTCTCGCTGTCGCATCGAAACATCTTGAATAACGGCATTCATATTG
      R  D  I  I  N  L  Q  F  T  S  G  T  T  G  L  P  K  G  V  S  L  S  H  R  N  I  L  N  N  G  I  H  I  G

1001 GAGATAACATGCGACTGACGGAAAAGGATTTGCTTTGCTGCCCGGTCCCGCTCTTTCACTGCTTTGGACTGGTGCTGGCAAGCTTGGCTGCAATGACCCA
      D  N  M  R  L  T  E  K  D  L  L  C  C  P  V  P  L  F  H  C  F  G  L  V  L  A  S  L  A  A  M  T  H

1101 TGGCGCAGGAATTATTTACCCTTCGCAGTCCTTTGATGCTGAGGCCACACTGAGGGCTGTTTCTGAGGAGGGTGCTACAGCGCTGCATGGCGTGCCGACT
      G  A  G  I  I  Y  P  S  Q  S  F  D  A  E  A  T  L  R  A  V  S  E  E  G  A  T  A  L  H  G  V  P  T

1201 ATGCTGTTGGAAGAGATGAACCACCCCAACTTTGCAAAGTACAACCTTTCGACACTTCGGACAGGAATTGCAGCTGGATCCCCTGTGCCCATTGAGGTCA
      M  L  L  E  E  M  N  H  P  N  F  A  K  Y  N  L  S  T  L  R  T  G  I  A  A  G  S  P  V  P  I  E  V  M

1301 TGAAGAACGTGCAGACAAAGATGAACCTGAAGGAGCTGACTATCTGTTACGGCATGACCGAGACCTCGCCCGTGTCCTTCATGACACTCACAACGGATGA
      K  N  V  Q  T  K  M  N  L  K  E  L  T  I  C  Y  G  M  T  E  T  S  P  V  S  F  M  T  L  T  T  D  E

1401 ATTACGGGATCGATGTGAGACTGTTGGACGAATTATGCCACATCTCGAGGCCAAAGTCGTCAACCCTGAGACGGGAGAGACTTTGCCAGTGAATTCATCA
      L  R  D  R  C  E  T  V  G  R  I  M  P  H  L  E  A  K  V  V  N  P  E  T  G  E  T  L  P  V  N  S  S

1501 GGAGAGTTGTGCACGCGCGGGTATGCTGTGATGGAGGGTGGTTACTGGCGATCCCAGGAGCAGACAGATGCAGTGGTGGACAAGGATGGCTGGATGCACA
      G  E  L  C  T  R  G  Y  A  V  M  E  G  G  Y  W  R  S  Q  E  Q  T  D  A  V  V  D  K  D  G  W  M  H  T

1601 CTGGCGACACTGCCGTGCTCGATGACCGTGGCTTTTGCAGGATCGACGGACGCATCAAGGACATGGTGATCGGAGGAGGCGAAAAAATCCATCCTGTAGA
      G  D  T  A  V  L  D  D  R  G  F  C  R  I  D  G  R  I  K  D  M  V  I  R  G  G  E  K  I  H  P  V  E

1701 GGTCGAGAACTGTCTCTTTGAGATGGACGGCGTCAAGAACGTGTCTGTGATTGGCGTTCCCGACAAGCGGTATGGCGAGCAGGTGTGTGCGTGGATCTCG
      V  E  N  C  L  F  E  M  D  G  V  K  N  V  S  V  I  G  V  P  D  K  R  Y  G  E  Q  V  C  A  W  I  S

1801 ACCAAGGACGGGAAGACGGTCAGTCTGGAGGCAGTGCAAAAGTTCTGTGAGGGCAAGATTGCGCACTACAAGGTGCCGCGGTATGTGGTTGTGGTGGAGT
      T  K  D  G  K  T  V  S  L  E  A  V  Q  K  F  C  E  G  K  I  A  H  Y  K  V  P  R  Y  V  V  V  E  S

1901 CCAATGAGTTCCCGACTACCCCCTCGGGCAAGATCCAAAAGAATGTGATGCGCGAGCTGACCAAGGCGAAGCTGCAGCTGCCTTGATGGTACTAGGATAT
      N  E  F  P  T  T  P  S  G  K  I  Q  K  N  V  M  R  E  L  T  K  A  K  L  Q  L  P

2001 GGAGCCGACGAAAGTAATAAAGGCGTATGCTGGCATGGCGCAAGATCTGAGCCCTGCGGTGAGGTGCATTCAGTGACGCCATTAG
```

```
   1 TGCTTTTCTCTTCTTCGTCACCGTCCTTCTTCCCATTCCTCCGGTCCTCCTCGGTTCCTAATCAGTTTCTCAGACCCTGTCCATTCCTCTGGCCTCCACA

101 CACACCCCACTCTCCCTTGAACAAATACCTTATCCAGATCAAAGACATGCCTTCCTTCAAAAAGTACAACCTCGACAAGCAGAGTGTTGAGGTCCCTGGC
                                             M  P  S  F  K  K  Y  N  L  D  K  Q  S  V  E  V  P  G

201 ACTCGGAAGCCTGGCGCTTCAGGCCACTACAGACATGCCGGCCTACGGCGATGCTCTTGTCACCAACATCCGTGAGGCCCCTCATATCGAAACTCTTTACG
      T  R  K  P  G  A  S  G  H  Y  R  H  A  A  Y  G  D  A  L  V  T  N  I  R  E  A  P  H  I  E  T  L  Y  D

301 ACATGTGGCAGAACTCTGTGACAAAGTATGGCGGCAATGACTTTTTGGGTCACCGTCCCTTCAACACTGTTGCCCAGACCTATGGTGGCTACAGTTGGGA
         M  W  Q  N  S  V  T  K  Y  G  G  N  D  F  L  G  H  R  P  F  N  T  V  A  Q  T  Y  G  G  Y  S  W  E

401 GACGTACCGCCAGATTAACCAGCGCGTTAATGCGTTCGGCAGGGGTATCATGCACCTGAACGAGGTGATCCTCGGCAACCGCCAGCTTAACCGCTGGGCG
         T  Y  R  Q  I  N  Q  R  V  N  A  F  G  S  G  I  M  H  L  N  E  V  I  L  G  N  R  Q  L  N  R  W  A

501 TTGGGCATCTGGTCCCACGGTCGCCCTGAGTGGTTCATTACGGAGATGAGCTGCAACTGCTACAACCTCATTTCTGTTGCATTGTACGACACCCTTGGAC
         L  G  I  W  S  H  G  R  P  E  W  F  I  T  E  M  S  C  N  C  Y  N  L  I  S  V  A  L  Y  D  T  L  G  P

601 CTGATGCAGTCGAGTACATTGTCAACCACGCCGAGATTGAGATTGTTGTCTCAAGTGCCAACCATATCGCCTCTTTGCTCGAGAACGCCGAGAAGCTCCC
         D  A  V  E  Y  I  V  N  H  A  E  I  E  I  V  V  S  S  A  N  H  I  A  S  L  L  E  N  A  E  K  L  P

701 CAAGCTCAAGGCCATTGTCAGCATGGATGCTCTTCACGATACCGTCCCCGGTGCCCGGCGCCACCTCTGCCGCACAGGTTCTTCGTGCCTGGGGTGCACAA
         K  L  K  A  I  V  S  M  D  A  L  H  D  T  V  P  V  P  G  A  T  S  A  A  G  V  L  R  A  W  G  A  G

801 AAGGGCATCAAGGTCTATGACTTTAACGAGATTGAGTCCCTCGGTGCCGAGTTCCCTCGGCAAGCACCTGCCTCCCACGGCTGATGAGGTCGCCTCCATCT
         K  G  I  K  V  Y  D  F  N  E  I  E  S  L  G  A  E  F  P  R  K  H  L  P  P  T  A  D  E  V  A  S  I  C

901 GCTACACTTCGGGCACCACCGGTCAGCCTAAAGGAGCCATGCTCACCCACAGAAACTTTGTTGCTACTGTTGGTACCAACCGCGAGGGCATGCTTCTCAC
         Y  T  S  G  T  T  G  Q  P  K  G  A  M  L  T  H  R  N  F  V  A  T  V  G  T  N  R  E  G  M  L  L  T

1001 CGAGGACGACGTTTTGATCAGTTTCTTGCCCTTGGCTCACATTATGGGACGCGTCATTGACACTTGCTCGATGTACAGCGGTGGCAAGATTGGTTACTTC
         E  D  D  V  L  I  S  F  L  P  L  A  H  I  M  G  R  V  I  D  T  C  S  M  Y  S  G  G  K  I  G  Y  F

1101 CGTGGAGATATTCTTTTGCTTCTCGAGGACGTTGCTGAGGTCCGTCCCACATTCTTCCCAGCTGTGCCTCGCCTCTTGAACGGCATTTATGCCAAGCTGG
         R  G  D  I  L  L  L  L  E  D  V  A  E  L  R  P  T  F  F  P  A  V  P  R  L  L  N  R  I  Y  A  K  L  V

1201 TTGCCTCTACCATTGAGGCCCCCGGTTTGGTCGGTGCCTTGGCCCGTCGCGGTGTCGCCGGCCAAGATGGCCAACCTTGCTGCCGGAAAGGGTGTCAACCA
         A  S  T  I  E  A  P  G  L  V  G  A  L  A  R  R  G  V  A  A  K  M  A  N  L  A  A  G  K  G  V  N  H

1301 CGCTCTCTGGGACAGACTGCTGTTCAACAAGGTCAAGATGGCCCTGGGTGGTCGCGTTCAGGTCATCCTGACTGGATCTGCGCCCATTGCCAAGGAGGTT
         A  L  W  D  R  L  L  F  N  K  V  K  M  A  L  G  G  R  V  Q  V  I  L  T  G  S  A  P  I  A  K  E  V

1401 CTCAGCTTCTTGAGAATTGCTTTCGGATGCGTGGTTTTGGAGGGATACGGCTGCACTGAGGGCATGGCTACCGCCACCATCACAATGGCTGATGAGTACA
         L  S  F  L  R  I  A  F  G  C  V  V  L  E  G  Y  G  S  T  E  G  M  A  T  A  T  I  T  M  A  D  E  Y  I

1501 TTCCTGGTCACATTGGCTGCCCTCGTGCTGGATGCGAGCTCAAGCTGGTGGATGTGCCCGCGATGAACTACCTCTCTACCGACCAGCCCTACCCCCGTGG
         P  G  H  I  G  C  P  R  A  G  C  E  L  K  L  V  D  V  P  A  M  N  Y  L  S  T  D  Q  P  Y  P  R  G

1601 AGAGATCTGGATCCGTGGTGACACTGTTTTCAAAGGATACTTCAAGGACGAGAAGAACACTAGTGAGACTATCGACTCTGAAGGCTGGCTCGCTACCGGT
         E  I  W  I  R  G  D  T  V  F  K  G  Y  F  K  D  E  K  N  T  S  E  T  I  D  S  E  G  W  L  A  T  G

1701 GATATTGGATTTGTGGATAAGCGTGGATGCTTTACGATCATTGACCGCAAGAAGAACATCTTCAAGTTGGCACAAGGTGAATACATTGCTCCTGAAAAGA
         D  I  G  F  V  D  K  R  G  C  F  T  I  I  D  R  K  K  N  I  F  K  L  A  Q  G  E  Y  I  A  P  E  K  I

1801 TTGAGAACGTCTTGGGCGCACGCTGCAATCTTGTCCAGCAGATCTATGTTCATGGTGATTCGCTTGAGTCCACCTTGGTCGCAGTTCTTATTCCCGAGCC
         E  N  V  L  G  A  R  C  N  L  V  Q  Q  I  Y  V  H  G  D  S  L  E  S  T  L  V  A  V  L  I  P  E  P

1901 CGAGACCTTCCTGCCCTTCGCGAATGCCATTGCTGGTGCCTCCGTCACTGCTGGAGATGTTGAGGGTTTGAACAAGCTGTGCCAAGATCCCAAGGTCAAG
         E  T  F  L  P  F  A  N  A  I  A  G  A  S  V  T  A  G  D  V  E  G  L  N  K  L  C  Q  D  P  K  V  K
```

Figure 15B

```
2001    ATCGCGGTTCTGAAGGAGTTGGAGAAGGCCGGAAAGGCCGGTGCGATGCGCGGATTGGAGTTCGTGAAGCGTGTCCACTTGACCACGGATGCATTCTCGG
          I  A  V  L  K  E  L  E  K  A  G  K  A  G  A  M  R  G  F  E  F  V  K  R  V  H  L  T  T  D  A  F  S  V

2101    TCGACAACGGCATGATGACACCTACCTTCAAGGTCCGTCGCCCACAAGTAGCCGAGCATTTCAGGGAGCAAATCACGGGCCATGTATAAGGAGATCAATGC
          D  N  G  M  M  T  P  T  F  K  V  R  R  P  Q  V  A  E  H  F  R  E  Q  I  T  A  M  Y  K  E  I  N  A

2201    CTCGACCCCTGTTGCCAAGCTGTAGATAGAAAACTGTTTGCCCCTTATTACCCTTTGAATAGAAGGTGACACGTTGTTTGATTCACACAAAAAAAAAAAA
          S  T  P  V  A  K  L

2301    AAAAAA
```

```
            2801     2816
genome   TGTTGCGAAGCTGTAG
   CDS   TGTTGCGAAGCTGTAG
```

Figure 17

```
   1  TCGCTATCTATCACCCCTCAGTCCCCACTCCGCACTCTGCTCTTCCTTTTTCCTTTCTCTCTCTCACCGTCGCCACTGTCTCTACTTTCTTTACCACCCA

101  CGCATCAGTCACAGCATGGTTGCTCTCCCGACTCGTCGCAGCAGCTGTCCCAGCTGCCATGTATGTGAGCTCAAAGCTGGCACTTCCTCGGGATATGAAGT
                       M  V  A  L  P  L  V  A  A  A  V  P  A  A  M  Y  V  S  S  K  L  A  L  P  R  D  M  K  L

201  TGATTAAGAGCTTGATCGGAGCCAAGATGGCCTACAGTGCCATGGAAAAGAACGACGCCCTCAACCTGACACTCCGCTTCGACGAGTGCTACCGCAAGTA
       I  K  S  L  I  G  A  K  M  A  Y  S  A  M  E  K  N  D  A  L  N  L  T  L  R  F  D  E  C  Y  R  K  Y

301  TCCTGACCGTGAAGCCCTGGTCTTTGAGGGCAAATCCTATTCATTCCGTGATATTCAGCTTGCCTCCAACAGGTGCGGCAACTGGTTGCTGGCCAAAGGG
       P  D  R  E  A  L  V  F  E  G  K  S  Y  S  F  R  D  I  Q  L  A  S  N  R  C  G  N  W  L  L  A  K  G

401  ATCAAGCGAGGAGATATCGTCTCGCTTTTCATGTTGAACAGGCCAGAGTTCATCTTCTGCTGGCTGGGTCTCAACAAGATTGGAGCCACTGGTGCCTTCA
       I  K  R  G  D  I  V  S  L  F  M  L  N  R  P  E  F  I  F  C  W  L  G  L  N  K  I  G  A  T  G  A  F  I

501  TCAATACCAACCTTACGGGCAAACCCCTGACACATTCCCTCCGGACAGCCACGTCGTCAATGTTGATCATGGACACGGAGTTGACAGACGCGATCGCCAA
       N  T  N  L  T  G  K  P  L  T  H  S  L  R  T  A  T  S  S  M  L  I  M  D  T  E  L  T  D  A  I  A  N

601  GTCCCTGGATGAGATTCAGGAGATGGGCTATTCAATTTACTCTTACGGACCCGAAGCCGTGGACTTTGCTACCCCGATGGATATCTCGCAGGTCCAGAC
       S  L  D  E  I  Q  E  M  G  Y  S  I  Y  S  Y  G  P  E  A  V  D  F  A  T  P  M  D  I  S  Q  V  P  D

701  ACCGATACACCCGAACACCTGCGCCGGAACACGACCGCGGATGACATTGCGATGCTCATCTACACCTCTGGAACTACTGGTCTTCCCAAGGCCGGTCGTG
       T  D  T  P  E  H  L  R  R  N  T  T  A  D  D  I  A  M  L  I  Y  T  S  G  T  T  G  L  P  K  A  G  R  V

801  TCTCTCATGCGCGTGCCTCTATGGGACCTCAGTTTTGGAACCGATTCTATCACTTCAGTGAGAGCGACAGGGTCTATCTGTCCTTGCCCTTGTACCACAG
       S  H  A  R  A  S  M  G  P  Q  F  W  N  R  F  Y  H  F  S  E  S  D  R  V  Y  L  S  L  P  L  Y  H  S

901  TGCTGGCGCCATCTTGGGAGTGATTGCTTGTTGGACCTCGGGAGCAACCTTGATCCTGGCCCGCAAGTTCTCCGCGACACATTTCTGGGAGGATTGCCGC
       A  G  A  I  L  G  V  I  A  C  W  T  S  G  A  T  L  I  L  A  R  K  F  S  A  T  H  F  W  E  D  C  R

1001  GTGAACAACGCAACTGTGATTCAATACATTGGAGAAATTTGCAGATATCTGCTCAACACGCCAGAATCACCCCTGGACAAGGCACACTCGATACGACTGG
       V  N  N  A  T  V  I  Q  Y  I  G  E  I  C  R  Y  L  L  N  T  P  E  S  P  L  D  K  A  H  S  I  R  L  A

1101  GACATGGTAATGGAATGCGACCCGATGTCTGGACTCGCTTCAGAGATCGGTTCGGCATCCCGTTGATTGGCGAGTGGTATGCATCGACTGAGGGAACTGG
       H  G  N  G  M  R  P  D  V  W  T  R  F  R  D  R  F  G  I  P  L  I  G  E  W  Y  A  S  T  E  G  T  G

1201  AGCCTTGTCGAATTATAACACAGGCCCAGGCGGCGCTGGAGCGATTGGATACCGCGGTACCCTTGCCAGAGCATTGGATAAAGGACTCAGGATTGCGAGA
       A  L  S  N  Y  N  T  G  P  G  G  A  G  A  I  G  Y  R  G  T  L  A  R  A  L  D  K  G  L  R  I  A  R

1301  TTTGATGTCCAGACAGAGGAGTTGGTTCGGGACAAAAACGGTTATTGCATTGAGTGCAAACCTGGCGAGCCCGGAGAATTGCTGACGCTTGTTGATGCTA
       F  D  V  Q  T  E  E  L  V  R  D  K  N  G  Y  C  I  E  C  K  P  G  E  P  G  E  L  L  T  L  V  D  A  K

1401  AAGAGCCCGAACAAAGACTTCAAAGGATACCATCAAAACCCAGGCAGCGACCAACAAAAAGATTGTCAAAGATGTTTTCAAAGCCGCCGACATGTACTTCCG
       E  P  N  K  D  F  K  G  Y  H  Q  N  Q  A  A  T  N  K  K  I  V  K  D  V  F  K  A  G  D  M  Y  F  R

1501  TACCGGAGATATCCTTCGCCGCGATAGCGATGGGTACTTTTACTTTGGCGACCGTGTGGGCGATACATTCGGGTGGAAGTCCGAGAATGTGTCTACGGCC
       T  G  D  I  L  R  R  D  S  D  G  Y  F  Y  F  G  D  R  V  G  D  T  F  R  W  K  S  E  N  V  S  T  A

1601  GAGGTGTCTGAAGTCCTCTCGCAGTATCCGGACTGTATCGAAGTCAATGTGTATGGAGTTCAGATCCCAGGGCAGGACGGACGCGCCGGTATGGCAGCGA
       E  V  S  E  V  L  S  Q  Y  P  D  C  I  E  V  N  V  Y  G  V  Q  I  P  G  Q  D  G  R  A  G  M  A  A  I

1701  TTGTGTCCAAGAGCACGATGGATTGGGAGAAATTTGCGGCGTATGCACTCAAGAACCTGCCGCGGGTATTCTGTTCCGATCTTTATCCGCAAGATGCCGA
       V  S  K  S  T  M  D  W  E  K  F  A  A  Y  A  L  K  N  L  P  R  Y  S  V  P  I  F  I  R  K  M  P  E

1801  GATGGAGATCACAGGGACGTTCAAGCAGCGCAAAGTCGAGTTGGTGAATGAGGGAATCGACCCCAAGACGATTGCCAACGAGATGCTGTGGTTGGACGGA
       M  E  I  T  G  T  F  K  Q  R  K  V  E  L  V  N  E  G  I  D  P  K  T  I  A  N  E  M  L  W  L  D  G

1901  GACCACTATAAGCCGTTCAAGGCGGCCGAGCACCAGCGCGTCATCAGCGGCAAGGCCAAGCTATAGTAGGGCGCGTGCGCCAATGCAGTAGCAATAGTAT
       H  H  Y  K  P  F  K  A  A  E  H  Q  R  V  I  S  G  K  A  K  L

2001  TCCCCGCTTTGTCCATTAAAAAAAAAAAAAAAAAAAAAAAAA
```

```
   1  ATGGAAACCTTGGTTAACGGAAAGTATGCGGTGGAGTACGACGAGGTCGATCACATCTATCGCAACGTCATGGCTACAGGCGGGCTCCTCGACAGGCCTA
      M  E  T  L  V  N  G  K  Y  A  V  E  Y  D  E  V  D  H  I  Y  R  N  V  M  A  T  G  G  L  L  D  R  P  M

101  TGCCTCCATACTACGACATCAAGGAGCGCACCATGGCCCACCTCTTTGAGTATATGGCCAACACCTACGAAGACAAAGACGCCATGGGCTGGCGAGACAT
       P  P  Y  Y  D  I  K  E  R  T  M  A  H  L  F  E  Y  M  A  N  T  Y  E  D  K  D  A  M  G  W  R  D  I

201  TATCAAGGTCCACAAGGTCGAGAAGCAGGCTGCCAATCCTGGCGAGAAGCCAAAGACCTGGATCACTTATGAGCTCTCGGACTACAACTGGATGTCGTAC
       I  K  V  H  K  V  E  K  Q  A  A  N  P  G  E  K  P  K  T  W  I  T  Y  E  L  S  D  Y  N  W  M  S  Y

301  CGGCCAAGCCAAGAACTATGCAGATCGAGTTGGCTTGGGCATCAGACGCCTTGGAGTTGAGAAGGGAGACTTTGTCATGATCTTTGCTAGCACATGTCCG
       R  Q  A  K  N  Y  A  D  R  V  G  L  G  I  T  R  L  G  V  E  K  G  D  F  V  M  I  F  A  S  T  C  P  E

401  AATGGTTCCTGACAGCGCATGGATGCTTCTCGCAGTCAGTGACTATCGTGACAGCCTACGACTCGATGGACGAGAAGTCGATCCAGTTTATTGTTGACCA
       W  F  L  T  A  H  G  C  F  S  Q  S  V  T  I  V  T  A  Y  D  S  M  D  E  K  S  I  Q  F  I  V  D  Q

501  GTCCCAGCCCAAGGCCATCTTTGCTGATGCGCACACGCTCCCTGTGGTGTCCAAACTCATGCAGAAGGGCAACAGTGGTGTCAAGGCAGTCATTTACACA
       S  Q  P  K  A  I  F  A  D  A  H  T  L  P  V  V  S  K  L  M  Q  K  G  N  S  G  V  K  A  V  I  Y  T

601  GGCCAAGAGTGGGAAGTGACCGATGCAATCAAGAAGATGGAGCAAGTAGAAAACCGCTCATTTGAGCTGGTTCATATCGAGGAACTCAAGAAGACCAAGT
       G  Q  E  W  E  V  T  D  A  I  K  K  M  E  Q  V  E  N  R  S  F  E  L  V  H  I  D  E  L  K  K  T  K  S

701  CAGCATCTAACGGCGAACAGTCTGCCGGAAAGGGGAAGCAGAGATCATCTGAGGATGCCGAAGGCGCTCAGGACGAGATCGAGGTCATATACCCTAAGGC
       A  S  N  G  E  Q  S  A  G  K  G  K  Q  R  S  S  E  D  A  E  G  A  Q  D  E  I  E  V  I  Y  P  K  A

801  GGATGATCTGGCCTGTATTATGTATACCTCTGGGTCGACGGGTCAGCCCAAGGGCGCGCAATTGACACATGGCAACTTGATGGCGGCCATTGGAAGTGCT
       D  D  L  A  C  I  M  Y  T  S  G  S  T  G  Q  P  K  G  A  Q  L  T  H  G  N  L  M  A  A  I  G  S  A

901  GGGGCCATGGAGGGCGACCAGCTGGACAAGGAAACAGACATTGTTATTTCATATCTGCCATTGGGCCATGTCCTCGAGTTTGTCATTTCCCACTTTGTGG
       A  A  M  E  G  D  Q  L  D  K  E  T  D  I  V  I  S  Y  L  P  L  A  H  V  L  E  F  V  I  S  H  F  V  V

1001  TATCCATGGGCTGCCGTCTTGGATTCGGACGAGCACGCACTCTGATGGATGATGCAGTCGCTCCCACCGCAGGAAGTGGCAGGTCCAAGGGCCTTGGTGA
       S  M  G  C  R  L  G  F  G  R  A  R  T  L  M  D  D  A  V  A  P  T  A  G  S  G  R  S  K  G  L  G  D

1101  TCTGAAGGCGCTCCAGCCAACATTGATGGCTGGTGTGCCAACGATCTGGGAGCGTATCCGCAAGGGCATCCTGGCCGAGGTCAACAAGCAATCCTTCCCT
       L  K  A  L  Q  P  T  L  M  A  G  V  P  T  I  W  E  R  I  R  K  G  I  L  A  E  V  N  K  Q  S  F  P

1201  ATCCGTACACTCTTCTTTGCTGCACTCAACACCAAGTGGGCTATCGTCCAGGCTACCGGATCTGAGAAGTTTGTCACCAAGACTATTGACTCGTTGGTCT
       I  R  T  L  F  F  A  A  L  N  T  K  W  A  I  V  Q  A  T  G  S  E  N  F  V  T  K  T  I  D  S  L  V  F

1301  TTAGTAAGGCTAAGGAGCTCGTTGGAGGCAAGCTGCGCCTTACCTTGACTGGAGGGGCCGGAATCAGTGATGAGACGCACCGGTTCTTGAGCATGGTAAT
       S  K  A  K  E  L  V  G  G  K  L  R  L  T  L  T  G  G  A  G  I  S  D  E  T  H  R  F  L  S  M  V  M

1401  GTGCTACGTTATCTCGGGATATGGTCTCACTGAAGTCTGTGGTGTTGCCGCTGTCACCCTGCCACGTATGGGTCACCGTCTCAGGACGGTTGGACCACCC
       C  Y  V  I  S  G  Y  G  L  T  E  V  C  G  V  A  A  V  T  L  P  R  M  G  H  R  L  R  T  V  G  P  P

1501  GCGCCCAGTCTTGAGCTGAAGTTGGTGAATGTGCCCGACACCGAGTACACAGGAGACAATGGATGGGCGAAATCTGGTTCCGTGGACCTGCAGTGATGA
       A  P  S  L  E  L  K  L  V  N  V  P  D  T  E  Y  T  G  D  N  G  S  G  E  I  W  F  R  G  P  A  V  M  K

1601  AGGGATACTTCAAACTCGAGGAAGAGACCAAGAAGGTGATGACCGGGGATGGTTGGTTCAAGACAGGCGACATTGGCACGATGAACCCAGACGGCACACT
       G  Y  F  K  L  E  E  E  T  K  K  V  M  T  G  D  G  W  F  K  T  G  D  I  G  T  M  N  P  D  G  T  L

1701  GTCAATCAAGGACAGGGTCAAGAATCTGGTCAAGCTGTCTCATGGAGAATATGTCGCCCTGGAGAAATGTGAAGCCGTTTATCGCGATTCCAAGGAGATC
       S  I  K  D  R  V  K  N  L  V  K  L  S  H  G  E  Y  V  A  L  E  K  C  E  A  V  Y  R  D  S  K  E  I

1801  AAGAGCATTTGCATCGTTGCGGACAATGGGTGCCCTGTGTTGCTGGCCGTTGTGGAACCGAGCCACGCAGGGGCGTCTGACAAGGAGATTTTGGATATCC
       K  S  I  C  I  V  A  D  N  G  C  P  V  L  L  A  V  V  E  P  S  H  A  G  A  S  D  K  E  I  L  D  I  L
```

Figure 19B

1901 TGAAGAGCCAAGCCAAGGCGGCGGGCCTCTCCAAGTCCGAGACTGTGCAAGGCGTTATCATTGATGATTCGGACTGGATGACGAATGGGTTCATGACCTC
. K S Q A K A A G L S K S E T V Q G V I I D D S D W M T N G F M T S .

2001 GAGCAGCAAGGTCAAGAGACGCGAGGTCCGCAAGGCACACAACAAGGATATTGAGGAGATGTGGAAGAAGTTCTAG
. S S K V K R R E V R K A H N K D I E E M W K K F *

Figure 20A

```
            1                                                                                                   100
genome      ATGGAAACCTTCGTTAACGGAAAGTATGCGTCGAGTACGACGAGGTCGATCAGATCTATCGGAACGTCATGGCTACAGCGCGGCTCCTCGACAGCGCTA
CDS         ATGGAAACCTTCGTTAACGGAAAGTATGCGTCGAGTACGACGAGGTCGATCAGATCTATCGGAACGTCATGGCTACAGCGCGGCTCCTCGACAGCGCTA 101                                                                                                 200
genome      TGGCTGCATACTAGGACATCAAGGAGCGCAGCCATGGCCGAGCTCTTTGAGTATATGGGCAAGACCTACGAAGACAAAGACGGCATGGCCGTGGCGAGACAT
CDS         TGGCTGCATACTAGGACATCAAGGAGCGCAGCCATGGCCGAGCTCTTTGAGTATATGGGCAAGACCTACGAAGACAAAGACGGCATGGCCGTGGCGAGACAT 201                                                                                                 300
genome      TATCAAGGGATTGACTGCCCCGGCCTATCACTTTTTACCCCACACGATCGTCCCTTTTTTTTCTCTCCCATTCTTCTATCCTGACCGTATCGCTATCGAA
CDS         TATCAAGGG----------------------------------------------------------------------------------------

301                                                                                                 400
genome      CGAGTCAACGAGATCAGTTCCCACGCTTACTTTACTCCCTCGTCTGATTCTGATTATTTTCTCTCTCTGCCTCTTCGTGATTTGTTCGCAGGTGCAGAAG
CDS         ---------------------------------------------------------------------------------------GCAGAAG 401                                                                                                 500
genome      GTGGAGAAGCAGGCTGCCAATCCTGCGAGAAGCCAAAGACCTGGATCACTTATCAGCTCTCGGACTACAACTGGATGTCGTACGCGCCAAGCCAAGAAGT
CDS         GTGGAGAAGCAGGCTGCCAATCCTGCGAGAAGCCAAAGACCTGGATCACTTATCAGCTCTCGGACTACAACTGGATGTCGTACGCGCCAAGCCAAGAAGT 501                                                                                                 600
genome      ATGCAGATGGACTTGGCTTGGCATCGACACGGCTTGCAGTTGACAAGGCGAGACTTGTCATGATGTTTGCTAGGACATGGTATAACCTCATGCAGACAAC
CDS         ATGCAGATGGACTTGGCTTGGCATCGACACGGCTTGCAGTTGACAAGGCGAGACTTGTCATGATCTTGCTAGGACATG-----------------------

601                                                                                                 700
genome      TTTCGCATCCATGACAGCATCGCAAGAAAAAAAAAGAGAAGGAAATTATGATAATTCGGGCCAAGCGACTAAAACACCGCTATCGCACGCTTTTTTTTTT
CDS         --------------------------------------------------------------------------------------------------

701                                                                                                 800
genome      TTTTTTCGCTATCTTGCATTTCTTATCGTTCAAATAGTCCGAATTGGTTCGTGACAGCGGATGGTAAGCTTTTTCTTTTTGCGGATGATGATTTCTTCTT
CDS         --------------------------------------TCCGAATTGGTTCGTGACAGCGCAT-----------------------------------

801                                                                                                 900
genome      ATGACAGCATGATGAGATTCAACCGGGATTAGGTGACGGCTGTTGATTGTGCAAAAGGGGGCCGGACAATTTGAAGAGACTTGGGGAGGTGTTTGTGAT
CDS         --------------------------------------------------------------------------------------------------

901                                                                                                 1000
genome      GACGACAAATCCAAGATTCAACAGAAGACTGGTGCCAGGGAAGAGTAGAGAGGGTGCCTCGTTCTTTGGCATATGAAAGTGGATTACGATATGGCTGAGT
CDS         --------------------------------------------------------------------------------------------------

1001                                                                                                1100
genome      TAGGAGTCTAATTCATCGCGGAAAAAGAGTCGCGACTGAAGTCCCAAGTCGGGGACTGTAGAAAGTATTCCACTCGTGTCTGGTGAAATGAGGAGGACTG
CDS         --------------------------------------------------------------------------------------------------

1101                                                                                                1200
genome      GGTTGGGGTTTGGAGTGCCGACGAGAAATCATGGAATACGCTTCTCGGTCTTCAGTCCACTGATCACTCATGGCGCAATTGACTCTACAATAATAGGATG
CDS         -----------------------------------------------------------------------------------------------GATG 1201                                                                                                1300
genome      CTTCTGCGCAGTCAGTGACTATCGTGACAGCCTACGACTCGATGGACGAGAAGTCGATCGAGTTTATTGTTGACCAGTCGCAGCCAAGCGCATCTTTGGT
CDS         CTTCTGCGCAGTCAGTGACTATCGTGACAGCCTACGACTCGATGGACGAGAAGTCGATCGAGTTTATTGTTGACCAGTCGCAGCCAAGCGCATCTTTGGT 1301                                                                                                1400
genome      GATGCGCAGAGGCTCGGCTGTGCTGTCGAAACTCGATGCAGAAGGCAACAGTGGTCTCAAGGCAGTCATTACAGAGGCGAAGAGTGGCAAGTGACGGATG
CDS         GATGCGCAGAGGCTCGGCTGTGCTGTCGAAACTCGATGCAGAAGGCAACAGTGGTCTCAAGGCAGTCATTACAGAGGCGAAGAGTGGCAAGTGACGGATG
```

```
              2901                                                                                       3000
genome  GTGGAACGGAGCCACGGCAGGGGTGAGTGAGACGCTTTTGGCCTGACAAGGTCTCGTTCTTATGGGAATGTGGATCATTACTCTATCACTAACGAGAGG
CDS     GTGGAACGGAGCCACGGCAGGGG--------------------------------------------------------------------------

3001                                                                                       3100
genome  CTGTATTATTCTACTTGCGTAACGTGGCATAGGGGTCTGACAAGGAGATTTTGGATATCCTGAAGAGCCAAGCCAAGGCGGCGGCGCTCTCAAGTCCGA
CDS     ---------------------------------GGTCTGACAAGGAGATTTTGGATATCCTGAAGAGCCAAGCCAAGGCGGCGGCGCTCTCAAGTCCGA 3101                                                                                       3200
genome  GACTGTCAAGGCGTTATCATTGATGATTCGGACTGGATGACGAATGGGTTCATGACCTCGAGCAGCAAGGTCAAGAGACGGCAGGTCGGCAAGGCACAC
CDS     GACTGTCAAGGCGTTATCATTGATGATTCGGACTGGATGACGAATGGGTTCATGACCTCGAGCAGCAAGGTCAAGAGACGGCAGGTCGGCAAGGCACAC 3201                 3236
genome  AACAAGGATATTGAGGAGATGTGGAAGAAGTTCTAG
CDS     AACAAGGATATTGAGGAGATGTGGAAGAAGTTCTAG
```

Figure 21A

```
  1  CATGGCAAAGTGCTTTACCGTCAACGTCGGCCCCGAGGACGTCAAGGGCGAGACTCGGATCCGTCGCTCCATCCAGGCCGTCGACAAACTCATGGACTCA
      M  P  K  C  F  T  V  N  V  G  P  E  D  V  K  G  E  T  R  I  R  R  S  I  Q  A  V  D  K  L  M  D  S

101  CCCTCAAGCGACATCAAGACCTTGTACGATGTCATCCAGTACTCTGCCAAGGTCCGCCCCAACCTCAACGCCATCGGCTACCGCAAGATTGTCAAGATGA
      P  S  S  D  I  K  T  L  Y  D  V  I  Q  Y  S  A  K  V  R  P  N  L  N  A  I  G  Y  R  K  I  V  K  M  I

201  TCGAAGAGGAAAAGGAGATCACCAAGATGGTCAGCGGCGAGCCTGTCAAGGAGAAAAAGACGTGGAAATACTTCAAGCTCTCCGGCTACCACTATCTGAC
      .  E  E  E  K  E  I  T  K  M  V  S  G  E  P  V  K  E  K  K  T  W  K  Y  F  K  L  S  G  Y  H  Y  L  T

301  CTACAAGGACACCAAGGCCGTCATCGACAGCATTGGAAGTGGCCTGCGCAAGTGGGGTGTTGAGCCCAAGGAGAGGATCACCGTCTTTGGTTCCACAAGT
      .  Y  K  D  T  K  A  V  I  D  S  I  G  S  G  L  R  K  W  G  V  E  P  K  E  R  I  T  V  F  G  S  T  S

401  GCCAACTGGCTGCTGGTCGCTCATGGTGCCTTCACGCAGTCCATGACCATCGTCACCGTGTATGACACTTTGGGCGAGGAAGGATTGCTGCACTCGATGA
      A  N  W  L  L  V  A  H  G  A  F  T  Q  S  M  T  I  V  T  V  Y  D  T  L  G  E  E  G  L  L  H  S  M  N

501  ACGAGGCCGAGGTGGGAACGGCCTACACGAACGCTGATTTGATCAAGACAATGACCAACGTTTCAGGACGCTGCCCGACCCTCAAGAGGATCGTCTATGA
      .  E  A  E  V  G  T  A  Y  T  N  A  D  L  I  K  T  M  T  N  V  S  G  R  C  P  T  L  K  R  I  V  Y  D

601  CGGCGAAGCCAACGCAGCAGACGTGATCGCCCTTCAGACGGCCCATCCTCACCTTCAGCTTATCACTCTGGAGGAGCTGAAGCAGCTCGGTGTGGATCAC
      .  G  E  A  N  A  A  D  V  I  A  L  Q  T  A  H  P  H  L  Q  L  I  T  L  E  E  L  K  Q  L  G  V  D  H

701  CCTGTGGAGCCCACTCCTCCCACCGGCGAGGATTGCTCCTGCATCATGTACACTTCTGGATCGACCGGAAACCCTAAGGGAGTCATCCTCACTCACGGAA
      P  V  E  P  T  P  P  T  A  E  D  C  S  C  I  M  Y  T  S  G  S  T  G  N  P  K  G  V  I  L  T  H  G  N

801  ACCTCATTGCCGCCATTGGCGGAGTTAACAAGATGCTGGAAAAGTACATTCGCGAAGGCGATGTCTTGCTTGCCTACCTTCCCTTGGCTCACGTTCTGGA
      .  L  I  A  A  I  G  G  V  N  K  M  L  E  K  Y  I  R  E  G  D  V  L  L  A  Y  L  P  L  A  H  V  L  E

901  ATTCATGGTTGAGAACCTCTGTCTCTTCTGGGGTGTAACCCTTGGATATGGTACTGTCCGCACGCTGACGGATGCCTCTGTGCGTGAGTGCCAGGGTGAT
      .  F  M  V  E  N  L  C  L  F  W  G  V  T  L  G  Y  G  T  V  R  T  L  T  D  A  S  V  R  E  C  Q  G  D

1001 ATCAAGGAATTGCGGCCTACGCTTATGACCGGCGTTCCAGCAGTGTGGGAGACCATCCGGAAAGGTGTTCTCGCCCAAGTAAACCAGGGTTCACCTCTGG
      I  K  E  L  R  P  T  L  M  T  G  V  P  A  V  W  E  T  I  R  K  G  V  L  A  Q  V  N  Q  G  S  P  L  V

1101 TTCAATCCGTCTTCAACGCGGGCTCTGAACGCCAAGGCCTGGTGCATGGACCGCAAACTAGGCGCTTTGACTGGAATTTTCGACACTGTGGTGTTCAACAA
      .  Q  S  V  F  N  A  A  L  N  A  K  A  W  C  M  D  R  K  L  G  A  L  T  G  I  F  D  T  V  V  F  N  K

1201 GGTCCGTCAGCAAACTGGAGGTCGTCTTCGCTACGCGCTCTCGGGCGGCGCGGCCTATCTCCCAGGAGACCCAGGCGCTTCTTGACCACAGCACTGTGCCCT
      V  R  Q  Q  T  G  G  R  L  R  Y  A  L  S  G  G  A  P  I  S  Q  E  T  Q  R  F  L  T  T  A  L  C  P

1301 ATCCTTCAAGCCTATGGCATGACTGAGTCGTGCGGCATGTGCTCGATCATGACTCCAGAGGCGTTCAACTACAACCGCGTCGGTTCCCCTGTTCCCTGCA
      I  L  Q  A  Y  G  M  T  E  S  C  G  M  C  S  I  M  T  P  E  A  F  N  Y  N  R  V  G  S  P  V  P  C  T

1401 CAGAGGTCAAGCTCGTGGATGTGCCCGATGCAGGATACTTTTCGGACTGATTCGCCCCGGCCTCGTGGTGAGATTTGGATTCGGGACCCTCCATCACCTC
      .  E  V  K  L  V  D  V  P  D  A  G  Y  F  S  T  D  S  P  R  P  R  G  E  I  W  I  R  G  P  S  I  T  S

1501 TGGATACTTCAAGAACGCTGAGGAGACCTCGGCAGCCATCACAGAGGACCGCTGGCTCAAGACTGGAGATATTGGAGAGTGGCATGCTGATGGCACACTC
      .  G  Y  F  K  N  A  E  E  T  S  A  A  I  T  E  D  R  W  L  K  T  G  D  I  G  E  W  H  A  D  G  T  L

1601 TCGGTCATTGATCGCAAGAAGAACTTGGTCAAGTTGTCGCATGGGGAGTACATTGCTCTAGAGAAACTTGAGTCGGTGTACAAGAGCACGGCTTACTGCA
      S  V  I  D  R  K  K  N  L  V  K  L  S  H  G  E  Y  I  A  L  E  K  L  E  S  V  Y  K  S  T  A  Y  C  N

1701 ACAACATCTGCGTTTATGCCGATTCCATGCAAAACAAGCCTGTGGCGCTGATTGTTGCGAGTGAACCCCGCATCCTCGAGCTGGCCAAGGCCAAGGGCCT
      .  N  I  C  V  Y  A  D  S  M  Q  N  K  P  V  A  L  I  V  A  S  E  P  R  I  L  E  L  A  K  A  K  G  L

1801 GGAGAGCCGCGACTTTGCAGTGCTCTGCCACGATAAGGTGATCATCAAGGCTGTCCTCGACGCCTGTCTCGCGACTGCCAAAAAGGCTGGCCTCAAGCCC
      .  E  S  R  D  F  A  V  L  C  H  D  K  V  I  I  K  A  V  L  D  A  C  L  A  T  A  K  K  A  G  L  K  P
```

Figure 21B

1901 GCCGAGTTGCTGCAGGGTGTGTACCTGGAGTCTGAGGAGTGGACCGCTCAAGGCGGTTTGTTGACTGCTGCTCAGAAATTGAAGCGCAAGGAAATCAACC
      A  E  L  L  Q  G  V  Y  L  E  S  E  E  W  T  A  Q  G  G  L  L  T  A  A  Q  K  L  K  R  K  E  I  N  Q

2001 AGGCTTATGCTGACCAGATCAAGCAGATCTATGGCTCCAAGTAAAAATGAAC
      A  Y  A  D  Q  I  K  Q  I  Y  G  S  K

```
   1  CCTTTATCCCGGCACCGCCATCTCTCGCCGCCACCATCTCGCATTCCTTTGAATCCACACTCCCACCTGTGCCCCCTGCTTTTCACGTCCCGCTCTCATC

101  CCGCCTTCTCCTTTCATCACCCCAATTCAACATGACAAAGTGCCTCACCGTCGAAGTCGGACCCGCCGACGTCCAGGGCGAGACCCGCATCCGCCGCTCC
                                     M  T  K  C  L  T  V  E  V  G  P  A  D  V  Q  G  E  T  R  I  R  R  S

201  GTCCTCTCTGCAAAGCGCCTCATGTCCTCGCCCTCGGATGACATCAAGACCCTCTACGACGTCTTCAACCACTCCGTCAGCGTCCGCCCCAACCTCAACG
       V  L  S  A  K  R  L  M  S  S  P  S  D  D  I  K  T  L  Y  D  V  F  N  H  S  V  T  V  R  P  N  L  N  A

301  CGATCGGATACCGCAAGGTCGTCAAGATTGTCGAGGAAGAAAAGGAGGTCGTCAAGGTTGTCAACGGCGAGGAAGTCAAGGAAAAGAAGACCTGGAAGTT
        I  G  Y  R  K  V  V  K  I  V  E  E  E  K  E  V  V  K  V  V  N  G  E  E  V  K  E  K  K  T  W  K  F

401  CTTCAAGATGTCGGGCTACCACTGGCTCACCTACAAGGATGCGAAGCAGGTCGTCGACAGCATCGGATGCGGTCTTCGCAAGTTTGGCGTCGAGCCCAAG
        F  K  M  S  G  Y  H  W  L  T  Y  K  D  A  K  Q  V  V  D  S  I  G  C  G  L  R  K  F  G  V  E  P  K

501  GACAAGCTGACCGTTTTCGGTGCCACAAGTGCCAACTGGCTCCTGCTTGCCCACGGTGCTTTCACCCAGTCCATCACCATTGTTACCGCCTACGACACCC
        D  K  L  T  V  F  G  A  T  S  A  N  W  L  L  L  A  H  G  A  F  T  Q  S  I  T  I  V  T  A  Y  D  T  L

601  TGGGCGAGGACGGTCTTTTGCACTCTATGAACGAGGCCGAGGTGGCCACCGCTTACACAAACGGCGACTTGCTCAACACTATCAAGAACGTTGCCGGCAA
         G  E  D  G  L  L  H  S  M  N  E  A  E  V  A  T  A  Y  T  N  A  D  L  L  N  T  I  K  N  V  A  G  K

701  ATGCCCCACCCTGAAGAAGATCATCTACGACGGCGATGCCAAGCCCGCAGATGTCATTGCCCTCCAGGAGGCCCATCCTCACCTCCAGCTCATCACCCTC
         C  P  T  L  K  K  I  I  Y  D  G  D  A  K  P  A  D  V  I  A  L  Q  E  A  H  P  H  L  Q  L  I  T  L

801  GAGGAGCTGAAGCAGCTCGGAGTGGACAACCCTGTCGCCCCAACCCCTGCTGCTGCCAAGGACTACTGCTGCATCATGTACACTTCGGGATCGACTGGCA
         E  E  L  K  Q  L  G  V  D  N  P  V  A  P  T  P  A  A  K  D  Y  C  C  I  M  Y  T  S  G  S  T  G  N

901  ACCCCAAGGGAGTGTTGCTGACCCATGGAAACCTCGTTGCTGCCATCGGAGGTGTGAACAAGATGCTGACAAAGTACGTTCACGAGGGAGACGTCTTGCT
         P  K  G  V  L  L  T  H  G  N  L  V  A  A  I  G  G  V  N  K  M  L  T  K  Y  V  H  E  G  D  V  L  L

1001  CGCGTACTTGCCTCTTGCTCACGTTCTCGAGTTCCTGGTCGAAAACGTCTGTCTCTTCTGGGGTGTGACTCTTGGCTACGGTACCGTCCGCACATTGACT
         A  Y  L  P  L  A  H  V  L  E  F  L  V  E  N  V  C  L  F  W  G  V  T  L  G  Y  G  T  V  R  T  L  T

1101  GATGCCTCAGTCCGTGAGTGCCAGGGTGATATCAAGGAGTTGCGCCCTACATTGATGACCGGTGTTCCTGCTGTGTGGGAGACGATTCGTAAGGGAGTGT
         D  A  S  V  R  E  C  Q  G  D  I  K  E  L  R  P  T  L  M  T  G  V  P  A  V  W  E  T  I  R  K  G  V  L

1201  TGGCTCAGGTTTCCCAGGGGCTCACCTCTTGTTCAAAAGATCTTCCATGCTGCTTTGAACGCCAAGGCCTGGTGCCTGGACCGCAAGTTGGGTGCGTTGAC
          A  Q  V  S  Q  G  S  P  L  V  Q  K  I  F  H  A  A  L  N  A  K  A  W  C  L  D  R  K  L  G  A  L  T

1301  TGGAATCTTCGATACTGTCGTCTTCAACAAGGTCAAGCAGCAGACAGGAGGACGTCTTCGCTTCGCCCTTTCGGGAGGTGCACCCATCTCTCAGGAGACC
          G  I  F  D  T  V  V  F  N  K  V  K  Q  Q  T  G  G  R  L  R  F  A  L  S  G  G  A  P  I  S  Q  E  T

1401  CAGCGCTTCTTGACGACAGCTTTGTGCCCTATCCTCCAGGGCTACGGTATGACAGAGTCTTGCGGCATGTGCGCCATTTTGACCCCCGATGTCTTCAACT
          Q  R  F  L  T  T  A  L  C  P  I  L  Q  G  Y  G  M  T  E  S  C  G  M  C  A  I  L  T  P  D  V  F  N  Y

1501  ACAGCCGTGTCGGATCCCCAGTTCCTTGCACGGAGGTCAAGTTGGTGGATGTGCCCGATGCAGGATACCACTCAACGGACTTGCCTCTCCCCGTGGTGA
           S  R  V  G  S  P  V  P  C  T  E  V  K  L  V  D  V  P  D  A  G  Y  H  S  T  D  L  P  L  P  R  G  E

1601  GGTCTGCATTCGTGGACCCTCCATCACTGCTGGATACTTGAAGAACCCCGAGGAGACCTCCGCCACATTGACTGCTGATCGCTGGCTCAAGACTGGAGAT
          V  C  I  R  G  P  S  I  T  A  G  Y  F  K  N  P  E  E  T  S  A  T  L  T  A  D  R  W  L  K  T  G  D

1701  ATCGGAGAGTGGCACCCCGACGGCACTATCTCGATCATTGACCGCAAGAAGAACTTGGTCAAGCTGTCACACGGAGAGTACATTGCTTTGGAGAAGCTTG
           I  G  E  W  H  P  D  G  T  I  S  I  I  D  R  K  K  N  L  V  K  L  S  H  G  E  Y  I  A  L  E  K  L  E

1801  AGTCTGTCTACAAGAGCACAGCCTACTGCAACAACATTTGCGTGTATGCCGACTCGATGCAGAACAAGCCCGTTGCCATTATTGTTGCCAGCGAACCCCG
           S  V  Y  K  S  T  A  Y  C  N  N  I  C  V  Y  A  D  S  M  Q  N  K  P  V  A  I  I  V  A  S  E  P  R

1901  CATCCTCGAGTTGGCCAAGGCCAAGGGCATTGAGAGCCGCGACTTTGCTGCTCTCTGCCACGACAAGGTTATCATCAAGGCTGTCCACGATGCCTGCCTC
           I  L  E  L  A  K  A  K  G  I  E  S  R  D  F  A  A  L  C  H  D  K  V  I  I  K  A  V  H  D  A  C  L
```

Figure 23B

```
2001    GCCACTGCCAAGCGTGCTGGACTCAAGCCCGCTGAGATGCTTCAGGGAGTGTACTTGGAGTCAGAAGAATGGACGGCCCAGGCTGGCATGTTGACTGCCG
         A  T  A  K  R  A  G  L  K  P  A  E  M  L  Q  G  V  Y  L  E  S  E  E  W  T  A  Q  A  G  M  L  T  A  A

2101    CTCAGAAGCTCAAGCGCAAGGAGATCAACCAGGCCTATGTCTCACAGATCAAGCAGCTTTATGGAACGGCCTAAGTCGCTGAAAGGTGTGCCTTTGTCCG
         Q  K  L  K  R  K  E  I  N  Q  A  Y  V  S  Q  I  K  Q  L  Y  G  T  A

2201    TCTCTTCAACCCCACAAGTGCTATGTATAATGACCCGCGCGGGCCCTCCTTTAATCCTATACCGACCCTTTTTTACACGTTAAAGAAGCCACATTTTTGGT

2301    TCTTTTTTTTGTCTCGGCACACACTACACACTCCCCATCCATTCCCTGCAAACAGGATGGTTGTCTGCAAATAAATTGACGAATTTTCTCTTGAAAAAAAA

2401    AAAAAAAAAAAAA
```

Figure 24A

```
                    1                                                                                              100
        genome      ATGACAAACTGCCTCACCGTGGAAGTCGGACCGGCGACGTCAAGGCGGAGAGCGGCATGCGCGGCTGCCTCCTCTCTGCAAAGCGGCTCATGTCCTCGG
        CDS         ATGACAAACTGCCTCACCGTGGAAGTCCGACCGGCGACGTCAAGGCGGAGACCGCATCGCCCGTGCTCCTCTCTGCAAAGCGGCTCATGTGCTGCG 101                                                                                            200
        genome      CCTCGGATGACATCAAGACCGTCTACGACGTCTTGAAGCACTCCGTCACCGTCCGCCCGAACCTCAACGCGATCGGATACCGCAAGGTCGTCAAGATTCT
        CDS         GCTCGGATGACATCAAGACCGTCTACGACGTCTTGAAGCACTCCGTCACCGTCCGCCCGAACCTCAACGCGATCGGATACCGCAAGGTCGTCAAGATTCT 201                                                                                            300
        genome      GGAGGAAGAAAAGGAGGTCGTCAAGGTTGTGAAGGCGGAGGAAGTGAAGGAAAAGAAGACCTGGAAGTTCTTCAAGATGTGCGGCTACCGACTGGCTCACC
        CDS         GGAGGAAGAAAAGGAGGTCGTCAAGGTTGTGAAGGCGGAGGAAGTGAAGGAAAAGAAGACCTGGAAGTTCTTCAAGATGTCCGGCTACCACTGGCTCACC 301                                                                                            400
        genome      TACAAGGATCCGCAAGCAGGTGGTGGACAGGATCGGATGCGTGTTGGCAAGCTTGGCGTCGAGCGCAAGGACAAGGTGACCGTTTCGGTGGCACAAGGT
        CDS         TACAAGGATCCGCAAGCAGGTCCTCAACAGGATCGGATGCGTGTTGGCAAGCTTGGCGTCGAGCCCAAGGAGAAGGTGACCGTTTCGGTGGCACAAAG---

401                                                                                            500
        genome      AAGAAAGAGGCATAACAAGAAAATGCAAGAGAGGCAAAAAAAATGGCTTGACGTGAGAGCATAAGGGAACCAACAGACAGGTGTTTGTGTGGGTTGCGGA
        CDS         --------------------------------------------------------------------------------------------------

501                                                                                            600
        genome      TAGTGGGTGAGCATGCTTCGTTATCGAATGTGGGAGAAGAGAGCGGACGCGAATATGGCTCTCGTCTCTGGCGGGATGCGAGTGGCCAAGTGTGGGATAC
        CDS         --------------------------------------------------------------------------------------------------

601                                                                                            700
        genome      ATATCCTCGCGGTGGGGTGTCCGGGTCGGCCCCTTGAATCTTGTTGAAGCATGATAATGTGAATGTGGACCGCAATCACGCTCAGATTATGCGTAGCAAGC
        CDS         --------------------------------------------------------------------------------------------------

701                                                                                            800
        genome      GTGTTGCTAGTCTACATCATGCTCACACGTATTCACATTTATTCATTTTCACTCTATCTCGCTCTTAGTGCGAACTGGCTCCTGCTTGCGCACGGTGCTT
        CDS         ---------------------------------------------------------------TGCGAACTGGCTCCTGCTTGCGCACGGTGCTT 801                                                                                            900
        genome      TCACCGAGTCCATCACCATTGTTACCCGCTACGACACCGTGGCGAGGACGGTCTTTTGCACTCTATGAAGGAGGCGGAGGTGGCCACCGCTTACACAAA
        CDS         TCACCGAGTCCATCACCATTGTTACCCGCTACGACACCGTGGCGAGGACGGTCTTTTGCACTCTATGAAGGAGGCGGAGGTGGCCACCGCTTACACAAA 901                                                                                            1000
        genome      GGCCGACTTGCTCAACACTATCAAGAACGTTGCCGGCGAAATGCCCCACCCTGAAGAAGATCATCTACGACGGCGATGCCAACGCGCAGATGTGATTGCC
        CDS         GGCCGACTTGCTCAACACTATCAAGAACGTTGCCGGCGAAATGCCCCACCCTGAAGAAGATCATCTACGACGGCGATGCCAACGCGCAGATGTGATTGCC 1001                                                                                           1100
        genome      GTGCAGGAGGCCGATCCTCAGCTCCAGCTGATCACCCTCGAGGAGCTGAAGCAGCTCGGAGTGGACAAGCCTGTCGCCGCAACGCCTCCTGCTGCCAAGG
        CDS         GTGCAGGAGGCCGATCCTCAGCTCCAGCTGATCACCCTCGAGGAGCTGAAGCAGCTCGGAGTGGACAAGCCTGTCGCCGCAACGCCTCCTGCTGCCAAGG 1101                                                                                           1200
        genome      ACTACTGGTGCATCATGTACACGTTCGGGATCGAGTGGCAAGCCCAAGGGAGTGTTGCTGACCCATGAAAAGCTGGTTGCTGCCAGTACGTATCTTTCTCG
        CDS         ACTACTGCTGCATCATGTACACGTTCGGGATCGAGTGGCAAGCCCAAGGGAGTGTTGCTGACCCATGAAAAGCTGCTTGCTGCCA---------------

1201                                                                                           1300
        genome      TCATGATCGTCCTCCCGGCATTTCCACTGCGCTTGTTACCATTTGATGGGAAATGTATTTAACCCGAACCACACATTTTTTCTTTTTCTCACACTTGCCAC
        CDS         --------------------------------------------------------------------------------------------------

1301                                                                                           1400
        genome      GTCACTAGTCGGCACCGTCTGAACAACATGCTGACAAAGTACGTTCAGCAGGAGACGTCTTGCTCCGCGTACTTCCTCTCCTCACGGTCGTCGAGTTCCTG
        CDS         -----------TCGGCACCGTCTGAACAACATGCTGACAAAGTACGTTCAGCAGGAGACGTCTTGCTCCGCGTACTTCCTCTCCTCACGGTCGTCGAGTTCCTG
```

```
             801
   MaACS-3   ----------
   MaACS-4   IHQKESKL--
   MaACS-5   IH--------
   MaACS-6   IA--------
   MaACS-8   INASTPVAKL
   MaACS-10  F---------
   MaACS-11  K---------
   MaACS-12  A---------
   ScFAA1    S---------
   ScFAA2    GSLVKTEKL-
   ScFAA3    NS--------
   ScFAA4    NT--------
```

```
         601                                                                                          700
MaACS-1  MAAIVSKDTMNWDS------------------------FAKFALNNLPKYSVNIEIRKVP-----EMEITGTFKQRNELVNEGMDPSKIKDEMLNLDG-HSYRPF
MaACS-2  MAALVLKNSIVQMAGGSQAKFHVDEAALNAFLRDLSKDVVKKLPAYAIRRELRIAEQ---ELETGTFKNKNELKKEGFDLGKVKERLYNWTPKGEYAPF
MaACS-9  MAAIVSKSTMDWEK------------------------FAAYALNNLPRYSVNIEIRKMP-----EMEITGTFKQRNELVNEGIDPKTIANEMLNLDG-HHYKPF
MaACS-7  AWISTKDGKTVSLEAVQK--------------------FCEGKIAH---YKNGRYGVVNESNEFPTNPSGKINKNNMRELTKAKLGLP------------
ScFAT1   FAVNKLTDNSLDITAKTKLLN-----------------DSLSRLNLPSYAMNLNYKFNDE---IKMNDNHKILKNYREQKLPKGLDGNDTIFNKNYKRNEVL
ScFAT2   ANIVLKNGEKMTYEELVN--------------------FLKKHLAS---FKINTKNYFNDK---LPKNATGKINRRNIANTFAKSSRNKSKL---------

701            726
MaACS-1  KENNHTRVVSNKNRN-------------
MaACS-2  GVNENEGILANRNRN-------------
MaACS-9  KANNHQRVISNKNKN-------------
MaACS-7  ----------------------------
ScFAT1   TANDWEAIDAQTIKN-------------
ScFAT2   ----------------------------
```

POLYNUCLEOTIDE ENCODING ACYL-COA SYNTHETASE HOMOLOG AND USE THEREOF

CROSS-REFERENCE TO RELATED APPLICATIONS

This application is a Divisional of U.S. application Ser. No. 13/574,026, filed Jul. 19, 2012, now U.S. Pat. No. 9,289,007, which is the National Stage of International Application No. PCT/JP2011/052035, filed Feb. 1, 2011, which claims priority to Japanese Patent Application No. 2010-019967, filed Feb. 1, 2010. The disclosure of application Ser. Nos. 13/574,026 and PCT/JP2011/052035 are expressly incorporated by reference herein in their entireties.

SEQUENCE LISTING

The instant application contains a Sequence Listing which has been submitted electronically in ASCII format and is hereby incorporated by reference in its entirety. Said ASCII copy, created on Sep. 24, 2015, is named P42026_SL.txt and is 294,294 bytes in size.

TECHNICAL FIELD

The present invention relates to a polynucleotide encoding an acyl-CoA synthetase homolog and use thereof.

BACKGROUND ART

Fatty acids containing two or more unsaturated bonds are collectively referred to as polyunsaturated fatty acids (PUFAs) and known to specifically include arachidonic acid (ARA), dihomo-γ-linolenic acid (DGLA), eicosapentaenoic acid (EPA), docosahexaenoic acid (DHA), etc. Some of these polyunsaturated fatty acids cannot be synthesized in the animal body. It is therefore necessary to compensate these polyunsaturated fatty acids as essential amino acids from food.

Polyunsaturated fatty acids are widely distributed; for instance, arachidonic acid can be separated from lipids extracted from the adrenal glands and livers of animals. However, polyunsaturated fatty acids contained in animal organs are only in a small quantity and cannot be obtained sufficiently for large supplies when simply extracted or separated from animal organs. For this reason, microbial techniques have been developed for obtaining polyunsaturated fatty acids by cultivation of various microorganisms. Above all, microorganisms of the genus *Mortierella* are known to produce lipids containing polyunsaturated fatty acids such as arachidonic acid and the like.

Other attempts have also been made to produce polyunsaturated fatty acids in plants. Polyunsaturated fatty acids constitute storage lipids such as triacylglycerols and are known to be accumulated within microorganism mycelia or plant seeds.

Acyl-CoA synthetase (ACS) is an enzyme catalyzing the thioesterification of fatty acids and coenzyme A (CoA) and catalyzes the following reaction.

Fatty acid+CoASH+ATP→Acyl-CoA+AMP+PPi

Acyl-CoA produced by ACS is involved in various life phenomena including the biosynthesis and remodeling of lipids, energy production by β-oxidation, acylation of proteins, expression regulation by fatty acids, etc. Furthermore, ACS is reportedly associated with extracellular uptake of fatty acids, intracellular transport of fatty acids, etc. (Non-Patent Documents 1 and 2). In view of the foregoing, it is considered to control the activity of ACS when polyunsaturated fatty acids or the like are produced by utilizing microorganisms or plants.

In the yeast *Saccharomyces cerevisiae* used as a model eukaryote, six (6) acyl-CoA synthetase genes (ScFAA1, ScFAA2, ScFAA3, ScFAA4, ScFAT1 and ScFAT2) are known (Non-Patent Document 1). The proteins encoded by these genes are different in substrate specificity, timing of expression, intracellular localization and function.

Patent Document 1 discloses nine (9) genes as the acyl-CoA synthetase gene (ScACS) derived from *Schizochytrium* sp. Patent Document 1 also discloses an increased production of DPA (n-6) (docosapentanoic acid (n-6)) or DHA when the gene encoding the *Schizochytrium* sp. PUFA synthase system is co-expressed with ScACS, as compared to the case where the co-expression with ScACS is not involved.

In addition, acyl-CoA synthetase genes derived from animals and plants are also reported (Non-Patent Document 2 and Patent Document 2).

[Patent Document 1] Japanese Unexamined Patent Application Publication (Translation of PCT Application) No. 2009-529890

[Patent Document 2] PCT International Publication Pamphlet WO 0209295

[Non-Patent Document 1] B. B. A. 1771, 286-298, 2007

[Non-Patent Document 2] Exp. Biol. Med., 233 (5), 507-521, 2008

DISCLOSURE OF THE INVENTION

Under the foregoing circumstances, it has been desired to isolate a novel gene that increases the amount of the fatty acids produced in a host cell or changes the composition of fatty acids produced, when the gene is expressed in the host cell.

As a result of extensive investigations, the present inventors have succeeded in cloning a gene encoding an ACS homolog of lipid-producing fungus *Mortierella alpina* (hereinafter "*M. alpina*") (MaACS), and accomplished the present invention. That is, the present invention provides the following polynucleotides, proteins, expression vectors, transformants, and a method for producing lipids or lipid compositions and foods, etc. using the transformants, as well as foods produced by the method, etc.

That is, the present invention is characterized as follows.

[1] A polynucleotide according to any one selected from the group consisting of (a) to (e) below:

(a) a polynucleotide comprising any one nucleotide sequence selected from the group consisting of the nucleotide sequences shown by SEQ ID NOs: 1, 6, 11, 16, 21, 26, 31, 36, 41, 46, 51 and 56;

(b) a polynucleotide encoding a protein consisting of any one amino acid sequence selected from the group consisting of the amino acid sequences shown by SEQ ID NOs: 2, 7, 12, 17, 22, 27, 32, 37, 42, 47, 52 and 57;

(c) a polynucleotide encoding a protein consisting of an amino acid sequence wherein 1 to 100 amino acids are deleted, substituted, inserted and/or added in any one amino acid sequence selected from the group consisting of the amino acid sequences shown by SEQ ID NOs: 2, 7, 12, 17, 22, 27, 32, 37, 42, 47, 52 and 57, and having an acyl-CoA synthetase activity or an activity of increasing the amount or changing the composition, of the fatty acids produced in a host cell when expressed in the host cell;

(d) a polynucleotide encoding a protein having an amino acid sequence having at least 60% identity to any one amino acid sequence selected from the group consisting of the amino acid sequences shown by SEQ ID NOs: 2, 7, 12, 17, 22, 27, 32, 37, 42, 47, 52 and 57, and having an acyl-CoA synthetase activity or an activity of increasing the amount or changing the composition, of the fatty acids produced in a host cell when expressed in the host cell; and, (e) a polynucleotide which hybridizes to a polynucleotide consisting of a nucleotide sequence complementary to any one nucleotide sequence selected from the group consisting of the nucleotide sequences shown by SEQ ID NOs: 1, 6, 11, 16, 21, 26, 31, 36, 41, 46, 51 and 56 under stringent conditions, and which encodes a protein having an acyl-CoA synthetase activity or an activity of increasing the amount or changing the composition, of the fatty acids produced in a host cell when expressed in the host cell.

[2] The polynucleotide according to claim 1, which is either one defined in (f) or (g) below:

(f) a polynucleotide encoding a protein consisting of an amino acid sequence wherein 1 to 10 amino acids are deleted, substituted, inserted and/or added in any one amino acid sequence selected from the group consisting of the amino acid sequences shown by SEQ ID NOs: 2, 7, 12, 17, 22, 27, 32, 37, 42, 47, 52 and 57, and having an acyl-CoA synthetase activity or an activity of increasing the amount or changing the composition, of the fatty acids produced in a host cell when expressed in the host cell; and, (g) a polynucleotide encoding a protein having an amino acid sequence having at least 90% identity to any one amino acid sequence selected from the group consisting of the amino acid sequences shown by SEQ ID NOs: 2, 7, 12, 17, 22, 27, 32, 37, 42, 47, 52 and 57, and an acyl-CoA synthetase activity or an activity of increasing the amount or changing the composition, of the fatty acids produced in a host cell when expressed in the host cell.

[3] The polynucleotide according to [1] above, comprising any one nucleotide sequence selected from the group consisting of the nucleotide sequences shown by SEQ ID NOs: 1, 6, 11, 16, 21, 26, 31, 36, 41, 46, 51 and 56.

[4] The polynucleotide according to [1] above, encoding a protein consisting of any one amino acid sequence selected from the group consisting of the amino acid sequences shown by SEQ ID NOs: 2, 7, 12, 17, 22, 27, 32, 37, 42, 47, 52 and 57.

[5] The polynucleotide according to any one of [1] to [4] above, which is a DNA.

[6] A protein encoded by the polynucleotide according to any one of [1] to [5] above.

[7] A vector comprising the polynucleotide according to any one of [1] to [5] above.

[8] A non-human transformant, into which the polynucleotide according to any one of [1] to [5] above, or the vector according to [7] above is introduced.

[9] A method for producing a lipid or fatty acid composition, which comprises collecting the lipid or fatty acid composition from the culture of the transformant according to [8] above.

[10] The method according to [9] above, wherein the lipid is a triacylglycerol.

[11] The method according to [9] above, wherein the fatty acid is a polyunsaturated fatty acid having at least 18 carbon atoms.

[12] A food product, pharmaceutical, cosmetic or soap comprising the lipid or fatty acid composition obtained by the production method according to [9] above.

The polynucleotide of the present invention can be used for transformation of an appropriate host cell. The transformant thus produced can be used to produce fatty acid compositions, food products, cosmetics, pharmaceuticals, soaps, etc.

More specifically, the transformant of the present invention provides an extremely high production efficiency of lipids and fatty acids. Accordingly, the present invention can be effectively used to manufacture pharmaceuticals or health foods which require a large quantity of lipids or fatty acids.

BRIEF DESCRIPTION OF DRAWINGS

FIG. 1 shows the correspondence between the cDNA sequence of MaACS-1 (SEQ ID NO: 4) and putative amino acid sequence of MaACS-1 (SEQ ID NO: 2).

FIG. 2A shows the alignment between the genome sequence of MaACS-1 (SEQ ID NO: 5) and CDS sequence of MaACS-1 (SEQ ID NO: 3).

FIG. 2B is a continuation from FIG. 2A.

FIG. 3A shows the correspondence between the cDNA sequence of MaACS-2 (SEQ ID NO: 9) and putative amino acid sequence of MaACS-2 (SEQ ID NO: 7).

FIG. 3B is a continuation from FIG. 3A.

FIG. 4A shows the alignment between the genome sequence of MaACS-2 (SEQ ID NO: 10) and CDS sequence of MaACS-2 (SEQ ID NO: 8).

FIG. 4B is a continuation from FIG. 4A.

FIG. 4C is a continuation from FIG. 4B.

FIG. 5 shows the correspondence between the cDNA sequence of MaACS-3 (SEQ ID NO: 14) and putative amino acid sequence of MaACS-3 (SEQ ID NO: 12).

FIG. 6A shows the alignment between the genome sequence of MaACS-3 (SEQ ID NO: 15) and CDS sequence of MaACS-3 (SEQ ID NO: 13).

FIG. 6B is a continuation from FIG. 6A.

FIG. 7A shows the correspondence between the cDNA sequence of MaACS-4 (SEQ ID NO: 19) and putative amino acid sequence of MaACS-4 (SEQ ID NO: 17).

FIG. 7B is a continuation from FIG. 7A.

FIG. 8A shows the alignment between the genome sequence of MaACS-4 (SEQ ID NO: 20) and CDS sequence of MaACS-4 (SEQ ID NO: 18).

FIG. 8B is a continuation from FIG. 8A

FIG. 8C is a continuation from FIG. 8B.

FIG. 9A shows the correspondence between the cDNA sequence of MaACS-5 (SEQ ID NO: 24) and putative amino acid sequence of MaACS-5 (SEQ ID NO: 22).

FIG. 9B is a continuation from FIG. 9A.

FIG. 10A shows the alignment between the genome sequence of MaACS-5 (SEQ ID NO: 25) and CDS sequence of MaACS-5 (SEQ ID NO: 23).

FIG. 10B is a continuation from FIG. 10A.

FIG. 11A shows the correspondence between the cDNA sequence of MaACS-6 (SEQ ID NO: 29) and putative amino acid sequence of MaACS-6 (SEQ ID NO: 27).

FIG. 11B is a continuation from FIG. 11A.

FIG. 12A shows the alignment between the genome sequence of MaACS-6 (SEQ ID NO: 30) and CDS sequence of MaACS-6 (SEQ ID NO: 28).

FIG. 12B is a continuation from FIG. 12A.

FIG. 13 shows the correspondence between the cDNA sequence of MaACS-7 (SEQ ID NO: 34) and putative amino acid sequence of MaACS-7 (SEQ ID NO: 32).

FIG. 14A shows the alignment between the genome sequence of MaACS-7 (SEQ ID NO: 35) and CDS sequence of MaACS-7 (SEQ ID NO: 33).

FIG. 14B is a continuation from FIG. 14A.

FIG. 15A shows the correspondence between the cDNA sequence of MaACS-8 (SEQ ID NO: 39) and putative amino acid sequence of MaACS-8 (SEQ ID NO: 37).

FIG. 15B is a continuation from FIG. 15A.

FIG. 16A shows the alignment between the genome sequence of MaACS-8 (SEQ ID NO: 40) and CDS sequence of MaACS-8 (SEQ ID NO: 38).

FIG. 16B is a continuation from FIG. 16A.

FIG. 16C is a continuation from FIG. 16B.

FIG. 17 shows the correspondence between the cDNA sequence of MaACS-9 (SEQ ID NO: 44) and putative amino acid sequence of MaACS-9 (SEQ ID NO: 42).

FIG. 18B is a continuation from FIG. 18A.

FIG. 19A shows the correspondence between the cDNA sequence of MaACS-10 (SEQ ID NO: 49) and putative amino acid sequence of MaACS-10 (SEQ ID NO: 47).

FIG. 19B is a continuation from FIG. 19A.

FIG. 20A shows the alignment between the genome sequence of MaACS-10 (SEQ ID NO: 50) and CDS sequence of MaACS-10 (SEQ ID NO: 48).

FIG. 20B is a continuation from FIG. 20A.

FIG. 20C is a continuation from FIG. 20B.

FIG. 21A shows the correspondence between the cDNA sequence of MaACS-11 (SEQ ID NO: 54) and putative amino acid sequence of MaACS-11 (SEQ ID NO: 52).

FIG. 21B is a continuation from FIG. 21A

FIG. 22A shows the alignment between the genome sequence of MaACS-11 (SEQ ID NO: 55) and CDS sequence of MaACS-11 (SEQ ID NO: 53).

FIG. 22B is a continuation from FIG. 22A.

FIG. 23A shows the correspondence between the cDNA sequence of MaACS-12 (SEQ ID NO: 59) and putative amino acid sequence of MaACS-12 (SEQ ID NO: 57).

FIG. 23B is a continuation from FIG. 23A

FIG. 24A shows the alignment between the genome sequence of MaACS-12 (SEQ ID NO: 60) and CDS sequence of MaACS-12 (SEQ ID NO: 58).

FIG. 24B is a continuation from FIG. 24A

FIG. 25A shows the alignment between MaACS having relatively high amino acid sequence homology to *S. cerevisiae*-derived FAA protein (FAA: fatty acid activation) and the FAA protein (SEQ ID NOS: 12, 17, 22, 27, 37, 47, 52, 57, and 124-127, in order of appearance). The single underlined and double underlined sequences denote the ATP-AMP motif and the FACS/VLACS-FATP motif, respectively.

FIG. 25B is a continuation from FIG. 25A.

FIG. 25C is a continuation from FIG. 25B.

FIG. 26A shows the alignment between MaACS having relatively high amino acid sequence homology to *S. cerevisiae*-derived FAT protein (FAT: fatty acid transferase) and the FAT protein (SEQ ID NOS: 2, 7, 42, 32, and 128-129, in order of appearance). The single underlined and double underlined sequences denote the ATP-AMP motif and the FACS/VLACS-FATP motif, respectively.

FIG. 26B is a continuation from FIG. 26A.

BEST MODE FOR CARRYING OUT THE INVENTION

Figure 18A:
FIG. 18A shows the alignment between the genome sequence of MaACS-9 (SEQ ID NO: 45) and CDS sequence of MaACS-9 (SEQ ID NO: 43).

Hereinafter, the present invention is described in detail. The embodiments described below are intended to be presented by way of example merely to describe the invention but not limited only to the following embodiments. The present invention may be implemented in various ways without departing from the gist of the invention.

All of the publications, published patent applications, patents and other patent documents cited in this application are herein incorporated by reference in their entirety. This application hereby incorporates by reference the contents of the specification and drawings in the Japanese Patent Application (No. 2010-19967) filed Feb. 1, 2010, from which the priority was claimed.

As will be later described in detail in EXAMPLES below, the present inventors have succeeded for the first time in cloning the full-length cDNA of lipid-producing fungus *M. alpina*-derived ACS homolog genes (MaACS-1~12). The present inventors have also identified the nucleotide sequences of genomic DNAs of MaACS-1~12 from *M. alpina* and putative amino acid sequences thereof. The ORF sequences, putative amino acid sequences, CDS sequences, cDNA sequences and genome sequences of MaACS-1, 2, 3, 4, 5, 6, 7, 8, 9, 10, 11 and 12 are SEQ ID NOs: 1, 6, 11, 16, 21, 26, 31, 36, 41, 46, 51 and 56 (hereinafter these sequences are collectively referred to as "ORF sequences of MaACS-1~12"), SEQ ID NOs: 2, 7, 12, 17, 22, 27, 32, 37, 42, 47, 52 and 57 (hereinafter these sequences are collectively referred to as "amino acid sequences of MaACS-1~12"), SEQ ID NOs: 3, 8, 13, 18, 23, 28, 33, 38, 43, 48, 53 and 58 (hereinafter these sequences are collectively referred to as "CDS sequences of MaACS-1~12"), SEQ ID NOs: 4, 9, 14, 19, 24, 29, 34, 39, 44, 49, 54 and 59 (hereinafter these sequences are collectively referred to as "cDNA sequences of MaACS-1~12") and SEQ ID NOs: 5, 10, 15, 20, 25, 30, 35, 40, 45, 50, 55 and 60 (hereinafter these sequences are collectively referred to as "genome sequences of MaACS-1~12"), respectively. These polynucleotides and proteins may be obtained by the methods described in EXAMPLES below, known genetic engineering techniques, known methods for synthesis, and so on.

1. Polynucleotide of the Invention

First, the present invention provides the polynucleotide described in any one selected from the group consisting of (a) to (g) below:

(a) a polynucleotide comprising any one nucleotide sequence selected from the group consisting of the ORF sequences of MaACS-1~12;

(b) a polynucleotide comprising any one nucleotide sequence selected from the group consisting of the cDNA sequences of MaACS-1~12;

(c) a polynucleotide encoding a protein consisting of any one amino acid sequence selected from the group consisting of the amino acid sequences of MaACS-1~12;

(d) a polynucleotide encoding a protein consisting of an amino acid sequence wherein 1 to 100 amino acids are deleted, substituted, inserted and/or added in any one amino acid sequence selected from the group consisting of the amino acid sequences of MaACS-1~12, and having an acyl-CoA synthetase activity or an activity of increasing the amount and/or changing the composition, of the fatty acids produced in a host cell when expressed in the host cell;

(e) a polynucleotide encoding a protein having an amino acid sequence having at least 60% identity to any one amino acid sequence selected from the group consisting of the amino acid sequences of MaACS-1~12, and having an acyl-CoA synthetase activity or an activity of increasing the amount and/or changing the composition, of the fatty acids produced in a host cell when expressed in the host cell; and, (f) a polynucleotide which hybridizes to a polynucleotide consisting of a nucleotide sequence complementary to any one nucleotide sequence selected from the group consisting of the ORF sequences of MaACS-1~12 under stringent conditions, and which encodes a protein having an acyl-CoA synthetase activity or an activity of increasing the amount and/or changing the composition, of the fatty acids produced in a host cell when expressed in the host cell; and,.

(g) a polynucleotide which hybridizes to a polynucleotide consisting of a nucleotide sequence complementary to any one nucleotide sequence selected from the group consisting of the cDNA sequences of MaACS-1~12 under stringent conditions, and which encodes a protein having an acyl-CoA synthetase activity or an activity of increasing the amount and/or changing the composition, of the fatty acids produced in a host cell when expressed in the host cell.

As used herein, the term "polynucleotide" means a DNA or RNA.

As used herein, the term "polynucleotide which hybridizes under stringent conditions" refers to a polynucleotide obtained by the colony hybridization method, plaque hybridization method, Southern hybridization method or the like, using as a probe, for example, a polynucleotide consisting of a nucleotide sequence complementary to any one nucleotide sequence selected from the group consisting of the ORF sequences of MaACS-1~12 or any one nucleotide sequence selected from the group consisting of the cDNA sequences of MaACS-1~12, or the whole or part of a polynucleotide consisting of the nucleotide sequence encoding any one amino acid sequence selected from the group consisting of the amino acid sequences of MaACS-1~12. For the methods of hybridization, there are used the methods described in, e.g., "Sambrook & Russell, Molecular Cloning: A Laboratory Manual Vol. 3, Cold Spring Harbor, Laboratory Press 2001," "Ausubel, Current Protocols in Molecular Biology, John Wiley & Sons 1987-1997," etc.

As used herein, the term "stringent conditions" may be any of low stringent conditions, moderate stringent conditions and high stringent conditions. The term "low stringent conditions" are, for example, 5×SSC, 5× Denhardt's solution, 0.5% SDS, 50% formamide at 32° C. The term "moderate stringent conditions" are, for example, 5×SSC, 5× Denhardt's solution, 0.5% SDS, 50% formamide at 42° C., or 5×SSC, 1% SDS, 50 mM Tris-HCl (pH 7.5), 50% formamide at 42° C. The term "high stringent conditions" are, for example, 5×SSC, 5× Denhardt's solution, 0.5% SDS, 50% formamide at 50° C. or 0.2×SSC, 0.1% SDS at 65° C. Under these conditions, a DNA with higher identity is expected to be obtained efficiently at higher temperatures, though multiple factors are involved in hybridization stringency including temperature, probe concentration, probe length, ionic strength, time, salt concentration and others, and a person skilled in the art may appropriately select these factors to achieve similar stringency.

When commercially available kits are used for hybridization, for example, an Alkphos Direct Labeling and Detection System (GE Healthcare) may be used. In this case, according to the attached protocol, after cultivation with a labeled probe overnight, the membrane is washed with a primary wash buffer containing 0.1% (w/v) SDS at 55° C. to detect the hybridized DNA. Alternatively, in producing a probe based on the nucleotide sequence complementary to any one nucleotide sequence selected from the group consisting of the ORF sequences of MaACS-1~12 or any one nucleotide sequence selected from the group consisting of the cDNA sequences of MaACS-1~12, or based on the entire or part of the nucleotide sequence encoding any one amino acid sequence selected from the group consisting of the amino acid sequences of MaACS-1~12, hybridization can be detected with a DIG Nucleic Acid Detection Kit (Roche Diagnostics) when the probe is labeled with digoxigenin (DIG) using a commercially available reagent (e.g., a PCR Labeling Mix (Roche Diagnostics), etc.).

In addition to those described above, other polynucleotides that can be hybridized include DNAs having 50% or higher, 51% or higher, 52% or higher, 53% or higher, 54% or higher, 55% or higher, 56% or higher, 57% or higher, 58% or higher, 59% or higher, 60% or higher, 61% or higher, 62% or higher, 63% or higher, 64% or higher, 65% or higher, 66% or higher, 67% or higher, 68% or higher, 69% or higher, 70% or higher, 71% or higher, 72% or higher, 73% or higher, 74% or higher, 75% or higher, 76% or higher, 77% or higher, 78% or higher, 79% or higher, 80% or higher, 81% or higher, 82% or higher, 83% or higher, 84% or higher, 85% or higher, 86% or higher, 87% or higher, 88% or higher, 89% or higher, 90% or higher, 91% or higher, 92% or higher, 93% or higher, 94% or higher, 95% or higher, 96% or higher, 97% or higher, 98% or higher, 99% or higher, 99.1% or higher, 99.2% or higher, 99.3% or higher, 99.4% or higher, 99.5% or higher, 99.6% or higher, 99.7% or higher, 99.8% or higher or 99.9% or higher identity with the DNA for any one nucleotide sequence selected from the group consisting of the ORF sequences of MaACS-1~12 or for any one nucleotide sequence selected from the group consisting of the cDNA sequences of MaACS-1~12, or with the DNA encoding any one amino acid sequence selected from the group consisting of the amino acid sequences of MaACS-1~12, as calculated by a homology search software, such as FASTA, BLAST, etc. using default parameters.

Identity between amino acid sequences or nucleotide sequences may be determined using FASTA (Science 227 (4693): 1435-1441, (1985)), algorithm BLAST (Basic Local Alignment Search Tool) by Karlin and Altschul (Proc. Natl. Acad. Sci. USA, 87: 2264-2268, 1990; Proc. Natl. Acad. Sci. USA, 90: 5873, 1993). Programs called blastn, blastx, blastp, tblastn and tblastx based on the BLAST algorithm have been developed (Altschul S. F. et al., J. Mol. Biol. 215: 403, 1990). When a nucleotide sequence is sequenced using blastn, the parameters are, for example, score=100 and wordlength=12. When an amino acid sequence is sequenced using blastp, the parameters are, for example, score=50 and wordlength=3. When BLAST and Gapped BLAST programs are used, default parameters for each of the programs are employed.

The polynucleotides of the present invention described above can be obtained by known genetic engineering techniques or known methods for synthesis.

2. Protein of the Invention

The present invention provides the proteins shown below.

(i) A protein encoded by the polynucleotide of any one of (a) to (g) above.

(ii) A protein comprising any one amino acid sequence selected from the group consisting of the amino acid sequences of MaACS-1~12.

(iii) A protein consisting of an amino acid sequence wherein one or more amino acids are deleted, substituted, inserted and/or added in any one amino acid sequence selected from the group consisting of the amino acid sequences of MaACS-1~12, and having an acyl-CoA synthetase activity or an activity of increasing the amount and/or changing the composition, of the fatty acids produced in a host cell when expressed in the host cell.

(iv) A protein having an amino acid sequence having at least 90% identity to any one amino acid sequence selected from the group consisting of the amino acid sequences of MaACS-1~12, and having an acyl-CoA synthetase activity or an activity of increasing the amount and/or changing the composition, of the fatty acids produced in a host cell when expressed in the host cell.

The proteins described in (iii) or (iv) above are typically naturally occurring mutants of the protein consisting of any one amino acid sequence selected from the group consisting of the amino acid sequences of MaACS-1~12 and include those proteins which may be artificially obtained using site-directed mutagenesis described in, e.g., "Sambrook & Russell, Molecular Cloning: A Laboratory Manual Vol. 3, Cold Spring Harbor Laboratory Press 2001," "Ausubel, Current Protocols in Molecular Biology, John Wiley & Sons 1987-1997," "Nuc. Acids. Res., 10, 6487 (1982)," "Proc. Natl. Acad. Sci. USA, 79, 6409 (1982)," "Gene, 34, 315 (1985)," "Nuc. Acids. Res., 13, 4431 (1985)," "Proc. Natl. Acad. Sci. USA, 82, 488 (1985)," etc.

As used herein, the "protein consisting of an amino acid sequence wherein one or several acids are deleted, substituted, inserted and/or added in any one amino acid sequence selected from the group consisting of the amino acid sequences of MaACS-1~12, and having an acyl-CoA synthetase activity or an activity of increasing the amount and/or changing the composition, of the fatty acids produced in a host cell when expressed in the host cell" includes proteins consisting of an amino acid sequence wherein, e.g., 1 to 100, 1 to 90, 1 to 80, 1 to 70, 1 to 60, 1 to 50, 1 to 40, 1 to 39, 1 to 38, 1 to 37, 1 to 36, 1 to 35, 1 to 34, 1 to 33, 1 to 32, 1 to 31, 1 to 30, 1 to 29, 1 to 28, 1 to 27, 1 to 26, 1 to 25, 1 to 24, 1 to 23, 1 to 22, 1 to 21, 1 to 20, 1 to 19, 1 to 18, 1 to 17, 1 to 16, 1 to 15, 1 to 14, 1 to 13, 1 to 12, 1 to 11, 1 to 10, 1 to 9 (1 to several), 1 to 8, 1 to 7, 1 to 6, 1 to 5, 1 to 4, 1 to 3, 1 to 2, or one amino acid is/are deleted, substituted, inserted and/or added in any one amino acid sequence selected from the group consisting of the amino acid sequences of MaACS-1~12, and having the acyl-CoA synthetase activity or the activity of increasing the amount and/or changing the composition, of the fatty acids produced in a host cell when expressed in the host cell. In general, the number of deletions, substitutions, insertions, and/or additions is preferably smaller.

Such proteins include a protein having an amino acid sequence having the identity of approximately 60% or higher, 61% or higher, 62% or higher, 63% or higher, 64% or higher, 65% or higher, 66% or higher, 67% or higher, 68% or higher, 69% or higher, 70% or higher, 71% or higher, 72% or higher, 73% or higher, 74% or higher, 75% or higher, 76% or higher, 77% or higher, 78% or higher, 79% or higher, 80% or higher, 81% or higher, 82% or higher, 83% or higher, 84% or higher, 85% or higher, 86% or higher, 87% or higher, 88% or higher, 89% or higher, 90% or higher, 91% or higher, 92% or higher, 93% or higher, 94% or higher, 95% or higher, 96% or higher, 97% or higher, 98% or higher, 99% or higher, 99.1% or higher, 99.2% or higher, 99.3% or higher, 99.4% or higher, 99.5% or higher, 99.6% or higher, 99.7% or higher, 99.8% or higher, or 99.9% or higher, to any one amino acid sequence selected from the group consisting of the amino acid sequences of MaACS-1~12, and having the diacylglycerol acyltransferase activity. As the identity percentage described above is higher, the protein is preferable in general.

The term deletion, substitution, insertion and/or addition of one or more amino acid residues in the amino acid sequence of the protein of the invention is intended to mean that one or more amino acid residues are deleted, substituted, inserted and/or added at optional and one or more positions in the same sequence. Two or more types of deletions, substitutions, insertions and additions may occur at the same time.

Examples of the amino acid residues which are mutually substitutable are given below. Amino acid residues in the same group are mutually substitutable. Group A: leucine, isoleucine, norleucine, valine, norvaline, alanine, 2-aminobutanoic acid, methionine, o-methylserine, t-butylglycine, t-butylalanine and cyclohexylalanine; Group B: aspartic acid, glutamic acid, isoaspartic acid, isoglutamic acid, 2-aminoadipic acid and 2-aminosuberic acid; Group C: asparagine and glutamine; Group D: lysine, arginine, ornithine, 2,4-diaminobutanoic acid and 2,3-diaminopropionic acid; Group E: proline, 3-hydroxyproline and 4-hydroxyproline; Group F: serine, threonine and homoserine; and Group G: phenylalanine and tyrosine.

The protein of the present invention may also be produced by chemical synthesis methods such as the Fmoc method (fluorenylmethyloxycarbonyl method), the tBoc method (t-butyloxycarbonyl method), etc. In addition, peptide synthesizers available from Advanced Automation Peptide Protein Technologies, Perkin Elmer, Protein Technologies, PerSeptive, Applied Biosystems, SHIMADZU Corp., etc. may also be used for the chemical synthesis.

Figure 25A:
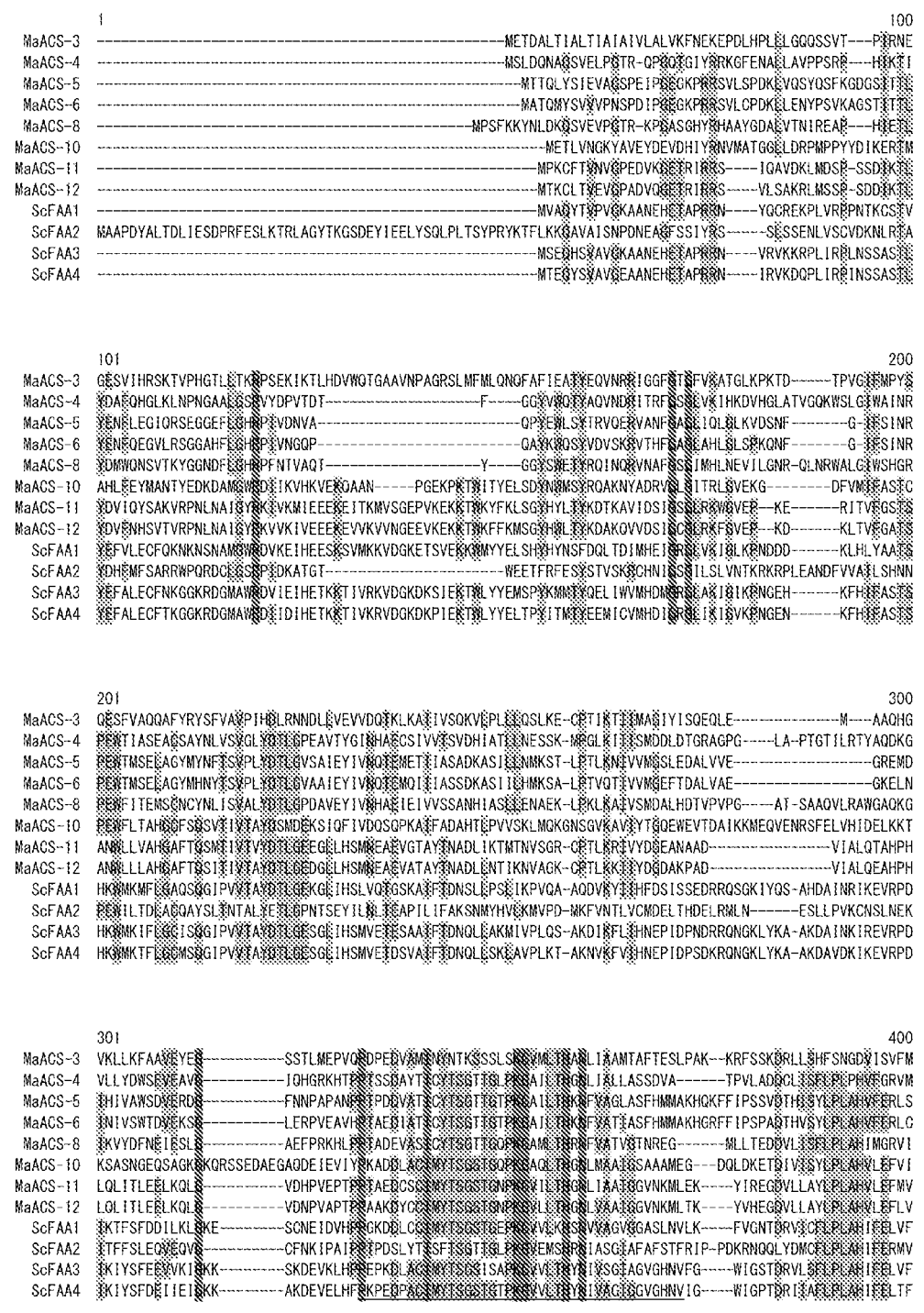
Figure 25B:
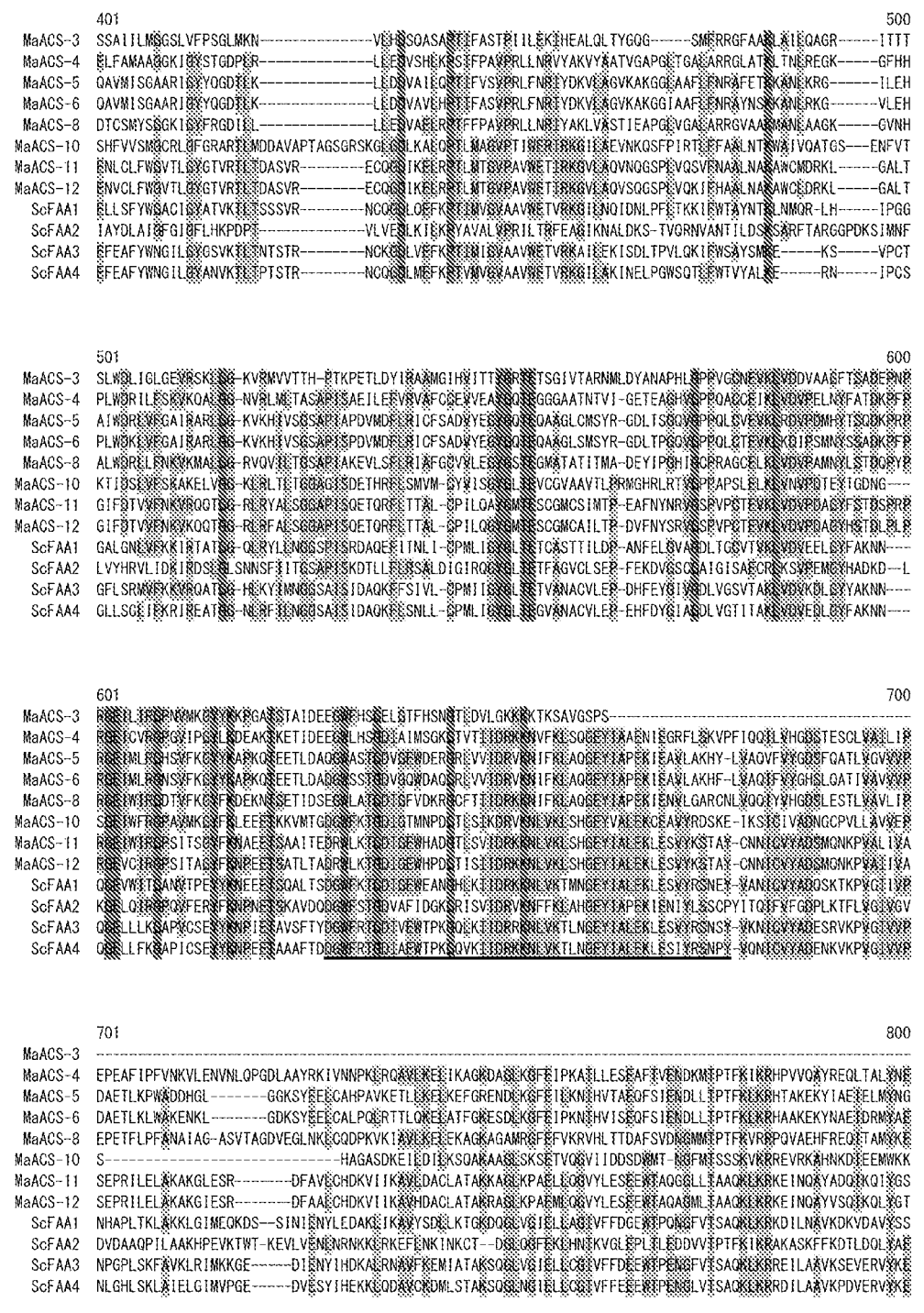
Figure 26A:
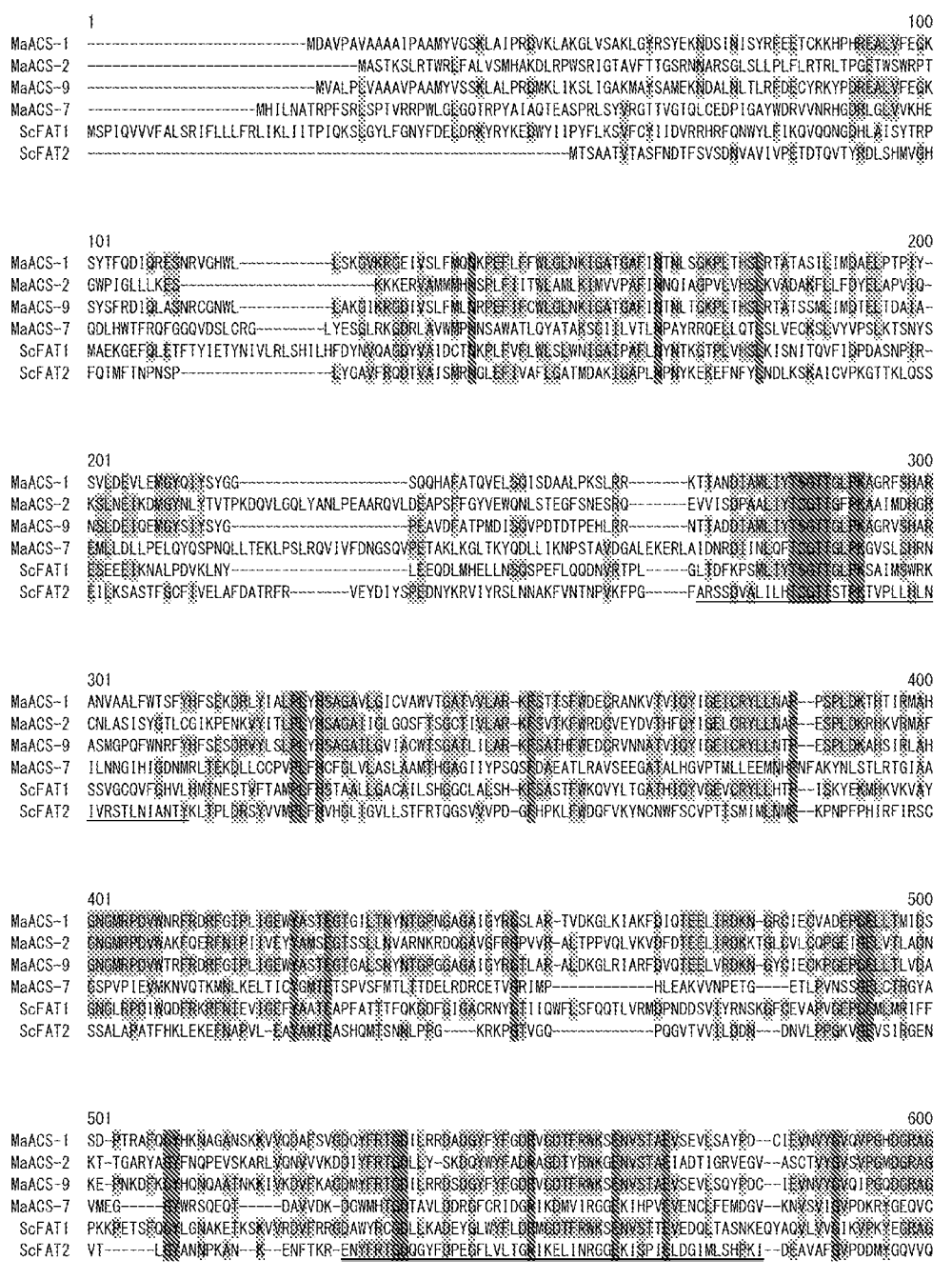

The protein encoded by the polynucleotide of the invention and the protein of the invention are both ACS homolog proteins and considered to have the acyl-CoA synthetase activity since the ATP-AMP motif and FACS/VLACS-FATP motif, which are important for the acyl-CoA synthetase activity, are conserved. As used herein, ATP, AMP, FACS, VLACS and FATP are intended to mean adenosine triphosphate, adenosine monophosphate, fatty acyl-CoA synthetase, very long chain acyl-CoA synthetase and fatty acid transport protein, respectively. Specific amino acid sequences of the ATP-AMP motif and FACS/VLACS-FATP motif contained in the protein of the present invention are shown in FIGS. 25 and 26 at the single underlined and double underlined sequences, respectively. With regard to representative amino acid sequences of the ATP-AMP motif and FACS/VLACS-FATP motif, reference may be made to databases including pfam (http://pfam.sanger.ac.uk/), etc.

As used herein, the term "acyl-CoA synthetase activity (ACS activity)" is intended to mean the activity of promoting the acyl-CoA-forming reaction through formation of a thioester bond between a fatty acid and coenzyme A (chemical reaction equation below).

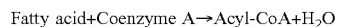

Fatty acid+Coenzyme A→Acyl-CoA+$H_2O$

The acyl-CoA synthetase activity can be quantitatively confirmed, for example, by cultivating for a certain period of time host cells, into which the polypeptide of the present invention is introduced, preparing the lysate of the host cells, mixing the cell lysate with a labeled fatty acid (e.g., polyunsaturated fatty acid labeled with a radioactive isotope, etc.) and coenzyme A, reacting them for a certain period of time, then extracting free fatty acids with n-heptane, and quantifying the fatty acyl-CoA which is formed during the above reaction and remained in the aqueous fraction, using a scintillation counter. For details of the method for confirming the acyl-CoA synthetase activity, reference may be made to Black P. N., et al. (J. B. C., 272 (8), 4896-4903, 1997). Alternatively, the acyl-CoA synthetase activity may also be assayed by the method described in "Evaluation of ACS Activity" of EXAMPLE 2, which involves no radioactive label.

The "activity of increasing the amount of the fatty acids produced in a host cell when expressed in the host cell" is intended to mean the activity that, when the polynucleotide of the present invention or the polynucleotide encoding the protein of the present invention is introduced (transformed) into a host cell and expressed in the host cell, increases the total fatty acid production, as compared to a reference cell (control) derived from the same strain as the host cell in which the polynucleotide described above is not introduced.

The "activity of changing the composition of the fatty acids produced in a host cell when expressed in the host cell" is intended to mean the activity that, when the polynucleotide of the present invention or the polynucleotide encoding the protein of the present invention is introduced (transformed) into a host cell and expressed in the host cell, changes the amount or ratio of various fatty acids produced, as compared to a reference cell (control) derived from the same strain as the host cell in which the polynucleotide described above is not introduced.

As used herein, the term "fatty acid" is intended to mean an aliphatic monocarboxylic acid (a carboxylic acid having one carboxylic residue and carbon atoms connected to each other in a chain) represented by general formula RCOOH (wherein R is an alkyl). The fatty acid includes a saturated fatty acid having no double bond and an unsaturated fatty acid containing a double bond(s) in the hydrocarbon chain. The fatty acid is preferably an unsaturated fatty acid, and more preferably, a polyunsaturated fatty acid containing a plurality of double bonds in the hydrocarbon chain. The polyunsaturated fatty acid includes preferably an unsaturated fatty acid having carbon atoms of 18 or more, e.g., an unsaturated fatty acid having carbon atoms of 18 or 20, and examples include, but not limited to, oleic acid, linoleic acid, linolenic acid (γ-linolenic acid, dihomo-γ-linolenic acid, etc.), arachidonic acid, and the like. The polyunsaturated fatty acids are particularly preferably linoleic acid, γ-linolenic acid, dihomo-γ-linolenic acid and arachidonic acid, more preferably, linoleic acid, dihomo-γ-linolenic acid and arachidonic acid, and most preferably, dihomo-γ-linolenic acid and arachidonic acid.

In the present invention, the "host cell" is not particularly limited so long as the cell is capable of expressing the polynucleotide of the invention when the polynucleotide is introduced. The cells include cells derived from mammals (excluding human), insects, plants, fungi, bacteria, etc., preferably cells from plants and fungi, more preferably, cells from fungi, and most preferably, lipid-producing fungi or yeast.

The lipid-producing fungi which can be used are the lipid-producing fungi described in, e.g., MYCOTAXON, Vol. XLIV, No. 2, pp. 257-265 (1992). Specific examples include, but not limited to, microorganisms belonging to the genus *Mortierella* including microorganisms belonging to the subgenus *Mortierella*, e.g., *Mortierella elongata* IFO8570, *Mortierella exigua* IFO8571, *Mortierella hygrophila* IFO5941, *Mortierella alpina* IFO8568, ATCC16266, ATCC32221, ATCC42430, CBS 219.35, CBS224.37, CBS250.53, CBS343.66, CBS527.72, CBS528.72, CBS529.72, CBS608.70 and CBS754.68, etc., or microorganisms belonging to the subgenus *Micromucor*, e.g., *Mortierella isabellina* CBS194.28, IFO6336, IFO7824, IFO7873, IFO7874, IFO8286, IFO8308 and IFO7884, *Mortierella nana* IFO8190, *Mortierella ramanniana* IFO5426, IFO8186, CBS112.08, CBS212.72, IFO7825, IFO8184, IFO8185 and IFO8287, *Mortierella vinacea* CBS236.82, etc. Among others, *Mortierella alpina* is preferable.

Specific examples of the yeast include the genus *Saccharomyces*, the genus *Candida*, the genus *Zygosaccharomyces*, the genus *Pichia* and the genus *Hansenula,* and preferably, *Saccharomyces cerevisiae* in the genus *Saccharomyces*. In wild strains of yeast such as *Saccharomyces cerevisiae*, etc., saturated fatty acids or monovalent fatty acids having mainly 18 or less carbon atoms can be synthesized within the cells, but polyunsaturated fatty acids cannot be synthesized therein. For this reason, when yeast such as Saccharomyces cerevisiae, etc. is used as a host cell, it is preferred to impart the ability to synthesize polyunsaturated fatty acids to the yeast cells by genetic engineering, etc. The ability to synthesize polyunsaturated fatty acids can be imparted by introducing a gene encoding a protein derived from an organism that already possesses the ability to synthesize polyunsaturated fatty acids and takes part in fatty acid synthesis.

The "organism that already possesses the ability to synthesize polyunsaturated fatty acids" includes, for example, lipid-producing fungi. Specific examples of the lipid-producing fungi are the same as those given hereinabove.

Examples of the gene encoding a protein derived from an organism that already possesses the ability to synthesize polyunsaturated fatty acids and "gene encoding the protein that takes part in fatty acid synthesis" include, but not limited to, Δ12 fatty acid desaturase gene, Δ6 fatty acid desaturase gene, GLELO fatty acid elongase gene and Δ5 fatty acid desaturase gene, etc. The nucleotide sequences of Δ12 fatty acid desaturase gene, Δ6 fatty acid desaturase gene, GLELO fatty acid elongase gene and Δ5 fatty acid desaturase gene are available by having access to databases including GenBank, etc. For example, in GenBank, Accession No. AB020033, No. AB020032, No. AB193123 and No. AB188307 are entered to access the respective sequences.

The genes for fatty acid synthesis-related proteins described above are inserted into appropriate vectors (e.g., pESC (Stratagene), pYES (Invitrogen), etc.), which are then introduced into yeast by the electroporation method, the spheroplast method (Proc. Natl. Acad. Sci. USA, 75 p1929 (1978)), the lithium acetate method (J. Bacteriology, 153, p163 (1983)), and the methods described in Proc. Natl. Acad. Sci. USA, 75 p1929 (1978), Methods in Yeast Genetics, 2000 Edition: A Cold Spring Harbor Laboratory Course Manual, etc.

Fatty acids can be extracted from the host cells transformed by the polynucleotide of the present invention or the polynucleotide encoding the protein of the present invention in the following manner. A host cell is cultured and then treated in a conventional manner, e.g., by centrifugation, filtration, etc. to obtain cultured cells. The cells are thoroughly washed with water and preferably dried. Drying may be accomplished by lyophilization, air-drying, etc. Depending upon necessity, the dried cells are disrupted using a Dynomil or by ultrasonication, and then extracted with an organic solvent preferably in a nitrogen flow. Examples of the organic solvent include ether, hexane, methanol, ethanol, chloroform, dichloromethane, petroleum ether and so on. Alternatively, good results can also be obtained by alternating extraction with methanol and petroleum ether or by extraction with a single-phase solvent system of chloroform-methanol-water. Removal of the organic solvent from the extract by distillation under reduced pressure may give fatty acid-containing lipids. The fatty acids extracted may be converted into the methyl esters by the hydrochloric acid methanol method, etc.

The quantity or ratio of various fatty acids may be determined by analyzing the fatty acids extracted as described above using various chromatography techniques. Examples of the chromatography techniques include, but not limited to, high performance liquid chromatography and gas chromatography, and particularly preferably, gas chromatography.

3. Vector of the Invention and Vector-Introduced Transformants

In another embodiment, the present invention further provides the expression vector comprising the polynucleotide of the invention.

The vector of the invention is generally constructed to contain an expression cassette comprising:
  (i) a promoter that can be transcribed in a host cell;
  (ii) any of the polynucleotides defined in (a) to (g) above that is linked to the promoter; and,
  (iii) an expression cassette comprising as a component a signal that functions in the host cell with respect to the transcription termination and polyadenylation of RNA molecule.

The vector thus constructed is introduced into a host cell. Examples of host cells which may be appropriately used in the present invention are the same as described above.

In these host cells transformed by the vector of the present invention, the ACS activity is more increased, fatty acids are more produced or the quantity or ratio of various fatty acids contained in the cells are changed, when compared to the host cells which are not transformed by the vector of the present invention.

Examples of the vectors available for introducing into lipid-producing fungi include, but not limited to, pDura5 (Appl. Microbiol. Biotechnol., 65, 419-425, (2004)).

Any vector is available as the vector used to introduce into the yeast and not particularly limited so long as it is a vector capable of expressing the insert in the yeast cells. The vector includes, e.g., pYE22m (Biosci. Biotech. Biochem., 59, 1221-1228, 1995).

Promoters/terminators for regulating gene expression in host cells may be used in an optional combination as far as they function in the host cells. For example, a promoter of the histone H4.1 gene, a promoter of the glyceraldehyde-3-phosphate dehydrogenase, etc. may be used.

As selection markers used for the transformation, there may be utilized auxotrophic markers (ura5, niaD), hygromycin-resistant gene, zeocin-resistant gene, genecitin-resistant gene (G418r), copper-resistant gene (CUP1) (Marin et al., Proc. Natl. Acad. Sci. USA, 81, 337 1984), cerulenin-resistant gene (fas2m, PDR4) (Junji Inokoshi, et al., Biochemistry, 64, 660, 1992; and Hussain et al., Gene, 101: 149, 1991, respectively), and the like.

For the transformation of host cells, generally known methods may be used. In lipid-producing fungi, the transformation may be performed, e.g., by the electroporation method (Mackenzie, D. A. et al., Appl. Environ. Microbiol., 66, 4655-4661, 2000) and the particle delivery method (the method described in JPA 2005-287403 "Method of Breeding Lipid-Producing Fungus"). On the other hand, the electroporation method, the spheroplast method (Proc. Natl. Acad. Sci. USA, 75 p1929 (1978)) and the lithium acetate method (J. Bacteriology, 153 p163 (1983)) as well as the methods described in Proc. Natl. Acad. Sci. USA, 75 p1929 (1978), Methods in yeast genetics, 2000 Edition: A Cold Spring Harbor Laboratory Course Manual, etc) may be used for the transformation of yeast. However, the method for transformation is not limited to those described above.

For general cloning techniques, reference may be made to "Sambrook & Russell, Molecular Cloning: A Laboratory Manual Vol. 3, Cold Spring Harbor Laboratory Press 2001", "Methods in Yeast Genetics, A laboratory manual (Cold Spring Harbor Laboratory Press, Cold Spring Harbor, N.Y.)," etc.

4. Method for Producing the Lipid or Fatty Acid Composition of the Invention

In another embodiment, the present invention further provides a method for preparing a lipid or fatty acid composition which comprises using the transformant described above.

As used herein, the term "lipid" is intended to mean a simple lipid including a compound (e.g., a glyceride) which is composed of a fatty acid and an alcohol attached via an ester linkage, or its analog (e.g., a cholesterol ester), etc.; a complex lipid in which phosphoric acid, amino acid(s), saccharide(s) or the like are bound to a part of the simple lipid; or a derived lipid which is a hydrolysate of the lipid and is insoluble in water.

As used herein, the term "oil and fat" is intended to mean an ester of glycerol and a fatty acid (glyceride).

The term "fatty acid" is the same as defined above.

The method for extracting the lipid or fatty acid composition of the present invention is the same as the method for extracting fatty acids described above.

Fatty acids can be separated from the above fatty acid-containing lipids in a state of mixed fatty acids or mixed fatty acid esters by concentration and separation in a conventional manner (e.g., urea addition, separation under cooling, column chromatography, etc.).

The lipids produced by the method of the present invention include preferably unsaturated fatty acids, and more preferably, polyunsaturated fatty acids. Preferred examples of the polyunsaturated fatty acids are unsaturated fatty acids having 18 or more carbon atoms, e.g., unsaturated fatty acids having 18 to 20 carbon atoms, and include, but not limited to, oleic acid, linoleic acid, linolenic acid (γ-linolenic acid and dihomo-γ-linolenic acid, etc.), arachidonic acid, etc. Particularly preferred polyunsaturated fatty acids are linoleic acid, γ-linoleic acid, dihomo-γ-linoleic acid and arachidonic acid, more preferably, linoleic acid, dihomo-γ-linoleic acid and arachidonic acid, and most preferably, dihomo-γ-linolenic acid and arachidonic acid.

The lipids produced by the method of the present invention and the composition of the fatty acids contained in the lipids may be confirmed by the lipid extraction method or fatty acid separation method described above, or a combination thereof.

The lipid or fatty acid composition obtained by the production method of the present invention can be provided for use in producing, e.g., food products, pharmaceuticals, industrial materials (raw materials for cosmetics, soaps, etc.), which contain oils and fats, in a conventional manner.

In a still other embodiment, the present invention provides a method for preparing food products, cosmetics, pharmaceuticals, soaps, etc. using the transformant of the present invention. The method involves the step of forming lipids or fatty acids using the transformant of the present invention.

Food products, cosmetics, pharmaceuticals, soaps, etc. containing the lipids or fatty acids produced are prepared in a conventional manner. As such, the food products, cosmetics, pharmaceuticals, soaps, etc. produced by the method of the present invention contain the lipids or fatty acids produced using the transformant of the present invention. The present invention further provides the food products, cosmetics, pharmaceuticals, soaps, etc. produced by such a method.

The form of the cosmetic (composition) or pharmaceutical (composition) of the present invention is not particularly limited and may be any form including the state of a solution, paste, gel, solid or powder. The cosmetic composition or pharmaceutical composition of the present invention may also be used as cosmetics or topical agents for the skin, including an oil, lotion, cream, emulsion, gel, shampoo, hair rinse, hair conditioner, enamel, foundation, lipstick, face powder, facial pack, ointment, perfume, powder, eau de cologne, tooth paste, soap, aerosol, cleansing foam, etc., an anti-aging skin care agent, anti-inflammatory agent for the skin, bath agent, medicated tonic, skin beauty essence, sun protectant, or protective and improving agent for skin troubles caused by injury, chapped or cracked skin, etc.

The cosmetic composition of the present invention may further be formulated appropriately with other oils and fats and/or dyes, fragrances, preservatives, surfactants, pigments, antioxidants, etc., if necessary. The formulation ratio of these materials may be appropriately determined by those skilled in the art, depending upon purpose (for example, oils and fats may be contained in the composition in 1 to 99.99 wt %, preferably, 5 to 99.99 wt %, and more preferably, 10 to 99.95 wt%). If necessary, the pharmaceutical composition of the present invention may also contain other pharmaceutically active components (e.g., anti-inflammatory components) or aid components (e.g., lubricants or vehicle components). Examples of the other components commonly used in a cosmetic or a skin preparation for external use include an agent for acne, an agent for preventing dandruff or itching, an antiperspirant and deodorant agent, an agent for burn injury, an anti-mite and lice agent, an agent for softening keratin, an agent for xeroderma, an antiviral agent, a percutaneous absorption promoting agent, and the like.

The food product of the present invention includes a dietary supplement, health food, functional food, food product for young children, baby food, infant modified milk, premature infant modified milk, geriatric food, etc. As used herein, the food or food product is intended to mean a solid, fluid and liquid food as well as a mixture thereof, and collectively means an edible stuff.

The term dietary supplement refers to food products enriched with specific nutritional ingredients. The term health food refers to food products which are healthful or beneficial to health, and encompasses dietary supplements, natural foods, diet foods, etc. The term functional food refers to a food product for replenishing nutritional ingredients which assist body control functions and is synonymous with a food for specified health use. The term food for young children refers to a food product given to children up to about 6 years old. The term geriatric food refers to a food product treated to facilitate digestion and absorption when compared to untreated foods. The term infant modified milk refers to modified milk given to children up to about one year old. The term premature infant modified milk refers to modified milk given to premature infants until about 6 months after birth.

The form of these food products includes natural foods (treated with fats and oils) such as meat, fish and nuts; foods supplemented with fats and oils during cooking, e.g., Chinese foods, Chinese noodles, soups, etc.; foods prepared using fats and oils as heating media, e.g., tempura or deep-fried fish and vegetables, deep-fried foods, fried bean curd, Chinese fried rice, doughnuts, Japanese fried dough cookies or karinto; fat- and oil-based foods or processed foods supplemented with fats and oils during processing, e.g., butter, margarine, mayonnaise, dressing, chocolate, instant noodles, caramel, biscuits, cookies, cakes, ice cream; and foods sprayed or coated with fats and oils upon finishing, e.g., rice crackers, hard biscuits, sweet bean paste bread, etc. However, the food product is not limited to foods containing fats and oils, and other examples include agricultural foods such as bakery products, noodles, cooked rice, sweets (e.g., candies, chewing gums, gummies, sweet tablets, Japanese sweets), bean curd or tofu and processed products thereof; fermented foods such as Japanese rice wine or sake, medicinal liquor, sweet cooking sherry or mirin, vinegar, soy sauce and bean paste or miso, etc.; livestock food products such as yoghurt, ham, bacon, sausage, etc.; seafood products such as minced and steamed fish cake or kamaboko, deep-fried fish cake or ageten and puffy fish cake or hanpen, etc.; as well as fruit drinks, soft drinks, sports drinks, alcoholic beverages, tea, etc.

The food product of the present invention may also be in the form of pharmaceutical preparations such as capsules, etc., or in the form of a processed food such as natural liquid diets, defined formula diets and elemental diets formulated with the oil and fat of the present invention together with proteins, sugars, trace elements, vitamins, emulsifiers, aroma chemicals, etc., health drinks, enteral nutrients, and the like.

As described above, fatty acids can be efficiently produced by expressing the ACS homolog gene of the present invention in host cells.

Furthermore, the expression level of the gene can be used as an indicator to study conditions for cultivation, cultivation control, etc. for efficient fatty acid production.

EXAMPLES

Hereinafter, the present invention is described in more detail with reference to EXAMPLES but it should be understood that the invention is not deemed to limit the scope of the invention to these EXAMPLES.

Example 1

Genome Analysis of *M. alpina*

The *M. alpina* 1S-4 strain was plated on 100 ml of GY2:1 medium (2% glucose and 1% yeast extract, pH 6.0) followed by shake culture at 28° C. for 2 days. The mycelial cells were collected by filtration, and genomic DNA was prepared using DNeasy (QIAGEN). The nucleotide sequence of the genomic DNA described above was determined using a Roche 454 GS FLX Standard. On this occasion, nucleotide sequencing of a fragment library was performed in two runs and nucleotide sequencing of a mate paired library in three runs. The resulting nucleotide sequences were assembled to give 300 supercontigs.

Synthesis of cDNA and Construction of cDNA Library

The *M. alpina* strain 1S-4 was plated on 100 ml of medium (1.8% glucose, 1% yeast extract, pH 6.0) and precultured for 3 days at 28° C. A 10 L culture vessel (Able Co., Tokyo) was charged with 5 L of medium (1.8% glucose, 1% soybean powder, 0.1% olive oil, 0.01% Adekanol, 0.3% $KH_2PO_4$, 0.1% $Na_2SO_4$, 0.05% $CaCl_2.2H_2O$ and 0.05% $MgCl_2.6H_2O$, pH 6.0), and the whole amount of the precultured product was plated thereon, followed by aerobic spinner culture under conditions of 300 rpm, 1 vvm and 26° C. for 8 days. On Days 1, 2 and 3 of the cultivation, glucose was added in an amount corresponding to 2%, 2% and 1.5%, respectively. The mycelial cells were collected at each stage on Days 1, 2, 3, 6 and 8 of the cultivation to prepare total RNA by the guanidine hydrochloride/CsCl method. Using an Oligotex-dT30<Super>mRNA Purification Kit (Takara Bio Inc.)("dT30" disclosed as SEQ ID NO: 130), poly(A)+ RNA was purified from the total RNA. A cDNA library was constructed for each stage using a ZAP-cDNA Gigapack III Gold Cloning Kit (STRATAGENE).

Search for ACS Homolog

Using as a query the amino acid sequences of ScFAA1 (YOR317W), ScFAA2 (YER015W), ScFAA3 (YIL009W), ScFAA4 (YMR246W), ScFAT1 (YBR041W) and ScFAT2 (YBR222C), which are ACS from yeast, a tblastn search was performed against the genome nucleotide sequence of the *M. alpina* strain 1S-4. As a result, hits were found in twelve (12) sequences. That is, hit was found on supercontigs containing the sequence shown by SEQ ID NO: 5, SEQ ID NO: 10, SEQ ID NO: 15, SEQ ID NO: 20, SEQ ID NO: 25, SEQ ID NO: 30, SEQ ID NO: 35, SEQ ID NO: 40, SEQ ID NO: 45, SEQ ID NO: 50, SEQ ID NO: 55 or SEQ ID NO: 60. The genes bearing SEQ ID NO: 5, SEQ ID NO: 10, SEQ ID NO: 15, SEQ ID NO: 20, SEQ ID NO: 25, SEQ ID NO: 30, SEQ ID NO: 35, SEQ ID NO: 40, SEQ ID NO: 45, SEQ ID NO: 50, SEQ ID NO: 55 and SEQ ID NO: 60 were designated respectively as MaACS-1, MaACS-2, MaACS-3, MaACS-4, MaACS-5, MaACS-6, MaACS-7, MaACS-8, MaACS-9, MaACS-10, MaACS-11 and MaACS-12.

Cloning of ACS Homolog

For cloning of the cDNAs corresponding to the MaACS-1~12 genes, screening of the cDNA library described above was performed. Probe labeling was performed by PCR using an ExTaq (Takara Bio Inc.). That is, digoxigenin (DIG)-labeled amplified DNA probes were prepared using a PCR Labeling Mix (Roche Diagnostics) instead of dNTP mix attached to ExTaq.

Conditions for hybridization were set as follows.

Buffer: 5×SSC, 1% SDS, 50 mM Tris-HCl (pH 7.5), 50% formaldehyde;

Temperature: 42° C. (overnight);

Wash conditions: 0.2×SSC, in 0.1% SDS solution (65° C.) for 20 mins.×3

Detection was performed using a DIG Nucleic Acid Detection Kit (Roche Diagnositcs). Phage clones were obtained by screening and plasmids were excised from the phage clones by in vivo excision to give the respective plasmid DNAs. Primers for preparing the probes used for screening of the respective genes, the number of nucleotides in CDS of the respective genes, the number of amino acids in the amino acid sequences deduced from the nucleotide sequences of CDS, and the number of exons and introns by comparison of genomic DNA sequences with CDS sequences are given below.

(1) MaACS-1

(SEQ ID NO: 61)
Primer ACS-1-1F: 5'-GTCGGCTCCAAGCTTGCAATCC-3'

(SEQ ID NO: 62)
Primer ACS-1-2R: 5'-GGACAGCTCCAGCACTGTGGTAAAG-3' cDNA (SEQ ID NO: 4)
CDS (SEQ ID NO: 3): 1857 bp
ORF (SEQ ID NO: 1): 1854 bp
Amino acid sequence (SEQ ID NO: 2): 618 amino acids (see FIG. 1)
Number of exons: 5, number of introns: 4 (see FIG. 2)

(2) MaACS-2

(SEQ ID NO: 63)
Primer ACS-2-1F: 5'-GACCACGGGATTCCCCAAGGCTGC-3'

Figure 4B:
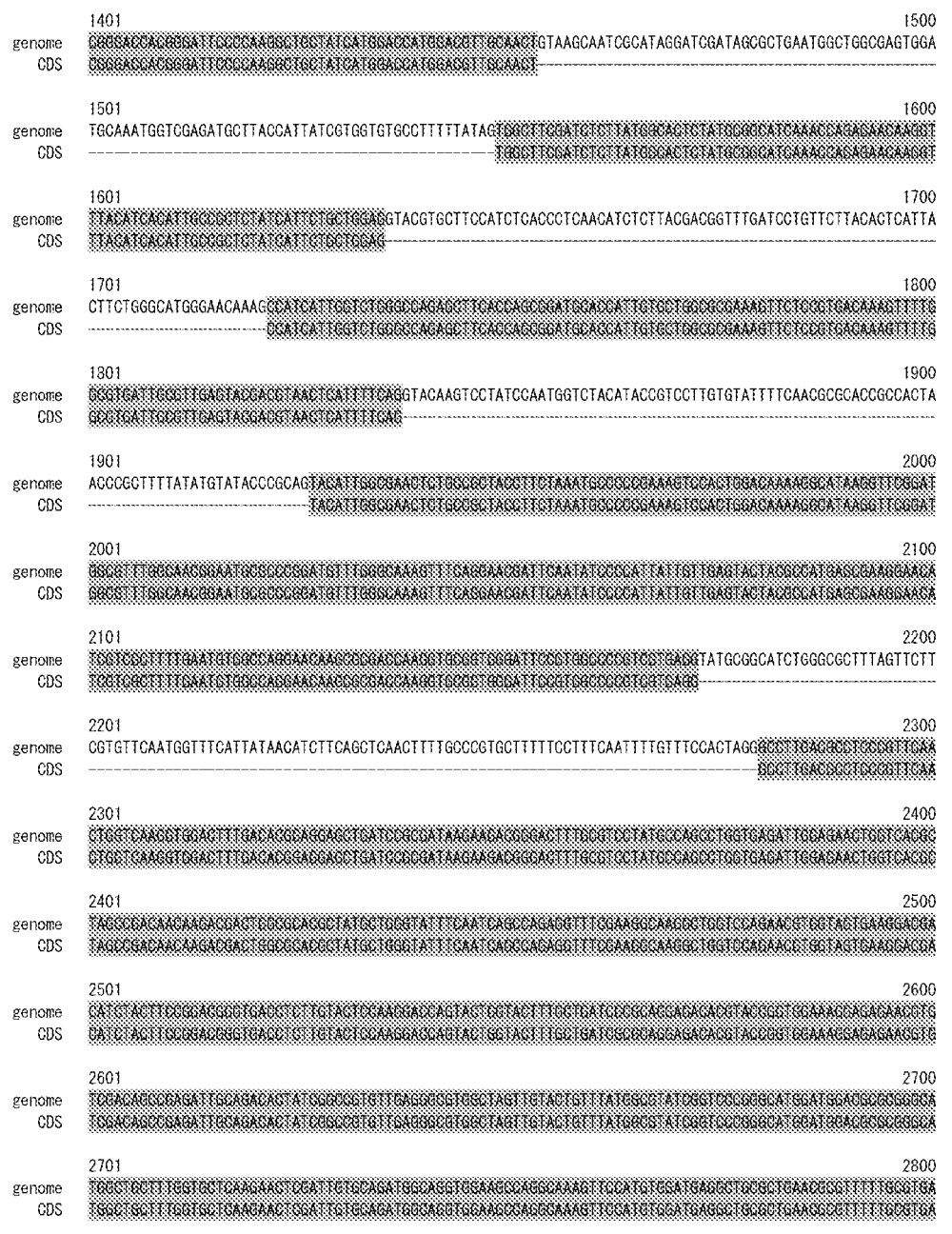
Figure 4C:
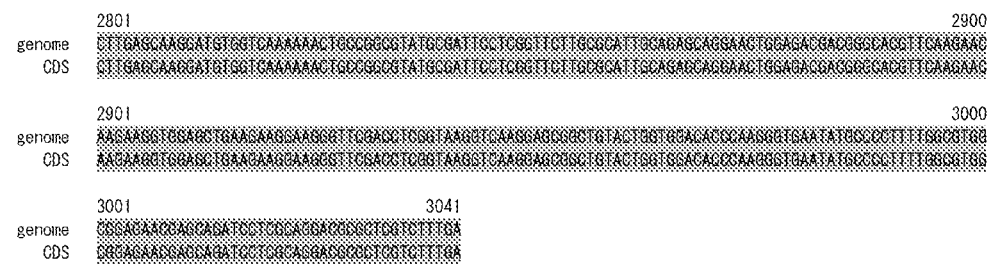

(SEQ ID NO: 64)
Primer ACS-2-2R: 5'-CTTGGTCGCGCTTGTTCCTGGCCAC-3' cDNA (SEQ ID NO: 9)
CDS (SEQ ID NO: 8): 1929 bp
ORF (SEQ ID NO: 6): 1926 bp
Amino acid sequence (SEQ ID NO: 7): 642 amino acids (see FIG. 3)
Number of exons: 8, number of introns: 7 (see FIG. 4)

(3) MaACS-3

(SEQ ID NO: 65)
Primer ACS-3-1F: 5'-TACAGCTTTGTTGCTGTCCCCATC-3'

Figure 6A:
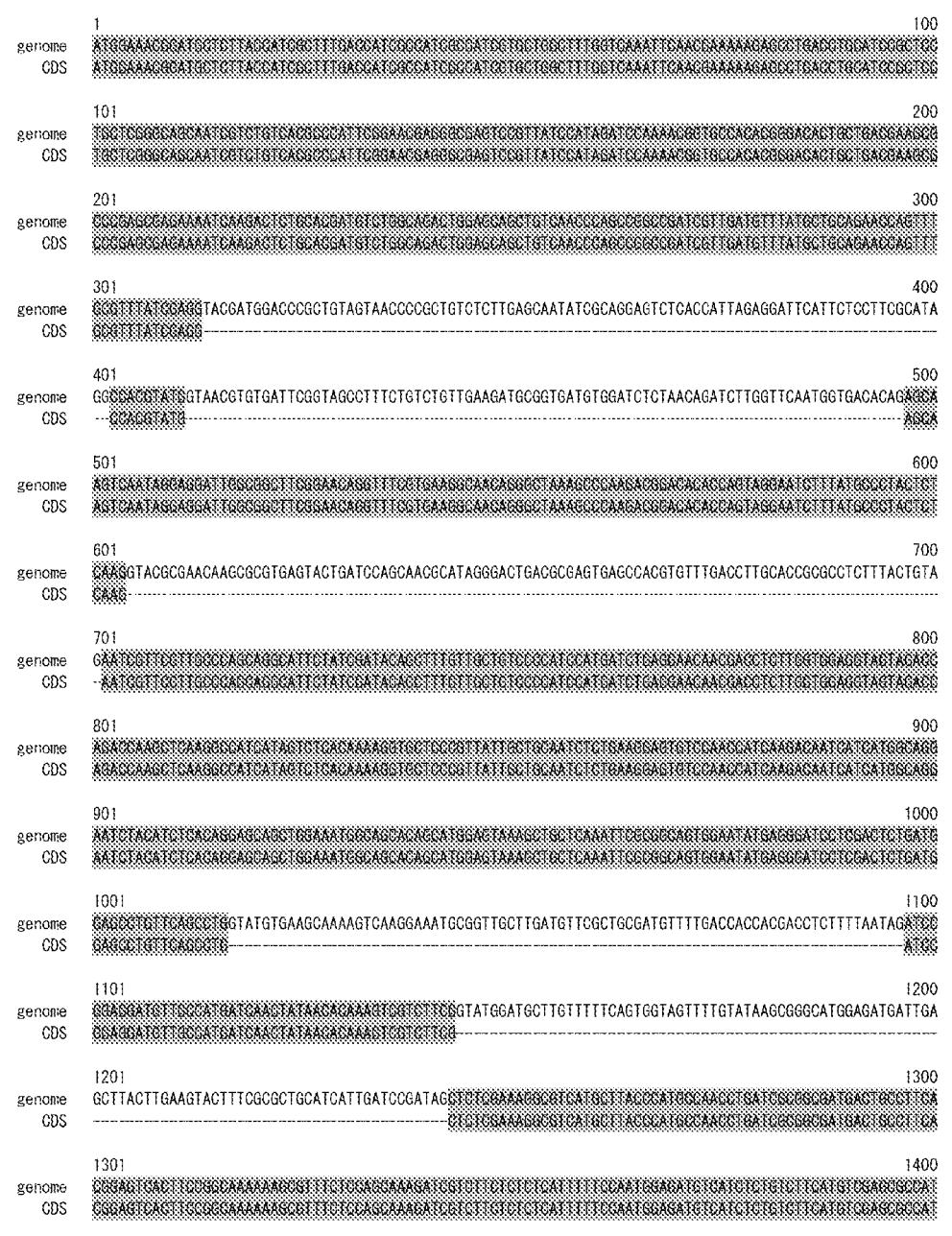

(SEQ ID NO: 66)
Primer ACS-3-2R: 5'-GATGATGGGTGTGCTTGCAAAGATC-3' cDNA (SEQ ID NO: 14)
CDS (SEQ ID NO: 13): 1653 bp
ORF (SEQ ID NO: 11): 1650 bp
Amino acid sequence (SEQ ID NO: 12): 550 amino acids (see FIG. 5)
Number of exons: 9, number of introns: 8 (see FIG. 6)

(4) MaACS-4

(SEQ ID NO: 67)
Primer ACS-4-1F: 5'-AACCCAAAGCTGCGCCAGGCTGTCC-3'

Figure 8A:
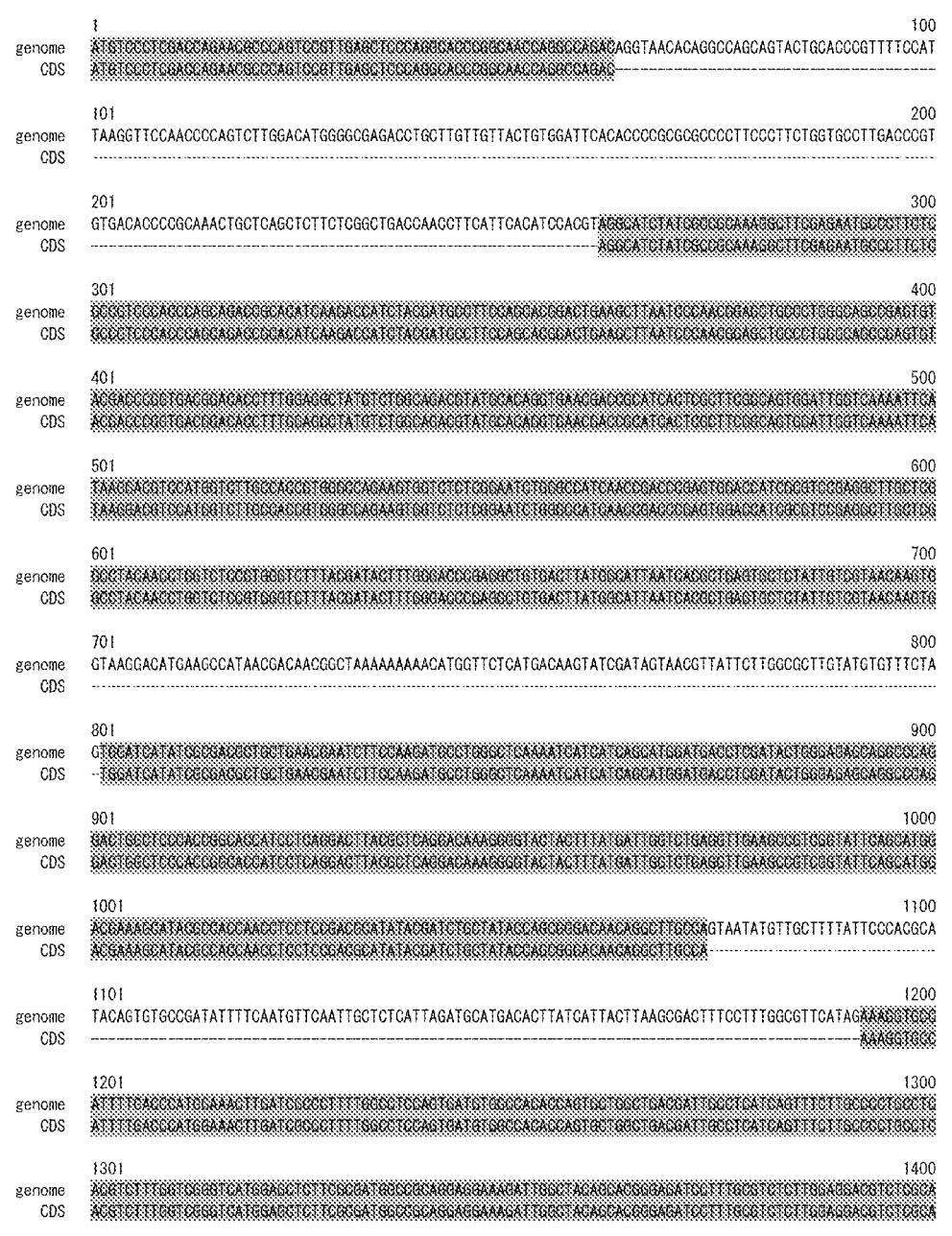
Figure 8B:
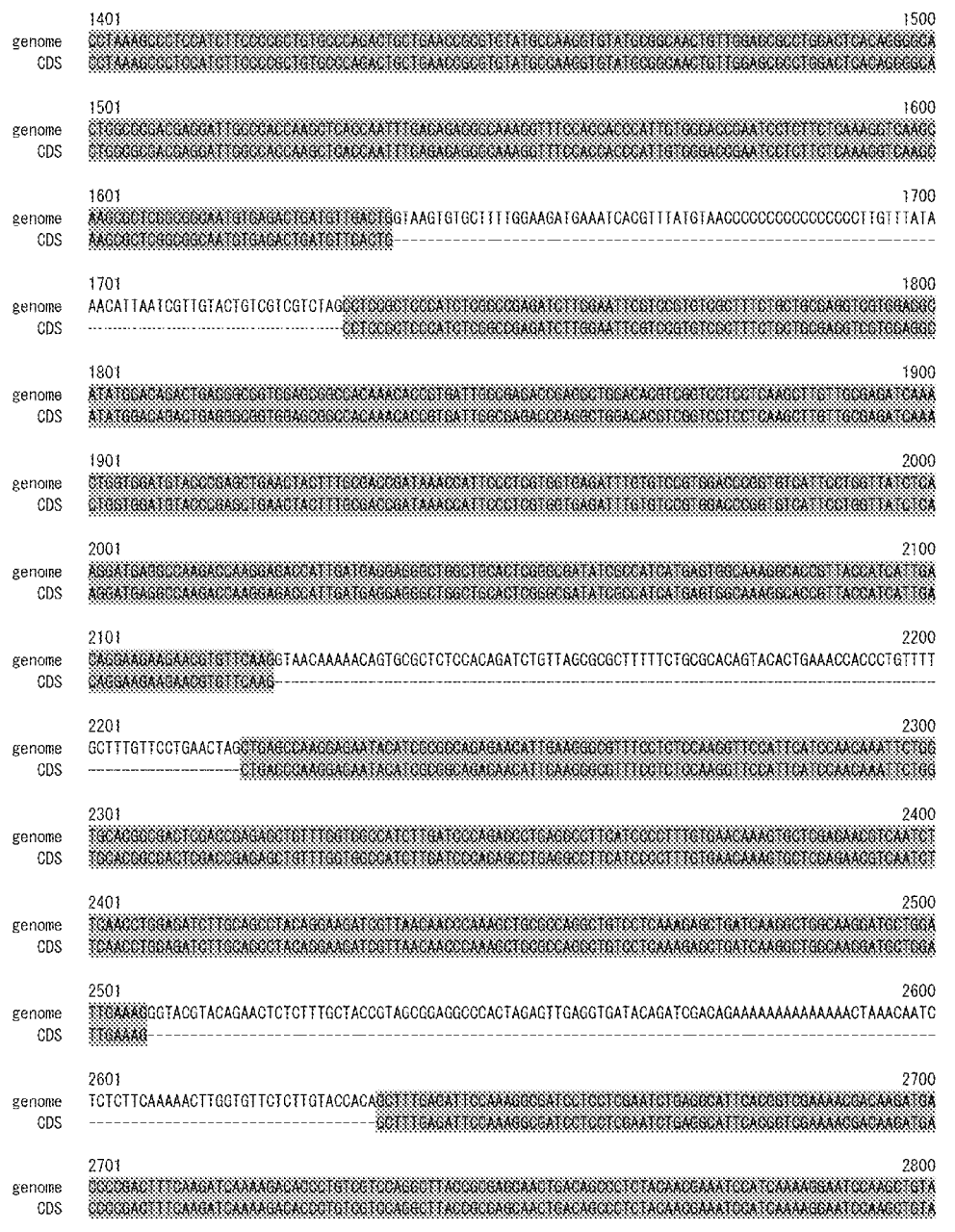

(SEQ ID NO: 68)
Primer ACS-4-2R: 5'-TTACAGCTTGGATTCCTTTTGATGG-3' cDNA (SEQ ID NO: 19)
CDS (SEQ ID NO: 18): 2067 bp
ORF (SEQ ID NO: 16): 2064 bp
Amino acid sequence (SEQ ID NO: 17): 688 amino acids (see FIG. 7)
Number of exons: 7, number of introns: 6 (see FIG. 8)

(5) MaACS-5

(SEQ ID NO: 69)
Primer ACS-5-1F: 5'-GTCGTGCCCGATGCGGAGACGC-3'

Figure 10B:
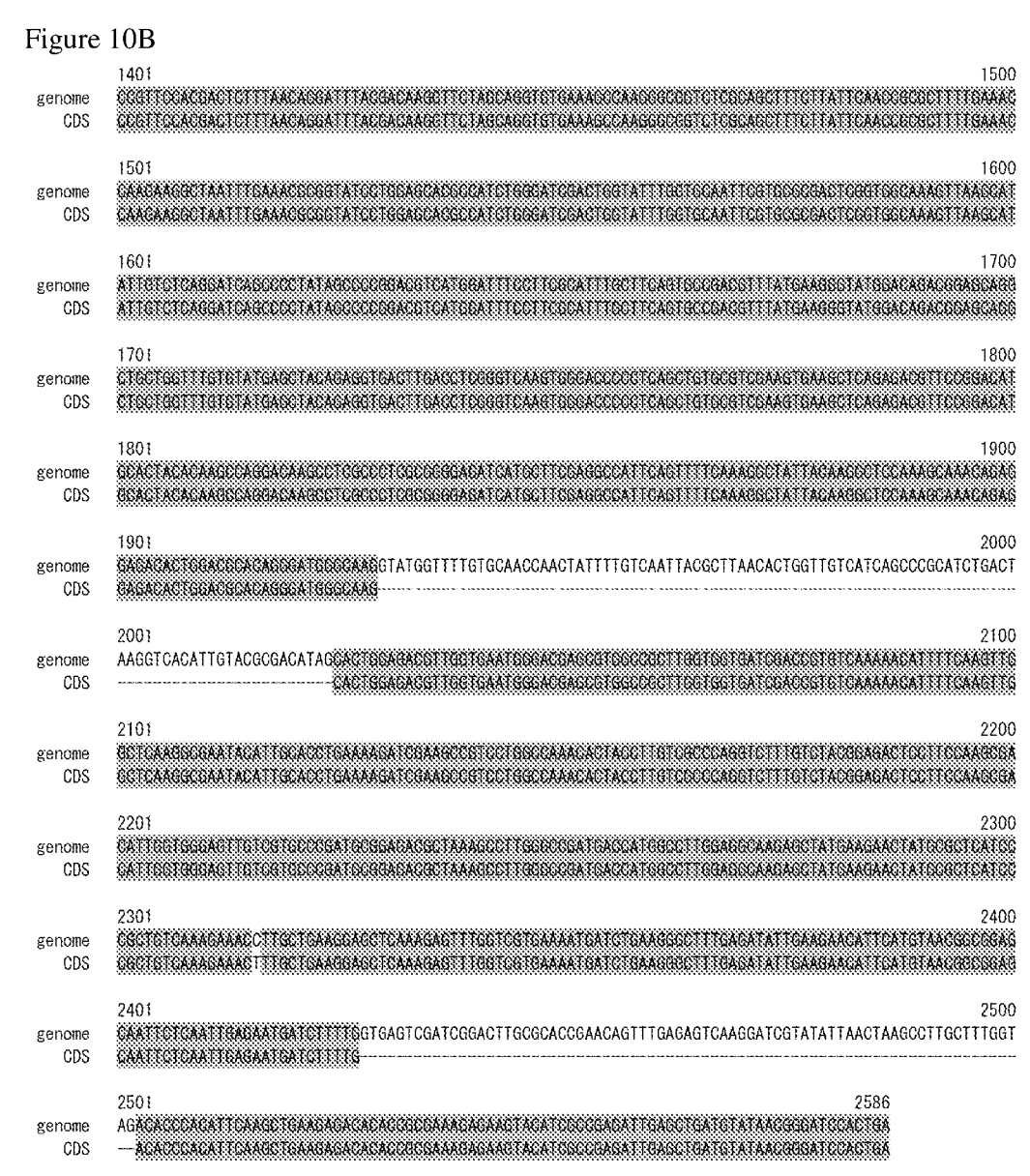

(SEQ ID NO: 70)
Primer ACS-5-2R: 5'-TCAGTGGATCCCGTTATACATCAG-3' cDNA (SEQ ID NO: 24)
CDS (SEQ ID NO: 23): 1980 bp
ORF (SEQ ID NO: 21): 1977 bp
Amino acid sequence (SEQ ID NO: 22): 659 amino acids (see FIG. 9)
Number of exons: 6, number of introns: 5 (see FIG. 10)

(6) MaACS-6

(SEQ ID NO: 71)
Primer ACS-6-1F: 5'-GCGTCCCCCTCTATGATACATTG-3'

(SEQ ID NO: 72)
Primer ACS-6-2R: 5'-GTGGGATGCAGGACGGCAACATCG-3' cDNA (SEQ ID NO: 29)
CDS (SEQ ID NO: 28): 1980 bp
ORF (SEQ ID NO: 26): 1977 bp

Figure 12A:
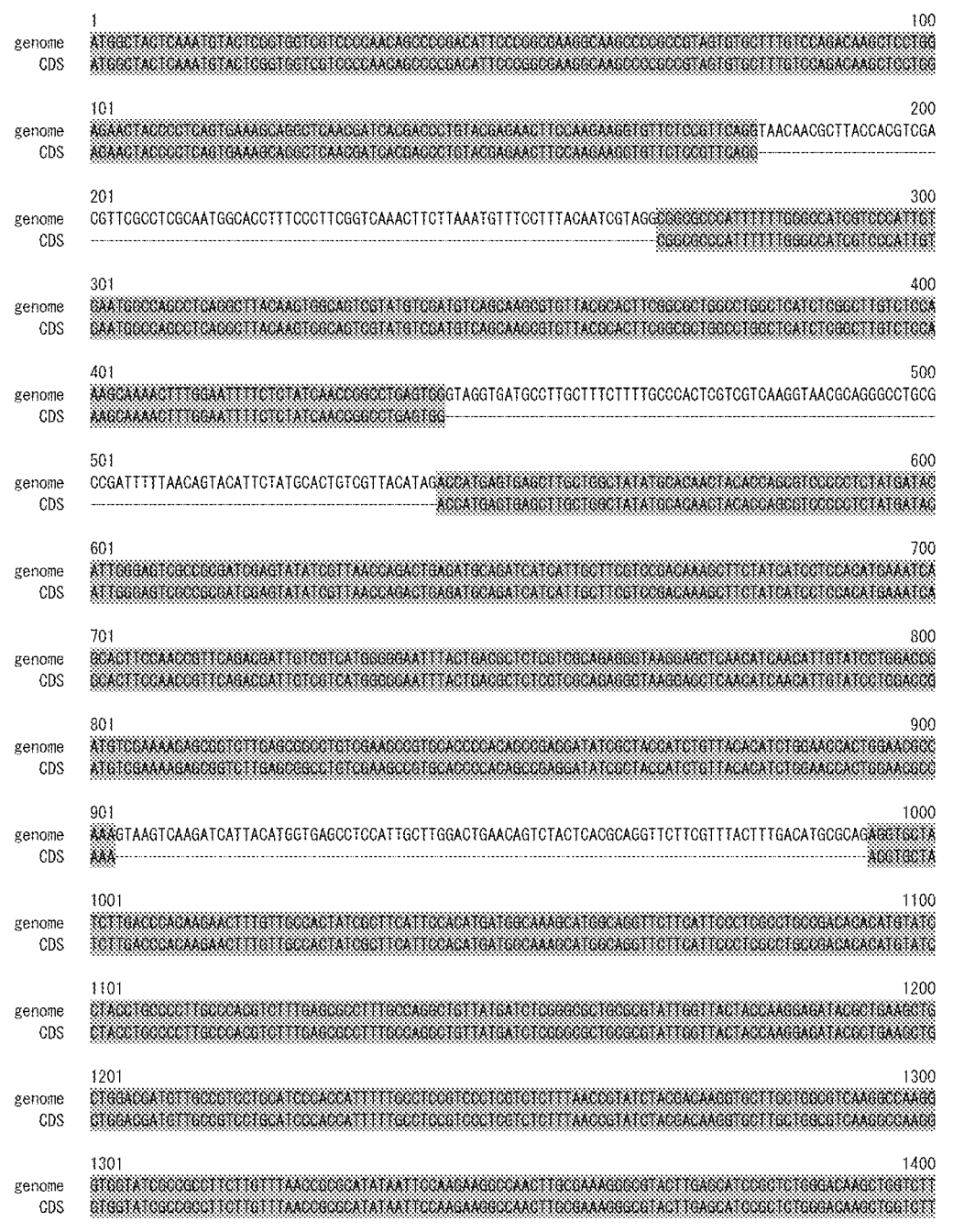

Amino acid sequence (SEQ ID NO: 27): 659 amino acids (see FIG. 11)
Number of introns: at least 5 (see FIG. 12)

(7) MaACS-7
(SEQ ID NO: 73)
Primer ACS-7-1F: 5'-GGATGCCGAACAACAGCGCGTGG-3'

Figure 14A:
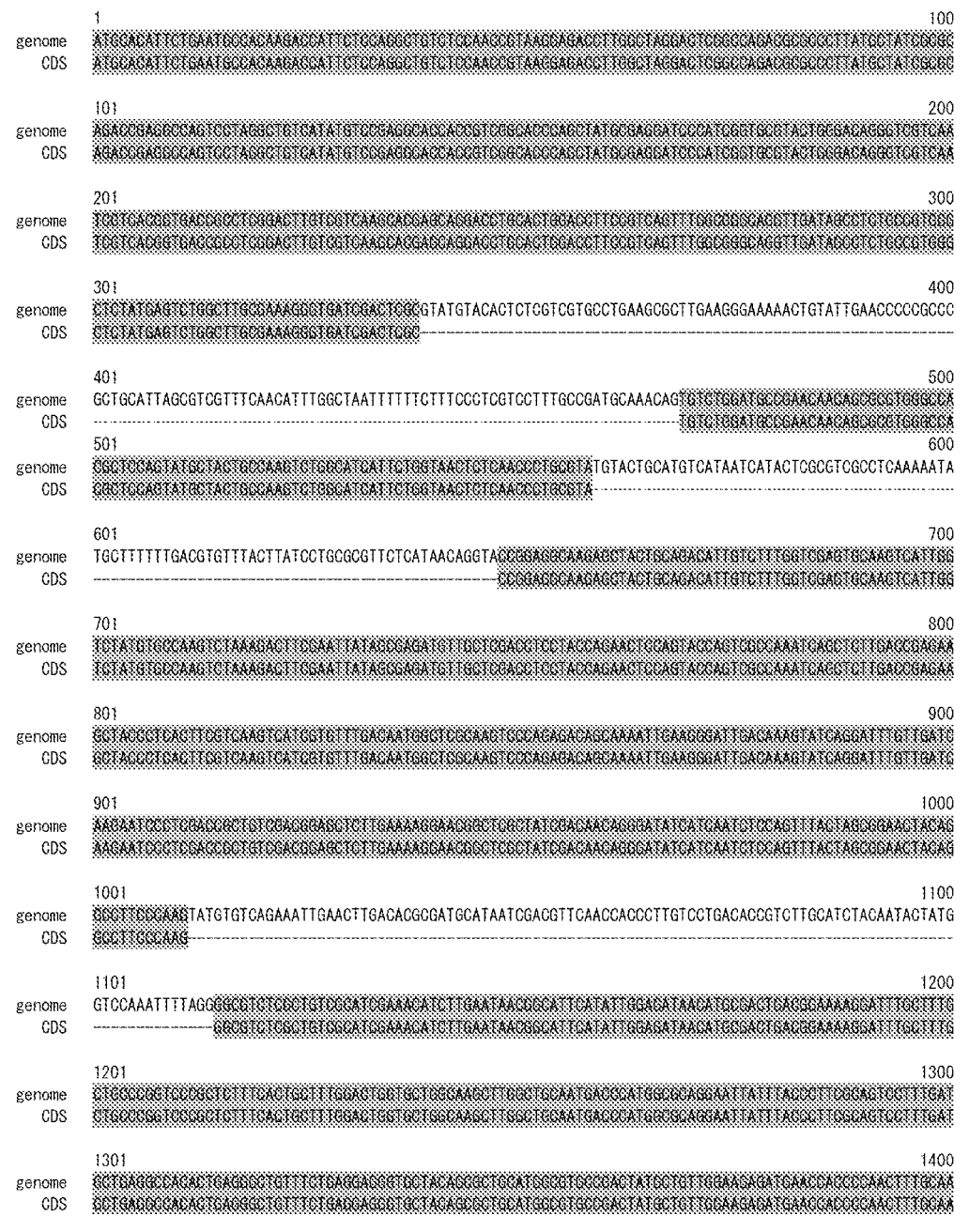
Figure 14B:
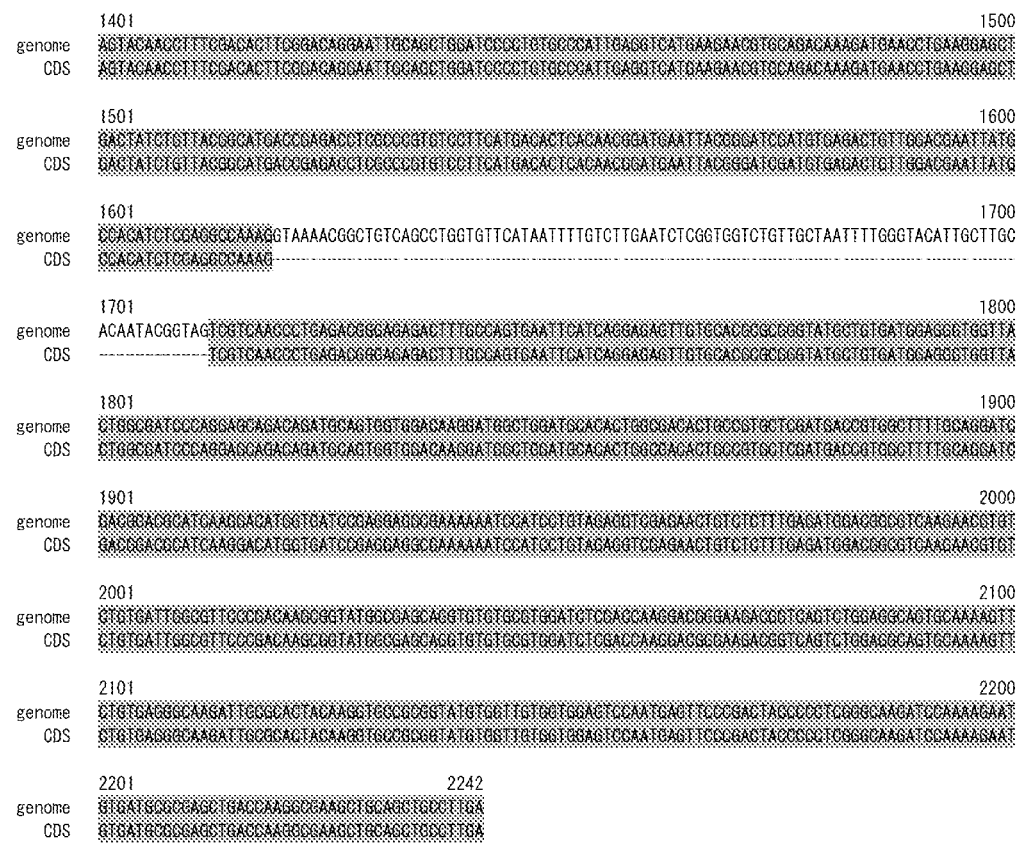

(SEQ ID NO: 74)
Primer ACS-7-2R: 5'-GCACCCTCCTCAGAAACAGCCCTC-3' cDNA (SEQ ID NO: 34)
CDS (SEQ ID NO: 33): 1827 bp
ORF (SEQ ID NO: 31): 1824 bp
Amino acid sequence (SEQ ID NO: 32): 608 amino acids (see FIG. 13)
Number of exons: 5, number of introns: 4 (see FIG. 14)

(8) MaACS-8
(SEQ ID NO: 75)
Primer ACS-8-1F: 5'-CAGTCGAGTACATTGTCAACCACG-3'

Figure 16A:
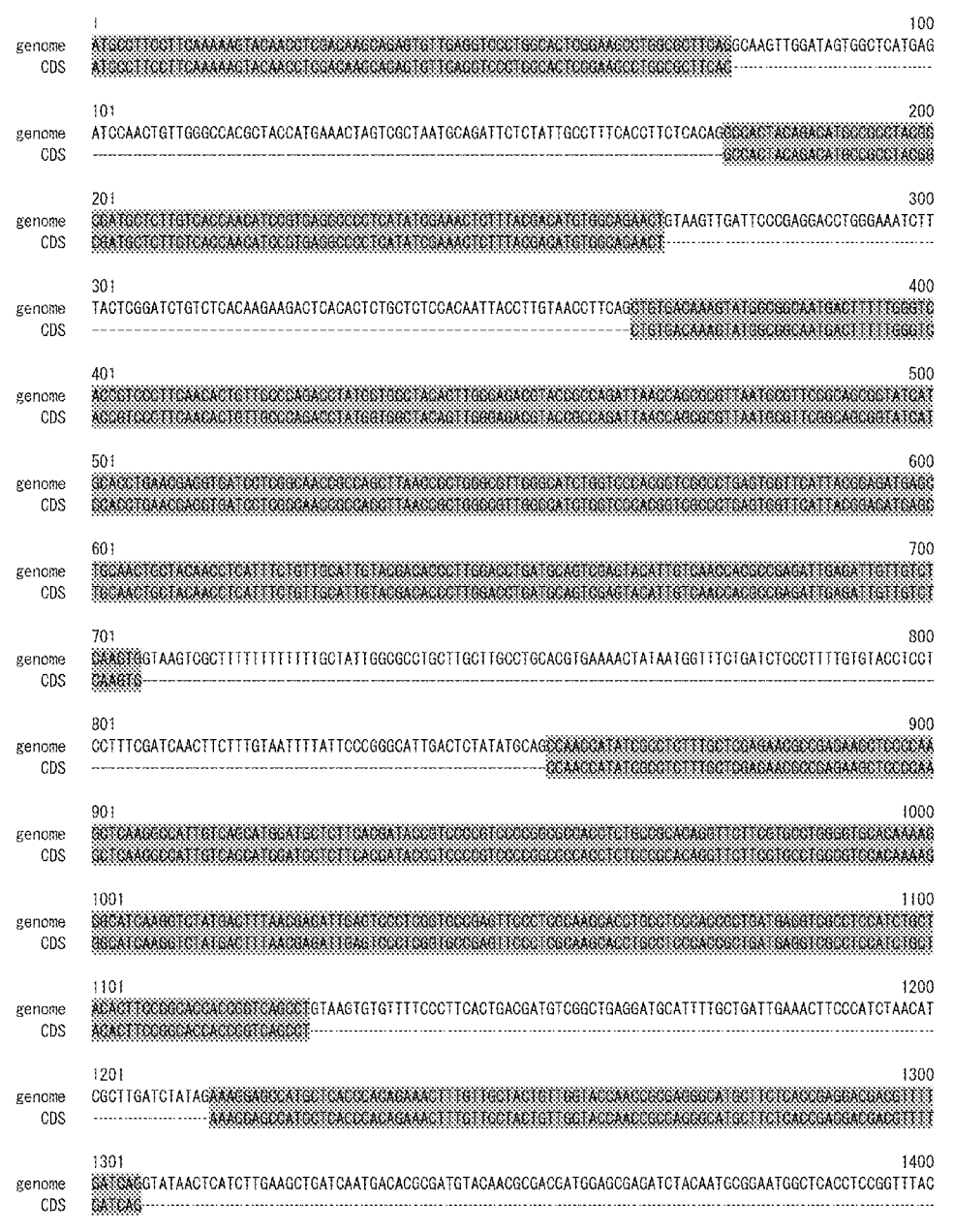
Figure 16B:
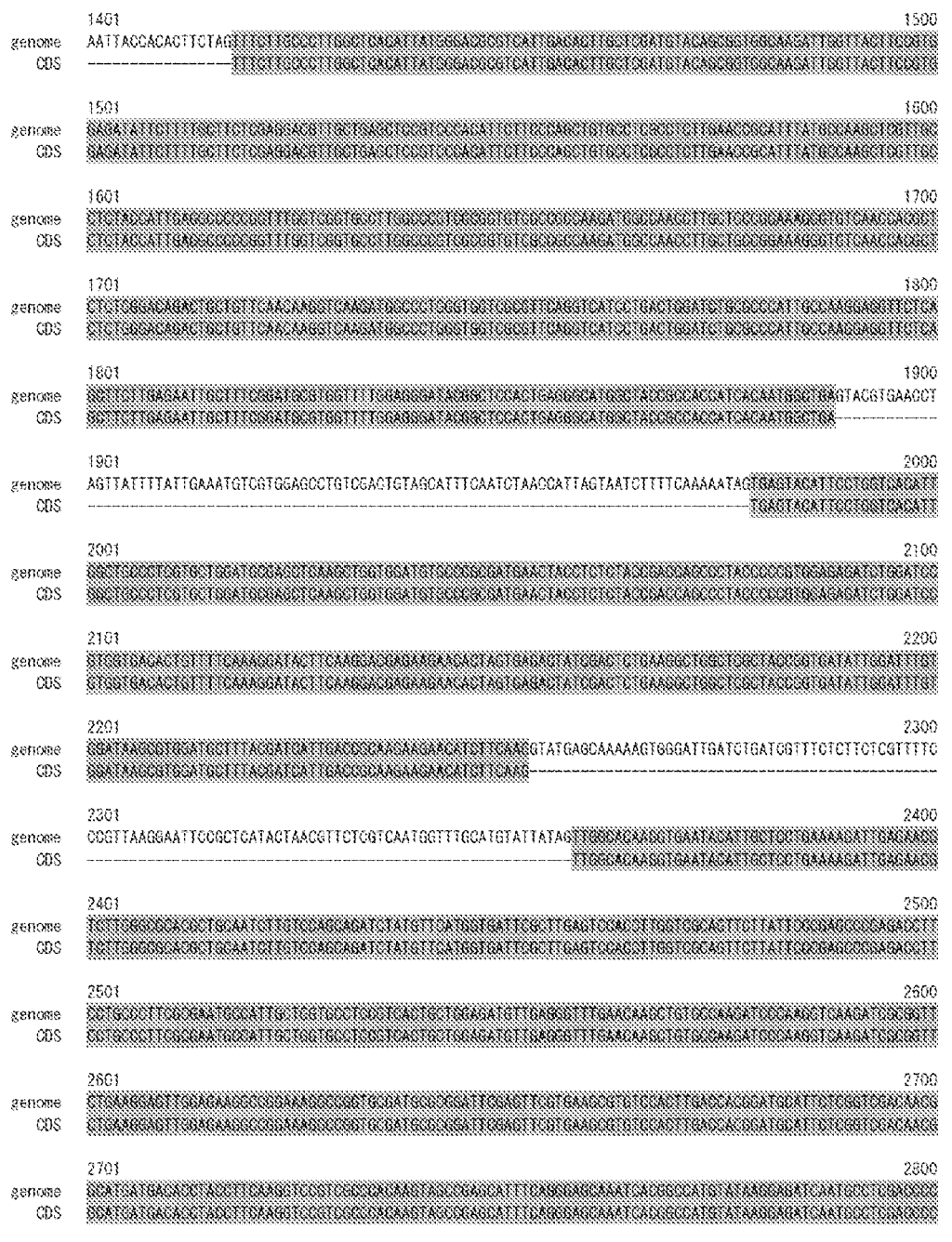

(SEQ ID NO: 76)
Primer ACS-8-2R: 5'-GCGGTTCAAGAGGCGAGGCACAGC-3' cDNA (SEQ ID NO: 39)
CDS (SEQ ID NO: 38): 2079 bp
ORF (SEQ ID NO: 36): 2076 bp
Amino acid sequence (SEQ ID NO: 37): 692 amino acids (see FIG. 15)
Number of exons: 8, number of introns: 7 (see FIG. 16)

(9) MaACS-9
(SEQ ID NO: 77)
Primer ACS-9-1F: 5'-GTTCATCTTCTGCTGGCTGGGTCTC-3'

Figure 18B:
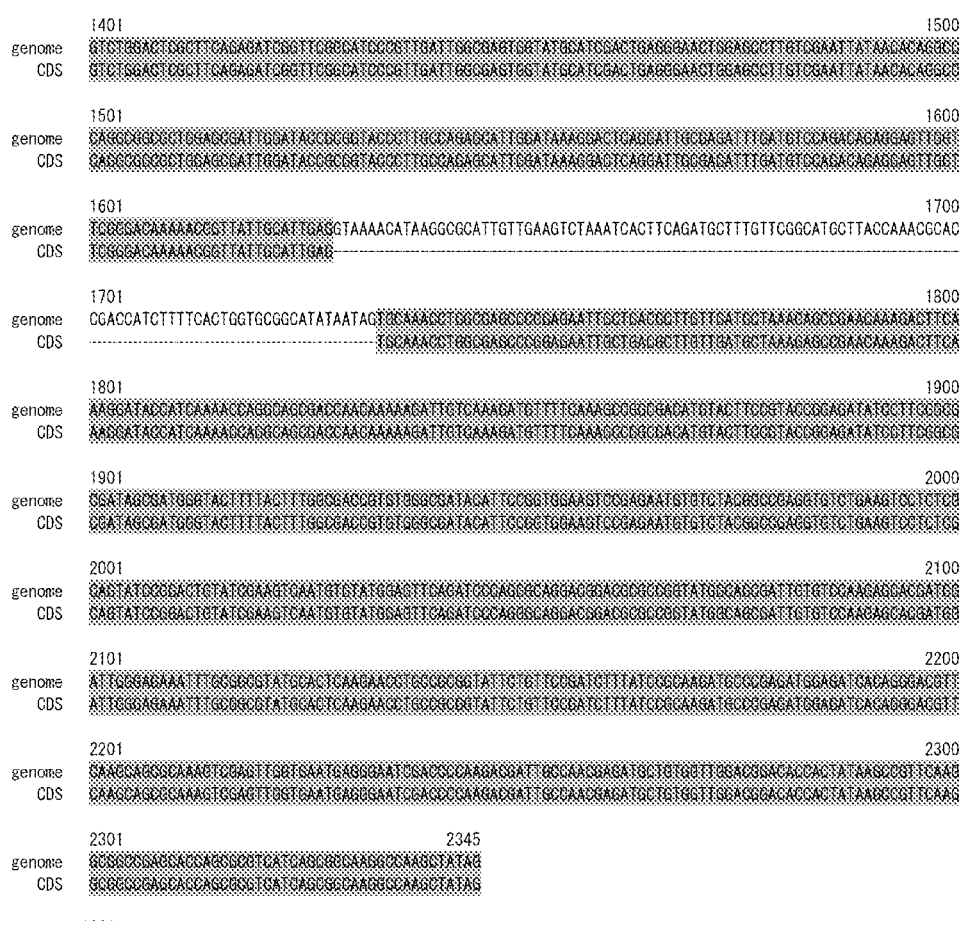

(SEQ ID NO: 78)
Primer ACS-9-2R: 5'-GTTGCGTTGTTCACGCGGCAATCC-3' cDNA (SEQ ID NO: 44)
CDS (SEQ ID NO: 43): 1851 bp
ORF (SEQ ID NO: 41): 1848 bp
Amino acid sequence (SEQ ID NO: 42): 616 amino acids (see FIG. 17)
Number of exons: 5, number of introns: 4 (see FIG. 18)

(10) MaACS-10
(SEQ ID NO: 79)
Primer ACS-10-1F: 5'-ATGGAAACCTTGGTTAACGGAAAG-3'

Figure 20B:
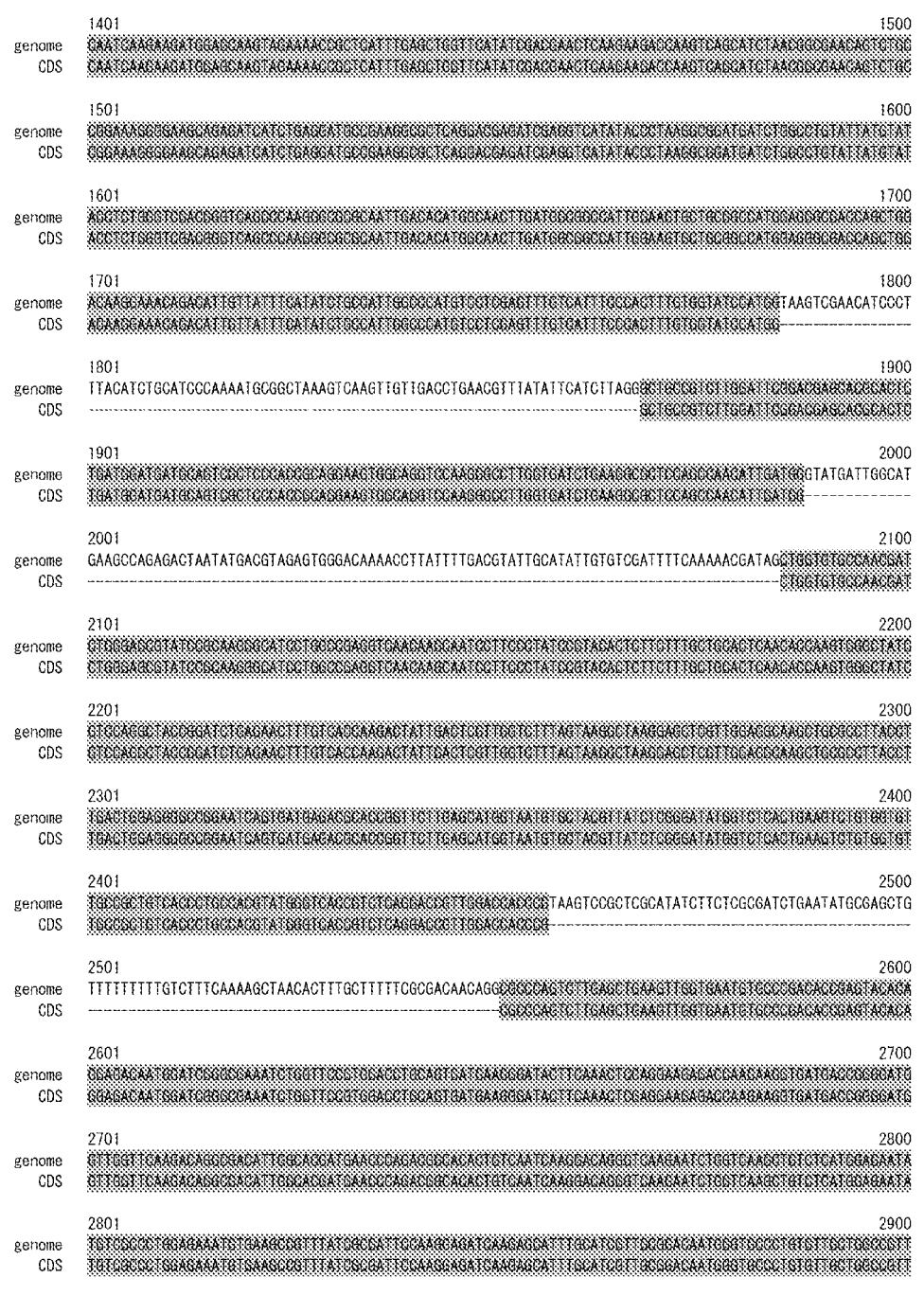

(SEQ ID NO: 80)
Primer ACS-10-2R: 5'-TCAGCAAAGATGGCCTTGGGCTGG-3' cDNA (SEQ ID NO: 49)
CDS (SEQ ID NO: 48): 2076 bp
ORF (SEQ ID NO: 46): 2073 bp
Amino acid sequence (SEQ ID NO: 47): 691 amino acids (see FIG. 19)
Number of exons: 8, number of introns: 7 (see FIG. 20)

(11) MaACS-11
(SEQ ID NO: 81)
Primer ACS-11-1F: 5'-GTCAAGGGCGAGACTCGCATCC-3'

Figure 22A:
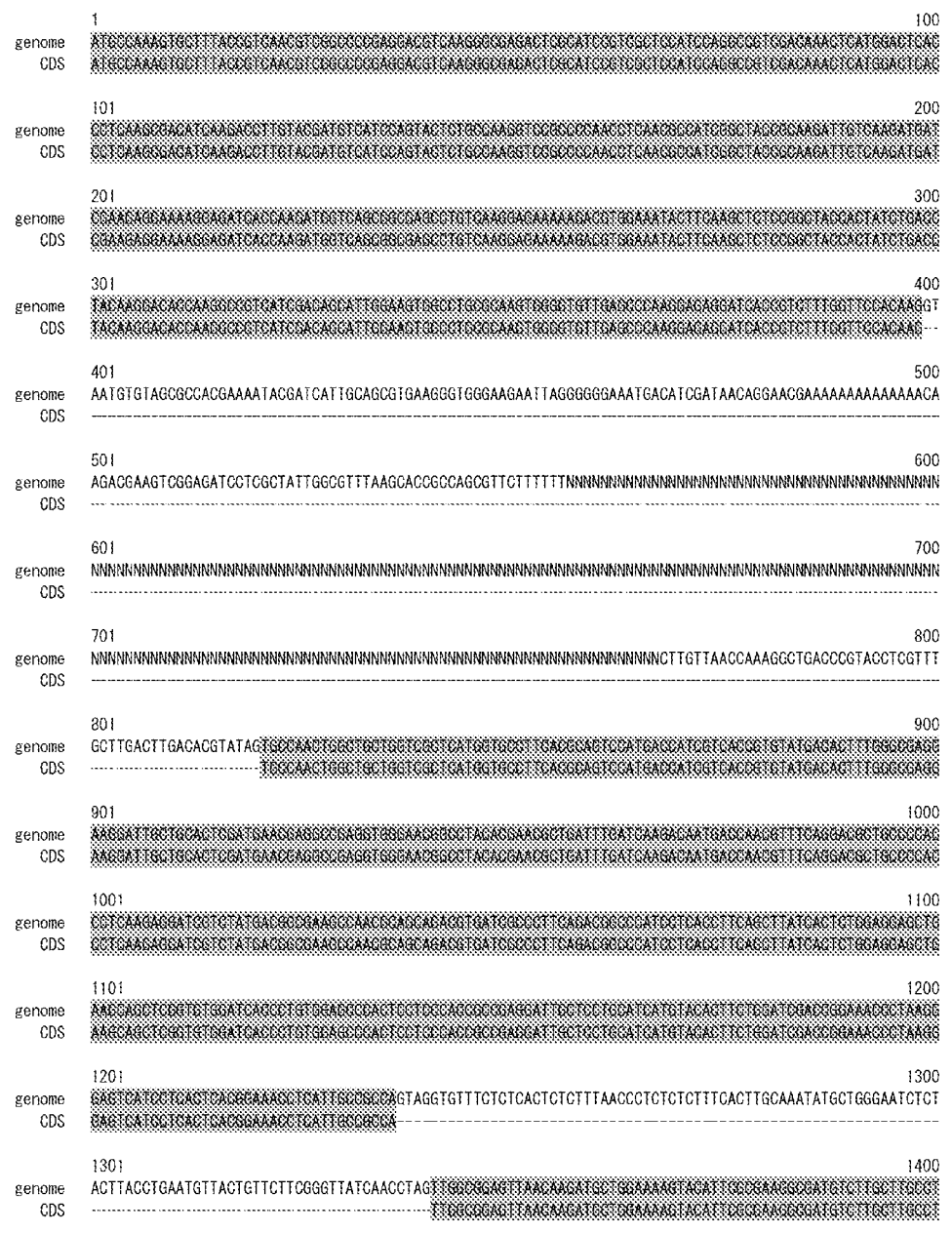
Figure 22B:
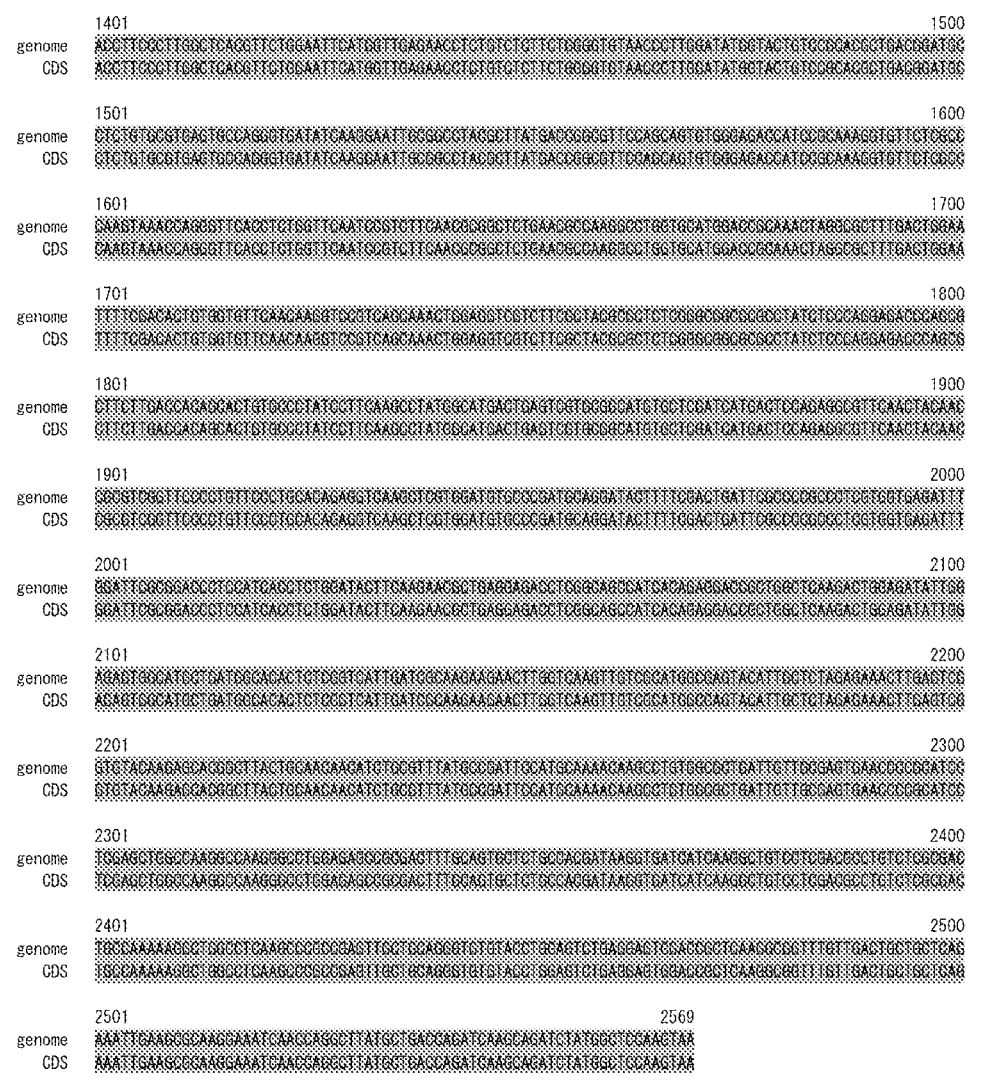

(SEQ ID NO: 82)
Primer ACS-11-2R: 5'-CGGTGACGATGGTCATGGACTGC-3' cDNA (SEQ ID NO: 54)
CDS (SEQ ID NO: 53): 2043 bp
ORF (SEQ ID NO: 51): 2040 bp
Amino acid sequence (SEQ ID NO: 52): 680 amino acids (see FIG. 21)
Number of exons: 3, number of introns: 2 (see FIG. 22)

(12) MaACS-12
(SEQ ID NO: 83)
Primer ACS-12-1F: 5'-GCGAGACCCGCATCCGCCGCTCC-3'

Figure 24B:
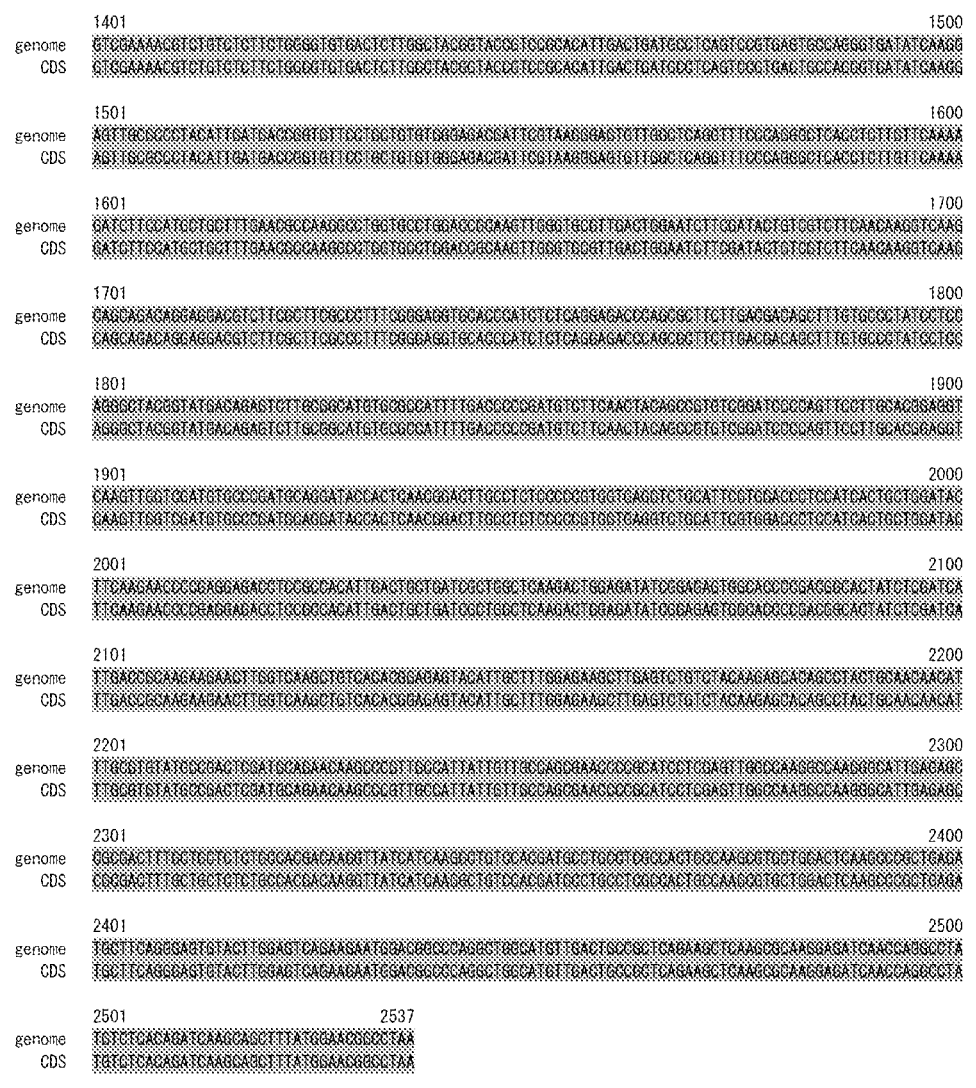

(SEQ ID NO: 84)
Primer ACS-12-2R: 5'-GACCGTCCTCGCCCAGGGTGTCG-3' cDNA (SEQ ID NO: 59)
CDS (SEQ ID NO: 58): 2043 bp
ORF (SEQ ID NO: 56): 2040 bp
Amino acid sequence (SEQ ID NO: 57): 680 amino acids (see FIG. 23)
Number of exons: 3, number of introns: 2 (see FIG. 24)

Sequencing Analysis

The identity between the CDS nucleotide sequences of 12 ACS homologs from *M. alpina* is shown in TABLE 1 and the identity between the amino acid sequences is shown in TABLE 2. MaACS-11 and MaACS-12 showed high identity of 80.2% in the nucleotide sequence and 84.3% in the amino acid sequence.

TABLE 1

Sequence identity among CDS nucleotide sequences of ACS homologs from *M. alpina*

| | MaACS-1 | MaACS-2 | MaACS-3 | MaACS-4 | MaACS-5 | MaACS-6 |
|---|---|---|---|---|---|---|
| MaACS-1 | — | 51.3 | 42.9 | 45.4 | 44.7 | 46.6 |
| MaACS-2 | | — | 43.4 | 46.8 | 46.9 | 45.7 |
| MaACS-3 | | | — | 38.0 | 38.2 | 38.9 |
| MaACS-4 | | | | — | 50.4 | 51.6 |
| MaACS-5 | | | | | — | 70.8 |
| MaACS-6 | | | | | | — |
| MaACS-7 | | | | | | |
| MaACS-8 | | | | | | |
| MaACS-9 | | | | | | |
| MaACS-10 | | | | | | |
| MaACS-11 | | | | | | |
| MaACS-12 | | | | | | |

TABLE 1-continued

Sequence identity among CDS nucleotide sequences of ACS homologs from *M. alpina*

|         | MaACS-7 | MaACS-8 | MaACS-9 | MaACS-10 | MaACS-11 | MaACS-12 |
|---------|---------|---------|---------|----------|----------|----------|
| MaACS-1 | 46.0 | 45.6 | 69.5 | 44.7 | 46.2 | 45.8 |
| MaACS-2 | 46.5 | 44.6 | 52.5 | 44.9 | 44.9 | 44.0 |
| MaACS-3 | 43.7 | 37.5 | 42.8 | 41.5 | 39.0 | 39.1 |
| MaACS-4 | 43.8 | 57.7 | 44.2 | 47.0 | 49.7 | 49.3 |
| MaACS-5 | 44.7 | 53.0 | 44.9 | 46.6 | 48.9 | 47.2 |
| MaACS-6 | 46.2 | 53.0 | 45.2 | 47.9 | 49.2 | 49.4 |
| MaACS-7 | — | 44.2 | 45.9 | 42.3 | 45.0 | 44.6 |
| MaACS-8 |  | — | 44.3 | 48.1 | 50.7 | 50.8 |
| MaACS-9 |  |  | — | 42.7 | 46.2 | 47.8 |
| MaACS-10 |  |  |  | — | 51.8 | 52.1 |
| MaACS-11 |  |  |  |  | — | 80.2 |
| MaACS-12 |  |  |  |  |  | — |

TABLE 2

Sequence identity among amino acid sequences of ACS homologs from *M. alpina*

|         | MaACS-1 | MaAGS-2 | MaACS-3 | MaACS-4 | MaACS-5 | MaACS-6 |
|---------|---------|---------|---------|---------|---------|---------|
| MaACS-1 | — | 36.6 | 11.8 | 13.9 | 15.1 | 15.8 |
| MaACS-2 |  | — | 11.0 | 14.0 | 15.4 | 15.0 |
| MaACS-3 |  |  | — | 21.7 | 21.5 | 20.8 |
| MaACS-4 |  |  |  | — | 37.5 | 37.5 |
| MaACS-5 |  |  |  |  | — | 77.9 |
| MaACS-6 |  |  |  |  |  | — |
| MaACS-7 |  |  |  |  |  |  |
| MaACS-8 |  |  |  |  |  |  |
| MaACS-9 |  |  |  |  |  |  |
| MaACS-10 |  |  |  |  |  |  |
| MaACS-11 |  |  |  |  |  |  |
| MaACS-12 |  |  |  |  |  |  |

|         | MaACS-7 | MaACS-8 | MaACS-9 | MaACS-10 | MaACS-11 | MaACS-12 |
|---------|---------|---------|---------|----------|----------|----------|
| MaACS-1 | 18.0 | 14.8 | 71.9 | 13.5 | 14.6 | 15.0 |
| MaACS-2 | 17.2 | 13.2 | 37.0 | 12.3 | 12.7 | 13.8 |
| MaACS-3 | 13.1 | 21.1 | 10.5 | 17.7 | 18.5 | 17.9 |
| MaACS-4 | 17.0 | 50.9 | 15.4 | 22.8 | 29.8 | 29.5 |
| MaACS-5 | 17.0 | 41.2 | 16.4 | 25.2 | 29.1 | 29.8 |
| MaACS-6 | 16.6 | 39.8 | 16.6 | 25.3 | 29.9 | 29.4 |
| MaACS-7 | — | 15.5 | 17.0 | 15.3 | 16.2 | 16.7 |
| MaACS-8 |  | — | 15.2 | 24.9 | 27.8 | 28.6 |
| MaACS-9 |  |  | — | 14.1 | 14.5 | 14.7 |
| MaACS-10 |  |  |  | — | 32.8 | 32.6 |
| MaACS-11 |  |  |  |  | — | 84.3 |
| MaACS-12 |  |  |  |  |  | — |

Using as query sequences the putative amino acid sequences for the CDS sequences of MaACS-1~12, BLASTp search was performed against the amino acid sequences registered in GenBank. The proteins having the amino acid sequence which matched the putative amino acid sequences of MaACS-1~12 with highest score and the identity between these proteins and the putative amino acid sequences of MaACS-1~12 are shown in TABLE 3. The identity of the putative amino acid sequences of MaACS-1~12 with the amino acid sequences of *S. cerevisiae*-derived acyl-CoA synthetases are also shown in TABLE 4.

TABLE 3

Sequence identity between the amino acid sequences of *M. alpina*-derived ACS homologs and known amino acid sequences

|         | identity(%) | gi |  |
|---------|-------------|----|--|
| MaACS-1 | 41.8 | 71014575 | Putative protein from *Ustilago maydis* |
| MaACS-2 | 35.4 | 71014575 | Putative protein from *Ustilago maydis* |
| MaACS-3 | 23.5 | 71895089 | Chick ACS long-chain family member 5 |
| MaACS-4 | 36.9 | 115487304 | Putative protein from *Oryza sativa* |
| MaACS-5 | 42.5 | 168065128 | Putative protein from *Physcomitrella patens* |
| MaACS-6 | 40.9 | 13516481 | Long-chain acyl-CoA synthetase from *Arabidopsis thaliana* |
| MaACS-7 | 45.7 | 120612991 | Putative protein from *Acidovorax avenae* subsp. *citrulli* |

TABLE 3-continued

Sequence identity between the amino acid sequences of M. alpina-derived ACS homologs and known amino acid sequences

|  | identity(%) | gi | |
|---|---|---|---|
| MaACS-8 | 40.0 | 13516481 | Long-chain acyl-CoA synthetase from *Arabidopsis thaliana* |
| MaACS-9 | 37.8 | 67538044 | Putative protein from *Aspergillus nidulans* |
| MaACS-10 | 33.2 | 171682488 | Putative protein from *Podospora Anserina* |
| MaACS-11 | 48.8 | 169854433 | Putative protein from *Coprinopsis atramentarius* |
| MaACS-12 | 45.1 | 156045509 | Putative protein from *Sclerotinia sclerotiorum* |

TABLE 4

Comparison of amino acid sequences of M. alpina-derived ACS homologs and amino acid sequences of S. cerevisiae-derived ACS

|  | ScFAA1 | ScFAA2 | ScFAA3 | ScFAA4 | ScFAT1 | ScFAT2 |
|---|---|---|---|---|---|---|
| MaACS-1 | 13.8 | 15.3 | 13.6 | 13.5 | 29.8 | 18.1 |
| MaACS-2 | 12.5 | 13.6 | 13.4 | 13.5 | 26.3 | 17.5 |
| MaACS-3 | 15.8 | 14.0 | 15.0 | 14.8 | 13.6 | 12.9 |
| MaACS-4 | 26.3 | 28.3 | 23.9 | 24.2 | 14.0 | 16.0 |
| MaACS-5 | 25.6 | 28.2 | 25.5 | 25.8 | 13.2 | 18.6 |
| MaACS-6 | 25.3 | 28.4 | 25.8 | 25.5 | 13.0 | 18.1 |
| MaACS-7 | 16.5 | 17.5 | 16.0 | 16.9 | 16.6 | 20.6 |
| MaACS-8 | 23.0 | 28.0 | 21.3 | 22.8 | 12.2 | 14.8 |
| MaACS-9 | 15.6 | 15.5 | 14.3 | 14.7 | 30.1 | 18.3 |
| MaACS-10 | 30.8 | 20.6 | 30.6 | 30.6 | 14.0 | 14.2 |
| MaACS-11 | 39.6 | 22.6 | 37.3 | 38.7 | 12.9 | 15.8 |
| MaACS-12 | 41.3 | 22.3 | 39.8 | 39.0 | 14.4 | 16.2 |

FIG. 25 shows the alignment between MaACS from MaACS-1~12, which have relatively high amino acid sequence homology to the *S. cerevisiae*-derived FAA proteins, and the FAA proteins. FIG. 26 shows the alignment of the ACS homologs having relatively high amino acid sequence homology to *S. cerevisiae*-derived FAT proteins. The regions of the ATP-AMP motif and FACS/VLACS-FATP motif, which are important motifs for the ACS activity, are highly conserved in both groups shown in FIGS. 25 and 26.

Construction of Expression Vector

Vectors for expressing MaACS-1, MaACS-10, MaACS-11, MaACS-6, MaACS-8 and MaACS-9, respectively, in yeast were constructed as follows, using the expression vector pYE22m (Biosci. Biotech. Biochem., 59, 1221-1228, 1995).

The plasmid containing SEQ ID NO: 29, which was obtained by screening MaACS-6, was digested with restriction enzymes BamHI and XhoI. The resulting DNA fragment of approximately 2.1 kbp was ligated to the DNA fragment obtained by digestion of vector pYE22m with restriction enzymes BamHI and SalI using a Ligation High (TOYOBO) to give plasmid pYE-ACS-6.

Using the plasmid containing cDNA of MaACS-8 as a template, PCR was performed with the primers below using ExTaq (Takara Bio Inc.). The thus amplified DNA fragment was cloned by a TOPO-TA Cloning Kit (Invitrogen).

Primer EcoRI-ACS-8-F:
(SEQ ID NO: 85)
5'-GGATCCATGCCTTCCTTCAAAAAGTACAACC-3'

Primer SmaI-ACS-8-R:
(SEQ ID NO: 86)
5'-CCCGGGCAAAGAGTTTTCTATCTACAGCTT-3'

The nucleotide sequence of the insert was verified and the plasmid containing the correct nucleotide sequence was digested with restriction enzymes EcoRI and SmaI. Using a Ligation High (TOYOBO), the resulting DNA fragment of approximately 2.1 kbp was ligated to the DNA fragment obtained by digesting vector pYE22m with restriction enzymes EcoRII and SmaI to give plasmid pYE-ACS-8.

Using the plasmid containing cDNA of MaACS-9 as a template, PCR was performed with the primers below using ExTaq (Takara Bio Inc.). The thus amplified DNA fragment was cloned by a TOPO-TA Cloning Kit (Invitrogen).

Primer EcoRI-ACS-9-F:
(SEQ ID NO: 87)
5'-GAATTCATGGTTGCTCTCCCACTCG-3'

Primer BamHI-ACS-9-R:
(SEQ ID NO: 88)
5'-GGATCCCTACTATAGCTTGGCCTTGCC-3'

The nucleotide sequence of the insert was verified and the plasmid containing the correct nucleotide sequence was digested with restriction enzymes EcoRI and BamHI. Using a Ligation High (TOYOBO), the resulting DNA fragment of approximately 2.0 kbp was ligated to the DNA fragment obtained by digesting vector pYE22m with restriction enzymes EcoRII and BamHI to give plasmid pYE-ACS-9.

Using the plasmid containing cDNA of MaACS-1 as a template, PCR was performed with the primers below using ExTaq (Takara Bio Inc.). The thus amplified DNA fragment was cloned by a TOPO-TA Cloning Kit (Invitrogen).

Primer EcoRI-ACS-1-F:
(SEQ ID NO: 89)
5'-GGATCCATGTATGTCGGCTCCAAGCTTGC-3'

Primer SalI-ACS-1-R:
(SEQ ID NO: 90)
5'-GTCGACTCAAAGCCTGGCTTTGCCGCTGACG-3'

The nucleotide sequence of the insert was verified and the plasmid containing the correct nucleotide sequence was digested with restriction enzymes EcoRI and SalI. Using a Ligation High (TOYOBO), the resulting DNA fragment of approximately 1.9 kbp was ligated to the DNA fragment obtained by digesting vector pYE22m with restriction enzymes EcoRI and SalI to give plasmid pYE-ACS-1.

Using the plasmid containing cDNA of MaACS-10 as a template, PCR was performed with the primers below using ExTaq (Takara Bio Inc.). The thus amplified DNA fragment was cloned by a TOPO-TA Cloning Kit (Invitrogen).

Primer ACS-10-1F:
(SEQ ID NO: 91)
5'-GGATCCATGGAAACCTTGGTTAACGGAAAG-3'

Primer KpnI-ACS-10-R:
(SEQ ID NO: 92)
5'-GGTACCTAGAACTTCTTCCACATCTCCTC-3'

The nucleotide sequence of the insert was verified and the plasmid containing the correct nucleotide sequence was digested with restriction enzymes EcoRI and KpnI. Using a Ligation High (TOYOBO), the resulting DNA fragment of approximately 2.1 kbp was ligated to the DNA fragment obtained by digesting vector pYE22m with restriction enzymes EcoRI and KpnI. Plasmid pYE-ACS-10 was obtained by screening for the orientation that the GAPDH promoter of vector pYE22m was located at its 5' end of CDS of MaACS-10.

Using the plasmid containing cDNA of MaACS-11 as a template, PCR was performed with the primers below using ExTaq (Takara Bio Inc.). The thus amplified DNA fragment was cloned by a TOPO-TA Cloning Kit (Invitrogen).

```
Primer SacI-ACS-11-F:
                                    (SEQ ID NO: 93)
5'-GAGCTCATGCCAAAGTGCTTTACCGTCAACG-3'

Primer BamHI-ACS-11-R:
                                    (SEQ ID NO: 94)
5'-GGATCCTTACTTGGAGCCATAGATCTGCTTG-3'
```

The nucleotide sequence of the insert was verified and the plasmid containing the correct nucleotide sequence was digested with restriction enzymes SacI and BamHI. Using a Ligation High (TOYOBO), the resulting DNA fragment of approximately 2.0 kbp was ligated to the DNA fragment obtained by digesting vector pYE22m with restriction enzymes SacI and BamHI to give plasmid pYE-ACS-11.

Expression in Yeast

Acquisition of Transformants

The yeast *S. cerevisiae* EH13-15 strain (trp1, MATα) (Appl. Microbiol. Biotechnol., 30, 515-520, 1989) was transformed with plasmids pYE22m, pYE-MaACS-6, pYE-MaACS-8 and pYE-MaACS-9, respectively, by the lithium acetate method. The transformants were screened for the ability to grow on SC-Trp agar medium (2% agar) (per liter, 6.7 g Yeast Nitrogen Base w/o Amino Acids (DIFCO), 20 g glucose, 1.3 g amino acid powders (a mixture of 1.25 g adenine sulfate, 0.6 g arginine, 3 g aspartic acid, 3 g glutamic acid, 0.6 g histidine, 1.8 g leucine, 0.9 g lysine, 0.6 g methionine, 1.5 g phenylalanine, 11.25 g serine, 0.9 g tyrosine, 4.5 g valine, 6 g threonine and 0.6 g uracil).

Cultivation of Yeast

One each from the transformants obtained using the respective plasmids was provided for the following cultivation experiment.

One platinum loop of the yeast was plated on 10 ml of SC-Trp and cultured with shaking for preincubation at 30° C. for a day. After 1 ml of the preincubation was added to the SC-Trp medium, main cultivation was performed by shake culturing at 30° C. for a day.

Analysis of Fatty Acids in Mycelia

The yeast culture broth was centrifuged to recover the mycelial cells. After washing with 10 ml of sterile water, the mycelial cells were again centrifuged, recovered and lyophilized The fatty acids in the mycelial cells were converted into the methyl esters by the hydrochloric acid-methanol method followed by extraction with hexane. After hexane was removed by distillation, the fatty acids were analyzed by gas chromatography.

The fatty acid production per medium is shown in TABLE 5. In the strains transformed by ppYE-MaACS-6, pYE-MaACS-8 or pYE-MaACS-9, the fatty acid production per medium was increased as compared to the control which was transformed by pYE22m.

TABLE 5

| Fatty Acid Production by Transformant per Medium | | | | |
|---|---|---|---|---|
|  | Control | MaACS-6 | MaACS-8 | MaACS-9 |
| Fatty acid production (mg/L) | 135 | 159 | 196 | 187 |

Expression in Arachidonic Acid-Producing Yeast (1) Breeding of Arachidonic Acid-Producing Yeast Strains To breed arachidonic acid-producing yeast strain (*S. cerevisiae*), the following plasmids were constructed.

First, using the cDNA prepared from *M. alpina* strain 1S-4 as a template, PCR was performed with ExTaq using the primer pair of Δ12-f and Δ12-r, Δ6-f and Δ6-r, GLELO-f and GLELO-r, or Δ5-f and Δ5-r to amplify the Δ12 fatty acid desaturase gene (GenBank Accession No. AB020033) (hereinafter "Δ12 gene"), the Δ6 fatty acid desaturase gene (GenBank Accession No. AB020032) (hereinafter "Δ6 gene"), the GLELO fatty acid elongase gene (GenBank Accession No. AB193123) (hereinafter "GLELO gene") and the Δ5 fatty acid desaturase gene (GenBank Accession No. AB188307) (hereinafter "Δ5 gene") in the *M. alpina* strain 1S-4.

```
Δ12-f:
                                    (SEQ ID NO: 95)
5'-TCTAGAATGGCACCTCCCAACACTATTG-3'

Δ12-r:
                                    (SEQ ID NO: 96)
5'-AAGCTTTTACTTCTTGAAAAAGACCACGTC-3'

Δ6-f:
                                    (SEQ ID NO: 97)
5'-TCTAGAATGGCTGCTGCTCCCAGTGTGAG-3'

Δ6-r:
                                    (SEQ ID NO: 98)
5'-AAGCTTTTACTGTGCCTTGCCCATCTTGG-3'

GLELO-f:
                                    (SEQ ID NO: 99)
5'-TCTAGAATGGAGTCGATTGCGCAATTCC-3'

GLELO-r:
                                    (SEQ ID NO: 100)
5'-GAGCTCTTACTGCAACTTCCTTGCCTTCTC-3'

Δ5-f:
                                    (SEQ ID NO: 101)
5'-TCTAGAATGGGTGCGGACACAGGAAAAACC-3'

Δ5-r:
                                    (SEQ ID NO: 102)
5'-AAGCTTTTACTCTTCCTTGGGACGAAGACC-3'
```

These genes were cloned with the TOPO-TA-Cloning Kit. The clones were confirmed by their nucleotide sequences. The clones containing the nucleotide sequences of the Δ12 gene, Δ6 gene, GLELO gene and Δ5 gene were designated as plasmids pCR-MAΔ12DS (containing the nucleotide sequence of the Δ12 gene), pCR-MAΔ6DS (containing the nucleotide sequence of the Δ6 gene), pCR-MAGLELO (containing the nucleotide sequence of the GLELO gene) and pCR-MAΔ5DS (containing the nucleotide sequence of the Δ5 gene), respectively.

On the other hand, the plasmid pURA34 (JPA 2001-120276) was digested with restriction enzyme HindIII. The resulting DNA fragment of approximately 1.2 kb was inserted into the HindIII site of the vector, which was obtained by digesting pUC18 vector (Takara Bio Inc.) with restriction enzymes EcoRI and SphI, then blunt ending and self ligating said vector. The clone in which the EcoRI site of the vector was located at its 5' end of URA3 was designated as pUC-URA3. Also, the DNA fragment of approximately 2.2 kb, which was obtained by digesting YEp 13 with restriction enzymes SalI and XhoI, was inserted into the SalI site of vector pUC18. The clone in which the EcoRI site of the vector was located at its 5' end of LUE2 was designated as pUC-LEU2.

Next, the plasmid pCR-MAΔ12DS was digested with restriction enzyme HindIII, followed by blunt ending and further digestion with restriction enzyme XbaI. The resulting DNA fragment of approximately 1.2 kbp was ligated to the DNA fragment of approximately 6.6 kbp, which was obtained by digesting vector pESC-URA (STRATAGENE) with restriction enzyme SacI, blunt ending and further digesting with restriction enzyme SpeI. Thus, the plasmid pESC-U-Δ12 was obtained. The plasmid pCR-MAΔ6DS was digested with restriction enzyme XbaI, followed by blunt ending and further digestion with restriction enzyme HindIII. The resulting DNA fragment of approximately 1.6 kbp was ligated to the DNA fragment of approximately 8 kbp, which was obtained by digesting the plasmid pESC-U-Δ12 with restriction enzyme SalI, blunt ending and further digesting with restriction enzyme HindIII, thereby to give the plasmid pESC-U-Δ12:Δ6. This plasmid was partially digested with restriction enzyme PvuII. The resulting fragment of approximately 4.2 kb was inserted into the SmaI site of pUC-URA3 to give the plasmid pUC-URA-Δ12:Δ6.

Also, the plasmid pCR-MAGLELO was digested with restriction enzymes XbaI and SacI. The resulting DNA fragment of approximately 0.95 kbp was ligated to the DNA fragment of approximately 7.7 kbp, which was obtained by digesting vector pESC-LEU (STRATAGENE) with restriction enzymes XbaI and SacI. Thus, the plasmid pESC-L-GLELO was obtained. The plasmid pCR-MAΔ5DS was digested with restriction enzyme XbaI, followed by blunt ending and further digestion with restriction enzyme HindIII. The resulting DNA fragment of approximately 1.3 kbp was ligated to the DNA fragment of approximately 8.7 kbp, which was obtained by digesting the plasmid pESC-L-GLELO with restriction enzyme ApaI, blunt ending and further digesting with restriction enzyme HindIII, thereby to give the plasmid pESC-L-GLELO:Δ5. This plasmid was digested with restriction enzyme PvuII and the resulting fragment of approximately 3.2 kbp was inserted into the SmaI site of pUC-LEU2 to give plasmid pUC-LEU-GLELO:Δ5. The *Saccharomyces cerevisiae* strain YPH499 (STRATAGENE) was co-transformed by the plasmid pUC-URA-Δ12:Δ6 and plasmid pUC-LEU-GLELO:Δ5. The transformants were screened for the ability to grow on SC-Leu,Ura agar medium. Among the transformants thus obtained, random one strain was designated as the strain ARA3-1. By cultivating the strain in a galactose-supplemented medium, the strain became capable of expressing from the GAL1/10 promoter the Δ12 fatty acid desaturase gene, the Δ6 fatty acid desaturase gene, the GLELO gene and the Δ5 fatty acid desaturase gene.

(2) Transformation into Arachidonic Acid-Producing Yeast and Analysis

The ARA3-1 strain was transformed by plasmids pYE22m, pYE-ACS-1, pYE-ACS-10 and pYE-ACS-11, respectively. Transformants were screened for the ability to grow on SC-Trp,Leu,Ura agar medium (2% agar) (per liter, 6.7 g Yeast Nitrogen Base w/o Amino Acids (DIFCO), 20 g glucose and 1.3 g amino acid powders (a mixture of 1.25 g adenine sulfate, 0.6 g arginine, 3 g aspartic acid, 3 g glutamic acid, 0.6 g histidine, 0.9 g lysine, 0.6 g methionine, 1.5 g phenylalanine, 11.25 g serine, 0.9 g tyrosine, 4.5 g valine and 6 g of threonine). Random four strains from the respective plasmid-transfected strains were used for the subsequent cultivation.

These strains were cultivated at 30° C. for a day in 10 ml of the SC-Trp,Leu,Ura liquid medium described above. One milliliter of the culture was plated on 10 ml of SG-Trp,Leu, Ura liquid medium (per liter, 6.7 g Yeast Nitrogen Base w/o Amino Acids (DIFCO), 20 g galactose and 1.3 g amino acid powders (a mixture of 1.25 g adenine sulfate, 0.6 g arginine, 3 g aspartic acid, 3 g glutamic acid, 0.6 g histidine, 0.9 g lysine, 0.6 g methionine, 1.5 g phenylalanine, 11.25 g serine, 0.9 g tyrosine, 4.5 g valine and 6 g threonine) and then cultivated at 15° C. for 6 days. The mycelial cells were collected, washed with water and then lyophilized After the fatty acids in the dried mycelial cells were converted to the methyl esters by the hydrochloric acid-methanol method, the analysis of fatty acids was performed by gas chromatography. The ratio of each PUFA to the total fatty acids in the control strain transformed by plasmid pYE22m, and in the strains transformed by each ACS homolog from *Mortierella* is shown in TABLE 6.

TABLE 6

% Ratio of PUFA in ACS homolog expression strains from *Mortierella*

| | control | MaACS-1 | MaACS-10 | MaACS-11 |
|---|---|---|---|---|
| 18:2 | 7.23 ± 0.11 | 8.15 ± 0.29 | 14.87 ± 0.28 | 10.57 ± 0.30 |
| 18:3 (n − 6) | 0.38 ± 0.01 | 0.44 ± 0.04 | 1.67 ± 0.10 | 0.92 ± 0.07 |
| DGLA | 0.41 ± 0.01 | 0.42 ± 0.02 | 0.30 ± 0.17 | 0.33 ± 0.03 |
| ARA | 0.42 ± 0.01 | 0.63 ± 0.04 | 0.47 ± 0.10 | 0.75 ± 0.10 |

Average ± Standard Deviation

As shown in TABLE 6, the ratio of fatty acids could be modified by expressing the ACS homolog from *Mortierella*. Particularly in the MaACS-11 expression strain, the ratios of arachidonic acid, linoleic acid and γ-linolenic acid were increased by about 1.8 times, about 1.5 times and about 2.4 times, respectively, as compared to the control strain. In the MaACS-1 expression strain, the ratio of arachidonic acid was increased by about 1.5 times, as compared to the control strain. Further in the MaACS-10 expression strain, the ratios of linoleic acid and γ-linolenic acid were increased by about 2 times and about 4 times, respectively, as compared to the control strain.

Example 2

Construction of Expression Vector
Expression Vector for Yeast

The vector pYE-ACS-12 for expressing MaACS-12 in yeast was constructed as follows. Using a plasmid containing the cDNA of MaACS-12 as a template, PCR was performed with the following primers using KOD-Plus- (TOYOBO).

```
Primer Eco-ACS-G-F:
                                      (SEQ ID NO: 103)
5'-GAATTCATGACAAAGTGCCTCACCGTCG-3'

Primer Sma-ACS-G-R:
                                      (SEQ ID NO: 104)
5'-CCCGGGACTTAGGCCGTTCCATAAAGCTG-3'
```

The amplified DNA fragment was cloned using a Zero Blunt TOPO PCR Cloning Kit (Invitrogen). The nucleotide sequence of the insert was verified and the plasmid containing the correct nucleotide sequence was digested with restriction enzymes EcoRI and SmaI. Using a Ligation High (TOYOBO), the resulting DNA fragment of approximately 2 kbp was ligated to the DNA fragment obtained by digesting vector pYE22m with restriction enzyme BamHI and then blunt ending with a Blunting Kit (TAKARA Bio) and further digesting with EcoRI, to give plasmid pYE-ACS-12.

Expression Vector for *M. alpina*

The vector for expressing MaACS-10 and MaACS-11 in *M. alpina* was constructed as follows.

First, pUC18 was digested with restriction enzymes EcoRI and HindIII and an adapter obtained by annealing oligo DNA MCS-for-pUC18-F2 with MCS-for-pUC18-R2 was inserted therein to construct plasmid pUC18-RF2.

```
MCS-for-pUC18-F2:
                                        (SEQ ID NO: 105)
5'-AATTCATAAGAATGCGGCCGCTAAACTATTCTAGACTAGGTCGA
CGGCGCGCCA-3'

MCS-for-pUC18-R2:
                                        (SEQ ID NO: 106)
5'-AGCTTGGCGCGCCGTCGACCTAGTCTAGAATAGTTTAGCGGCCG
CATTCTTATG-3'
```

Using the genome DNA of *M. alpina* as a template, PCR was performed with the primers Not1-GAPDHt-F and EcoR1-Asc1-GAPDHt-R using KOD-Plus-(Toyobo). The amplified DNA fragment of about 0.5 kbp was cloned using a Zero Blunt TOPO PCR Cloning Kit (Invitrogen). After the nucleotide sequence of the insert was verified, the DNA fragment of about 0.9 kbp obtained by digesting with restriction enzymes NotI and EcoRI was inserted into the NotI and EcoRI site of plasmid pUC18-RF2 to construct plasmid pDG-1.

```
Not1-GAPDHt-F:
                                        (SEQ ID NO: 107)
5'-AGCGGCCGCATAGGGGAGATCGAACC-3'

EcoR1-Asc1-GAPDHt-R:
                                        (SEQ ID NO: 108)
5'-AGAATTCGGCGCGCCATGCACGGGTCCTTCTCA-3'
```

Using the genome of *M. alpina* as a template, PCR was performed with the primers URASg-F1 and URASg-R1 using KOD-Plus-(Toyobo). The amplified DNA fragment was cloned using a Zero Blunt TOPO PCR Cloning Kit (Invitrogen). After the nucleotide sequence of the insert was verified, the DNA fragment of about 2 kbp obtained by digestion with SalI was inserted into the SalI site of plasmid pDG-1. The plasmid that the 5' end of URAS gene inserted was oriented toward the EcoRI side of the vector was designated as the plasmid pDuraG.

```
URA5g-F1:
                                        (SEQ ID NO: 109)
5'-GTCGACCATGACAAGTTTGC-3'

URA5g-R1:
                                        (SEQ ID NO: 110)
5'-GTCGACTGGAAGACGAGCACG-3'
```

Subsequently, PCR was performed with KOD-Plus-(TOYOBO) using the genome of *M. alpina* as a template and the primers hisHp+URAS-F and hisHp+MGt-E Using an In-Fusion (registered trade name) Advantage PCR Cloning Kit (TAKARA Bio), the amplified DNA fragment of about 1.0 kbp was ligated to the DNA fragment of about 5.3 kbp amplified by PCR with KOD-Plus-(TOYOBO) using pDuraG as a template and the primers pDuraSC-GAPt-F and URASgDNA-F, to give plasmid pDUra-RhG.

```
hisHp + URA5-F:
                                        (SEQ ID NO: 111)
5'-GGCAAACTTGTCATGAAGCGAAAGAGAGATTATGAAAACAAGC-3' hisHp + MGt-F:
                                        (SEQ ID NO: 112)
5'-CACTCCCTTTTCTTAATTGTTGAGAGAGTGTTGGGTGAGAGT-3' pDuraSC-GAPt-F:
                                        (SEQ ID NO: 113)
5'-TAAGAAAAGGGAGTGAATCGCATAGGG-3'

URA5gDNA-F:
                                        (SEQ ID NO: 114)
5'-CATGACAAGTTTGCCAAGATGCG-3'
```

Using the plasmid pDUra-RhG as a template, the DNA fragment of about 6.3 kbp was amplified by PCR with KOD-Plus-(TOYOBO) using the primers pDuraSC-GAPt-F and pDurahG-hisp-R.

```
pDurahG-hisp-R:
                                        (SEQ ID NO: 115)
5'-ATTGTTGAGAGAGTGTTGGGTGAGAGTG-3'
```

Using the plasmid containing cDNA of MaACS-10, the DNA fragment of about 2.1 kbp was amplified by PCR with KOD-Plus-(TOYOBO), using the primers below.

```
Primer ACS-10 + hisp-F:
                                        (SEQ ID NO: 116)
5'-CACTCTCTCAACAATATGGAAACCTTGGTTAACGGAAAGT-3'

Primer ACS-10 + MGt-R:
                                        (SEQ ID NO: 117)
5'-CACTCCCTTTTCTTACTAGAACTTCTTCCACATCTCCTCAATA
TC-3'
```

The resulting DNA fragment was ligated to the 6.3 kbp DNA fragment described above using an In-Fusion (registered trade name) Advantage PCR Cloning Kit (TAKARA BIO) to give plasmid pDUraRhG-ACS-10.

Using the plasmid containing cDNA of MaACS-11 as a template, the 2.1 kbp DNA fragment was amplified by PCR with KOD-Plus-(TOYOBO) using the primers below.

```
Primer ACS-11 + MGt-R:
                                        (SEQ ID NO: 118)
5'-CACTCCCTTTTCTTATTACTTGGAGCCATAGATCTGCTTGA-3'

Primer ACS-11 + hisp-F:
                                        (SEQ ID NO: 119)
5'-CACTCTCTCAACAATATGCCAAAGTGCTTTACCGTCAAC-3'
```

The resulting DNA fragment was ligated to the 6.3 kbp DNA fragment described above using an In-Fusion (registered trade name) Advantage PCR Cloning Kit (TAKARA BIO) to give the plasmid pDUraRhG-ACS-11.

Evaluation of ACS Activity

The yeast EH13-15 was transformed by plasmids pYE22m, pYE-ACS-5, pYE-ACS-8, pYE-ACS-10, pYE-ACS-11 and pYE-ACS-12, respectively, and random two transformants obtained were cultivated as follows. One platinum loop of the mycelial cells were plated on 10 ml of SC-Trp medium and cultivated with shaking for preincubation at 30° C. for a day. After 1% of the preincubation was added to 100 ml of the SD-Trp medium, main cultivation was performed by shake culturing at 28° C. for a day.

The crude enzyme solution was prepared as follows. The mycelial cells were collected by centrifugation, washed with water and temporarily stored at −80° C. The mycelial cells were suspended in 5 ml of Buffer B (50 mM sodium sulfate buffer (pH 6.0), 10% glycerol and 0.5 mM PMSF). The mycelial cells were then disrupted with a French press (16 kPa, 3 times). Centrifugation was carried out at 1,500×g at 4° C. for 10 minutes and centrifuged. The supernatant obtained was used as the crude enzyme solution.

The ACS activity was determined by the following procedures based on the description of a reference literature (J.B.C., 272 (8), 1896-4903, 1997). The reaction solution contained 200 mM Tris-HCl (pH7.5), 2.5 mM ATP, 8 mM $MgCl_2$, 2 mM EDTA, 20 mM NaF, 0.1% TritonX-100, 50 μg/ml fatty acids, 50 μM CoA and 100 μl of the crude enzyme solution (suitably diluted in Buffer B), and was made 500 μl in total. The reaction was carried out at 28° C. for 30 minutes. After completion of the reaction, 2.5 ml of stop solution (isopropanol:n-heptane:1 M sulfuric acid (40:20:1)) was added and the mixture was thoroughly agitated. Furthermore, 2 ml of n-heptane was added thereto. After thoroughly mixing them, the mixture was centrifuged to recover the upper layer. Further 2 ml of n-heptane was added to the lower layer and treated in the same manner to recover the upper layer. The upper layers recovered were combined and evaporated to dryness using a centrifugal concentrator. Then, 50 μl of 0.2 mg/ml tricosanoic acid (23:0) was added thereto as an internal standard. The fatty acids were converted into the methyl esters by the hydrochloric acid-methanol method, followed by fatty acid analysis using gas chromatography. The amount of the fatty acids, which were changed to acyl-CoA and thus distributed into the lower layer by the procedures above, was calculated from the amount of fatty acids detected. The results are shown in the table below. The ACS activity is expressed as the amount of fatty acids distributed into the lower layer by the procedures above, per weight of the protein in the crude enzyme solution. The control is the strain transformed by pYE22m and the others are the transformants in which the expression vectors of the respective genes were introduced.

TABLE 7

ACS Activity on Palmitic Acid

| | MaACS-5 | | MaACS-10 | | MaACS-11 | | MaACS-12 | | Control | |
|---|---|---|---|---|---|---|---|---|---|---|
| | #1 | #2 | #1 | #2 | #1 | #2 | #1 | #2 | #1 | #2 |
| mg/mg · protein | 0.26 | 0.20 | 0.41 | 0.34 | 0.49 | 0.43 | 0.31 | 0.40 | 0.11 | 0.12 |

When palmitic acid was used as substrate, MaACS-5, MaACS-10, MaACS-11 and MaACS-12 showed the ACS activity of approximately 2 to 4 times the control.

TABLE 8

ACS Activity on Oleic Acid

| | MaACS-10 | | MaACS-11 | | MaACS-12 | | Control | |
|---|---|---|---|---|---|---|---|---|
| | #1 | #2 | #1 | #2 | #1 | #2 | #1 | #2 |
| mg/mg · protein | 0.25 | 0.20 | 0.25 | 0.16 | 0.16 | 0.18 | 0.09 | 0.11 |

When oleic acid was used as substrate, MaACS-10, MaACS-11 and MaACS-12 showed the ACS activity of approximately twice the control.

TABLE 9

ACS Activity on Linoleic Acid

| | MaACS-5 | | MaACS-8 | | MaACS-10 | | MaACS-11 | | MaACS-12 | | Control | |
|---|---|---|---|---|---|---|---|---|---|---|---|---|
| | #1 | #2 | #1 | #2 | #1 | #2 | #1 | #2 | #1 | #2 | #1 | #2 |
| mg/mg · protein | 0.47 | 0.42 | 0.42 | 0.38 | 5.24 | 5.67 | 3.46 | 3.20 | 0.95 | 0.78 | 0.14 | 0.14 |

When linoleic acid was used as substrate, MaACS-5, MaACS-8 and MaACS-12 showed the ACS activity of several times (approximately 3, 3 and 6 times, respectively) the control, whereas MaACS-10 and MaACS-11 showed the ACS activity of several tens times (approximately 40 and 20 times, respectively) the control.

TABLE 10

ACS Activity on γ-Linoleic Acid

| | MaACS-5 | | MaACS-8 | | MaACS-10 | | MaACS-11 | | MaACS-12 | | Control | |
|---|---|---|---|---|---|---|---|---|---|---|---|---|
| | #1 | #2 | #1 | #2 | #1 | #2 | #1 | #2 | #1 | #2 | #1 | #2 |
| mg/mg · protein | 0.28 | 0.28 | 0.16 | 0.31 | 0.63 | 0.59 | 0.90 | 0.75 | 0.52 | 0.63 | 0.07 | 0.09 |

When γ-linoleic acid was used as substrate, all of MaACS-5, MaACS-8, MaACS-10, MaACS-11 and MaACS-12 showed the ACS activity of approximately 2 to 10 times the control.

TABLE 11

ACS Activity on Dihomo-γ-Linoleic Acid

| | MaACS-10 | | MaACS-11 | | MaACS-12 | | Control | |
|---|---|---|---|---|---|---|---|---|
| | #1 | #2 | #1 | #2 | #1 | #2 | #1 | #2 |
| mg/mg · protein | 4.98 | 4.21 | 2.75 | 2.98 | 2.04 | 1.86 | 0.09 | 0.05 |

When dihomo-γ-linoleic acid was used as substrate, all of MaACS-10, MaACS-11 and MaACS-12 showed the ACS activity of several tens times (approximately 60 times, 40 times and 30 times, respectively) the control.

TABLE 12

ACS Activity on Arachidonic Acid

| | MaACS-10 | | MaACS-11 | | MaACS-12 | | Control | |
|---|---|---|---|---|---|---|---|---|
| | #1 | #2 | #1 | #2 | #1 | #2 | #1 | #2 |
| mg/mg · protein | 8.12 | 7.19 | 2.73 | 2.87 | 1.08 | 0.87 | 0.13 | 0.03 |

When arachidonic acid was used as substrate, MaACS-10, MaACS-11 and MaACS-12 showed the ACS activity of several tens times (approximately 90 times, 30 times and 10 times, respectively) the control.

As above, MaACS-10, MaACS-11 and MaACS-12 in particular showed a higher activity on polyunsaturated fatty acids of 20 carbon atoms such as dihomo-γ-linoleic acid or arachidonic acid.

Arachidonic Acid Uptake Activity of ACS-Expressed Yeast

The yeast EH13-15 was transformed by plasmids pYE22m, pYE -ACS-10, pYE-ACS-11 and pYE-ACS-12, respectively, and random two transformants obtained were cultivated as follows. One platinum loop of the cells were plated on 10 ml of SC-Trp medium and cultivated with shaking for preincubation at 30° C. for a day. After 100 μl of the preincubation was added to 10 ml of the SC-Trp medium in which 50 μg/ml of arachidonic acid was supplemented, main cultivation was performed by shake culturing at 25° C. for a day. The mycelial cells were collected, lyophilized and subjected to fatty acid analysis. The ratio of arachidonic acid taken up into the mycelial cells to the added arachidonic acid was determined The results are shown in TABLE 14. The control is the strain transformed by pYE22m and the others are the transformants in which the expression vectors of the respective genes were introduced.

TABLE 13

Dry Mycelial Weight

| | Control | | MaACS-10 | | MaACS-11 | | MaACS-12 | |
|---|---|---|---|---|---|---|---|---|
| | #1 | #2 | #1 | #2 | #1 | #2 | #1 | #2 |
| % | 36.63 | 37.81 | 65.86 | 66.64 | 61.53 | 61.35 | 63.64 | 67.06 |

TABLE 14

Ratio of Arachidonic Acid Taken Up into Mycelia

| | Control | | MaACS-10 | | MaACS-11 | | MaACS-12 | |
|---|---|---|---|---|---|---|---|---|
| | #1 | #2 | #1 | #2 | #1 | #2 | #1 | #2 |
| mg/10 ml | 15.30 | 15.80 | 19.60 | 18.10 | 16.70 | 17.40 | 16.80 | 16.20 |

Acquisition of *M. Alpina* Transformants

Using as a host the uracil-auxotrophic strain Aura-3 derived from *M. alpina* strain 1S-4 as described in PCT International Publication Pamphlet WO 2005/019437 entitled "Method of Breeding Lipid-Producing Fungus"), transformation was performed by the particle delivery method using the plasmids pDUraRhG-ACS-10 and pDU-raRhG-ACS-11, respectively. For screening of the transformants, SC agar medium was used (0.5% Yeast Nitrogen Base w/o Amino Acids and Ammonium Sulfate (Difco), 0.17% ammonium sulfate, 2% glucose, 0.002% adenine, 0.003% tyrosine, 0.0001% methionine, 0.0002% arginine, 0.0002% histidine, 0.0004% lysine, 0.0004% tryptophan, 0.0005% threonine, 0.0006% isoleucine, 0.0006% leucine, 0.0006% phenylalanine, and 2% agar).

Evaluation of *M. Alpina* Transformants

The transformants obtained were plated on 4 ml of GY medium and cultured with shaking at 28° C. for 2 days. The mycelial cells were collected by filtration, and RNA was extracted with an RNeasy Plant Kit (QIAGEN). A SuperScript First Strand System for RT-PCR (Invitrogen) was used to synthesize cDNA. To confirm expression of the respective genes from the introduced constructs, RT-PCR was performed with the following primer pairs.

```
ACS10-RT1:
                                          (SEQ ID NO: 120)
5'-GTCCCGAATGGTTCCT-3'
```

```
ACS10-RT2:
                                (SEQ ID NO: 121)
5'-AGCGGTTTTCTACTTGC-3'

ACS11-RT1:
                                (SEQ ID NO: 122)
5'-AACTACAACCGCGTCG-3'

ACS11-RT2:
                                (SEQ ID NO: 123)
5'-CGGCATAAACGCAGAT-3'
```

Figure 27A:
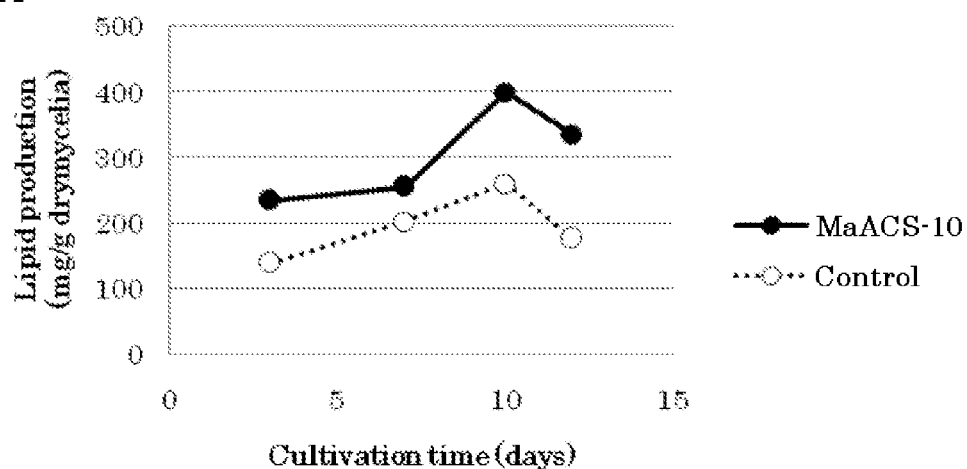
FIG. 27A and FIG. 27B show changes with the passage of time in lipid production (FIG. 27A) and arachidonic acid production (FIG. 27B), per mycelia in MaACS-10-overexpressed *M. alpina*.
Figure 27B:
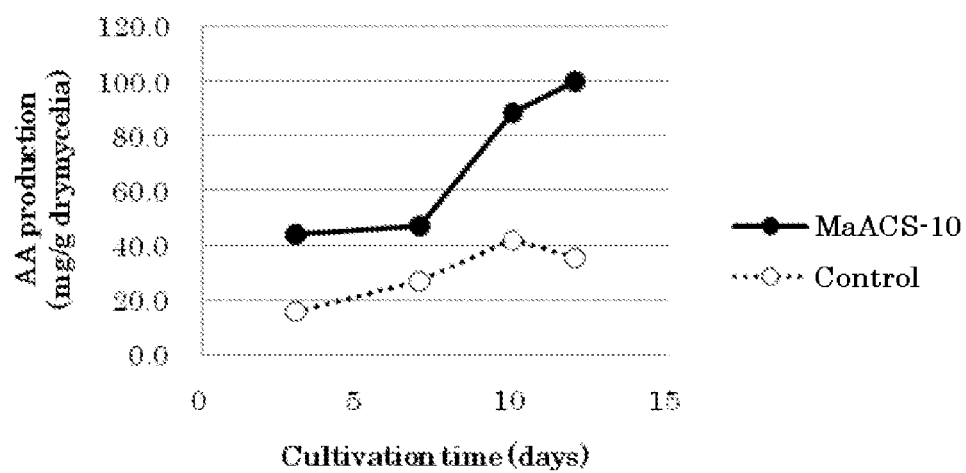
Figure 28A:
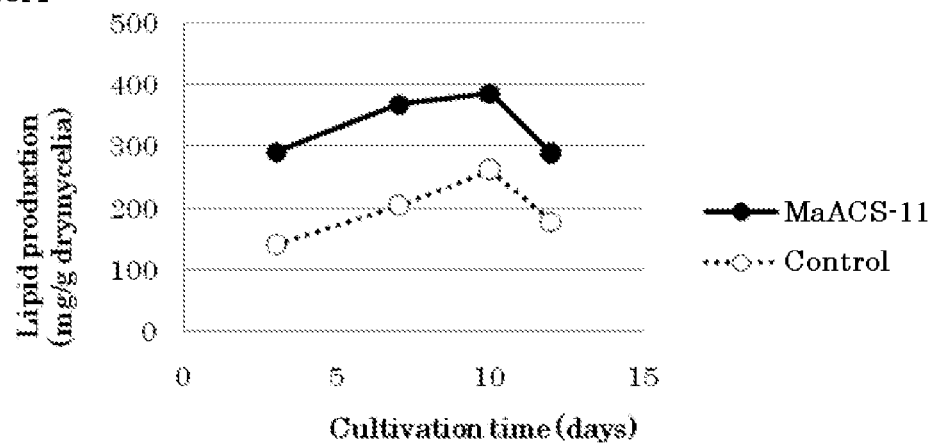
FIG. 28A and FIG. 28B show changes with the passage of time in lipid production (FIG. 28A) and arachidonic acid production (FIG. 28B), per mycelia in MaACS-11-overexpressed *M. alpina*.
Figure 28B:
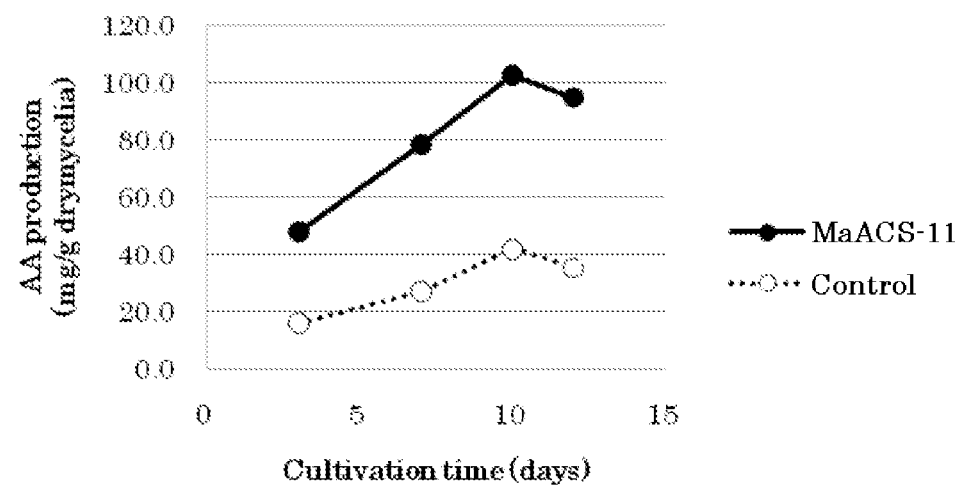

In the transformants that overexpression was confirmed, one transformant each was plated on 10 ml of GY medium (2% glucose and 1% yeast extract) and cultured with shaking at 28° C. at 300 rpm for 3 days. The whole volume of the culture was transferred to 500 ml of GY medium (2 Sakaguchi flask) and shake cultured at 28° C. and 120 rpm. Three, seven, ten and twelve days after this day, 5 ml each and 10 ml each were taken and filtered. After the mycelial cells were dried at 120° C., fatty acids were converted into the methyl esters by the hydrochloric acid-methanol method and analyzed by gas chromatography. The fatty acid production and the amount of arachidonic acid produced, per dried mycelial cells were monitored with the passage of time. The transformant host strain Δura-3 was used as control. The results are shown in FIG. 27A and FIG. 27B (MaACS-10) and FIG. 28A and FIG. 28B (MaACS-11).

As shown in FIGS. 27A, 27B, 28A, and 28B, when MaACS-10 and MaACS-11 were overexpressed in *M. alpina*, both the amount of fatty acids and the amount of arachidonic acid per mycelia were increased as compared to the control.

INDUSTRIAL APPLICABILITY

The polynucleotide of the present invention is expressed in an appropriate host cell to efficiently produce fatty acids, in particular, polyunsaturated fatty acids. The fatty acids produced in host cells according to the present invention can be used to produce fatty acid compositions, food products, cosmetics, pharmaceuticals, soaps, etc.

What is claimed is:

1. A polynucleotide, which is a cDNA, according to any one selected from t group consisting of (a) to (d) below:
   (a) a polynucleotide comprising the nucleotide sequence shown by SEQ ID NO: 58;
   (b) a polynucleotide encoding a protein consisting of the amino acid sequence shown by SEQ ID NO: 57;
   (c) a polynucleotide encoding a protein consisting of an amino acid sequence wherein 1 to 10 amino acids are deleted, substituted, inserted and/or added in the amino acid sequence shown by SEQ ID NO: 57, and having an acyl-CoA synthetase activity or an activity of increasing the amount or changing the composition, of the fatty acids produced in a host cell when expressed in the host cell; and
   (d) a polynucleotide encoding a protein having an amino acid sequence having at least 95% identity to the amino acid sequence shown by SEQ ID NO: 57, and having an acyl-CoA synthetase activity or an activity of increasing the amount or changing the composition, of the fatty acids produced in a host cell when expressed in the host cell.

2. The polynucleotide according to claim 1, comprising the nucleotide sequence shown by SEQ ID NO: 58.

3. The polynucleotide according to claim 1, encoding a protein consisting of the amino acid sequence shown by SEQ ID NO: 57.

4. The polynucleotide according to claim 1, which is a DNA.

5. A vector comprising the polynucleotide according to claim 1.

6. A non-human transformant, into which the polynucleotide according to claim 1 is introduced.

7. The polynucleotide according to claim 2, which is a DNA.

8. The polynucleotide according to claim 3, which is a DNA.

9. A vector comprising the polynucleotide according to claim 2.

10. A vector comprising the polynucleotide according to claim 3.

11. A non-human transformant, into which the polynucleotide according to claim 2 is introduced.

12. A non-human transformant, into which the polynucleotide according to claim 3 is introduced.

13. A non-human transformant, into which the vector according to claim 5 is introduced.

14. A method for producing a lipid or fatty acid composition, which comprises culturing the transformant according to claim 6, and collecting the lipid or fatty acid composition from the culture.

15. The method according to claim 14, wherein the lipid is a triacylglycerol.

16. The method according to claim 14, wherein the fatty acid is a polyunsaturated fatty acid having at least 18 carbon atoms.

* * * * *

SEQUENCE LISTING

```
<160> NUMBER OF SEQ ID NOS: 142

<210> SEQ ID NO 1
<211> LENGTH: 1854
<212> TYPE: DNA
<213> ORGANISM: Mortierella alpina

<400> SEQUENCE: 1
atggatgctg tccctgcagt tgctgctgcg gccatccccg cagccatgta tgtcggctcc      60
aagcttgcaa tcccccgtga tgtcaagtta gctaaaggcc tagtcagtgc caagctaggt     120
tacaggtcct acgagaagaa cgactcgatc aatatctctt atcgttttga agagacctgt     180
aagaagcacc ctcatcgcga agctttggtg tttgaaggca aatcgtacac cttccaggac     240
atccagcgag aatcgaatag ggtgggacac tggctgttgt ccaaaggcgt caagcgagga     300
gagatcgtgt cgctcttcat gcaaaataag ccagagtttc tcttcttctg gcttggactc     360
aacaagatcg gcgctacggg agcattcatc aacacgaacc tctcgggcaa acctctgacg     420
cactcattgc gtaccgcgac agcatccatt ctgattatgg atgcggaact gccgacgccc     480
atttatagtg tcctcgatga agtccttgag atgggatatc agatatattc ctacggagga     540
tcccagcaac acgcctttgc tacacaagtt gaactttctc aaatctcgga tgcggccttg     600
cccaagagtc tgcgaaggaa aaccactgca aatgatattg ccatgttgat ttacacctcc     660
ggaacgacgg gtttgcccaa agctggacgg ttctcccatg ctcgagccaa cgttgccgca     720
cttttctgga cgtctttcta ccacttcagc gaaaaagacc gcctgtacat cgccttgcct     780
ctttaccaca gtgctggagc tgtccttgga atatgtgtgg cctgggtcac cggtgctacg     840
gtggtcctgg cgcgcaagtt ttcaactact tccttctggg acgaatgcag ggccaacaag     900
gtcaccgtga tccagtatat tggagaaatc tgccgatact tactgaatgc tcctccttct     960
cccttggaca agacacacac gatccgaatg gcgcatggca acggcatgcg tccggatgta    1020
tggaacagat tcagagatcg tttcggcatc cctttgatcg gagaatggta tgcaagcact    1080
gagggcaccg gaatcttgac aaactataac acaggaccca atggcgctgg tgcgatagga    1140
tacagaggct cccttggccag aactgtcgat aagggtctga agattgcgaa gttcgacatc    1200
caaaccgagg aacttattcg tgacaaaaat ggtcgatgca ttgagtgtgt cgcagatgag    1260
```

```
cccggcgagc tcttgacaat gattgattca agtgatccca ctcgcgcttt ccaagggtac   1320
cataaaaatg caggtgcaaa ctccaagaaa gtcgtccagg atgcattcag tgttggcgac   1380
caatactttc gtactggtga catccttcgt cgcgacgctg atggctattt ctattttggc   1440
gatcgtgttg gagatacttt ccgctggaaa tctgaaaacg tgtcaactgc ggaggtttct   1500
gaggtgctct cagcataccc ggactgcatc gaggtcaacg tttatggcgt tcaagtccct   1560
ggacacgacg gccgcgcagg catggctgcc attgtctcca aggacaccat gaactgggat   1620
agtttcgcca gtttgcact caaaaatctg ccgaagtact ctgtgccgat tttcatccgc   1680
aaggtcccag atggagat tacgggaacg ttcaagcaac gaaaggttga actggtgaac   1740
gagggcatgg acccgagcaa gatcaaagac gaaatgctgt ggttggatgg cactcctac   1800 cggcccttca agaggcgga gcatactaga gtcgtcagcg caaagccag gctt          1854
```

```
<210> SEQ ID NO 2
<211> LENGTH: 618
<212> TYPE: PRT
<213> ORGANISM: Mortierella alpina

<400> SEQUENCE: 2

Met Asp Ala Val Pro Ala Val Ala Ala Ala Ile Pro Ala Ala Met
1               5                   10                  15

Tyr Val Gly Ser Lys Leu Ala Ile Pro Arg Asp Val Lys Leu Ala Lys
            20                  25                  30

Gly Leu Val Ser Ala Lys Leu Gly Tyr Arg Ser Tyr Glu Lys Asn Asp
        35                  40                  45

Ser Ile Asn Ile Ser Tyr Arg Phe Glu Glu Thr Cys Lys Lys His Pro
    50                  55                  60

His Arg Glu Ala Leu Val Phe Glu Gly Lys Ser Tyr Thr Phe Gln Asp
65                  70                  75                  80

Ile Gln Arg Glu Ser Asn Arg Val Gly His Trp Leu Leu Ser Lys Gly
                85                  90                  95

Val Lys Arg Gly Glu Ile Val Ser Leu Phe Met Gln Asn Lys Pro Glu
            100                 105                 110

Phe Leu Phe Phe Trp Leu Gly Leu Asn Lys Ile Gly Ala Thr Gly Ala
        115                 120                 125

Phe Ile Asn Thr Asn Leu Ser Gly Lys Pro Leu Thr His Ser Leu Arg
    130                 135                 140

Thr Ala Thr Ala Ser Ile Leu Ile Met Asp Ala Glu Leu Pro Thr Pro
145                 150                 155                 160

Ile Tyr Ser Val Leu Asp Glu Val Leu Glu Met Gly Tyr Gln Ile Tyr
                165                 170                 175

Ser Tyr Gly Gly Ser Gln Gln His Ala Phe Ala Thr Gln Val Glu Leu
            180                 185                 190

Ser Gln Ile Ser Asp Ala Ala Leu Pro Lys Ser Leu Arg Arg Lys Thr
        195                 200                 205

Thr Ala Asn Asp Ile Ala Met Leu Ile Tyr Thr Ser Gly Thr Thr Gly
    210                 215                 220

Leu Pro Lys Ala Gly Arg Phe Ser His Ala Arg Ala Asn Val Ala Ala
225                 230                 235                 240

Leu Phe Trp Thr Ser Phe Tyr His Phe Ser Glu Lys Asp Arg Leu Tyr
                245                 250                 255

Ile Ala Leu Pro Leu Tyr His Ser Ala Gly Ala Val Leu Gly Ile Cys
            260                 265                 270
```

```
Val Ala Trp Val Thr Gly Ala Thr Val Val Leu Ala Arg Lys Phe Ser
            275                 280                 285
Thr Thr Ser Phe Trp Asp Glu Cys Arg Ala Asn Lys Val Thr Val Ile
        290                 295                 300
Gln Tyr Ile Gly Glu Ile Cys Arg Tyr Leu Leu Asn Ala Pro Pro Ser
305                 310                 315                 320
Pro Leu Asp Lys Thr His Thr Ile Arg Met Ala His Gly Asn Gly Met
                325                 330                 335
Arg Pro Asp Val Trp Asn Arg Phe Asp Arg Phe Gly Ile Pro Leu
            340                 345                 350
Ile Gly Glu Trp Tyr Ala Ser Thr Glu Gly Thr Gly Ile Leu Thr Asn
        355                 360                 365
Tyr Asn Thr Gly Pro Asn Gly Ala Gly Ala Ile Gly Tyr Arg Gly Ser
370                 375                 380
Leu Ala Arg Thr Val Asp Lys Gly Leu Lys Ile Ala Lys Phe Asp Ile
385                 390                 395                 400
Gln Thr Glu Glu Leu Ile Arg Asp Lys Asn Gly Arg Cys Ile Glu Cys
                405                 410                 415
Val Ala Asp Glu Pro Gly Glu Leu Leu Thr Met Ile Asp Ser Ser Asp
            420                 425                 430
Pro Thr Arg Ala Phe Gln Gly Tyr His Lys Asn Ala Gly Ala Asn Ser
        435                 440                 445
Lys Lys Val Val Gln Asp Ala Phe Ser Val Gly Asp Gln Tyr Phe Arg
    450                 455                 460
Thr Gly Asp Ile Leu Arg Arg Asp Ala Asp Gly Tyr Phe Tyr Phe Gly
465                 470                 475                 480
Asp Arg Val Gly Asp Thr Phe Arg Trp Lys Ser Glu Asn Val Ser Thr
                485                 490                 495
Ala Glu Val Ser Glu Val Leu Ser Ala Tyr Pro Asp Cys Ile Glu Val
            500                 505                 510
Asn Val Tyr Gly Val Gln Val Pro Gly His Asp Gly Arg Ala Gly Met
        515                 520                 525
Ala Ala Ile Val Ser Lys Asp Thr Met Asn Trp Asp Ser Phe Ala Lys
    530                 535                 540
Phe Ala Leu Lys Asn Leu Pro Lys Tyr Ser Val Pro Ile Phe Ile Arg
545                 550                 555                 560
Lys Val Pro Glu Met Glu Ile Thr Gly Thr Phe Lys Gln Arg Lys Val
                565                 570                 575
Glu Leu Val Asn Glu Gly Met Asp Pro Ser Lys Ile Lys Asp Glu Met
            580                 585                 590
Leu Trp Leu Asp Gly His Ser Tyr Arg Pro Phe Lys Glu Ala Glu His
        595                 600                 605
Thr Arg Val Val Ser Gly Lys Ala Arg Leu
    610                 615

<210> SEQ ID NO 3
<211> LENGTH: 1857
<212> TYPE: DNA
<213> ORGANISM: Mortierella alpina

<400> SEQUENCE: 3
atggatgctg tccctgcagt tgctgctgcg gccatcccg cagccatgta tgtcggctcc    60
aagcttgcaa tccccgtga tgtcaagtta gctaaaggcc tagtcagtgc caagctaggt   120
tacaggtcct acgagaagaa cgactcgatc aatatctctt atcgttttga agagacctgt   180
```

```
aagaagcacc ctcatcgcga agctttggtg tttgaaggca aatcgtacac cttccaggac      240
atccagcgag aatcgaatag ggtgggacac tggctgttgt ccaaaggcgt caagcgagga      300
gagatcgtgt cgctcttcat gcaaaataag ccagagtttc tcttcttctg gcttggactc      360
aacaagatcg gcgctacggg agcattcatc aacacgaacc tctcgggcaa acctctgacg      420
cactcattgc gtaccgcgac agcatccatt ctgattatgg atgcggaact gccgacgccc      480
atttatagtg tcctcgatga agtccttgag atgggatatc agatatattc ctacggagga      540
tcccagcaac acgcctttgc tacacaagtt gaactttctc aaatctcgga tgcggccttg      600
cccaagagtc tgcgaaggaa aaccactgca atgatattg ccatgttgat ttacacctcc       660
ggaacgacgg gtttgcccaa agctggacgg ttctcccatg ctcgagccaa cgttgccgca      720
cttttctgga cgtctttcta ccacttcagc gaaaaagacc gcctgtacat cgccttgcct      780
ctttaccaca gtgctggagc tgtccttgga atatgtgtgg cctgggtcac cggtgctacg      840
gtggtcctgg cgcgcaagtt ttcaactact tccttctggg acgaatgcag gccaacaag       900 gtcaccgtga tccagtatat tggagaaatc tgccgatact tactgaatgc tcctccttct      960
cccttggaca agacacacac gatccgaatg gcgcatggca acggcatgcg tccggatgta     1020
tggaacagat tcagagatcg tttcggcatc cctttgatcg gagaatggta tgcaagcact     1080
gagggcaccg gaatcttgac aaactataac acaggaccca atggcgctgg tgcgatagga     1140
tacagaggct ccttggccag aactgtcgat aagggtctga agattgcgaa gttcgacatc     1200
caaaccgagg aacttattcg tgacaaaaat ggtcgatgca ttgagtgtgt cgcagatgag     1260
cccggcgagc tcttgacaat gattgattca agtgatccca ctcgcgcttt ccaagggtac     1320
cataaaaatg caggtgcaaa ctccaagaaa gtcgtccagg atgcattcag tgttggcgac     1380
caatactttc gtactggtga catccttcgt cgcgacgctg atggctattt ctattttggc     1440
gatcgtgttg agatactttt ccgctggaaa tctgaaaacg tgtcaactgc ggaggtttct     1500
gaggtgctct cagcataccc ggactgcatc gaggtcaacg tttatggcgt tcaagtccct     1560
ggacacgacg gccgcgcagg catggctgcc attgtctcca aggacaccat gaactgggat     1620
agtttcgcca agtttgcact caaaaaatctg ccgaagtact ctgtgccgat tttcatccgc     1680
aaggtcccag agatggagat tacgggaacg ttcaagcaac gaaaggttga actggtgaac     1740
gagggcatgg acccgagcaa gatcaaagac gaaatgctgt ggttggatgg gcactcctac     1800
cggcccttca agaggcgga gcatactaga gtcgtcagcg gcaaagccag gctttga        1857
```

<210> SEQ ID NO 4  
<211> LENGTH: 2077  
<212> TYPE: DNA  
<213> ORGANISM: Mortierella alpina

<400> SEQUENCE: 4

```
gctcttttt gttctgttct ttgccacccc actctgctgt gcctctccac tcccctgcc        60 cgtcgaacgt tcttctgtca cttttgcacag cagtatctcc tctgatctcg cttgrttata    120
ttccctctaa tctcgtttgg ttatattccc tctgatctcg ctcggttata ttcttcagat     180
atggatgctg tccctgcagt tgctgctgcg gccatccccg cagccatgta tgtcggctcc     240
aagcttgcaa tccccgtga tgtcaagtta gctaaaggcc tagtcagtgc caagctaggt     300
tacaggtcct acgagaagaa cgactcgatc aatatctctt atcgttttga agagacctgt    360
aagaagcacc ctcatcgcga agctttggtg tttgaaggca aatcgtacac cttccaggac     420
```

```
atccagcgag aatcgaatag ggtgggacac tggctgttgt ccaaaggcgt caagcgagga        480
gagatcgtgt cgctcttcat gcaaaataag ccagagtttc tcttcttctg gcttggactc        540
aacaagatcg gcgctacggg agcattcatc aacacgaacc tctcgggcaa acctctgacg        600
cactcattgc gtaccgcgac agcatccatt ctgattatgg atgcggaact gccgacgccc        660
atttatagtg tcctcgatga agtccttgag atgggatatc agatatattc ctacggagga        720
tcccagcaac acgcctttgc tacacaagtt gaactttctc aaatctcgga tgcggccttg        780
cccaagagtc tgcgaaggaa aaccactgca aatgatattg ccatgttgat ttacacctcc        840
ggaacgacgg gtttgcccaa agctggacgg ttctcccatg ctcgagccaa cgttgccgca        900
cttttctgga cgtctttcta ccacttcagc gaaaaagacc gcctgtacat cgccttgcct        960
ctttaccaca gtgctggagc tgtccttgga atatgtgtgg cctgggtcac cggtgctacg       1020
gtggtcctgg cgcgcaagtt ttcaactact tccttctggg acgaatgcag ggccaacaag       1080
gtcaccgtga tccagtatat tggagaaatc tgccgatact tactgaatgc tcctccttct       1140
cccttggaca agacacacac gatccgaatg gcgcatggca acggcatgcg tccggatgta       1200
tggaacagat tcagagatcg tttcggcatc cctttgatcg agaatggta tgcaagcact        1260 gagggcaccg gaatcttgac aaactataac acaggaccca atggcgctgg tgcgatagga       1320
tacagaggct ccttggccag aactgtcgat aagggtctga agattgcgaa gttcgacatc       1380
caaaccgagg aacttattcg tgacaaaaat ggtcgatgca ttgagtgtgt cgcagatgag       1440
cccggcgagc tcttgacaat gattgattca agtgatccca ctcgcgcttt ccaagggtac       1500
cataaaaatg caggtgcaaa ctccaagaaa gtcgtccagg atgcattcag tgttggcgac       1560
caatactttc gtactggtga catccttcgt cgcgacgctg atggctattt ctattttggc       1620
gatcgtgttg agatactttt ccgctggaaa tctgaaaacg tgtcaactgc ggaggtttct       1680
gaggtgctct cagcataccc ggactgcatc gaggtcaacg tttatggcgt tcaagtccct       1740
ggacacgacg gccgcgcagg catggctgcc attgtctcca aggacaccat gaactgggat       1800
agtttcgcca gtttgcact caaaaatctg ccgaagtact ctgtgccgat tttcatccgc       1860
aaggtcccag agatggagat tacgggaacg ttcaagcaac gaaaggttga actggtgaac       1920
gagggcatgg acccgagcaa gatcaaagac gaaatgctgt ggttggatgg gcactcctac       1980
cggcccttca aagaggcgga gcatactaga gtcgtcagcg gcaaagccag gctttgacga       2040
ataaaattat ttcgttttgt ccgttgaaaa aaaaaaa                                2077
```

<210> SEQ ID NO 5
<211> LENGTH: 2278
<212> TYPE: DNA
<213> ORGANISM: Mortierella alpina

<400> SEQUENCE: 5

```
atggatgctg tccctgcagt tgctgctgcg gccatccccg cagccatgta tgtcggctcc         60
aagcttgcaa tcccccgtga tgtcaagtta gctaaaggcc tagtcagtgc caagctaggt        120
tacaggtcct acgagaagaa cgactcgatc aatatctctt atcgttttga agagacctgt        180
aagaagcacc ctcatcgcga agctttggtg tttgaaggca aatcgtacac cttccaggac        240
atccagcgag gtaacaagaa aaacaattgt ccaaagtgac agtcgaacgc atccgaaatt        300
tttactcaag ataaattgga tcatcgcacc acacccctcc gtcgatttca ctaacccttg        360
acttggaatg tagaatcgaa tagggtggga cactggctgt tgtccaaagg cgtcaagcga        420
ggagagatcg tgtcgctctt catgcaaaat aagccagagt ttctcttctt ctggcttgga        480
```

-continued

```
ctcaacaaga tcggcgctac gggagcattc atcaacacga acctctcggg caaacctctg    540
acgcactcat tgcgtaccgc gacagcatcc attctgatta tggatgcgga actgccgacg    600
cccatttata gtgtcctcga tgaagtcctt gagatgggat atcagatata ttcctacgga    660
ggatcccagc aacacgcctt tgctacacaa gttgaacttt ctcaaatctc ggatgcggcc    720
ttgcccaaga gtctgcgaag gaaaaccact gcaaatgata ttgccatgtt gatttacacc    780
tccggaacga cgggtttgcc caaagctgga cggttctccc atgctcgagc caacggtagg    840 attataccccc ccctcctccc ccccccccctt tttttcatt tgctgtgaag ttattagctg    900
ttccactagc atattgactc atattcacgt tccttttaca cgtcgggatc cagttgccgc    960
acttttctgg acgtctttct accacttcag cgaaaaagac cgcctgtaca tcgccttgcc   1020
tctttaccac agtgctggag ctgtccttgg aatatgtgtg gcctgggtca ccggtgctac   1080
ggtggtcctg gcgcgcaagt tttcaactac ttccttctgg gacgaatgca gggccaacaa   1140
ggtcaccgtg atccagtata ttggagaaat ctgccgatac ttactgaatg ctcctccttc   1200
tcccttggac aagacacaca cgatccgaat ggcgcatggc aacggcatgc gtccggatgt   1260
atggaacaga ttcagagatc gtttcggcat ccctttgatc ggagaatggt atgcaagcac   1320
tgagggcacc ggaatcttga caaactataa cacaggaccc aatggcgctg gtgcgatagg   1380 atacagagc tccttggcca gaactgtcga taagggtctg aagattgcga agttcgacat   1440
ccaaaccgag gaacttattc gtgacaaaaa tggtcgatgc attgaggtaa agttgacagt   1500
attaagttga acatattcca cagtacccctt tgtcttcggt gtccaaaata ctgactactt   1560
gcttgatgcc ccttcaagtg tgtcgcagat gagcccggcg agctcttgac aatgattgat   1620
tcaagtgatc ccactcgcgc tttccaaggg taccataaaa atgcaggtgc aaactccaag   1680
aaagtcgtcc aggatgcatt cagtgttggt aggtgtaatc ttcaccttgc gtgccttcaa   1740
cagcaaactt tgtgatccgc gctgactcga tgaccctgtc ctgcctacat ttctaggcga   1800
ccaatacttt cgtactggtg acatccttcg tcgcgacgct gatggctatt tctattttgg   1860
cgatcgtgtt ggagatactt ccgctggaaa atctgaaaac gtgtcaactg cggaggtttc   1920
tgaggtgctc tcagcatacc cggactgcat cgaggtcaac gttatggcg ttcaagtccc   1980 tggacacgac ggccgcgcag gcatggctgc cattgtctcc aaggacacca tgaactggga   2040
tagtttcgcc aagtttgcac tcaaaaatct gccgaagtac tctgtgccga ttttcatccg   2100
caaggtccca gagatggaga ttacgggaac gttcaagcaa cgaaaggttg aactggtgaa   2160
cgagggcatg gacccgagca agatcaaaga cgaaatgctg tggttggatg gcactccta   2220 ccggcccttc aaagaggcgg agcatactag agtcgtcagc ggcaaagcca ggctttga    2278
```

<210> SEQ ID NO 6
<211> LENGTH: 1926
<212> TYPE: DNA
<213> ORGANISM: Mortierella alpina

<400> SEQUENCE: 6

```
atggcaagta ccaaatcact aaggacttgg cgcttgttcg cgttggtctc catgcacgca     60
aaagacttga ggccttggtc gagaatcggg actgcagtct ttacaacagg ttcgaggaac    120
aatgccagat ccggcctttc tctgttgccc ttgttttga aacacgtct tacacctgga    180 gagacttgga gctggcgtcc aacaggatgg cccattggtt tgttgctcaa ggaatccaaa    240 aaaaggagc gtgtggcgat gatgatgcat aactcgcctc tgttcattat cacctggctg    300
```

```
gcaatgctca agatcatggt tgtacctgct tttatcaata accagattgc aggacctgtt      360
ctggttcatt ctcttaaagt ggccgacgcc aagtttctct tgttcgatta cgagttggca      420
cctgtcatcc aaaagtcgct caatgagatc aaggacatgg ttacaatct ctacactgtc      480 acacccaagg atcaagttct aggtcaactt acgccaatc tgcccgaggc tgctcgtcag      540
gtgttggatg aggctccttc attctttggt tatgtcgaat ggcagaacct cagtaccgaa      600
ggtttctcga cgagagtcg tcaggaggtg gtgatctccg accccgcagc cttgatttac      660
accagcggga ccacgggatt ccccaaggct gctatcatgg accatggacg ttgcaacttg      720
gcttcgatct cttatggcac tctatgcggc atcaaaccag agaacaaggt ttacatcaca      780
ttgccgctct atcattctgc tggagccatc attggtctgg ccagagcttc accagcgga       840 tgcaccattg tgctggcgcg aaagttctcc gtgacaaagt tttggcgtga ttgcgttgag      900
tacgacgtaa ctcattttca gtacattggc gaactctgcc gctaccttct aaatgccccc      960
gaaagtccac tggacaaaag cataaggtt cggatggcgt ttggcaacgg aatgcgcccg       1020
gatgtttggg caaagtttca ggaacgattc aatatcccca ttattgttga gtactacgcc      1080
atgagcgaag aacatcgtc gcttttgaat gtggccagga acaagcgcga ccaaggtgcg       1140
gtgggattcc gtgccccgt cgtgagggcc ttgacgcctc ccgttcaact ggtcaaggtg       1200
gactttgaca cggaggagct gatccgcgat aagaagacgg actttgcgt cctatgccag       1260 cctggtgaga ttggagaact ggtcacgcta gccgacaaca agacgactgg cgcacgctat      1320
gctgggtatt tcaatcagcc agaggtttcg aaggcaaggc tggtccagaa cgtggtagtg      1380
aaggacgaca tctacttccg gacgggtgac ctcttgtact ccaaggacca gtactggtac      1440
tttgctgatc gcgcaggaga cacgtaccgg tggaaaggag agaacgtgtc gacagccgag      1500
attgcagaca ctatcggccg tgttgagggc gtggctagtt gtactgttta tggcgtatcg      1560
gtcccgggca tggatggacg cgcgggcatg gctgctttgg tgctcaagaa ctcgattgtg      1620
cagatggcag gtgaagccga ggcaaagttc catgtggatg aggctgcgct gaacgcgttt      1680
ttgcgtgact tgagcaagga tgtggtcaaa aaactgccgg cgtatgcgat tcctcggttc      1740
ttgcgcattg cagagcagga actggagacg acgggcacgt tcaagaacaa gaaggtggag      1800
ctgaagaagg aagggttcga cctcggtaag gtcaaggagc ggctgtactg gtggacaccc      1860
aagggtgaat atgcccctt tggcgtggcg gagaacgagc agatcctcgc aggacgcgct      1920
cgtctt                                                                 1926
```

<210> SEQ ID NO 7
<211> LENGTH: 642
<212> TYPE: PRT
<213> ORGANISM: Mortierella alpina

<400> SEQUENCE: 7

Met Ala Ser Thr Lys Ser Leu Arg Thr Trp Arg Leu Phe Ala Leu Val
1               5                   10                  15

Ser Met His Ala Lys Asp Leu Arg Pro Trp Ser Arg Ile Gly Thr Ala
            20                  25                  30

Val Phe Thr Thr Gly Ser Arg Asn Asn Ala Arg Ser Gly Leu Ser Leu
        35                  40                  45

Leu Pro Leu Phe Leu Arg Thr Arg Leu Thr Pro Gly Glu Thr Trp Ser
    50                  55                  60

Trp Arg Pro Thr Gly Trp Pro Ile Gly Leu Leu Leu Lys Glu Ser Lys
65                  70                  75                  80

-continued

```
Lys Lys Glu Arg Val Ala Met Met Met His Asn Ser Pro Leu Phe Ile
                 85                  90                  95

Ile Thr Trp Leu Ala Met Leu Lys Ile Met Val Val Pro Ala Phe Ile
            100                 105                 110

Asn Asn Gln Ile Ala Gly Pro Val Leu Val His Ser Leu Lys Val Ala
            115                 120                 125

Asp Ala Lys Phe Leu Leu Phe Asp Tyr Glu Leu Ala Pro Val Ile Gln
130                 135                 140

Lys Ser Leu Asn Glu Ile Lys Asp Met Gly Tyr Asn Leu Tyr Thr Val
145                 150                 155                 160

Thr Pro Lys Asp Gln Val Leu Gly Gln Leu Tyr Ala Asn Leu Pro Glu
                165                 170                 175

Ala Ala Arg Gln Val Leu Asp Glu Ala Pro Ser Phe Phe Gly Tyr Val
            180                 185                 190

Glu Trp Gln Asn Leu Ser Thr Glu Gly Phe Ser Asn Glu Ser Arg Gln
            195                 200                 205

Glu Val Val Ile Ser Asp Pro Ala Ala Leu Ile Tyr Thr Ser Gly Thr
210                 215                 220

Thr Gly Phe Pro Lys Ala Ala Ile Met Asp His Gly Arg Cys Asn Leu
225                 230                 235                 240

Ala Ser Ile Ser Tyr Gly Thr Leu Cys Gly Ile Lys Pro Glu Asn Lys
                245                 250                 255

Val Tyr Ile Thr Leu Pro Leu Tyr His Ser Ala Gly Ala Ile Ile Gly
            260                 265                 270

Leu Gly Gln Ser Phe Thr Ser Gly Cys Thr Ile Val Leu Ala Arg Lys
            275                 280                 285

Phe Ser Val Thr Lys Phe Trp Arg Asp Cys Val Glu Tyr Asp Val Thr
290                 295                 300

His Phe Gln Tyr Ile Gly Glu Leu Cys Arg Tyr Leu Leu Asn Ala Pro
305                 310                 315                 320

Glu Ser Pro Leu Asp Lys Arg His Lys Val Arg Met Ala Phe Gly Asn
                325                 330                 335

Gly Met Arg Pro Asp Val Trp Ala Lys Phe Gln Glu Arg Phe Asn Ile
            340                 345                 350

Pro Ile Ile Val Glu Tyr Tyr Ala Met Ser Glu Gly Thr Ser Ser Leu
            355                 360                 365

Leu Asn Val Ala Arg Asn Lys Arg Asp Gln Gly Ala Val Gly Phe Arg
370                 375                 380

Gly Pro Val Val Arg Ala Leu Thr Pro Pro Val Gln Leu Val Lys Val
385                 390                 395                 400

Asp Phe Asp Thr Glu Glu Leu Ile Arg Asp Lys Lys Thr Gly Leu Cys
                405                 410                 415

Val Leu Cys Gln Pro Gly Glu Ile Gly Glu Leu Val Thr Leu Ala Asp
            420                 425                 430

Asn Lys Thr Thr Gly Ala Arg Tyr Ala Gly Tyr Phe Asn Gln Pro Glu
            435                 440                 445

Val Ser Lys Ala Arg Leu Val Gln Asn Val Val Lys Asp Asp Ile
450                 455                 460

Tyr Phe Arg Thr Gly Asp Leu Leu Tyr Ser Lys Asp Gln Tyr Trp Tyr
465                 470                 475                 480

Phe Ala Asp Arg Ala Gly Asp Thr Tyr Arg Trp Lys Gly Glu Asn Val
                485                 490                 495

Ser Thr Ala Glu Ile Ala Asp Thr Ile Gly Arg Val Glu Gly Val Ala
```

|       |       |       |       | 500   |       |       |       |       | 505   |       |       |       |       | 510   |       |       |
|-------|-------|-------|-------|-------|-------|-------|-------|-------|-------|-------|-------|-------|-------|-------|-------|-------|

Ser Cys Thr Val Tyr Gly Val Ser Val Pro Gly Met Asp Gly Arg Ala
     515               520               525

Gly Met Ala Ala Leu Val Leu Lys Asn Ser Ile Val Gln Met Ala Gly
     530               535               540

Gly Ser Gln Ala Lys Phe His Val Asp Glu Ala Ala Leu Asn Ala Phe
545              550               555               560

Leu Arg Asp Leu Ser Lys Asp Val Val Lys Lys Leu Pro Ala Tyr Ala
              565               570               575

Ile Pro Arg Phe Leu Arg Ile Ala Glu Gln Glu Leu Glu Thr Thr Gly
     580               585               590

Thr Phe Lys Asn Lys Val Glu Leu Lys Lys Glu Gly Phe Asp Leu
     595               600               605

Gly Lys Val Lys Glu Arg Leu Tyr Trp Trp Thr Pro Lys Gly Glu Tyr
     610               615               620

Ala Pro Phe Gly Val Ala Glu Asn Glu Gln Ile Leu Ala Gly Arg Ala
625              630               635               640

Arg Leu

<210> SEQ ID NO 8
<211> LENGTH: 1929
<212> TYPE: DNA
<213> ORGANISM: Mortierella alpina

<400> SEQUENCE: 8

```
atggcaagta ccaaatcact aaggacttgg cgcttgttcg cgttggtctc catgcacgca      60
aaagacttga ggccttggtc gagaatcggg actgcagtct ttacaacagg ttcgaggaac     120
aatgccagat ccggcctttc tctgttgccc ttgtttttga aaacacgtct tacacctgga    180
gagacttgga gctggcgtcc aacaggatgg cccattggtt tgttgctcaa ggaatccaaa    240
aaaaaggagc gtgtggcgat gatgatgcat aactcgcctc tgttcattat cacctggctg    300
gcaatgctca agatcatggt tgtacctgct tttatcaata accagattgc aggacctgtt    360
ctggttcatt ctcttaaagt ggccgacgcc aagtttctct tgttcgatta cgagttggca    420
cctgtcatcc aaaagtcgct caatgagatc aaggacatgg gttacaatct ctacactgtc    480
acacccaagg atcaagttct aggtcaactt tacgccaatc tgcccgaggc tgctcgtcag    540
gtgttggatg aggctccttc attctttggt tatgtcgaat ggcagaacct cagtaccgaa    600
ggtttctcga cgagagtcg tcaggaggtg gtgatctccg accccgcagc cttgatttac    660
accagcggga ccacgggatt ccccaaggct gctatcatgg accatggacg ttgcaacttg    720
gcttcgatct cttatggcac tctatgcggc atcaaaccag agaacaaggt ttacatcaca    780
ttgccgctct atcattctgc tggagccatc attggtctgg ccagagcttc accagcgga    840
tgcaccattg tgctggcgcg aaagttctcc gtgacaaagt tttggcgtga ttgcgttgag    900
tacgacgtaa ctcattttca gtacattggc gaactctgcc gctaccttct aaatgcccc     960
gaaagtccac tggacaaaag gcataaggtt cggatggcgt ttgcaacgg aatgcgcccg    1020
gatgtttggg caaagtttca ggaacgattc aatatcccca ttattgttga gtactacgcc   1080
atgagcgaag gaacatcgtc gcttttgaat gtggccagga caagcgcga ccaaggtgcg   1140
gtgggattcc gtggccccgt cgtgagggcc ttgacgcctc ccgttcaact ggtcaaggtg   1200
gactttgaca cggaggagct gatccgcgat aagaagacgg actttgcgt cctatgccag   1260
cctggtgaga ttggagaact ggtcacgcta gccgacaaca agacgactgg cgcacgctat   1320
```

```

Actually 

gctgggtatt tcaatcagcc agaggtttcg aaggcaaggc tggtccagaa cgtggtagtg   1380
aaggacgaca tctacttccg gacgggtgac ctcttgtact ccaaggacca gtactggtac   1440
tttgctgatc gcgcaggaga cacgtaccgg tggaaaggag agaacgtgtc gacagccgag   1500
attgcagaca ctatcggccg tgttgagggc gtggctagtt gtactgttta tggcgtatcg   1560
gtcccgggca tggatggacg cgcgggcatg gctgctttgg tgctcaagaa ctcgattgtg   1620
cagatggcag gtggaagcca ggcaaagttc catgtggatg aggctgcgct gaacgcgttt   1680
ttgcgtgact tgagcaagga tgtggtcaaa aaactgccgg cgtatgcgat tcctcggttc   1740
ttgcgcattg cagagcagga actggagacg acgggcacgt tcaagaacaa gaaggtggag   1800
ctgaagaagg aagggttcga cctcggtaag gtcaaggagc ggctgtactg gtggacaccc   1860
aagggtgaat atgccccttt tggcgtggcg gagaacgagc agatcctcgc aggacgcgct   1920
cgtctttga                                                          1929
```

<210> SEQ ID NO 9
<211> LENGTH: 2155
<212> TYPE: DNA
<213> ORGANISM: Mortierella alpina

<400> SEQUENCE: 9

```
atccgcccat ccgctctctt gccactgatc tcaaagcgtg atccaaaggt cattcttagg     60
cagcactcac gcagctactt agaactctac ccacatatcc cttattgata caatggctcc    120
cgtcgctgca ctcgccgccg ctctggcggc aggatactat ctcaatggca agtaccaaat    180
cactaaggac ttggcgcttg ttcgcgttgg tctccatgca cgcaaaagac ttgaggcctt    240
ggtcgagaat cgggactgca gtctttacaa caggttcgag gaacaatgcc agatccggcc    300
tttctctgtt gcccttgttt ttgagaacac gtcttacacc tggagagact tggagctggc    360
gtccaacagg atggcccatt ggtttgttgc tcaaggaatc caaaaaaaag gagcgtgtgg    420
cgatgatgat gcataactcg cctctgttca ttatcacctg gctggcaatg ctcaagatca    480
tggttgtacc tgcttttatc aataaccaga ttgcaggacc tgttctggtt cattctctta    540
aagtggccga cgccaagttt ctcttgttcg attacgagtt ggcacctgtc atccaaaagt    600
cgctcaatga gatcaaggac atgggttaca atctctacac tgtcacaccc aaggatcaag    660
ttctaggtca actttacgcc aatctgcccg aggctgctcg tcaggtgttg gatgaggctc    720
cttcattctt tggttatgtc gaatggcaga acctcagtac cgaaggtttc tcgaacgaga    780
gtcgtcagga ggtggtgatc tccgaccccg cagccttgat ttacaccagc gggaccacgg    840
gattccccaa ggctgctatc atggaccatg gacgttgcaa cttggcttcg atctcttatg    900
gcactctatg cggcatcaaa ccagagaaca aggtttacat cacattgccg ctctatcatt    960
ctgctggagc catcattggt ctgggccaga gcttcaccag cggatgcacc attgtgctgg   1020
cgcgaaagtt ctccgtgaca aagttttggc gtgattgcgt tgagtacgac gtaactcatt   1080
ttcagtacat tggcgaactc tgccgctacc ttctaaatgc ccccgaaagt ccactggaca   1140
aaaggcataa ggttcggatg gcgtttggca acggaatgcg cccggatgtt tgggcaaagt   1200
ttcaggaacg attcaatatc cccattattg ttgagtacta cgccatgagc gaaggaacat   1260
cgtcgctttt gaatgtggcc aggaacaagc gcgaccaagg tgcggtggga ttccgtggcc   1320
ccgtcgtgag ggccttgacg cctcccgttc aactggtcaa ggtggacttt gacacggagg   1380
agctgatccg cgataagaag acgggacttt gcgtcctatg ccagcctggt gagattggag   1440
```

| | |
|---|---|
| aactggtcac gctagccgac aacaagacga ctggcgcacg ctatgctggg tatttcaatc | 1500 |
| agccagaggt ttcgaaggca aggctggtcc agaacgtggt agtgaaggac gacatctact | 1560 |
| tccggacggg tgacctcttg tactccaagg accagtactg gtactttgct gatcgcgcag | 1620 |
| gagacacgta ccggtggaaa ggagagaacg tgtcgacagc cgagattgca gacactatcg | 1680 |
| gccgtgttga gggcgtggct agttgtactg tttatggcgt atcggtcccg ggcatggatg | 1740 |
| gacgcgcggg catggctgct ttggtgctca agaactcgat tgtgcagatg gcaggtggaa | 1800 |
| gccaggcaaa gttccatgtg gatgaggctg cgctgaacgc gttttttgcgt gacttgagca | 1860 |
| aggatgtggt caaaaaactg ccggcgtatg cgattcctcg gttcttgcgc attgcagagc | 1920 |
| aggaactgga gacgacgggc acgttcaaga acaagaaggt ggagctgaag aaggaagggt | 1980 |
| tcgacctcgg taaggtcaag gagcggctgt actggtggac acccaagggt gaatatgccc | 2040 |
| cttttggcgt ggcggagaac gagcagatcc tcgcaggacg cgctcgtctt tgagcgatgt | 2100 |
| ttgtcaatga agtcatcggc atcatcatca tcatcaaaaa aaaaaaaaaa aaaaa | 2155 |

<210> SEQ ID NO 10
<211> LENGTH: 3041
<212> TYPE: DNA
<213> ORGANISM: Mortierella alpina
<220> FEATURE:
<221> NAME/KEY: modified_base
<222> LOCATION: (118)..(459)
<223> OTHER INFORMATION: n is a, c, g, or t

<400> SEQUENCE: 10

| | |
|---|---|
| atggcaagta ccaaatcact aaggacttgg cgcttgttcg cgttggtctc catgcacgca | 60 |
| aaaggtatga acgatgcact tggggacgc atctgtctca atgtgatttg cttgttcnnn | 120 |
| nnnnnnnnn nnnnnnnnnn nnnnnnnnnn nnnnnnnnnn nnnnnnnnnn nnnnnnnnnn | 180 |
| nnnnnnnnnn nnnnnnnnnn nnnnnnnnnn nnnnnnnnnn nnnnnnnnnn nnnnnnnnnn | 240 |
| nnnnnnnnnn nnnnnnnnnn nnnnnnnnnn nnnnnnnnnn nnnnnnnnnn nnnnnnnnnn | 300 |
| nnnnnnnnnn nnnnnnnnnn nnnnnnnnnn nnnnnnnnnn nnnnnnnnnn nnnnnnnnnn | 360 |
| nnnnnnnnnn nnnnnnnnnn nnnnnnnnnn nnnnnnnnnn nnnnnnnnnn nnnnnnnnnn | 420 |
| nnnnnnnnnn nnnnnnnnnn nnnnnnnnnc gtctactttt tttttttttt | 480 |
| ttttttgag agagaaaggt cgaatgtggg gaccgaacct atttttttc cgtgcctttt | 540 |
| aggtttgttg cttcagcgtt cttttgagct gatatctttt cgccactctt gcataccta | 600 |
| gacttgaggc cttggtcgag aatcgggact gcagtcttta caacaggttc gaggaacaat | 660 |
| gccagatccg gcctttctct gttgcccttg tttttgagaa cacgtcttac acctggagag | 720 |
| acttggagct gggtatgtgc agtaggattt tttggacgcc tgatgctgca ttctgtgata | 780 |
| gaggacatac attaaataat tgatatcatt tcgtctgtcg acctgtctgt ctatcgatat | 840 |
| acagcgtcca acaggatggt aagttggcaa ctgcatacaa gtacttcgtg ctctttatca | 900 |
| tgcgttactc acgcttcatt gcctcaatgt tccctttgaa ctaggcccat ggttttgttg | 960 |
| ctcaaggaat ccaaaaaaaa ggagcgtgtg gcgatgatga tgcataactc gcctctgttc | 1020 |
| attatcacct ggctggcaat gctcaagatc atggttgtac ctgctttat caataaccag | 1080 |
| attgcaggac ctgttctggt tcattctctt aaagtggccg acgccaagtt tctcttgttc | 1140 |
| gattacgagt tggcacctgt catccaaaag tcgctcaatg agatcaagga catgggttac | 1200 |
| aatctctaca ctgtcacacc caaggatcaa gttctaggtc aactttacgc caatctgccc | 1260 |
| gaggctgctc gtcaggtgtt ggatgaggct ccttcattct ttggttatgt cgaatggcag | 1320 |

```
aacctcagta ccgaaggttt ctcgaacgag agtcgtcagg aggtggtgat ctccgacccc   1380
gcagccttga tttacaccag cgggaccacg ggattcccca aggctgctat catgaccat    1440 ggacgttgca actgtaagca atcgcatagg atcgatagcg ctgaatggct ggcgagtgga   1500
tgcaaatggt cgagatgctt accattatcg tggtgtgcct ttttatagtg gcttcgatct   1560
cttatggcac tctatgcggc atcaaaccag agaacaaggt ttacatcaca ttgccgctct   1620
atcattctgc tggaggtacg tgcttccatc tcaccctcaa catctcttac gacgtttga    1680 tcctgttctt acactcatta cttctgggca tgggaacaaa gccatcattg gtctgggcca   1740
gagcttcacc agcggatgca ccattgtgct ggcgcgaaag ttctccgtga caaagttttg   1800
gcgtgattgc gttgagtacg acgtaactca ttttcaggta caagtcctat ccaatggtct   1860
acataccgtc cttgtgtatt ttcaacgcgc accgccacta cccgctttt atatgtatac    1920 ccgcagtaca ttggcgaact ctgccgctac cttctaaatg cccccgaaag tccactggac   1980
aaaaggcata aggttcggat ggcgtttggc aacggaatgc gcccgatgt ttgggcaaag    2040 tttcaggaac gattcaatat ccccattatt gttgagtact acgccatgag cgaaggaaca   2100
tcgtcgcttt tgaatgtggc caggaacaag cgcgaccaag gtgcggtggg attccgtggc   2160
cccgtcgtga ggtatgcggc atctgggcgc tttagttctt cgtgttcaat ggtttcatta   2220
taacatcttc agctcaactt tgcccgtgc ttttctttt caattttgtt tccactaggg     2280
ccttgacgcc tcccgttcaa ctggtcaagg tggactttga cacggaggag ctgatccgcg   2340
ataagaagac gggactttgc gtcctatgcc agcctggtga gattggagaa ctggtcacgc   2400
tagccgacaa caagacgact ggcgcacgct atgctgggta tttcaatcag ccagaggttt   2460
cgaaggcaag gctggtccag aacgtggtag tgaaggacga catctacttc cggacgggtg   2520
acctcttgta ctccaaggac cagtactggt actttgctga tcgcgcagga gacacgtacc   2580
ggtggaaagg agagaacgtg tcgacagccg agattgcaga cactatcggc cgtgttgagg   2640
gcgtggctag ttgtactgtt tatggcgtat cggtcccggg catggatgga cgcgcgggca   2700
tggctgcttt ggtgctcaag aactcgattg tgcagatggc aggtggaagc caggcaaagt   2760
tccatgtgga tgaggctgcg ctgaacgcgt ttttgcgtga cttgagcaag gatgtggtca   2820
aaaaactgcc ggcgtatgcg attcctcggt tcttgcgcat tgcagagcag gaactggaga   2880
cgacgggcac gttcaagaac aagaaggtgg agctgaagaa ggaagggttc gacctcgta    2940 aggtcaagga gcggctgtac tggtggacac ccaagggtga atatgcccct tttggcgtgg   3000
cggagaacga gcagatcctc gcaggacgcg ctcgtctttg a                       3041
```

<210> SEQ ID NO 11
<211> LENGTH: 1650
<212> TYPE: DNA
<213> ORGANISM: Mortierella alpina

<400> SEQUENCE: 11

```
atggaaacgg atgctcttac catcgctttg accatcgcca tcgccatcgt gctggctttg    60
gtcaaattca cgaaaaaga gcctgacctg catccgctcc tgctcgggca gcaatcgtct    120
gtcacgccca ttcggaacga gggcgagtcc gttatccata gatccaaaac ggtgccacac    180
gggacactgc tgacgaagcg cccgagcgag aaaatcaaga ctctgcacga tgtctggcag    240
actggagcag ctgtcaaccc agccggccga tcgttgatgt ttatgctgca gaaccagttt    300
gcgtttatcg aggccacgta tgagcaagtc aataggagga ttggcggctt cggaacaggt    360
```

```
ttcgtgaagg caacagggct aaagcccaag acggacacac cagtaggaat ctttatgccc    420
tactctcaag aatcgttcgt tgcccagcag gcattctatc gatacagctt tgttgctgtc    480
cccatccatg atctgaggaa caacgacctc ttggtggagg tagtagacca gaccaagctc    540
aaggccatca tagtctcaca aaaggtgctc ccgttattgc tgcaatctct gaaggagtgt    600
ccaaccatca agacaatcat catggcagga atctacatct cacaggagca gctggaaatg    660
gcagcacagc atggagtaaa gctgctcaaa ttcgcggcag tggaatatga gggatcctcg    720
actctgatgg agcctgttca gcctgatccg gaggatgttg ccatgatcaa ctataacaca    780
aagtcgtctt cgctctcgaa aggcgtcatg cttacccatg ccaacctgat cgcggcgatg    840
actgccttca cggagtcact tccggcaaaa aagcgtttct ccagcaaaga tcgtcttctc    900
tctcattttt ccaatggaga tgtcatctct gtcttcatgt cgagcgccat catcctgatg    960
ggaggttctt tggtctttcc atctggtttg atgaagaacg ttttgcatga ttcccaagct   1020
tctgcaccaa cgatctttgc aagcacaccc atcatcctgg aaaagattca cgaagcactt   1080
cagttgacgt atgccaaggc tccatgttc aggcgcggct tgctgccaa attggccata    1140 cttcaagctg gacgaatcac tacaacaagc ctatgggact tgattggact gggcgaggtc   1200
cgcagcaaac ttggtggaaa ggttcgaatg gttgtaacaa cacatcctac caaacctgag   1260
acgctggatt atatcagagc cgcgatgggc atccatgtca ttaccactta cggcaggaca   1320
gagacgtcgg gcattgtgac agcccgcaac atgctggatt atgccaacgc acctcattta   1380
ggaccaccag tgggttgcaa cgaggttaag cttgtggacg atgttgcagc tggctttaca   1440
agtgcagacg agcccaaccc acgaggcgag atccttatcc gaggcccaa tgtgatgaaa    1500 ggttattaca agaagccggg tgccacttca acggctatcg atgaggaagg gtggttccat   1560
tcaggagagc tgggcacatt ccactccaac ggcactttag acgtgttggg caagaagaag   1620
aagacgaagt ctgcagttgg atcaccgtca                                    1650
```

<210> SEQ ID NO 12
<211> LENGTH: 550
<212> TYPE: PRT
<213> ORGANISM: Mortierella alpina

<400> SEQUENCE: 12

```
Met Glu Thr Asp Ala Leu Thr Ile Ala Leu Thr Ile Ala Ile Ala Ile
 1               5                  10                  15

Val Leu Ala Leu Val Lys Phe Asn Glu Lys Glu Pro Asp Leu His Pro
                20                  25                  30

Leu Leu Leu Gly Gln Gln Ser Ser Val Thr Pro Ile Arg Asn Glu Gly
            35                  40                  45

Glu Ser Val Ile His Arg Ser Lys Thr Val Pro His Gly Thr Leu Leu
        50                  55                  60

Thr Lys Arg Pro Ser Glu Lys Ile Lys Thr Leu His Asp Val Trp Gln
 65                  70                  75                  80

Thr Gly Ala Ala Val Asn Pro Ala Gly Arg Ser Leu Met Phe Met Leu
                85                  90                  95

Gln Asn Gln Phe Ala Phe Ile Glu Ala Thr Tyr Glu Gln Val Asn Arg
            100                 105                 110

Arg Ile Gly Gly Phe Gly Thr Gly Phe Val Lys Ala Thr Gly Leu Lys
        115                 120                 125

Pro Lys Thr Asp Thr Pro Val Gly Ile Phe Met Pro Tyr Ser Gln Glu
    130                 135                 140
```

```
Ser Phe Val Ala Gln Gln Ala Phe Tyr Arg Tyr Ser Phe Val Ala Val
145                 150                 155                 160

Pro Ile His Asp Leu Arg Asn Asn Asp Leu Leu Val Glu Val Val Asp
            165                 170                 175

Gln Thr Lys Leu Lys Ala Ile Ile Val Ser Gln Lys Val Leu Pro Leu
        180                 185                 190

Leu Leu Gln Ser Leu Lys Glu Cys Pro Thr Ile Lys Thr Ile Ile Met
    195                 200                 205

Ala Gly Ile Tyr Ile Ser Gln Glu Gln Leu Glu Met Ala Ala Gln His
210                 215                 220

Gly Val Lys Leu Leu Lys Phe Ala Ala Val Glu Tyr Glu Gly Ser Ser
225                 230                 235                 240

Thr Leu Met Glu Pro Val Gln Pro Asp Pro Glu Asp Val Ala Met Ile
            245                 250                 255

Asn Tyr Asn Thr Lys Ser Ser Ser Leu Ser Lys Gly Val Met Leu Thr
            260                 265                 270

His Ala Asn Leu Ile Ala Ala Met Thr Ala Phe Thr Glu Ser Leu Pro
        275                 280                 285

Ala Lys Lys Arg Phe Ser Ser Lys Asp Arg Leu Leu Ser His Phe Ser
290                 295                 300

Asn Gly Asp Val Ile Ser Val Phe Met Ser Ser Ala Ile Ile Leu Met
305                 310                 315                 320

Gly Gly Ser Leu Val Phe Pro Ser Gly Leu Met Lys Asn Val Leu His
            325                 330                 335

Asp Ser Gln Ala Ser Ala Pro Thr Ile Phe Ala Ser Thr Pro Ile Ile
            340                 345                 350

Leu Glu Lys Ile His Glu Ala Leu Gln Leu Thr Tyr Gly Gln Gly Ser
            355                 360                 365

Met Phe Arg Arg Gly Phe Ala Ala Lys Leu Ala Ile Leu Gln Ala Gly
            370                 375                 380

Arg Ile Thr Thr Thr Ser Leu Trp Asp Leu Ile Gly Leu Gly Glu Val
385                 390                 395                 400

Arg Ser Lys Leu Gly Gly Lys Val Arg Met Val Val Thr Thr His Pro
            405                 410                 415

Thr Lys Pro Glu Thr Leu Asp Tyr Ile Arg Ala Ala Met Gly Ile His
            420                 425                 430

Val Ile Thr Thr Tyr Gly Arg Thr Glu Thr Ser Gly Ile Val Thr Ala
            435                 440                 445

Arg Asn Met Leu Asp Tyr Ala Asn Ala Pro His Leu Gly Pro Pro Val
450                 455                 460

Gly Cys Asn Glu Val Lys Leu Val Asp Asp Val Ala Ala Gly Phe Thr
465                 470                 475                 480

Ser Ala Asp Glu Pro Asn Pro Arg Gly Glu Ile Leu Ile Arg Gly Pro
            485                 490                 495

Asn Val Met Lys Gly Tyr Tyr Lys Lys Pro Gly Ala Thr Ser Thr Ala
            500                 505                 510

Ile Asp Glu Glu Gly Trp Phe His Ser Gly Glu Leu Gly Thr Phe His
            515                 520                 525

Ser Asn Gly Thr Leu Asp Val Leu Gly Lys Lys Lys Thr Lys Ser
            530                 535                 540

Ala Val Gly Ser Pro Ser
545                 550
```

<210> SEQ ID NO 13
<211> LENGTH: 1653
<212> TYPE: DNA
<213> ORGANISM: Mortierella alpina

<400> SEQUENCE: 13

| | | | | | |
|---|---|---|---|---|---|
| atggaaacgg | atgctcttac | catcgctttg | accatcgcca | tcgccatcgt | gctggctttg | 60 |
| gtcaaattca | acgaaaaaga | gcctgacctg | catccgctcc | tgctcgggca | gcaatcgtct | 120 |
| gtcacgccca | ttcggaacga | gggcgagtcc | gttatccata | gatccaaaac | ggtgccacac | 180 |
| gggacactgc | tgacgaagcg | cccgagcgag | aaaatcaaga | ctctgcacga | tgtctggcag | 240 |
| actggagcag | ctgtcaaccc | agccggccga | tcgttgatgt | ttatgctgca | gaaccagttt | 300 |
| gcgtttatcg | aggccacgta | tgagcaagtc | aataggagga | ttggcggctt | cggaacaggt | 360 |
| ttcgtgaagg | caacagggct | aaagcccaag | acggacacac | cagtaggaat | ctttatgccc | 420 |
| tactctcaag | aatcgttcgt | tgcccagcag | gcattctatc | gatacagctt | tgttgctgtc | 480 |
| cccatccatg | atctgaggaa | caacgacctc | ttggtggagg | tagtagacca | gaccaagctc | 540 |
| aaggccatca | tagtctcaca | aaaggtgctc | ccgttattgc | tgcaatctct | gaaggagtgt | 600 |
| ccaaccatca | agacaatcat | catggcagga | atctacatct | cacaggagca | gctggaaatg | 660 |
| gcagcacagc | atggagtaaa | gctgctcaaa | ttcgcggcag | tggaatatga | gggatcctcg | 720 |
| actctgatgg | agcctgttca | gcctgatccg | gaggatgttg | ccatgatcaa | ctataacaca | 780 |
| aagtcgtctt | cgctctcgaa | aggcgtcatg | cttacccatg | ccaacctgat | cgcggcgatg | 840 |
| actgccttca | cggagtcact | tccggcaaaa | aagcgtttct | ccagcaaaga | tcgtcttctc | 900 |
| tctcattttt | ccaatggaga | tgtcatctct | gtcttcatgt | cgagcgccat | catcctgatg | 960 |
| ggaggttctt | tggtctttcc | atctggtttg | atgaagaacg | ttttgcatga | ttcccaagct | 1020 |
| tctgcaccaa | cgatctttgc | aagcacaccc | atcatcctgg | aaaagattca | cgaagcactt | 1080 |
| cagttgacgt | atggccaagg | ctccatgttc | aggcgcggct | tgctgccaa | attggccata | 1140 |
| cttcaagctg | gacgaatcac | tacaacaagc | ctatgggact | tgattggact | gggcgaggtc | 1200 |
| cgcagcaaac | ttggtggaaa | ggttcgaatg | gttgtaacaa | cacatcctac | caaacctgag | 1260 |
| acgctggatt | atatcagagc | cgcgatgggc | atccatgtca | ttaccactta | cggcaggaca | 1320 |
| gagacgtcgg | gcattgtgac | agcccgcaac | atgctggatt | atgccaacgc | acctcattta | 1380 |
| ggaccaccag | tgggttgcaa | cgaggttaag | cttgtggacg | atgttgcagc | tggctttaca | 1440 |
| agtgcagacg | agcccaaccc | acgaggcgag | atccttatcc | gaggcccaa | tgtgatgaaa | 1500 |
| ggttattaca | agaagccggg | tgccacttca | acggctatcg | atgaggaagg | gtggttccat | 1560 |
| tcaggagagc | tgggcacatt | ccactccaac | ggcactttag | acgtgttggg | caagaagaag | 1620 |
| aagacgaagt | ctgcagttgg | atcaccgtca | tga | | | 1653 |

<210> SEQ ID NO 14
<211> LENGTH: 1773
<212> TYPE: DNA
<213> ORGANISM: Mortierella alpina

<400> SEQUENCE: 14

| | | | | | |
|---|---|---|---|---|---|
| gcctactttg | cgctcgcctc | atcgacccaa | aggcagcaat | ggaaacggat | gctcttacca | 60 |
| tcgctttgac | catcgccatc | gccatcgtgc | tggctttggt | caaattcaac | gaaaaagagc | 120 |
| ctgacctgca | tccgctcctg | ctcgggcagc | aatcgtctgt | cacgccatt | cggaacgagg | 180 |
| gcgagtccgt | tatccataga | tccaaaacgg | tgccacacgg | gacactgctg | acgaagcgcc | 240 |

```
cgagcgagaa aatcaagact ctgcacgatg tctggcagac tggagcagct gtcaacccag    300
ccggccgatc gttgatgttt atgctgcaga accagtttgc gtttatcgag gccacgtatg    360
agcaagtcaa taggaggatt ggcggcttcg gaacaggttt cgtgaaggca cagggctaa     420 agcccaagac ggacacacca gtaggaatct ttatgcccta ctctcaagaa tcgttcgttg    480
cccagcaggc attctatcga tacagctttg ttgctgtccc catccatgat ctgaggaaca    540
acgacctctt ggtggaggta gtagaccaga ccaagctcaa ggccatcata gtctcacaaa    600
aggtgctccc gttattgctg caatctctga aggagtgtcc aaccatcaag acaatcatca    660
tggcaggaat ctacatctca caggagcagc tggaaatggc agcacagcat ggagtaaagc    720
tgctcaaatt cgcggcagtg gaatatgagg gatcctcgac tctgatggag cctgttcagc    780
ctgatccgga ggatgttgcc atgatcaact ataacacaaa gtcgtcttcg ctctcgaaag    840
gcgtcatgct tacccatgcc aacctgatcg cggcgatgac tgccttcacg gagtcacttc    900
cggcaaaaaa gcgtttctcc agcaaagatc gtcttctctc tcattttttcc aatggagatg    960 tcatctctgt cttcatgtcg agcgccatca tcctgatggg aggttctttg gtctttccat    1020
ctggtttgat gaagaacgtt ttgcatgatt cccaagcttc tgcaccaacg atctttgcaa    1080
gcacacccat catcctggaa aagattcacg aagcacttca gttgacgtat ggccaaggct    1140
ccatgttcag gcgcggcttt gctgccaaat tggccatact tcaagctgga cgaatcacta    1200
caacaagcct atgggacttg attggactgg gcgaggtccg cagcaaactt ggtggaaagg    1260
ttcgaatggt tgtaacaaca catcctacca aacctgagac gctggattat atcagagccg    1320
cgatgggcat ccatgtcatt accacttacg gcaggacaga gacgtcgggc attgtgacag    1380
cccgcaacat gctggattat gccaacgcac ctcatttagg accaccagtg ggttgcaacg    1440
aggttaagct tgtggacgat gttgcagctg gctttacaag tgcagacgag cccaacccac    1500
gaggcgagat ccttatccga ggccccaatg tgatgaaagg ttattacaag aagccgggtg    1560
ccacttcaac ggctatcgat gaggaagggt ggttccattc aggagagctg gcacattcc     1620 actccaacgg cactttagac gtgttgggca agaagaagaa gacgaagtct gcagttggat    1680
caccgtcatg aaaggagatg ctgcatgtgc tacagaatat aaaaagggag aagatacgtt    1740
cggtaaccac atcaaaaaaa aaaaaaaaaa aaa                                  1773

<210> SEQ ID NO 15
<211> LENGTH: 2391
<212> TYPE: DNA
<213> ORGANISM: Mortierella alpina

<400> SEQUENCE: 15
atggaaacgg atgctcttac catcgctttg accatcgcca tcgccatcgt gctggctttg     60
gtcaaattca acgaaaaaga gcctgacctg catccgctcc tgctcgggca gcaatcgtct    120
gtcacgccca ttcggaacga gggcgagtcc gttatccata gatccaaaac ggtgccacac    180
gggacactgc tgacgaagcg cccgagcgag aaaatcaaga ctctgcacga tgtctggcag    240
actggagcag ctgtcaaccc agccggccga tcgttgatgt tatgctgca gaaccagttt    300 gcgtttatcg aggtacgatg gacccgctgt agtaaccccg ctgtctcttg agcaatatcg    360
caggagtctc accattagag gattcattct ccttcgcata ggccacgtat ggtaacgtgt    420
gattcggtag cctttctgtc tgttgaagat gcggtgatgt ggatctctaa cagatcttgg    480
ttcaatggtg acacagagca agtcaatagg aggattggcg gcttcggaac aggtttcgtg    540
aaggcaacag ggctaaagcc caagacggac acaccagtag gaatctttat gccctactct    600
```

```
caaggtacgc gaacaagcgc gtgagtactg atccagcaac gcatagggac tgacgcgagt    660
gagccacgtg tttgaccttg caccgcgcct ctttactgta gaatcgttcg ttgcccagca    720
ggcattctat cgatacagct tgttgctgt ccccatccat gatctgagga caacgacct     780
cttggtggag gtagtagacc agaccaagct caaggccatc atagtctcac aaaaggtgct    840
cccgttattg ctgcaatctc tgaaggagtg tccaaccatc aagacaatca tcatggcagg    900
aatctacatc tcacaggagc agctggaaat ggcagcacag catggagtaa agctgctcaa    960
attcgcggca gtggaatatg agggatcctc gactctgatg gagcctgttc agcctggtat   1020
gtgaagcaaa agtcaaggaa atgcggttgc ttgatgttcg ctgcgatgtt ttgaccacca   1080
cgacctcttt taatagatcc ggaggatgtt gccatgatca actataacac aaagtcgtct   1140
tcggtatgga tgcttgtttt tcagtggtag ttttgtataa gcgggcatgg agatgattga   1200
gcttacttga agtactttcg cgctgcatca ttgatccgat agctctcgaa aggcgtcatg   1260
cttacccatg ccaacctgat cgcggcgatg actgccttca cggagtcact tccggcaaaa   1320
aagcgtttct ccagcaaaga tcgtcttctc tctcattttt ccaatggaga tgtcatctct   1380
gtcttcatgt cgagcgccat catcctgatg ggaggttctt tggtctttcc atctggtttg   1440
atgaagaacg ttttgcatga ttcccaagct tctgcaccaa cgatctttgc aaggtacaag   1500
atgttccagt gtgatctgtg gattgtctcg ttattcatgt gcaagatact tacggcgctg   1560
ttccatttat ttttgacccc tcctagcaca cccatcatcc tggaaaagat tcacgaagca   1620
cttcagttga cgtatggcca aggctccatg ttcaggcgcg gctttgctgc caaattggcc   1680
atacttcaag ctggacgaat cactacaaca agcctatggg acttgattgg actgggcgag   1740
gtccgcagca aacttggtgg aaaggttcga atggttgtaa caacacgtaa gtctcctttt   1800
ttaccatgcg ggcttacgta cttgcagcat gatattcgaa gatactaaca gtctttttcat   1860
gacgctcctg tagatcctac caaacctgag acgctggatt atatcagagc cgcgatgggc   1920
atccatgtca ttaccactta cggcaggaca gagacgtcgg gcattgtgac agcccgcaac   1980
atgctggatt atgccaacgc acctcattta ggaccaccag tgggttgcaa cgaggttaag   2040
cttgtggacg atgttgcagc tggctttaca agtgcagacg agcccaaccc acgaggcgag   2100
gtaaggagtg catatctctt gctgcttcat gggcgataaa aaggctcaaa tgccgttgat   2160
tctactctaa cagcgttatt ttattgttca acaatatttt gtgcctagat ccttatccga   2220
ggccccaatg tgatgaaagg ttattacaag aagccgggtg ccacttcaac ggctatcgat   2280
gaggaaggg ggttccattc aggagagctg ggcacattcc actccaacgg cactttagac   2340
gtgttgggca agaagaagaa gacgaagtct gcagttggat caccgtcatg a            2391
```

<210> SEQ ID NO 16
<211> LENGTH: 2064
<212> TYPE: DNA
<213> ORGANISM: Mortierella alpina

<400> SEQUENCE: 16

```
atgtccctcg accagaacgc ccagtccgtt gagctcccag gcacccggca accaggccag     60
acaggcatct atcgccgcaa aggcttcgag aatgcccttc tcgccgtccc acccagcaga    120
ccgcacatca agaccatcta cgatgccttc agcacggac tgaagcttaa tcccaacgga    180
gctgccctgg gcagccgagt gtacgacccg gtgacggaca cctttggagg ctatgtctgg    240
cagacgtatg cacaggtgaa cgaccgcatc actcgcttcg gcagtggatt ggtcaaaatt    300
```

```
cataaggacg tccatggtct tgccaccgtg ggccagaagt ggtctctcgg aatctgggcc    360
atcaaccgac ccgagtggac catcgcgtcc gaggcttgct cggcctacaa cctggtctcc    420
gtgggtcttt acgatacttt gggacccgag gctgtgactt atggcattaa tcacgctgag    480
tgctctattg tcgtaacaag tgtggatcat atcgcgacgc tgctgaacga atcttccaag    540
atgcctgggc tcaaaatcat catcagcatg gatgacctcg atactgggag agcaggccca    600
ggactggctc ccaccggcac catcctcagg acttacgctc aggacaaagg gtactactt     660
tatgattggt ctgaggttga agccgtcggt attcagcatg gacgaaagca tacgccacca    720
acctcctccg acgcatatac gatctgctat accagcggga caacaggctt gccaaaaggt    780
gccattttga cccatggaaa cttgatcgcc cttttggcct ccagtgatgt ggccacacca    840
gtgctggctg acgattgcct catcagtttc ttgcccctgc ctcacgtctt tggtcgggtc    900
atggagctct tcgcgatggc cgcaggagga aagattggac acagcacggg agatcctttg    960
cgtctcttgg aggacgtctc gcacctaaag ccctccatct tccccgctgt gcccagactg   1020
ctgaaccgcg tgtatgccaa ggtgtatgcg gcaactgttg gagcgcctgg actcacaggg   1080
gcactggcgc gacgaggatt ggccaccaag ctcaccaatt tgagagaggg caaaggtttc   1140
caccacccat tgtgggaccg aatcctcttc tcaaaggtca gcaagcgct cggcggcaat    1200
gtgagactga tgttgactgc ctccgctccc atctcggccg agatcttgga attcgtccgt   1260
gtcgcttttct gctgcgaggt cgtggaggca tatggacaga ctgagggcgg tggagcggcc   1320
acaaacaccg tgattggcga accgaggct ggacacgtcg gtcctcctca gcttgttgc    1380
gagatcaaac tggtggatgt acccgagctg aactactttg cgaccgataa accattccct   1440
cgtggtgaga tttgtgtccg tggacccggt gtcattcctg gttatctcaa ggatgaggcc   1500
aagaccaagg agaccattga tgaggagggc tggctgcact cgggcgatat cgccatcatg   1560
agtggcaaag gcaccgttac catcattgac aggaagaaga acgtgttcaa gctgagccaa   1620
ggagaataca tcgcggcaga gaacattgaa gggcgtttcc tctccaaggt tccattcatc   1680
caacaaattc tggtgcacgg cgactcgacc gagagctgtt tggtggccat cttgatccca   1740
gagcctgagg ccttcatccc ctttgtgaac aaagtgctcg agaacgtcaa tcttcaacct   1800
ggagatcttg cagcctacag gaagatcgtt aacaacccaa agctgcgcca ggctgtcctc   1860
aaagagctga tcaaggctgg caaggatgct ggattgaaag ctttgagat tccaaaggcg    1920
atcctcctcg aatctgaggc attcacggtc gaaaacgaca agatgacccc gactttcaag   1980
atcaaaagac ccctgtcgt ccaggcttac cgcgagcaac tgacagccct ctacaacgaa    2040
atccatcaaa aggaatccaa gctg                                          2064
```

<210> SEQ ID NO 17
<211> LENGTH: 688
<212> TYPE: PRT
<213> ORGANISM: Mortierella alpina

<400> SEQUENCE: 17

Met Ser Leu Asp Gln Asn Ala Gln Ser Val Glu Leu Pro Gly Thr Arg
1               5                   10                  15

Gln Pro Gly Gln Thr Gly Ile Tyr Arg Arg Lys Gly Phe Glu Asn Ala
            20                  25                  30

Leu Leu Ala Val Pro Pro Ser Arg Pro His Ile Lys Thr Ile Tyr Asp
        35                  40                  45

Ala Phe Gln His Gly Leu Lys Leu Asn Pro Asn Gly Ala Ala Leu Gly
    50                  55                  60

-continued

```
Ser Arg Val Tyr Asp Pro Val Thr Asp Thr Phe Gly Tyr Val Trp
 65                  70                  75                  80

Gln Thr Tyr Ala Gln Val Asn Asp Arg Ile Thr Arg Phe Gly Ser Gly
                 85                  90                  95

Leu Val Lys Ile His Lys Asp Val His Gly Leu Ala Thr Val Gly Gln
                100                 105                 110

Lys Trp Ser Leu Gly Ile Trp Ala Ile Asn Arg Pro Glu Trp Thr Ile
                115                 120                 125

Ala Ser Glu Ala Cys Ser Ala Tyr Asn Leu Val Ser Val Gly Leu Tyr
130                 135                 140

Asp Thr Leu Gly Pro Glu Ala Val Thr Tyr Gly Ile Asn His Ala Glu
145                 150                 155                 160

Cys Ser Ile Val Val Thr Ser Val Asp His Ile Ala Thr Leu Leu Asn
                165                 170                 175

Glu Ser Ser Lys Met Pro Gly Leu Lys Ile Ile Ser Met Asp Asp
                180                 185                 190

Leu Asp Thr Gly Arg Ala Gly Pro Gly Leu Ala Pro Thr Gly Thr Ile
                195                 200                 205

Leu Arg Thr Tyr Ala Gln Asp Lys Gly Val Leu Leu Tyr Asp Trp Ser
210                 215                 220

Glu Val Glu Ala Val Gly Ile Gln His Gly Arg Lys His Thr Pro Pro
225                 230                 235                 240

Thr Ser Ser Asp Ala Tyr Thr Ile Cys Tyr Thr Ser Gly Thr Thr Gly
                245                 250                 255

Leu Pro Lys Gly Ala Ile Leu Thr His Gly Asn Leu Ile Ala Leu Leu
                260                 265                 270

Ala Ser Ser Asp Val Ala Thr Pro Val Leu Ala Asp Asp Cys Leu Ile
                275                 280                 285

Ser Phe Leu Pro Leu Pro His Val Phe Gly Arg Val Met Glu Leu Phe
290                 295                 300

Ala Met Ala Ala Gly Gly Lys Ile Gly Tyr Ser Thr Gly Asp Pro Leu
305                 310                 315                 320

Arg Leu Leu Glu Asp Val Ser His Leu Lys Pro Ser Ile Phe Pro Ala
                325                 330                 335

Val Pro Arg Leu Leu Asn Arg Val Tyr Ala Lys Val Tyr Ala Ala Thr
                340                 345                 350

Val Gly Ala Pro Gly Leu Thr Gly Ala Leu Ala Arg Arg Gly Leu Ala
                355                 360                 365

Thr Lys Leu Thr Asn Leu Arg Glu Gly Lys Gly Phe His His Pro Leu
                370                 375                 380

Trp Asp Arg Ile Leu Phe Ser Lys Val Lys Gln Ala Leu Gly Gly Asn
385                 390                 395                 400

Val Arg Leu Met Leu Thr Ala Ser Ala Pro Ile Ser Ala Glu Ile Leu
                405                 410                 415

Glu Phe Val Arg Val Ala Phe Cys Cys Glu Val Val Glu Ala Tyr Gly
                420                 425                 430

Gln Thr Glu Gly Gly Gly Ala Ala Thr Asn Thr Val Ile Gly Glu Thr
                435                 440                 445

Glu Ala Gly His Val Gly Pro Pro Gln Ala Cys Cys Glu Ile Lys Leu
                450                 455                 460

Val Asp Val Pro Glu Leu Asn Tyr Phe Ala Thr Asp Lys Pro Phe Pro
465                 470                 475                 480
```

```
Arg Gly Glu Ile Cys Val Arg Gly Pro Gly Val Ile Pro Gly Tyr Leu
                485                 490                 495
Lys Asp Glu Ala Lys Thr Lys Glu Thr Ile Asp Glu Glu Gly Trp Leu
            500                 505                 510
His Ser Gly Asp Ile Ala Ile Met Ser Gly Lys Gly Thr Val Thr Ile
        515                 520                 525
Ile Asp Arg Lys Lys Asn Val Phe Lys Leu Ser Gln Gly Glu Tyr Ile
    530                 535                 540
Ala Ala Glu Asn Ile Glu Gly Arg Phe Leu Ser Lys Val Pro Phe Ile
545                 550                 555                 560
Gln Gln Ile Leu Val His Gly Asp Ser Thr Glu Ser Cys Leu Val Ala
                565                 570                 575
Ile Leu Ile Pro Glu Pro Glu Ala Phe Ile Pro Phe Val Asn Lys Val
            580                 585                 590
Leu Glu Asn Val Asn Leu Gln Pro Gly Asp Leu Ala Ala Tyr Arg Lys
        595                 600                 605
Ile Val Asn Asn Pro Lys Leu Arg Gln Ala Val Leu Lys Glu Leu Ile
    610                 615                 620
Lys Ala Gly Lys Asp Ala Gly Leu Lys Gly Phe Glu Ile Pro Lys Ala
625                 630                 635                 640
Ile Leu Leu Glu Ser Glu Ala Phe Thr Val Glu Asn Asp Lys Met Thr
                645                 650                 655
Pro Thr Phe Lys Ile Lys Arg His Pro Val Val Gln Ala Tyr Arg Glu
            660                 665                 670
Gln Leu Thr Ala Leu Tyr Asn Glu Ile His Gln Lys Glu Ser Lys Leu
        675                 680                 685

<210> SEQ ID NO 18
<211> LENGTH: 2067
<212> TYPE: DNA
<213> ORGANISM: Mortierella alpina

<400> SEQUENCE: 18
atgtccctcg accagaacgc ccagtccgtt gagctcccag gcacccggca accaggccag    60
acaggcatct atcgccgcaa aggcttcgag aatgcccttc tcgccgtccc acccagcaga   120
ccgcacatca agaccatcta cgatgccttc agcacggac tgaagcttaa tccaacgga    180 gctgccctgg gcagccgagt gtacgacccg gtgacggaca ccttggagg ctatgtctgg   240 cagacgtatg cacaggtgaa cgaccgcatc actcgcttcg cagtggatt ggtcaaaatt   300 cataaggacg tccatggtct tgccaccgtg ggcagaagt ggtctctcgg aatctgggcc   360
atcaaccgac ccgagtggac catcgcgtcc gaggcttgct cggcctacaa cctggtctcc   420
gtgggtcttt acgatacttt gggacccgag gctgtgactt atggcattaa tcacgctgag   480
tgctctattg tcgtaacaag tgtggatcat atcgcgacgc tgctgaacga atcttccaag   540
atgcctgggc tcaaaatcat catcagcatg gatgacctcg atactgggag agcaggccca   600
ggactggctc ccaccggcac catcctcagg acttacgctc aggacaaagg ggtactactt   660
tatgattggt ctgaggttga agccgtcggt attcagcatg gacgaaagca tacgccacca   720
acctcctccg acgcatatac gatctgctat accagcggga caacaggctt gccaaaaggt   780
gccattttga cccatggaaa cttgatcgcc ctttttggcct ccagtgatgt ggccacacca   840
gtgctggctg acgattgcct catcagtttc ttgcccctgc ctcacgtctt tggtcgggtc   900
atggagctct tcgcgatggc cgcaggagga aagattggct acagcacggg agatcctttg   960
```

```
cgtctcttgg aggacgtctc gcacctaaag ccctccatct tccccgctgt gcccagactg    1020
ctgaaccgcg tgtatgccaa ggtgtatgcg gcaactgttg gagcgcctgg actcacaggg    1080
gcactggcgc gacgaggatt ggccaccaag ctcaccaatt tgagagaggg caaaggtttc    1140
caccacccat tgtgggaccg aatcctcttc tcaaaggtca agcaagcgct cggcggcaat    1200
gtgagactga tgttgactgc ctccgctccc atctcggccg agatcttgga attcgtccgt    1260
gtcgctttct gctgcgaggt cgtggaggca tatggacaga ctgagggcgg tggagcggcc    1320
acaaacaccg tgattggcga gaccgaggct ggacacgtcg gtcctcctca agcttgttgc    1380
gagatcaaac tggtggatgt acccgagctg aactactttg cgaccgataa accattccct    1440
cgtggtgaga tttgtgtccg tggacccggt gtcattcctg gttatctcaa ggatgaggcc    1500
aagaccaagg agaccattga tgaggagggc tggctgcact cggcgatat cgccatcatg    1560 agtggcaaag gcaccgttac catcattgac aggaagaaga acgtgttcaa gctgagccaa    1620
ggagaataca tcgcggcaga gaacattgaa gggcgtttcc tctccaaggt tccattcatc    1680
caacaaattc tggtgcacgg cgactcgacc gagagctgtt tggtgccat cttgatccca    1740 gagcctgagg ccttcatccc ctttgtgaac aaagtgctcg agaacgtcaa tcttcaacct    1800
ggagatcttg cagcctacag gaagatcgtt aacaacccaa agctgcgcca ggctgtcctc    1860
aaagagctga tcaaggctgg caaggatgct ggattgaaag gctttgagat tccaaaggcg    1920
atcctcctcg aatctgaggc attcacggtc gaaaacgaca gatgaccccc gactttcaag    1980
atcaaaagac accctgtcgt ccaggcttac cgcgagcaac tgacagcccct ctacaacgaa    2040 atccatcaaa aggaatccaa gctgtaa                                        2067

<210> SEQ ID NO 19
<211> LENGTH: 2337
<212> TYPE: DNA
<213> ORGANISM: Mortierella alpina

<400> SEQUENCE: 19
cacacgctca cgttcgctct caccccgaccc actccccact ctcgctctca ttctctccct     60
tgtccttccc ttgtcccttt caaggtctaa cagcatcaac atcagcatca gcatcaagct    120
tctcattcct ccctcgtcta aatctctgaa agagttcgct ttgcaattca gcaatgtccc    180
tcgaccagaa cgcccagtcc gttgagctcc caggcacccg gcaaccaggc cagacaggca    240
tctatcgccg caaaggcttc gagaatgccc ttctcgccgt cccacccagc agaccgcaca    300
tcaagaccat ctacgatgcc ttccagcacg gactgaagct taatcccaac ggagctgccc    360
tgggcagccg agtgtacgac ccggtgacgg acacctttgg aggctatgtc tggcagacgt    420
atgcacaggt gaacgaccgc atcactcgct tcggcagtgg attggtcaaa attcataagg    480
acgtccatgg tcttgccacc gtgggccaga agtggtctct cggaatctgg gccatcaacc    540
gacccgagtg gaccatcgcg tccgaggctt gctcggccta caacctggtc tccgtgggtc    600
tttacgatac tttgggaccc gaggctgtga cttatggcat taatcacgct gagtgctcta    660
ttgtcgtaac aagtgtggat catatcgcga cgctgctgaa cgaatcttcc aagatgcctg    720
ggctcaaaat catcatcagc atggatgacc tcgatactgg gagagcaggc ccaggactgg    780
ctcccaccgg caccatcctc aggacttacg ctcaggacaa agggggtacta ctttatgatt    840 ggtctgaggt tgaagccgtc ggtattcagc atggacgaaa gcatacgcca ccaacctcct    900
ccgacgcata tacgatctgc tataccgcg ggacaacagg cttgccaaaa ggtgccattt    960
tgacccatgg aaacttgatc gccctttggg cctccagtga tgtggccaca ccagtgctgg   1020
```

```
ctgacgattg cctcatcagt ttcttgcccc tgcctcacgt ctttggtcgg gtcatggagc      1080
tcttcgcgat ggccgcagga ggaaagattg gctacagcac gggagatcct ttgcgtctct      1140
tggaggacgt ctcgcaccta aagccctcca tcttccccgc tgtgcccaga ctgctgaacc      1200
gcgtgtatgc caaggtgtat gcggcaactg ttggagcgcc tggactcaca ggggcactgg      1260
cgcgacgagg attggccacc aagctcacca atttgagaga gggcaaaggt ttccaccacc      1320
cattgtggga ccgaatcctc ttctcaaagg tcaagcaagc gctcggcggc aatgtgagac      1380
tgatgttgac tgcctccgct cccatctcgg ccgagatctt ggaattcgtc cgtgtcgctt      1440
tctgctgcga ggtcgtggag gcatatggac agactgaggg cggtggagcg ccacaaaca      1500 ccgtgattgg cgagaccgag gctggacacg tcggtcctcc tcaagcttgt tgcgagatca      1560
aactggtgga tgtacccgag ctgaactact ttgcgaccga taaaccattc cctcgtggtg      1620
agatttgtgt ccgtggaccc ggtgtcattc ctggttatct caaggatgag gccaagacca      1680
aggagaccat tgatgaggag ggctggctgc actcgggcga tatcgccatc atgagtggca      1740
aaggcaccgt taccatcatt gacaggaaga agaacgtgtt caagctgagc caaggagaat      1800
acatcgcggc agagaacatt gaagggcgtt tcctctccaa ggttccattc atccaacaaa      1860
ttctggtgca cggcgactcg accgagagct gtttggtggc catcttgatc ccagagcctg      1920
aggccttcat cccctttgtg aacaaagtgc tcgagaacgt caatcttcaa cctgagatc      1980 ttgcagccta caggaagatc gttaacaacc caaagctgcg ccaggctgtc ctcaaagagc      2040
tgatcaaggc tggcaaggat gctggattga aaggctttga gattccaaag gcgatcctcc      2100
tcgaatctga ggcattcacg gtcgaaaacg acaagatgac cccgactttc aagatcaaaa      2160
gacaccctgt cgtccaggct taccgcgagc aactgcagc cctctacaac gaaatccatc      2220
aaaaggaatc caagctgtaa aaagaaaccc ttagaacctg cggtgctcgc agcaattaaa      2280
aaaaaaagag agatattact ctcacagcta aaaaaaaaaa aaaaaaaaaa aaaaaaa        2337

<210> SEQ ID NO 20
<211> LENGTH: 2801
<212> TYPE: DNA
<213> ORGANISM: Mortierella alpina

<400> SEQUENCE: 20
atgtccctcg accagaacgc ccagtccgtt gagctcccag gcacccggca accaggccag        60
acaggtaaca caggccagca gtactgcacc cgttttccat taaggttcca accccagtct       120
tggacatggg gcgagacctg cttgttgtta ctgtggattc acaccccgcg cgccccttcc       180
cttctggtgc cttgacccgt gtgacacccc gcaaactgct cagctcttct cggctgacca       240
accttcattc acatccacgt aggcatctat cgccgcaaag gcttcgagaa tgcccttctc       300
gccgtcccac ccagcagacc gcacatcaag accatctacg atgccttcca gcacggactg       360
aagcttaatc ccaacggagc tgccctgggc agccgagtgt acgacccggt gacggacacc       420
tttggaggct atgtctggca gacgtatgca caggtgaacg accgcatcac tcgcttcggc       480
agtggattgg tcaaaattca taaggacgtc catggtcttg ccaccgtggg ccagaagtgg       540
tctctcggaa tctgggccat caaccgaccc gagtggacca tcgcgtccga ggcttgctcg       600
gcctacaacc tggtctccgt gggtctttac gatactttgg acccgaggc tgtgacttat       660 ggcattaatc acgctgagtg ctctattgtc gtaacaagtg gtaaggacat gaagccataa       720
cgacaacggc taaaaaaaaa catggttctc atgacaagta tcgatagtaa cgttattctt       780
```

```
ggcgcttgta tgtgtttcta gtggatcata tcgcgacgct gctgaacgaa tcttccaaga      840
tgcctgggct caaaatcatc atcagcatgg atgacctcga tactgggaga gcaggcccag      900
gactggctcc caccggcacc atcctcagga cttacgctca ggacaaaggg gtactacttt      960
atgattggtc tgaggttgaa gccgtcggta ttcagcatgg acgaaagcat acgccaccaa     1020
cctcctccga cgcatatacg atctgctata ccagcgggac aacaggcttg ccagtaatat     1080
gttgctttta ttcccacgca tacagtgtgc cgatattttc aatgttcaat tgctctcatt     1140
agatgcatga cacttatcat tacttaagcg actttccttt ggcgttcata gaaaggtgcc     1200
attttgaccc atggaaactt gatcgccctt ttggcctcca gtgatgtggc cacaccagtg     1260
ctggctgacg attgcctcat cagtttcttg cccctgcctc acgtctttgg tcgggtcatg     1320
gagctcttcg cgatggccgc aggaggaaag attggctaca gcacgggaga tcctttgcgt     1380
ctcttggagg acgtctcgca cctaaagccc tccatcttcc ccgctgtgcc cagactgctg     1440
aaccgcgtgt atgccaaggt gtatgcggca actgttggag cgcctggact cacaggggca     1500
ctggcgcgac gaggattggc caccaagctc accaatttga gagagggcaa aggtttccac     1560
cacccattgt gggaccgaat cctcttctca aggtcaagc aagcgctcgg cggcaatgtg      1620
agactgatgt tgactggtaa gtgtgctttt ggaagatgaa atcacgttta tgtaaccccc     1680
cccccccccc cttgtttata aacattaatc gttgtactgt cgtcgtctag cctccgctcc     1740
catctcggcc gagatcttgg aattcgtccg tgtcgctttc tgctgcgagg tcgtggaggc     1800
atatggacag actgagggcg gtggagcggc cacaaacacc gtgattggcg agaccgaggc     1860
tggacacgtc ggtcctcctc aagcttgttg cgagatcaaa ctggtggatg tacccgagct     1920
gaactacttt gcgaccgata accattccc tcgtggtgag atttgtgtcc gtggacccgg      1980
tgtcattcct ggttatctca aggatgaggc caagaccaag gagaccattg atgaggaggg     2040
ctggctgcac tcgggcgata tcgccatcat gagtggcaaa ggcaccgtta ccatcattga     2100
caggaagaag aacgtgttca agtaacaaa acagtgcgc tctccacaga tctgttagcg       2160 cgcттттттct gcgcacagta cactgaaacc accctgtttt gctttgttcc tgaactagct     2220
gagccaagga gaatacatcg cggcagaaa cattgaaggg cgtttcctct ccaaggttcc      2280
attcatccaa caaattctgg tgcacggcga ctcgaccgag agctgtttgg tggccatctt     2340
gatcccagag cctgaggcct tcatcccctt tgtgaacaaa gtgctcgaga cgtcaatct      2400 tcaacctgga gatcttgcag cctacaggaa gatcgttaac aacccaaagc tgcgccaggc     2460
tgtcctcaaa gagctgatca aggctggcaa ggatgctgga ttgaaagggt acgtacagaa     2520
ctctctttgc taccgtagcg gaggcccact agagttgagg tgatacagat cgacagaaaa     2580
aaaaaaaaaa ctaaacaatc tctcttcaaa aacttggtgt tctcttgtac cacagctttg     2640
agattccaaa ggcgatcctc ctcgaatctg aggcattcac ggtcgaaaac gacaagatga     2700
ccccgacttt caagatcaaa agacaccctg tcgtccaggc ttaccgcgag caactgacag     2760
ccctctacaa cgaaatccat caaaaggaat ccaagctgta a                        2801
```

<210> SEQ ID NO 21
<211> LENGTH: 1977
<212> TYPE: DNA
<213> ORGANISM: Mortierella alpina

<400> SEQUENCE: 21

```
atgaccaccc aattgtactc catcgaagtg gcaggcagcc cagagattcc gggcgagggc       60
aaacctcggc gcagcgttct cagcccagac aaactcgtcc agagctatca gtctttcaag     120
```

```
ggcgacggct ccatcaccac tctatatgag aacttttgg agggcatcca gcgctcagag    180
ggaggagagt ttctcggaca ccgccccatc gtcgataatg tagctcagcc gtacgaatgg    240
ctaagctaca cgcgcgttca ggaacgtgtc gccaactttg cgctggtct catccagctg     300 ggcctgaaag tcgactcgaa cttttggcatc ttttccatca acaggcccga atggacaatg   360
agtgagctgg caggctacat gtacaacttt acatctgtgc cgctttacga cactctgggc    420
gtctcggcca tcgaatacat cgttaatcag accgagatgg agaccatcat cgcgtcggct    480
gataaagcct cgatcctgtt aaacatgaaa tcaactctgc cgacactcaa gaacattgtc    540
gttatgggct cgctcgaaga cgcgctcgtt gtcgagggta gggaaatgga tatccacatc    600
gttgcgtgga gtgacgtcga acgcgatggc ttcaacaacc ccgcgccagc caaccctcca    660
acaccggacg acgtcgccac catctgctac acgtcaggaa caaccgggac accaaagggc    720
gcaatcctga cccacaaaaa ctttgtggct ggccttgcct cgttccatat gatggcaaag    780
caccaaaagt ttttcatccc ctcgagcgtt gacactcaca tatcttacct gccctggca    840 catgtgttcg agcgtttgtc tcaggctgtt atgatttctg gcgcagctcg gattgggtat    900
taccaaggag acactttgaa gctactcgat gatgtggcga tcttgcagcc caccatcttt    960
gtgtccgttc cacgactctt aacaggatt tacgacaagg ttctagcagg tgtgaaagcc    1020
aagggcggtc tcgcagcttt cttattcaac cgcgcttttg aaaccaagaa ggctaatttg    1080
aaacgcggta tcctggagca cgccatctgg gatcgactgg tatttggtgc aattcgtgcg    1140
cgactcggtg gcaaagttaa gcatattgtc tcaggatcag cccctatagc cccgacgtc    1200 atggatttcc ttcgcatttg cttcagtgcc gacgtttatg aagggtatgg acagacggag    1260
caggctgctg gtttgtgtat gagctacaga ggtgacttga cctcgggtca agtgggaccc    1320
cctcagctgt gcgtcgaagt gaagctcaga gacgttccgg acatgcacta cacaagccag    1380
gacaagcctc gccctcgcgg ggagatcatg cttcgaggcc attcagtttt caaaggctat    1440
tacaaggctc caaagcaaac agaggagaca ctggacgcac agggatgggc aagcactgga    1500
gacgttggtg aatgggacga gcgtggccgc ttggtggtga tcgaccgtgt caaaacatt    1560 ttcaagttgg ctcaaggcga atacattgca cctgaaaaga tcgaagccgt cctggccaaa    1620
cactaccttg tcgcccaggt cttgtctac ggagactcct tccaagcgac attggtggga    1680
gttgtcgtgc ccgatgcgga gacgctaaag ccttgggccg atgaccatgg ccttggaggc    1740
aagagctatg aagaactatg cgctcatccc gctgtcaaag aaactttgct gaaggagctc    1800
aaagagtttg gtcgtgaaaa tgatctgaag gctttgaga tattgaagaa cattcatgta    1860
acggcggagc aattctcaat tgagaatgat ctttgacac ccacattcaa gctgaagaga    1920
cacaccgcga aagagaagta catcgccgag attgagctga tgtataacgg gatccac      1977
```

<210> SEQ ID NO 22
<211> LENGTH: 659
<212> TYPE: PRT
<213> ORGANISM: Mortierella alpina

<400> SEQUENCE: 22

Met Thr Thr Gln Leu Tyr Ser Ile Glu Val Ala Gly Ser Pro Glu Ile
1               5                   10                  15

Pro Gly Glu Gly Lys Pro Arg Arg Ser Val Leu Ser Pro Asp Lys Leu
            20                  25                  30

Val Gln Ser Tyr Gln Ser Phe Lys Gly Asp Gly Ser Ile Thr Thr Leu
        35                  40                  45

```
Tyr Glu Asn Phe Leu Glu Gly Ile Gln Arg Ser Gly Gly Glu Phe
     50                  55                  60
Leu Gly His Arg Pro Ile Val Asp Asn Val Ala Gln Pro Tyr Glu Trp
 65                  70                  75                  80
Leu Ser Tyr Thr Arg Val Gln Glu Arg Val Ala Asn Phe Gly Ala Gly
                 85                  90                  95
Leu Ile Gln Leu Gly Leu Lys Val Asp Ser Asn Phe Gly Ile Phe Ser
                100                 105                 110
Ile Asn Arg Pro Glu Trp Thr Met Ser Glu Leu Ala Gly Tyr Met Tyr
                115                 120                 125
Asn Phe Thr Ser Val Pro Leu Tyr Asp Thr Leu Gly Val Ser Ala Ile
    130                 135                 140
Glu Tyr Ile Val Asn Gln Thr Glu Met Glu Thr Ile Ile Ala Ser Ala
145                 150                 155                 160
Asp Lys Ala Ser Ile Leu Leu Asn Met Lys Ser Thr Leu Pro Thr Leu
                165                 170                 175
Lys Asn Ile Val Val Met Gly Ser Leu Glu Asp Ala Leu Val Val Glu
                180                 185                 190
Gly Arg Glu Met Asp Ile His Ile Val Ala Trp Ser Asp Val Glu Arg
                195                 200                 205
Asp Gly Phe Asn Asn Pro Ala Pro Ala Asn Pro Pro Thr Pro Asp Asp
    210                 215                 220
Val Ala Thr Ile Cys Tyr Thr Ser Gly Thr Thr Gly Thr Pro Lys Gly
225                 230                 235                 240
Ala Ile Leu Thr His Lys Asn Phe Val Ala Gly Leu Ala Ser Phe His
                245                 250                 255
Met Met Ala Lys His Gln Lys Phe Phe Ile Pro Ser Ser Val Asp Thr
                260                 265                 270
His Ile Ser Tyr Leu Pro Leu Ala His Val Phe Glu Arg Leu Ser Gln
                275                 280                 285
Ala Val Met Ile Ser Gly Ala Ala Arg Ile Gly Tyr Tyr Gln Gly Asp
                290                 295                 300
Thr Leu Lys Leu Leu Asp Asp Val Ala Ile Leu Gln Pro Thr Ile Phe
305                 310                 315                 320
Val Ser Val Pro Arg Leu Phe Asn Arg Ile Tyr Asp Lys Val Leu Ala
                325                 330                 335
Gly Val Lys Ala Lys Gly Gly Leu Ala Ala Phe Leu Phe Asn Arg Ala
                340                 345                 350
Phe Glu Thr Lys Lys Ala Asn Leu Lys Arg Gly Ile Leu Glu His Ala
                355                 360                 365
Ile Trp Asp Arg Leu Val Phe Gly Ala Ile Arg Ala Arg Leu Gly Gly
                370                 375                 380
Lys Val Lys His Ile Val Ser Gly Ser Ala Pro Ile Ala Pro Asp Val
385                 390                 395                 400
Met Asp Phe Leu Arg Ile Cys Phe Ser Ala Asp Val Tyr Glu Gly Tyr
                405                 410                 415
Gly Gln Thr Glu Gln Ala Ala Gly Leu Cys Met Ser Tyr Arg Gly Asp
                420                 425                 430
Leu Thr Ser Gly Gln Val Gly Pro Pro Gln Leu Cys Val Glu Val Lys
                435                 440                 445
Leu Arg Asp Val Pro Asp Met His Tyr Thr Ser Gln Asp Lys Pro Arg
    450                 455                 460
```

```
Pro Arg Gly Glu Ile Met Leu Arg Gly His Ser Val Phe Lys Gly Tyr
465                 470                 475                 480

Tyr Lys Ala Pro Lys Gln Thr Glu Glu Thr Leu Asp Ala Gln Gly Trp
                485                 490                 495

Ala Ser Thr Gly Asp Val Gly Glu Trp Asp Glu Arg Gly Arg Leu Val
            500                 505                 510

Val Ile Asp Arg Val Lys Asn Ile Phe Lys Leu Ala Gln Gly Glu Tyr
        515                 520                 525

Ile Ala Pro Glu Lys Ile Glu Ala Val Leu Ala Lys His Tyr Leu Val
    530                 535                 540

Ala Gln Val Phe Val Tyr Gly Asp Ser Phe Gln Ala Thr Leu Val Gly
545                 550                 555                 560

Val Val Val Pro Asp Ala Glu Thr Leu Lys Pro Trp Ala Asp Asp His
                565                 570                 575

Gly Leu Gly Gly Lys Ser Tyr Glu Glu Leu Cys Ala His Pro Ala Val
            580                 585                 590

Lys Glu Thr Leu Leu Lys Glu Leu Lys Glu Phe Gly Arg Glu Asn Asp
        595                 600                 605

Leu Lys Gly Phe Glu Ile Leu Lys Asn Ile His Val Thr Ala Glu Gln
    610                 615                 620

Phe Ser Ile Glu Asn Asp Leu Leu Thr Pro Thr Phe Lys Leu Lys Arg
625                 630                 635                 640

His Thr Ala Lys Glu Lys Tyr Ile Ala Glu Ile Glu Leu Met Tyr Asn
                645                 650                 655

Gly Ile His

<210> SEQ ID NO 23
<211> LENGTH: 1980
<212> TYPE: DNA
<213> ORGANISM: Mortierella alpina

<400> SEQUENCE: 23
atgaccaccc aattgtactc catcgaagtg gcaggcagcc cagagattcc gggcgagggc      60
aaacctcggc gcagcgttct cagcccagac aaactcgtcc agagctatca gtctttcaag     120
ggcgacggct ccatcaccac tctatatgag aacttttggg agggcatcca gcgctcagag     180
ggaggagagt ttctcggaca ccgccccatc gtcgataatg tagctcagcc gtacgaatgg     240
ctaagctaca cgcgcgttca ggaacgtgtc gccaactttg gcgctggtct catccagctg     300
ggcctgaaag tcgactcgaa ctttggcatc ttttccatca caggcccga atggacaatg     360 agtgagctgg caggctacat gtacaacttt acatctgtgc cgctttacga cactctgggc     420
gtctcggcca tcgaatacat cgttaatcag accgagatgg agaccatcat cgcgtcgggt     480
gataaagcct cgatcctgtt aaacatgaaa tcaactctgc cgacactcaa gaacattgtc     540
gttatgggct cgctcgaaga cgcgctcgtt gtcgagggta gggaaatgga tatccacatc     600
gttgcgtgga gtgacgtcga acgcgatggc ttcaacaacc ccgcgccagc caaccctcca     660
acaccggacg acgtcgccac catctgctac acgtcaggaa caaccgggac accaaagggc     720
gcaatcctga cccacaaaaa ctttgtggct ggccttgcct cgttccatat gatggcaaag     780
caccaaaagt ttttcatccc ctcgagcgtt gacactcaca tatcttacct gcccctggca     840
catgtgttcg agcgttttgt tcaggctgtt atgattctg gcgcagctcg gattgggtat     900
taccaaggag acactttgaa gctactcgat gatgtggcga tcttgcagcc caccatcttt     960
gtgtccgttc cacgactctt taacaggatt tacgacaagg ttctagcagg tgtgaaagcc    1020
```

```
aagggcggtc tcgcagcttt cttattcaac cgcgcttttg aaaccaagaa ggctaatttg   1080
aaacgcggta tcctggagca cgccatctgg gatcgactgg tatttggtgc aattcgtgcg   1140
cgactcggtg gcaaagttaa gcatattgtc tcaggatcag cccctatagc cccggacgtc   1200
atggatttcc ttcgcatttg cttcagtgcc gacgtttatg aagggtatgg acagacggag   1260
caggctgctg gtttgtgtat gagctacaga ggtgacttga cctcgggtca agtgggaccc   1320
cctcagctgt gcgtcgaagt gaagctcaga gacgttccgg acatgcacta cacaagccag   1380
gacaagcctc gccctcgcgg ggagatcatg cttcgaggcc attcagtttt caaaggctat   1440
tacaaggctc aaagcaaac agaggagaca ctggacgcac agggatgggc aagcactgga   1500
gacgttggtg aatgggacga gcgtggccgc ttggtggtga tcgaccgtgt caaaaacatt   1560
ttcaagttgg ctcaaggcga atacattgca cctgaaaaga tcgaagccgt cctggccaaa   1620
cactaccttg tcgcccaggt ctttgtctac ggagactcct tccaagcgac attggtggga   1680
gttgtcgtgc ccgatgcgga gacgctaaag ccttgggccg atgaccatgg ccttggaggc   1740
aagagctatg aagaactatg cgctcatccc gctgtcaaag aaactttgct gaaggagctc   1800
aaagagtttg tcgtgaaaa tgatctgaag ggctttgaga tattgaagaa cattcatgta   1860
acggcggagc aattctcaat tgagaatgat cttttgacac ccacattcaa gctgaagaga   1920
cacaccgcga aagagaagta catcgccgag attgagctga tgtataacgg gatccactga   1980

<210> SEQ ID NO 24
<211> LENGTH: 2216
<212> TYPE: DNA
<213> ORGANISM: Mortierella alpina

<400> SEQUENCE: 24 ttttttttt tttcttttct ctccaaccct ttcaccccca cgcctcggct cgtactcaag     60
cctcacgtcc acactctcgt cctctagcct gctgcattca cgattcacat tcctcctcga    120
ctccagcatc gctactccct cgtgctactt tcaccatgac cacccaattg tactccatcg    180
aagtggcagg cagcccagag attccgggcg agggcaaacc tcggcgcagc gttctcagcc    240
cagacaaact cgtccagagc tatcagtctt tcaagggcga cggctccatc accactctat    300
atgagaactt tttggagggc atccagcgct cagagggagg agagtttctc ggacaccgcc    360
ccatcgtcga taatgtagct cagccgtacg aatggctaag ctacacgcgc gttcaggaac    420
gtgtcgccaa cttggcgct ggtctcatcc agctgggcct gaaagtcgac tcgaactttg    480
gcatcttttc catcaacagg cccgaatgga caatgagtga gctggcaggc tacatgtaca    540
actttacatc tgtgccgctt tacgacactc tgggcgtctc ggccatcgaa tacatcgtta    600
atcagaccga gatggagacc atcatcgcgt cggctgataa agcctcgatc ctgttaaaca    660
tgaaatcaac tctgccgaca ctcaagaaca ttgtcgttat gggctcgctc gaagacgcgc    720
tcgttgtcga gggtagggaa atggatatcc acatcgttgc gtggagtgac gtcgaacgcg    780
atggcttcaa caaccccgcg ccagccaacc ctccaacacc ggacgacgtc gccaccatct    840
gctacacgtc aggaacaacc gggacaccaa agggcgcaat cctgacccac aaaaactttg    900
tggctggcct tgcctcgttc catatgatgg caaagcacca aaagttttc atcccctcga    960 gcgttgacac tcacatatct tacctgcccc tggcacatgt gttcgagcgt ttgtctcagg   1020
ctgttatgat ttctggcgca gctcggattg ggtattacca aggagacact ttgaagctac   1080
tcgatgatgt ggcgatcttg cagcccacca tctttgtgtc cgttccacga ctctttaaca   1140
```

```
ggatttacga caaggttcta gcaggtgtga aagccaaggg cggtctcgca gctttcttat    1200
tcaaccgcgc ttttgaaacc aagaaggcta atttgaaacg cggtatcctg gagcacgcca    1260
tctgggatcg actggtattt ggtgcaattc gtgcgcgact cggtggcaaa gttaagcata    1320
ttgtctcagg atcagcccct atagcccgga cgtcatgga tttccttcgc atttgcttca    1380
gtgccgacgt ttatgaaggg tatggacaga cggagcaggc tgctggtttg tgtatgagct    1440
acagaggtga cttgacctcg ggtcaagtgg accccctca gctgtgcgtc gaagtgaagc    1500
tcagagacgt tccggacatg cactacacaa gccaggacaa gcctcgccct cgcggggaga    1560
tcatgcttcg aggccattca gttttcaaag gctattacaa ggctccaaag caaacagagg    1620
agacactgga cgcacaggga tgggcaagca ctggagacgt tggtgaatgg gacgagcgtg    1680
gccgcttggt ggtgatcgac cgtgtcaaaa acatttttcaa gttggctcaa ggcgaataca    1740
ttgcacctga aaagatcgaa gccgtcctgg ccaaacacta ccttgtcgcc caggtctttg    1800
tctacggaga ctccttccaa gcgacattgg tgggagttgt cgtgcccgat gcggagacgc    1860
taaagccttg ggccgatgac catggccttg gaggcaagag ctatgaagaa ctatgcgctc    1920
atcccgctgt caaagaaact ttgctgaagg agctcaaaga gtttggtcgt gaaaatgatc    1980
tgaagggctt tgagatattg aagaacattc atgtaacggc ggagcaattc tcaattgaga    2040
atgatctttt gacacccaca ttcaagctga agagacacac cgcgaaagag aagtacatcg    2100
ccgagattga gctgatgtat aacgggatcc actgaaagag tctagccaaa gcagatcttt    2160
ttattactgt cgttaaaaaa actactcgta accatcaaaa aaaaaaaaaa aaaaaa       2216

<210> SEQ ID NO 25
<211> LENGTH: 2586
<212> TYPE: DNA
<213> ORGANISM: Mortierella alpina

<400> SEQUENCE: 25
atgaccaccc aattgtactc catcgaagtg gcaggcagcc cagagattcc gggcgagggc      60
aaacctcggc gcagcgttct cagcccagac aaactcgtcc agagctatca gtcttttcaag    120 ggcgacggct ccatcaccac tctatatgag aacttttttgg agggcatcca gcgctcaggt    180
actgacaccc cacatggtca gcgagacttc tccacatgac accagcgttt ctctattaac    240
gttatccctt ggcgccttttg gctttgttgt ggttaacgat gtgcctaatc atagagggag    300
gagagtttct cggacaccgc cccatcgtcg ataatgtagc tcagccgtac gaatggctaa    360
gctacacgcg cgttcaggaa cgtgtcgcca cttttggcgc tggtctcatc cagctgggcc    420
tgaaagtcga ctcgaacttt ggcatctttt ccatcaacag gcccgaatgg gtgagtgcag    480
tgggaggatc cttttttcttt tatgaaatgg gcccgtgcga gtctagattc gatgatggct    540
gcggttggac ccggcctcgg cccccaacca aacacgtgtg ggaaacccca accgactcta    600
atagaactcc gttcctctga tttggcgacg aacatactat tacctgtaga caatgagtga    660
gctggcaggc tacatgtaca actttacatc tgtgccgctt tacgacactc tgggcgtctc    720
ggccatcgaa tacatcgtta atcagaccga gatggagacc atcatcgcgt cggctgataa    780
agcctcgatc ctgttaaaca tgaaatcaac tctgccgaca ctcaagaaca ttgtcgttat    840
gggctcgctc gaagacgcgc tcgttgtcga gggtagggaa atggatatcc acatcgttgc    900
gtggagtgac gtcgaacgcg atggcttcaa caaccccgcg ccagccaacc ctccaacacc    960
ggacgacgtc gccaccatct gctacacgtc aggaacaacc gggacaccaa gtaacgttta   1020
agatgtcgat atgagaatat ctctaaaatg tggcatgcag cttgaatgag aattcactcc   1080
```

| | |
|---|---:|
| ttcatagaca cttgttgtcc tttctcaagt cactcacctc tcttcattta tcctacgtgt | 1140 |
| atgtgtatgt aggggcgcaa tcctgaccca caaaaacttt gtggctggcc ttgcctcgtt | 1200 |
| ccatatgatg gcaaagcacc aaaagttttt catccctcg agcgttgaca ctcacatatc | 1260 |
| ttacctgccc ctggcacatg tgttcgagcg tttgtctcag gctgttatga tttctggcgc | 1320 |
| agctcggatt gggtattacc aaggagacac tttgaagcta ctcgatgatg tggcgatctt | 1380 |
| gcagcccacc atctttgtgt ccgttccacg actctttaac aggatttacg acaaggttct | 1440 |
| agcaggtgtg aaagccaagg gcggtctcgc agctttctta ttcaaccgcg cttttgaaac | 1500 |
| caagaaggct aatttgaaac gcggtatcct ggagcacgcc atctgggatc gactggtatt | 1560 |
| tggtgcaatt cgtgcgcgac tcggtggcaa agttaagcat attgtctcag gatcagcccc | 1620 |
| tatagccccg gacgtcatgg atttccttcg catttgcttc agtgccgacg tttatgaagg | 1680 |
| gtatggacag acggagcagg ctgctggttt gtgtatgagc tacagaggtg acttgacctc | 1740 |
| gggtcaagtg ggaccccctc agctgtgcgt cgaagtgaag ctcagagacg ttccggacat | 1800 |
| gcactacaca agccaggaca agcctcgccc tcgcggggag atcatgcttc gaggccattc | 1860 |
| agttttcaaa ggctattaca aggctccaaa gcaaacagag gagacactgg acgcacaggg | 1920 |
| atgggcaagg tatggttttg tgcaaccaac tattttgtca attacgctta acactggttg | 1980 |
| tcatcagccc gcatctgact aaggtcacat tgtacgcgac atagcactgg agacgttggt | 2040 |
| gaatgggacg agcgtggccg cttggtggtg atcgaccgtg tcaaaaacat tttcaagttg | 2100 |
| gctcaaggcg aatacattgc acctgaaaag atcgaagccg tcctggccaa acactacctt | 2160 |
| gtcgcccagg tctttgtcta cggagactcc ttccaagcga cattggtggg agttgtcgtg | 2220 |
| cccgatgcgg agacgctaaa gccttgggcc gatgaccatg gccttggagg caagagctat | 2280 |
| gaagaactat gcgctcatcc cgctgtcaaa gaaaccttgc tgaaggagct caaagagttt | 2340 |
| ggtcgtgaaa atgatctgaa gggctttgag atattgaaga acattcatgt aacggcggag | 2400 |
| caattctcaa ttgagaatga tcttttggtg agtcgatcgg acttgcgcac cgaacagttt | 2460 |
| gagagtcaag gatcgtatat taactaagcc ttgctttggt agacacccac attcaagctg | 2520 |
| aagagacaca ccgcgaaaga gaagtacatc gccgagattg agctgatgta taacgggatc | 2580 |
| cactga | 2586 |

<210> SEQ ID NO 26
<211> LENGTH: 1977
<212> TYPE: DNA
<213> ORGANISM: Mortierella alpina

<400> SEQUENCE: 26

| | |
|---|---:|
| atggctactc aaatgtactc ggtggtcgtc cccaacagcc ccgacattcc cggcgaaggc | 60 |
| aagccccgcc gtagtgtgct ttgtccagac aagctcctgg agaactaccc ctcagtgaaa | 120 |
| gcaggctcaa cgatcacgac cctgtacgag aacttccaag aaggtgttct ccgttcaggc | 180 |
| ggcgcccatt ttttgggcca tcgtcccatt gtgaatggcc agcctcaggc ttacaagtgg | 240 |
| cagtcgtatg tcgatgtcag caagcgtgtt acgcacttcg cgctggcct ggctcatctc | 300 |
| ggcttgtctc caaagcaaaa cttggaatt ttctctatca accggcctga gtggaccatg | 360 |
| agtgagcttg ctggctatat gcacaactac accagcgtcc cctctatga tacattggga | 420 |
| gtcgccgcga tcgagtatat cgttaaccag actgagatgc agatcatcat tgcttcgtcc | 480 |
| gacaaagctt ctatcatcct ccacatgaaa tcagcacttc caaccgttca gacgattgtc | 540 |

```
gtcatggggg aatttactga cgctctcgtc gcagagggta aggagctcaa catcaacatt    600
gtatcctgga ccgatgtcga aaagagcggt cttgagcggc ctgtcgaagc cgtgcacccc    660
acagccgagg atatcgctac catctgttac acatctggaa ccactggaac gccaaaaggt    720
gctatcttga cccacaagaa ctttgttgcc actatcgctt cattccacat gatggcaaag    780
catggcaggt tcttcattcc ctcgcctgcc gacacacatg tatcctacct gccccttgcc    840
cacgtctttg agcgcctttg ccaggctgtt atgatctcgg gcgctgcgcg tattggttac    900
taccaaggag atacgctgaa gctgctggac gatgttgccg tcctgcatcc caccattttt    960
gcctccgtcc ctcgtctctt aaccgtatc tacgacaagg tgcttgctgg cgtcaaggcc   1020
aagggtggta tcgccgcctt cttgtttaac cgcgcatata attccaagaa ggccaacttg   1080
cgaaagggcg tacttgagca tccgctctgg gacaagctgg tctttggagc gattcgcgcg   1140
cgcttgggtg gcaaggttaa gcacatcgtg tcaggatctg cccccatctc tcctgatgtg   1200
atggatttcc tccgcatctg cttcagcgct gatgtgtatg agggatatgg ccagacggaa   1260
caggcagccg gattaagtat gagctatcgc ggtgatttga ctccaggaca ggttggccca   1320
cctcaactgt gcacagaggt caagttgaag gacatcccta gtatgaacta tagcagcgcg   1380
gacaagcctt tcccccgtgg agaaatcatg cttcgcggaa actctgtgtt caagggctat   1440
tacaaagcac caaagcagac tgaagaaaca ttggatgctg acggttggtc cagtaccgga   1500
gacgttggac agtgggatgc ccaaggccgt ctggtggtca ttgatcgcgt caagaacatc   1560
ttcaagttgg cgcaaggaga atatattgcg cctgaaaaga tcgaggctgt cctcgccaag   1620
cacttcctcg ttgcccagat ttttgtctat gggcactcgc tccaggccac cattgtcgcg   1680
gtggttgtcc ctgatgctga cgctcaag ttgtgggcta agaaaacaa gctgggtgac   1740
aagtcttacg aggagctgtg cgctctccct cagcttcgca caaccctcca aaaggagttg   1800
gctactttg caaagaatc ggatctgaag ggctttgaga ttcctaagaa cattcatgtt   1860
atctccgagc agtttcaat tgagaacgat cttttgaccc ccaccttcaa gctgaagaga   1920
catgctgcca agagaagta acgccgaa tcgaccgca tgtatgcaga aatcgct        1977
```

<210> SEQ ID NO 27
<211> LENGTH: 659
<212> TYPE: PRT
<213> ORGANISM: Mortierella alpina

<400> SEQUENCE: 27

Met Ala Thr Gln Met Tyr Ser Val Val Pro Asn Ser Pro Asp Ile
1               5                   10                  15

Pro Gly Glu Gly Lys Pro Arg Arg Ser Val Leu Cys Pro Asp Lys Leu
            20                  25                  30

Leu Glu Asn Tyr Pro Ser Val Lys Ala Gly Ser Thr Ile Thr Thr Leu
        35                  40                  45

Tyr Glu Asn Phe Gln Glu Gly Val Leu Arg Ser Gly Gly Ala His Phe
    50                  55                  60

Leu Gly His Arg Pro Ile Val Asn Gly Gln Pro Gln Ala Tyr Lys Trp
65                  70                  75                  80

Gln Ser Tyr Val Asp Val Ser Lys Arg Val Thr His Phe Gly Ala Gly
                85                  90                  95

Leu Ala His Leu Gly Leu Ser Pro Lys Gln Asn Phe Gly Ile Phe Ser
            100                 105                 110

Ile Asn Arg Pro Glu Trp Thr Met Ser Glu Leu Ala Gly Tyr Met His
        115                 120                 125

```
Asn Tyr Thr Ser Val Pro Leu Tyr Asp Thr Leu Gly Val Ala Ala Ile
    130                 135                 140

Glu Tyr Ile Val Asn Gln Thr Glu Met Gln Ile Ile Ala Ser Ser
145                 150                 155                 160

Asp Lys Ala Ser Ile Ile Leu His Met Lys Ser Ala Leu Pro Thr Val
                165                 170                 175

Gln Thr Ile Val Val Met Gly Glu Phe Thr Asp Ala Leu Val Ala Glu
            180                 185                 190

Gly Lys Glu Leu Asn Ile Asn Ile Val Ser Trp Thr Asp Val Glu Lys
        195                 200                 205

Ser Gly Leu Glu Arg Pro Val Glu Ala Val His Pro Thr Ala Glu Asp
    210                 215                 220

Ile Ala Thr Ile Cys Tyr Thr Ser Gly Thr Thr Gly Thr Pro Lys Gly
225                 230                 235                 240

Ala Ile Leu Thr His Lys Asn Phe Val Ala Thr Ile Ala Ser Phe His
                245                 250                 255

Met Met Ala Lys His Gly Arg Phe Phe Ile Pro Ser Pro Ala Asp Thr
            260                 265                 270

His Val Ser Tyr Leu Pro Leu Ala His Val Phe Glu Arg Leu Cys Gln
        275                 280                 285

Ala Val Met Ile Ser Gly Ala Ala Arg Ile Gly Tyr Tyr Gln Gly Asp
    290                 295                 300

Thr Leu Lys Leu Leu Asp Asp Val Ala Val Leu His Pro Thr Ile Phe
305                 310                 315                 320

Ala Ser Val Pro Arg Leu Phe Asn Arg Ile Tyr Asp Lys Val Leu Ala
                325                 330                 335

Gly Val Lys Ala Lys Gly Gly Ile Ala Ala Phe Leu Phe Asn Arg Ala
            340                 345                 350

Tyr Asn Ser Lys Lys Ala Asn Leu Arg Lys Gly Val Leu Glu His Pro
        355                 360                 365

Leu Trp Asp Lys Leu Val Phe Gly Ala Ile Arg Ala Arg Leu Gly Gly
    370                 375                 380

Lys Val Lys His Ile Val Ser Gly Ser Ala Pro Ile Ser Pro Asp Val
385                 390                 395                 400

Met Asp Phe Leu Arg Ile Cys Phe Ser Ala Asp Val Tyr Glu Gly Tyr
                405                 410                 415

Gly Gln Thr Glu Gln Ala Ala Gly Leu Ser Met Ser Tyr Arg Gly Asp
            420                 425                 430

Leu Thr Pro Gly Gln Val Gly Pro Gln Leu Cys Thr Glu Val Lys
        435                 440                 445

Leu Lys Asp Ile Pro Ser Met Asn Tyr Ser Ser Ala Asp Lys Pro Phe
    450                 455                 460

Pro Arg Gly Glu Ile Met Leu Arg Gly Asn Ser Val Phe Lys Gly Tyr
465                 470                 475                 480

Tyr Lys Ala Pro Lys Gln Thr Glu Glu Thr Leu Asp Ala Asp Gly Trp
                485                 490                 495

Ser Ser Thr Gly Asp Val Gly Gln Trp Asp Ala Gln Gly Arg Leu Val
            500                 505                 510

Val Ile Asp Arg Val Lys Asn Ile Phe Lys Leu Ala Gln Gly Glu Tyr
        515                 520                 525

Ile Ala Pro Glu Lys Ile Glu Ala Val Leu Ala Lys His Phe Leu Val
    530                 535                 540
```

```
Ala Gln Ile Phe Val Tyr Gly His Ser Leu Gln Ala Thr Ile Val Ala
545                 550                 555                 560

Val Val Val Pro Asp Ala Glu Thr Leu Lys Leu Trp Ala Lys Glu Asn
            565                 570                 575

Lys Leu Gly Asp Lys Ser Tyr Glu Glu Leu Cys Ala Leu Pro Gln Leu
        580                 585                 590

Arg Thr Thr Leu Gln Lys Glu Leu Ala Thr Phe Gly Lys Glu Ser Asp
            595                 600                 605

Leu Lys Gly Phe Glu Ile Pro Lys Asn Ile His Val Ile Ser Glu Gln
        610                 615                 620

Phe Ser Ile Glu Asn Asp Leu Leu Thr Pro Thr Phe Lys Leu Lys Arg
625                 630                 635                 640

His Ala Ala Lys Glu Lys Tyr Asn Ala Glu Ile Asp Arg Met Tyr Ala
            645                 650                 655

Glu Ile Ala

<210> SEQ ID NO 28
<211> LENGTH: 1980
<212> TYPE: DNA
<213> ORGANISM: Mortierella alpina

<400> SEQUENCE: 28
atggctactc aaatgtactc ggtggtcgtc cccaacagcc ccgacattcc cggcgaaggc      60
aagccccgcc gtagtgtgct ttgtccagac aagctcctgg agaactaccc ctcagtgaaa     120
gcaggctcaa cgatcacgac cctgtacgag aacttccaag aaggtgttct ccgttcaggc     180
ggcgcccatt ttttgggcca tcgtcccatt gtgaatggcc agcctcaggc ttacaagtgg     240
cagtcgtatg tcgatgtcag caagcgtgtt acgcacttcg gcgctggcct ggctcatctc     300
ggcttgtctc caaagcaaaa cttttggaatt ttctctatca accggctga gtggaccatg     360 agtgagcttg ctggctatat gcacaactac accagcgtcc ccctctatga tacattggga     420
gtcgccgcga tcgagtatat cgttaaccag actgagatgc agatcatcat tgcttcgtcc     480
gacaaagctt ctatcatcct ccacatgaaa tcagcacttc caaccgttca gacgattgtc     540
gtcatggggg aatttactga cgctctcgtc gcagagggta aggagctcaa catcaacatt     600
gtatcctgga ccgatgtcga aaagagcggt cttgagcggc ctgtcgaagc cgtgcacccc     660
acagccgagg atatcgctac catctgttac acatctggaa ccactggaac gccaaaaggt     720
gctatcttga cccacaagaa ctttgttgcc actatcgctt cattccacat gatggcaaag     780
catggcaggt tcttcattcc ctcgcctgcc gacacacatg tatcctacct gccccttgcc     840
cacgtctttg agcgcctttg ccaggctgtt atgatctcgg gcgctgcgcg tattggttac     900
taccaaggag atacgctgaa gctgctggac gatgttgccg tcctgcatcc caccattttt     960
gcctccgtcc ctcgtctctt taaccgtatc tacgacaagg tgcttgctgg cgtcaaggcc    1020
aagggtggta tcgccgcctt cttgtttaac gcgcatata attccaagaa ggccaacttg    1080
cgaaagggcg tacttgagca tccgctctgg gacaagctgg tctttggagc gattcgcgcg    1140
cgcttgggtg gcaaggttaa gcacatcgtg tcaggatctg ccccccatctc tcctgatgtg    1200 atggatttcc tccgcatctg cttcagcgct gatgtgtatg agggatatgg ccagacggaa    1260
caggcagccg gattaagtat gagctatcgc ggtgatttga ctccaggaca ggttggccca    1320
cctcaactgt gcacagaggt caagttgaag gacatcccta gtatgaacta tagcagcgcg    1380
gacaagcctt tcccccgtgg agaaatcatg cttcgcggaa actctgtgtt caagggctat    1440
```

```
tacaaagcac caaagcagac tgaagaaaca ttggatgctg acggttggtc cagtaccgga    1500
gacgttggac agtgggatgc ccaaggccgt ctggtggtca ttgatcgcgt caagaacatc    1560
ttcaagttgg cgcaaggaga atatattgcg cctgaaaaga tcgaggctgt cctcgccaag    1620
cacttcctcg ttgcccagat ttttgtctat gggcactcgc tccaggccac cattgtcgcg    1680
gtggttgtcc ctgatgctga cgctcaag ttgtgggcta agaaaacaa gctgggtgac       1740 aagtcttacg aggagctgtg cgctctccct cagcttcgca caaccctcca aaaggagttg    1800 gctactttg gcaaagaatc ggatctgaag ggctttgaga ttcctaagaa cattcatgtt     1860
atctccgagc agttttcaat tgagaacgat cttttgaccc ccaccttcaa gctgaagaga    1920
catgctgcca agagaagta taacgccgaa atcgaccgca tgtatgcaga aatcgcttaa    1980

<210> SEQ ID NO 29
<211> LENGTH: 2123
<212> TYPE: DNA
<213> ORGANISM: Mortierella alpina

<400> SEQUENCE: 29
tttcctcacc ttccctccgc tgccctctgc tgcacactcc tctggcttat accatccacc      60
cctctagccc cgccacttcg ccgccaacct catccgactc acaccgcaat ggctactcaa     120
atgtactcgg tggtcgtccc caacagcccc gacattcccg gcgaaggcaa gccccgccgt     180
agtgtgcttt gtccagacaa gctcctggag aactacccct cagtgaaagc aggctcaacg     240
atcacgaccc tgtacgagaa cttccaagaa ggtgttctcc gttcaggcgg cgcccatttt     300
ttgggccatc gtcccattgt gaatggccag cctcaggctt acaagtggca gtcgtatgtc     360
gatgtcagca gcgtgttac gcacttcggc gctggcctgg ctcatctcgg cttgtctcca      420
aagcaaaact ttggaatttt ctctatcaac cggcctgagt ggaccatgag tgagcttgct     480
ggctatatgc acaactacac cagcgtcccc ctctatgata cattgggagt cgccgcgatc    540
gagtatatcg ttaaccagac tgagatgcag atcatcattg cttcgtccga caaagcttct    600
atcatcctcc acatgaaatc agcacttcca accgttcaga cgattgtcgt catggggaa      660 tttactgacg ctctcgtcgc agagggtaag gagctcaaca tcaacattgt atcctggacc    720
gatgtcgaaa agagcggtct tgagcggcct gtcgaagccg tgcaccccac agccgaggat    780
atcgctacca tctgttacac atctggaacc actggaacgc caaaaggtgc tatcttgacc    840
cacaagaact tgttgccac tatcgcttca ttccacatga tggcaaagca tggcaggttc     900
ttcattccct cgcctgccga cacacatgta tcctacctgc cccttgccca cgtcttgag     960 cgccttgcc aggctgttat gatctcgggc gctgcgcgta ttggttacta ccaaggagat    1020
acgctgaagc tgctggacga tgttgccgtc ctgcatccca ccattttgc ctccgtccct     1080 cgtctcttta accgtatcta cgacaaggtg cttgctggcg tcaaggccaa gggtggtatc    1140
gccgccttct tgtttaaccg cgcatataat tccaagaagg ccaacttgcg aaagggcgta    1200
cttgagcatc cgctctggga caagctggtc tttgagcga ttcgcgcgcg cttgggtggc     1260
aaggttaagc acatcgtgtc aggatctgcc cccatctctc ctgatgtgat ggatttcctc    1320
cgcatctgct tcagcgctga tgtgtatgag ggatatggcc agacggaaca ggcagccgga    1380
ttaagtatga gctatcgcgg tgatttgact ccaggacagg ttggcccacc tcaactgtgc    1440
acagaggtca agttgaagga catccctagt atgaactata gcagcgcgga caagcctttc    1500
ccccgtggag aaatcatgct tcgcggaaac tctgtgttca agggctatta caaagccacca   1560 aagcagactg aagaaacatt ggatgctgac ggttggtcca gtaccggaga cgttggacag    1620
```

-continued

| | |
|---|---|
| tgggatgccc aaggccgtct ggtggtcatt gatcgcgtca agaacatctt caagttggcg | 1680 |
| caaggagaat atattgcgcc tgaaaagatc gaggctgtcc tcgccaagca cttcctcgtt | 1740 |
| gcccagattt ttgtctatgg gcactcgctc caggccacca ttgtcgcggt ggttgtccct | 1800 |
| gatgctgaga cgctcaagtt gtgggctaaa gaaaacaagc tgggtgacaa gtcttacgag | 1860 |
| gagctgtgcg ctctccctca gcttcgcaca accctccaaa aggagttggc tacttttggc | 1920 |
| aaagaatcgg atctgaaggg ctttgagatt cctaagaaca ttcatgttat ctccgagcag | 1980 |
| ttttcaattg agaacgatct tttgaccccc accttcaagc tgaagagaca tgctgccaaa | 2040 |
| gagaagtata acgccgaaat cgaccgcatg tatgcagaaa tcgcttaata taaataatgg | 2100 |
| ttgtactcaa tataaaaaaa aaa | 2123 |

<210> SEQ ID NO 30
<211> LENGTH: 2581
<212> TYPE: DNA
<213> ORGANISM: Mortierella alpina
<220> FEATURE:
<221> NAME/KEY: modified_base
<222> LOCATION: (1538)..(1937)
<223> OTHER INFORMATION: n is a, c, g, or t

<400> SEQUENCE: 30

| | |
|---|---|
| atggctactc aaatgtactc ggtggtcgtc cccaacagcc ccgacattcc cggcgaaggc | 60 |
| aagccccgcc gtagtgtgct tgtccagac aagctcctgg agaactaccc ctcagtgaaa | 120 |
| gcaggctcaa cgatcacgac cctgtacgag aacttccaag aaggtgttct ccgttcaggt | 180 |
| aacaacgctt accacgtcga cgttcgcctc gcaatggcac ctttcccttc ggtcaaactt | 240 |
| cttaaatgtt tcctttacaa tcgtaggcgg cgcccatttt ttgggccatc gtcccattgt | 300 |
| gaatggccag cctcaggctt acaagtggca gtcgtatgtc gatgtcagca agcgtgttac | 360 |
| gcacttcggc gctggcctgg ctcatctcgg cttgtctcca aagcaaaact ttggaatttt | 420 |
| ctctatcaac cggcctgagt gggtaggtga tgccttgctt tcttttgccc actcgtcgtc | 480 |
| aaggtaacgc agggcctgcg ccgatttta acagtacatt ctatgcactg tcgttacata | 540 |
| gaccatgagt gagcttgctg gctatatgca caactacacc agcgtccccc tctatgatac | 600 |
| attgggagtc gccgcgatcg agtatatcgt taaccagact gagatgcaga tcatcattgc | 660 |
| ttcgtccgac aaagcttcta tcatcctcca catgaaatca gcattccaa ccgttcagac | 720 |
| gattgtcgtc atgggggaat ttactgacgc tctcgtcgca gagggtaagg agctcaacat | 780 |
| caacattgta tcctggaccg atgtcgaaaa gagcggtctt gagcggcctg tcgaagccgt | 840 |
| gcaccccaca gccgaggata tcgctaccat ctgttacaca tctggaacca ctggaacgcc | 900 |
| aaagtaagtc aagatcatta catggtgagc ctccattgct tggactgaac agtctactca | 960 |
| cgcaggttct tcgtttactt tgacatgcgc agaggtgcta tcttgaccca caagaacttt | 1020 |
| gttgccacta tcgcttcatt ccacatgatg gcaaagcatg gcaggttctt cattccctcg | 1080 |
| cctgccgaca cacatgtatc ctacctgccc cttgcccacg tctttgagcg cctttgccag | 1140 |
| gctgttatga tctcgggcgc tgcgcgtatt ggttactacc aaggagatac gctgaagctg | 1200 |
| ctggacgatg ttgccgtcct gcatcccacc attttttgcct ccgtccctcg tctctttaac | 1260 |
| cgtatctacg acaaggtgct tgctggcgtc aaggccaagg gtggtatcgc cgccttcttg | 1320 |
| tttaaccgcg catataattc caagaaggcc aacttgcgaa agggcgtact tgagcatccg | 1380 |
| ctctgggaca agctggtctt tggagcgatt cgcgcgcgct gggtggcaa ggttaagcac | 1440 |

```
atcgtgtcag gatctgcccc catctctcct gatgtgatgg atttcctccg catctgcttc    1500
agcgctgatg tgtatgaggg atatggccag acggaacnnn nnnnnnnnnn nnnnnnnnnn    1560
nnnnnnnnnn nnnnnnnnnn nnnnnnnnnn nnnnnnnnnn nnnnnnnnnn nnnnnnnnnn    1620
nnnnnnnnnn nnnnnnnnnn nnnnnnnnnn nnnnnnnnnn nnnnnnnnnn nnnnnnnnnn    1680
nnnnnnnnnn nnnnnnnnnn nnnnnnnnnn nnnnnnnnnn nnnnnnnnnn nnnnnnnnnn    1740
nnnnnnnnnn nnnnnnnnnn nnnnnnnnnn nnnnnnnnnn nnnnnnnnnn nnnnnnnnnn    1800
nnnnnnnnnn nnnnnnnnnn nnnnnnnnnn nnnnnnnnnn nnnnnnnnnn nnnnnnnnnn    1860
nnnnnnnnnn nnnnnnnnnn nnnnnnnnnn nnnnnnnnnn nnnnnnnnnn nnnnnnnnnn    1920
nnnnnnnnnn nnnnnnntta ccccacgact ttcttttgtc tcggcctgtt ccgcaatcat    1980
agtaccggag acgttggaca gtgggatgcc caaggccgtc tggtggtcat tgatcgcgtc    2040
aagaacatct tcaagttggc gcaaggagaa tatattgcgc ctgaaaagat cgaggctgtc    2100
ctcgccaagc acttcctcgt tgcccagatt tttgtctatg ggcactcgct ccaggccacc    2160
attgtcgcgg tggttgtccc tgatgctgag acgctcaagt tgtgggctaa agaaaacaag    2220
ctgggtgaca gtcttacga ggagctgtgc gctctccctc agcttcgcac aaccctccaa    2280
aaggagttgg ctacttttgg caaagaatcg gatctgaagg gctttgagat tcctaagaac    2340
attcatgtta tctccgagca gttttcaatt gagaacgatc ttttggtgag tgtgcttccg    2400
agtatgaacc actgtgtcgt atgtacgttc gcattctgaa agctaactct ccgtacccttt   2460 ctacttcaat tgtgaattct cctcttgtcg catacagacc cccaccttca agctgaagag    2520
acatgctgcc aaagagaagt ataacgccga atcgaccgc atgtatgcag aaatcgctta    2580
a                                                                   2581

<210> SEQ ID NO 31
<211> LENGTH: 1824
<212> TYPE: DNA
<213> ORGANISM: Mortierella alpina

<400> SEQUENCE: 31
atgcacattc tgaatgccac aagaccattc tccaggctgt ctccaaccgt aaggagacct      60
tggctaggac tcggccagac gcgcccttat gctatcgcgc agaccgaggc cagtcctagg     120
ctgtcatatg tccgaggcac caccgtcggc acccagctat gcgaggatcc catcggtgcg     180
tactgggaca gggtcgtcaa tcgtcacggt gaccgcctcg gacttgtcgt caagcacgag     240
caggacctgc actggacctt ccgtcagttt ggcgggcagg ttgatagcct ctgccgtggg     300
ctctatgagt ctggcttgcg aaagggtgat cgactcgctg tctggatgcc gaacaacagc     360
gcgtgggcca cgctccagta tgctactgcc aagtctggca tcattctggt aactctcaac     420
cctgcgtacc ggaggcaaga gctactgcag acattgtctt tggtcgagtg caagtcattg     480
gtctatgtgc caagtctaaa gacttcgaat tatagcgaga tgttgctcga cctcctacca     540
gaactccagt accagtcgcc aaatcagctc ttgaccgaga agctaccctc acttcgtcaa     600
gtcatcgtgt ttgacaatgg ctcgcaagtc ccagagacag caaaattgaa gggattgaca     660
aagtatcagg atttgttgat caagaatccc tcgaccgctg tcgacggagc tcttgaaaag     720
gaacggctcg ctatcgacaa cagggatatc atcaatctcc agtttactag cggaactaca     780
ggccttccca agggcgtctc gctgtcgcat cgaaacatct tgaataacgg cattcatatt     840
ggagataaca tgcgactgac ggaaaaggat ttgctttgct gcccggtccc gctctttcac     900
tgctttggac tggtgctggc aagcttggct gcaatgaccc atggcgcagg aattatttac     960
```

```
ccttcgcagt cctttgatgc tgaggccaca ctgagggctg tttctgagga gggtgctaca    1020
gcgctgcatg gcgtgccgac tatgctgttg aagagatga accaccccaa ctttgcaaag    1080
tacaaccttt cgacacttcg dacaggaatt gcagctggat ccctgtgcc cattgaggtc    1140 atgaagaacg tgcagacaaa gatgaacctg aaggagctga ctatctgtta cggcatgacc    1200
gagacctcgc ccgtgtcctt catgacactc acaacggatg aattacggga tcgatgtgag    1260
actgttggac gaattatgcc acatctcgag gccaaagtcg tcaaccctga cgggagag     1320 actttgccag tgaattcatc aggagagttg tgcacgcgcg gtatgctgt gatggagggt    1380 ggttactggc gatcccagga gcagacagat gcagtggtgg acaaggatgg ctggatgcac    1440
actggcgaca ctgccgtgct cgatgaccgt ggcttttgca ggatcgacgg acgcatcaag    1500
gacatggtga tccgaggagg cgaaaaaatc catcctgtag aggtcgagaa ctgtctcttt    1560
gagatggacg gcgtcaagaa cgtgtctgtg attggcgttc ccgacaagcg gtatggcgag    1620
caggtgtgtg cgtggatctc gaccaaggac gggaagacgg tcagtctgga ggcagtgcaa    1680
aagttctgtg agggcaagat tgcgcactac aaggtgccgc ggtatgtggt tgtggtggag    1740
tccaatgagt tcccgactac cccctcgggc aagatccaaa agaatgtgat gcgcgagctg    1800
accaaggcga agctgcagct gcct                                          1824
```

<210> SEQ ID NO 32
<211> LENGTH: 608
<212> TYPE: PRT
<213> ORGANISM: Mortierella alpina

<400> SEQUENCE: 32

Met His Ile Leu Asn Ala Thr Arg Pro Phe Ser Arg Leu Ser Pro Thr
1               5                   10                  15

Val Arg Arg Pro Trp Leu Gly Leu Gly Gln Thr Arg Pro Tyr Ala Ile
            20                  25                  30

Ala Gln Thr Glu Ala Ser Pro Arg Leu Ser Tyr Val Arg Gly Thr Thr
        35                  40                  45

Val Gly Thr Gln Leu Cys Glu Asp Pro Ile Gly Ala Tyr Trp Asp Arg
    50                  55                  60

Val Val Asn Arg His Gly Asp Arg Leu Gly Leu Val Val Lys His Glu
65                  70                  75                  80

Gln Asp Leu His Trp Thr Phe Arg Gln Phe Gly Gln Val Asp Ser
                85                  90                  95

Leu Cys Arg Gly Leu Tyr Glu Ser Gly Leu Arg Lys Gly Asp Arg Leu
            100                 105                 110

Ala Val Trp Met Pro Asn Asn Ser Ala Trp Ala Thr Leu Gln Tyr Ala
        115                 120                 125

Thr Ala Lys Ser Gly Ile Ile Leu Val Thr Leu Asn Pro Ala Tyr Arg
    130                 135                 140

Arg Gln Glu Leu Leu Gln Thr Leu Ser Leu Val Glu Cys Lys Ser Leu
145                 150                 155                 160

Val Tyr Val Pro Ser Leu Lys Thr Ser Asn Tyr Ser Glu Met Leu Leu
                165                 170                 175

Asp Leu Leu Pro Glu Leu Gln Tyr Gln Ser Pro Asn Gln Leu Leu Thr
            180                 185                 190

Glu Lys Leu Pro Ser Leu Arg Gln Val Ile Val Phe Asp Asn Gly Ser
        195                 200                 205

Gln Val Pro Glu Thr Ala Lys Leu Lys Gly Leu Thr Lys Tyr Gln Asp

```
              210                 215                 220
Leu Leu Ile Lys Asn Pro Ser Thr Ala Val Asp Gly Ala Leu Glu Lys
225                 230                 235                 240

Glu Arg Leu Ala Ile Asp Asn Arg Asp Ile Ile Asn Leu Gln Phe Thr
                245                 250                 255

Ser Gly Thr Thr Gly Leu Pro Lys Gly Val Ser Leu Ser His Arg Asn
                260                 265                 270

Ile Leu Asn Asn Gly Ile His Ile Gly Asp Asn Met Arg Leu Thr Glu
                275                 280                 285

Lys Asp Leu Leu Cys Cys Pro Val Pro Leu Phe His Cys Phe Gly Leu
                290                 295                 300

Val Leu Ala Ser Leu Ala Ala Met Thr His Gly Ala Gly Ile Ile Tyr
305                 310                 315                 320

Pro Ser Gln Ser Phe Asp Ala Glu Ala Thr Leu Arg Ala Val Ser Glu
                325                 330                 335

Glu Gly Ala Thr Ala Leu His Gly Val Pro Thr Met Leu Leu Glu Glu
                340                 345                 350

Met Asn His Pro Asn Phe Ala Lys Tyr Asn Leu Ser Thr Leu Arg Thr
                355                 360                 365

Gly Ile Ala Ala Gly Ser Pro Val Pro Ile Glu Val Met Lys Asn Val
                370                 375                 380

Gln Thr Lys Met Asn Leu Lys Glu Leu Thr Ile Cys Tyr Gly Met Thr
385                 390                 395                 400

Glu Thr Ser Pro Val Ser Phe Met Thr Leu Thr Thr Asp Glu Leu Arg
                405                 410                 415

Asp Arg Cys Glu Thr Val Gly Arg Ile Met Pro His Leu Glu Ala Lys
                420                 425                 430

Val Val Asn Pro Glu Thr Gly Glu Thr Leu Pro Val Asn Ser Ser Gly
                435                 440                 445

Glu Leu Cys Thr Arg Gly Tyr Ala Val Met Glu Gly Gly Tyr Trp Arg
                450                 455                 460

Ser Gln Glu Gln Thr Asp Ala Val Val Asp Lys Asp Gly Trp Met His
465                 470                 475                 480

Thr Gly Asp Thr Ala Val Leu Asp Asp Arg Gly Phe Cys Arg Ile Asp
                485                 490                 495

Gly Arg Ile Lys Asp Met Val Ile Arg Gly Gly Glu Lys Ile His Pro
                500                 505                 510

Val Glu Val Glu Asn Cys Leu Phe Glu Met Asp Gly Val Lys Asn Val
                515                 520                 525

Ser Val Ile Gly Val Pro Asp Lys Arg Tyr Gly Glu Gln Val Cys Ala
                530                 535                 540

Trp Ile Ser Thr Lys Asp Gly Lys Thr Val Ser Leu Glu Ala Val Gln
545                 550                 555                 560

Lys Phe Cys Glu Gly Lys Ile Ala His Tyr Lys Val Pro Arg Tyr Val
                565                 570                 575

Val Val Val Glu Ser Asn Glu Phe Pro Thr Thr Pro Ser Gly Lys Ile
                580                 585                 590

Gln Lys Asn Val Met Arg Glu Leu Thr Lys Ala Lys Leu Gln Leu Pro
                595                 600                 605

<210> SEQ ID NO 33
<211> LENGTH: 1827
<212> TYPE: DNA
<213> ORGANISM: Mortierella alpina
```

<400> SEQUENCE: 33

```
atgcacattc tgaatgccac aagaccattc tccaggctgt ctccaaccgt aaggagacct    60
tggctaggac tcggccagac gcgcccttat gctatcgcgc agaccgaggc cagtcctagg   120
ctgtcatatg tccgaggcac caccgtcggc acccagctat gcgaggatcc catcggtgcg   180
tactgggaca gggtcgtcaa tcgtcacggt gaccgcctcg acttgtcgt caagcacgag    240
caggacctgc actggacctt ccgtcagttt ggcgggcagg ttgatagcct ctgccgtggg   300
ctctatgagt ctggcttgcg aaagggtgat cgactcgctg tctggatgcc gaacaacagc   360
gcgtgggcca cgctccagta tgctactgcc aagtctggca tcattctggt aactctcaac   420
cctgcgtacc ggaggcaaga gctactgcag acattgtctt tggtcgagtg caagtcattg   480
gtctatgtgc caagtctaaa gacttcgaat tatagcgaga tgttgctcga cctcctacca   540
gaactccagt accagtcgcc aaatcagctc ttgaccgaga agctacctc acttcgtcaa    600
gtcatcgtgt ttgacaatgg ctcgcaagtc ccagagacag caaaattgaa gggattgaca   660
aagtatcagg atttgttgat caagaatccc tcgaccgctg tcgacggagc tcttgaaaag   720
gaacggctcg ctatcgacaa cagggatatc atcaatctcc agtttactag cggaactaca   780
ggccttccca agggcgtctc gctgtcgcat cgaaacatct tgaataacgg cattcatatt   840
ggagataaca tgcgactgac ggaaaaggat ttgctttgct gcccggtccc gctctttcac   900
tgctttggac tggtgctggc aagcttggct gcaatgaccc atggcgcagg aattatttac   960
ccttcgcagt cctttgatgc tgaggccaca ctgagggctg tttctgagga gggtgctaca  1020
gcgctgcatg gcgtgccgac tatgctgttg aagagatga ccaccccaa ctttgcaaag   1080
tacaaccttt cgacacttcg acaggaatt gcagctggat cccctgtgcc cattgaggtc   1140
atgaagaacg tgcagacaaa gatgaacctg aaggagctga ctatctgtta cggcatgacc  1200
gagacctcgc ccgtgtcctt catgacactc acaacggatg aattacggga tcgatgtgag  1260
actgttggac gaattatgcc acatctcgag gccaaagtcg tcaaccctga cgggagag    1320
actttgccag tgaattcatc aggagagttg tgcacgcgcg gtatgctgtt gatggagggt  1380
ggttactggc gatcccagga gcagacagat gcagtggtgg acaaggatgg ctggatgcac  1440
actggcgaca ctgccgtgct cgatgaccgt ggcttttgca ggatcgacgg acgcatcaag  1500
gacatggtga tccgaggagg cgaaaaaatc catcctgtag aggtcgagaa ctgtctcttt  1560
gagatggacg cgtcaagaa cgtgtctgtg attggcgttc ccgacaagcg gtatggcgag  1620
caggtgtgtg cgtggatctc gaccaaggac gggaagacgg tcagtctgga ggcagtgcaa  1680
aagttctgtg agggcaagat tgcgcactac aaggtgccgc ggtatgtggt tgtggtggag  1740
tccaatgagt tcccgactac ccctcgggc aagatccaaa agaatgtgat gcgcgagctg  1800
accaaggcga agctgcagct gccttga                                       1827
```

<210> SEQ ID NO 34
<211> LENGTH: 2085
<212> TYPE: DNA
<213> ORGANISM: Mortierella alpina

<400> SEQUENCE: 34

```
ggcacgaggc tctactctcc attgcccact cactcattgc ccctctgtcc atcaccggca    60
ttgctcgttc gcgccttccg ccactccact ctttctttca ttccttcttt acaacggcca   120
tctcccctc gctctgcgct tctcccatcc acgctaacaa tgcacattct gaatgccaca   180
```

```
agaccattct ccaggctgtc tccaaccgta aggagacctt ggctaggact cggccagacg    240
cgcccttatg ctatcgcgca gaccgaggcc agtcctaggc tgtcatatgt ccgaggcacc    300
accgtcggca cccagctatg cgaggatccc atcggtgcgt actgggacag ggtcgtcaat    360
cgtcacggtg accgcctcgg acttgtcgtc aagcacgagc aggacctgca ctggaccttc    420
cgtcagtttg cgggcaggt tgatagcctc tgccgtgggc tctatgagtc tggcttgcga     480
aagggtgatc gactcgctgt ctggatgccg aacaacagcg cgtgggccac gctccagtat    540
gctactgcca agtctggcat cattctggta actctcaacc ctgcgtaccg gaggcaagag    600
ctactgcaga cattgtcttt ggtcgagtgc aagtcattgg tctatgtgcc aagtctaaag    660
acttcgaatt atagcgagat gttgctcgac ctcctaccag aactccagta ccagtcgcca    720
aatcagctct tgaccgagaa gctaccctca cttcgtcaag tcatcgtgtt tgacaatggc    780
tcgcaagtcc cagagacagc aaaattgaag ggattgacaa agtatcagga tttgttgatc    840
aagaatccct cgaccgctgt cgacggagct cttgaaaagg aacggctcgc tatcgacaac    900
agggatatca tcaatctcca gtttactagc ggaactacag gccttcccaa gggcgtctcg    960
ctgtcgcatc gaaacatctt gaataacggc attcatattg gagataacat gcgactgacg   1020
gaaaaggatt tgctttgctg cccggtcccg ctctttcact gctttggact ggtgctggca   1080
agcttggctg caatgaccca tggcgcagga attatttacc cttcgcagtc ctttgatgct   1140
gaggccacac tgagggctgt ttctgaggag ggtgctacag cgctgcatgg cgtgccgact   1200
atgctgttgg aagagatgaa ccaccccaac tttgcaaagt acaacctttc gacacttcgg   1260
acaggaattg cagctggatc ccctgtgccc attgaggtca tgaagaacgt gcagacaaag   1320
atgaacctga aggagctgac tatctgttac ggcatgaccg agacctcgcc cgtgtccttc   1380
atgacactca aacgatga attacggat cgatgtgaga ctgttggacg aattatgcca       1440
catctcgagg ccaaagtcgt caaccctgag acgggagaga ctttgccagt gaattcatca   1500
ggagagttgt gcacgcgcgg gtatgctgtg atggagggtg gttactggcg atcccaggag   1560
cagacagatg cagtggtgga caaggatggc tggatgcaca ctggcgacac tgccgtgctc   1620
gatgaccgtg gcttttgcag gatcgacgga cgcatcaagg acatggtgat ccgaggaggc   1680
gaaaaaatcc atcctgtaga ggtcgagaac tgtctctttg agatggacgg cgtcaagaac   1740
gtgtctgtga ttggcgttcc cgacaagcgg tatggcgagc aggtgtgtgc gtggatctcg   1800
accaaggacg ggaagacggt cagtctggag gcagtgcaaa agttctgtga gggcaagatt   1860
gcgcactaca aggtgccgcg gtatgtggtt gtggtggagt ccaatgagtt cccgactacc   1920
ccctcgggca agatccaaaa gaatgtgatg cgcgagctga ccaaggcgaa gctgcagctg   1980
ccttgatggt actaggatat ggagccgacg aaagtaataa aggcgtatgc tggcatggcg   2040
caagatctga gccctgcggt gaggtgcatt cagtgacgcc attag                   2085

<210> SEQ ID NO 35
<211> LENGTH: 2242
<212> TYPE: DNA
<213> ORGANISM: Mortierella alpina

<400> SEQUENCE: 35
atgcacattc tgaatgccac aagaccattc tccaggctgt ctccaaccgt aaggagacct     60
tggctaggac tcggccagac gcgcccttat gctatcgcgc agaccgaggc cagtcctagg    120
ctgtcatatg tccgaggcac caccgtcggc acccagctat gcgaggatcc catcggtgcg    180
tactgggaca gggtcgtcaa tcgtcacggt gaccgcctcg gacttgtcgt caagcacgag    240
```

```
caggacctgc actggacctt ccgtcagttt ggcgggcagg ttgatagcct ctgccgtggg      300
ctctatgagt ctggcttgcg aaagggtgat cgactcgcgt atgtacactc tcgtcgtgcc      360
tgaagcgctt gaagggaaaa actgtattga accccgccc gctgcattag cgtcgtttca       420
acatttggct aattttttct ttccctcgtc ctttgccgat gcaaacagtg tctggatgcc      480
gaacaacagc gcgtgggcca cgctccagta tgctactgcc aagtctggca tcattctggt      540
aactctcaac cctgcgtatg tactcatgt cataatcata ctcgcgtcgc ctcaaaaata       600
tgcttttttg acgtgtttac ttatcctgcg cgttctcata acaggtaccg gaggcaagag      660
ctactgcaga cattgtcttt ggtcgagtgc aagtcattgg tctatgtgcc aagtctaaag      720
acttcgaatt atagcgagat gttgctcgac ctcctaccag aactccagta ccagtcgcca      780
aatcagctct tgaccgagaa gctaccctca cttcgtcaag tcatcgtgtt tgacaatggc      840
tcgcaagtcc cagagacagc aaaattgaag ggattgacaa agtatcagga tttgttgatc      900
aagaatccct cgaccgctgt cgacggagct cttgaaaagg aacggctcgc tatcgacaac      960
agggatatca tcaatctcca gtttactagc ggaactacag gccttcccaa gtatgtgtca     1020
gaaattgaac ttgacacgcg atgcataatc gacgttcaac caccccttgtc ctgacaccgt    1080 cttgcatcta caatactatg gtccaaattt tagggggcgtc tcgctgtcgc atcgaaacat    1140
cttgaataac ggcattcata ttggagataa catgcgactg acggaaaagg atttgctttg     1200
ctgcccggtc ccgctctttc actgctttgg actggtgctg gcaagcttgg ctgcaatgac     1260
ccatggcgca ggaattattt acccttcgca gtcctttgat gctgaggcca cactgagggc     1320
tgtttctgag gagggtgcta cagcgctgca tggcgtgccg actatgctgt tggaagagat     1380
gaaccacccc aactttgcaa agtacaacct ttcgacactt cggacaggaa ttgcagctgg     1440 atccctgtg cccattgagg tcatgaagaa cgtgcagaca aagatgaacc tgaaggagct     1500
gactatctgt tacggcatga ccgagaccctc gcccgtgtcc ttcatgacac tcacaacgga    1560
tgaattacgg gatcgatgtg agactgttgg acgaattatg ccacatctcg aggccaaagg    1620
taaaacggct gtcagcctgg tgttcataat tttgtcttga atctcggtgg tctgttgcta    1680 atttttgggta cattgcttgc acaatacggt agtcgtcaac cctgagacgg gagagacttt     1740
gccagtgaat tcatcaggag agttgtgcac gcgcgggtat gctgtgatgg agggtggtta    1800
ctggcgatcc caggagcaga cagatgcagt ggtggacaag gatggctgga tgcacactgg    1860
cgacactgcc gtgctcgatg accgtggctt ttgcaggatc gacggacgca tcaaggacat    1920
ggtgatccga ggaggcgaaa aaatccatcc tgtagaggtc gagaactgtc tctttgagat    1980
ggacggcgtc aagaacgtgt ctgtgattgg cgttcccgac aagcggtatg cgagcaggt    2040 gtgtgcgtga atctcgacca aggacgggaa gacggtcagt ctggaggcag tgcaaaagtt    2100
ctgtgagggc aagattgcgc actacaaggt gccgcggtat gtggttgtgg tggagtccaa    2160
tgagttcccg actacccct cgggcaagat ccaaaagaat gtgatgcgcg agctgaccaa     2220
ggcgaagctg cagctgcctt ga                                             2242
```

<210> SEQ ID NO 36
<211> LENGTH: 2076
<212> TYPE: DNA
<213> ORGANISM: Mortierella alpina

<400> SEQUENCE: 36

```
atgccttcct tcaaaaagta caacctcgac aagcagagtg ttgaggtccc tggcactcgg       60
```

```
aagcctggcg cttcaggcca ctacagacat gccgcctacg gcgatgctct tgtcaccaac    120
atccgtgagg cccctcatat cgaaactctt tacgacatgt ggcagaactc tgtgacaaag    180
tatggcggca atgactttt gggtcaccgt cccttcaaca ctgttgccca gacctatggt    240
ggctacagtt gggagacgta ccgccagatt aaccagcgcg ttaatgcgtt cggcagcggt    300
atcatgcacc tgaacgaggt gatcctcggc aaccgccagc ttaaccgctg gcgttgggc    360 atctggtccc acggtcgccc tgagtggttc attacggaga tgagctgcaa ctgctacaac    420
ctcatttctg ttgcattgta cgacacccett ggacctgatg cagtcgagta cattgtcaac    480
cacgccgaga ttgagattgt tgtctcaagt gccaaccata tcgcctcttt gctcgagaac    540
gccgagaagc tccccaagct caaggccatt gtcagcatgg atgctcttca cgataccgtc    600
cccgtccccg gcgccacctc tgccgcacag gttcttcgtg cctggggtgc acaaagggc    660 atcaaggtct atgactttaa cgagattgag tccctcggtg ccgagttccc tcgcaagcac    720
ctgcctccca ccgctgatga ggtcgcctcc atctgctaca cttccggcac caccggtcag    780
cctaaaggag ccatgctcac ccacagaaac tttgttgcta ctgttggtac caaccgcgag    840
ggcatgcttc tcaccgagga cgacgttttg atcagtttct tgcccttggc tcacattatg    900
ggacgcgtca ttgacacttg ctcgatgtac agcggtggca agattggtta cttccgtgga    960
gatattcttt tgcttctcga ggacgttgct gagctccgtc ccacattctt cccagctgtg   1020
cctcgcctct tgaaccgcat ttatgccaag ctcgttgcct ctaccattga ggccccggt   1080 ttggtcggtg ccttggcccg tcgcggtgtc gccgccaaga tggccaacct tgctgccgga   1140
aagggtgtca ccacgctctc tgggacagac tgctgttca acaaggtcaa gatggccctg   1200
ggtggtcgcg ttcaggtcat cctgactgga tctgcgccca ttgccaagga ggttctcagc   1260
ttcttgagaa ttgctttcgg atgcgtggtt ttggagggat acggctccac tgagggcatg   1320
gctaccgcca ccatcacaat ggctgatgag tacattcctg gtcacattgg ctgccctcgt   1380
gctggatgcg agctcaagct ggtggatgtg cccgcgatga actacctctc taccgaccag   1440 cctaccccc gtggagagat ctggatccgt ggtgacactg ttttcaaagg atacttcaag   1500
gacgagaaga acactagtga gactatcgac tctgaaggct ggctcgctac cggtgatatt   1560
ggatttgtgg ataagcgtgg atgctttacg atcattgacc gcaagaagaa catcttcaag   1620
ttggcacaag gtgaatacat tgctcctgaa aagattgaga cgtcttgggg cgcacgctgc   1680
aatcttgtcc agcagatcta tgttcatggt gattcgcttg agtccacctt ggtcgcagtt   1740
cttattcccg agcccgagac cttcctgccc ttcgcgaatg ccattgctgg tgcctccgtc   1800
actgctggag atgttgaggg tttgaacaag ctgtgccaag atcccaaggt caagatcgcg   1860
gttctgaagg agttggagaa ggccggaaag gccggtgcga tgcgcggatt cgagttcgtg   1920
aagcgtgtcc acttgaccac ggatgcattc tcggtcgaca acggcatgat gacacctacc   1980
ttcaaggtcc gtcgcccaca gtagccgag catttcaggg agcaaatcac ggccatgtat   2040
aaggagatca atgcctcgac ccctgttgcc aagctg                             2076
```

<210> SEQ ID NO 37
<211> LENGTH: 692
<212> TYPE: PRT
<213> ORGANISM: Mortierella alpina

<400> SEQUENCE: 37

Met Pro Ser Phe Lys Lys Tyr Asn Leu Asp Lys Gln Ser Val Glu Val
1               5                   10                  15

-continued

```
Pro Gly Thr Arg Lys Pro Gly Ala Ser Gly His Tyr Arg His Ala Ala
            20                  25                  30
Tyr Gly Asp Ala Leu Val Thr Asn Ile Arg Glu Ala Pro His Ile Glu
        35                  40                  45
Thr Leu Tyr Asp Met Trp Gln Asn Ser Val Thr Lys Tyr Gly Gly Asn
    50                  55                  60
Asp Phe Leu Gly His Arg Pro Phe Asn Thr Val Ala Gln Thr Tyr Gly
65                  70                  75                  80
Gly Tyr Ser Trp Glu Thr Tyr Arg Gln Ile Asn Gln Arg Val Asn Ala
                85                  90                  95
Phe Gly Ser Gly Ile Met His Leu Asn Glu Val Ile Leu Gly Asn Arg
            100                 105                 110
Gln Leu Asn Arg Trp Ala Leu Gly Ile Trp Ser His Gly Arg Pro Glu
        115                 120                 125
Trp Phe Ile Thr Glu Met Ser Cys Asn Cys Tyr Asn Leu Ile Ser Val
    130                 135                 140
Ala Leu Tyr Asp Thr Leu Gly Pro Asp Ala Val Glu Tyr Ile Val Asn
145                 150                 155                 160
His Ala Glu Ile Glu Ile Val Val Ser Ser Ala Asn His Ile Ala Ser
                165                 170                 175
Leu Leu Glu Asn Ala Glu Lys Leu Pro Lys Leu Lys Ala Ile Val Ser
            180                 185                 190
Met Asp Ala Leu His Asp Thr Val Pro Val Pro Gly Ala Thr Ser Ala
        195                 200                 205
Ala Gln Val Leu Arg Ala Trp Gly Ala Gln Lys Gly Ile Lys Val Tyr
    210                 215                 220
Asp Phe Asn Glu Ile Glu Ser Leu Gly Ala Glu Phe Pro Arg Lys His
225                 230                 235                 240
Leu Pro Pro Thr Ala Asp Glu Val Ala Ser Ile Cys Tyr Thr Ser Gly
                245                 250                 255
Thr Thr Gly Gln Pro Lys Gly Ala Met Leu Thr His Arg Asn Phe Val
            260                 265                 270
Ala Thr Val Gly Thr Asn Arg Glu Gly Met Leu Leu Thr Glu Asp Asp
        275                 280                 285
Val Leu Ile Ser Phe Leu Pro Leu Ala His Ile Met Gly Arg Val Ile
    290                 295                 300
Asp Thr Cys Ser Met Tyr Ser Gly Gly Lys Ile Gly Tyr Phe Arg Gly
305                 310                 315                 320
Asp Ile Leu Leu Leu Leu Glu Asp Val Ala Glu Leu Arg Pro Thr Phe
                325                 330                 335
Phe Pro Ala Val Pro Arg Leu Leu Asn Arg Ile Tyr Ala Lys Leu Val
            340                 345                 350
Ala Ser Thr Ile Glu Ala Pro Gly Leu Val Gly Ala Leu Ala Arg Arg
        355                 360                 365
Gly Val Ala Ala Lys Met Ala Asn Leu Ala Ala Gly Lys Gly Val Asn
    370                 375                 380
His Ala Leu Trp Asp Arg Leu Leu Phe Asn Lys Val Lys Met Ala Leu
385                 390                 395                 400
Gly Gly Arg Val Gln Val Ile Leu Thr Gly Ser Ala Pro Ile Ala Lys
                405                 410                 415
Glu Val Leu Ser Phe Leu Arg Ile Ala Phe Gly Cys Val Val Leu Glu
            420                 425                 430
Gly Tyr Gly Ser Thr Glu Gly Met Ala Thr Ala Thr Ile Thr Met Ala
```

```
                435                440                445
Asp Glu Tyr Ile Pro Gly His Ile Gly Cys Pro Arg Ala Gly Cys Glu
    450                455                460
Leu Lys Leu Val Asp Val Pro Ala Met Asn Tyr Leu Ser Thr Asp Gln
465                470                475                480
Pro Tyr Pro Arg Gly Glu Ile Trp Ile Arg Gly Asp Thr Val Phe Lys
                485                490                495
Gly Tyr Phe Lys Asp Glu Lys Asn Thr Ser Glu Thr Ile Asp Ser Glu
            500                505                510
Gly Trp Leu Ala Thr Gly Asp Ile Gly Phe Val Asp Lys Arg Gly Cys
            515                520                525
Phe Thr Ile Ile Asp Arg Lys Lys Asn Ile Phe Lys Leu Ala Gln Gly
            530                535                540
Glu Tyr Ile Ala Pro Glu Lys Ile Glu Asn Val Leu Gly Ala Arg Cys
545                550                555                560
Asn Leu Val Gln Gln Ile Tyr Val His Gly Asp Ser Leu Glu Ser Thr
                565                570                575
Leu Val Ala Val Leu Ile Pro Glu Pro Glu Thr Phe Leu Pro Phe Ala
            580                585                590
Asn Ala Ile Ala Gly Ala Ser Val Thr Ala Gly Asp Val Glu Gly Leu
            595                600                605
Asn Lys Leu Cys Gln Asp Pro Lys Val Lys Ile Ala Val Leu Lys Glu
610                615                620
Leu Glu Lys Ala Gly Lys Ala Gly Ala Met Arg Gly Phe Glu Phe Val
625                630                635                640
Lys Arg Val His Leu Thr Thr Asp Ala Phe Ser Val Asp Asn Gly Met
                645                650                655
Met Thr Pro Thr Phe Lys Val Arg Arg Pro Gln Val Ala Glu His Phe
                660                665                670
Arg Glu Gln Ile Thr Ala Met Tyr Lys Glu Ile Asn Ala Ser Thr Pro
            675                680                685
Val Ala Lys Leu
    690

<210> SEQ ID NO 38
<211> LENGTH: 2079
<212> TYPE: DNA
<213> ORGANISM: Mortierella alpina

<400> SEQUENCE: 38
atgccttcct tcaaaaagta caacctcgac aagcagagtg ttgaggtccc tggcactcgg      60
aagcctggcg cttcaggcca ctacagacat gccgcctacg gcgatgctct tgtcaccaac     120
atccgtgagg cccctcatat cgaaactctt tacgacatgt ggcagaactc tgtgacaaag     180
tatggcggca atgactttt gggtcaccgt cccttcaaca ctgttgccca gacctatggt     240
ggctacagtt gggagacgta ccgccagatt aaccagcgcg ttaatgcgtt cggcagcggt     300
atcatgcacc tgaacgaggt gatcctcggc aaccgccagc ttaaccgctg gcgttgggc      360 atctggtccc acgtcgccc tgagtggttc attacggaga tgagctgcaa ctgctacaac     420
ctcatttctg ttgcattgta cgacacctt ggacctgatg cagtcgagta cattgtcaac     480
cacgccgaga ttgagattgt tgtctcaagt gccaaccata tcgcctcttt gctcgagaac     540
gccgagaagc tccccaagct caaggccatt gtcagcatgg atgctcttca cgataccgtc     600
cccgtccccg gcgccaccct ctgccgcacag gttcttcgtg cctggggtgc acaaaagggc     660
```

| | |
|---|---|
| atcaaggtct atgactttaa cgagattgag tccctcggtg ccgagttccc tcgcaagcac | 720 |
| ctgcctccca ccgctgatga ggtcgcctcc atctgctaca cttccggcac caccggtcag | 780 |
| cctaaaggag ccatgctcac ccacagaaac tttgttgcta ctgttggtac caaccgcgag | 840 |
| ggcatgcttc tcaccgagga cgacgttttg atcagtttct tgcccttggc tcacattatg | 900 |
| ggacgcgtca ttgacacttg ctcgatgtac agcggtggca agattggtta cttccgtgga | 960 |
| gatattcttt tgcttctcga ggacgttgct gagctccgtc ccacattctt cccagctgtg | 1020 |
| cctcgcctct tgaaccgcat ttatgccaag ctcgttgcct ctaccattga ggcccccggt | 1080 |
| ttggtcggtg ccttggcccg tcgcggtgtc gccgccaaga tggccaacct tgctgccgga | 1140 |
| aagggtgtca ccacgctct ctgggacaga ctgctgttca acaaggtcaa gatggccctg | 1200 |
| ggtggtcgcg ttcaggtcat cctgactgga tctgcgccca ttgccaagga ggttctcagc | 1260 |
| ttccttgagaa ttgctttcgg atgcgtggtt ttggagggat acggctccac tgagggcatg | 1320 |
| gctaccgcca ccatcacaat ggctgatgag tacattcctg gtcacattgg ctgccctcgt | 1380 |
| gctggatgcg agctcaagct ggtggatgtg cccgcgatga actacctctc taccgaccag | 1440 |
| ccctaccccc gtggagagat ctggatccgt ggtgacactg ttttcaaagg atacttcaag | 1500 |
| gacgagaaga acactagtga gactatcgac tctgaaggct ggctcgctac cggtgatatt | 1560 |
| ggatttgtgg ataagcgtgg atgctttacg atcattgacc gcaagaagaa catcttcaag | 1620 |
| ttggcacaag gtgaatacat tgctcctgaa aagattgaga acgtcttggg cgcacgctgc | 1680 |
| aatcttgtcc agcagatcta tgttcatggt gattcgcttg agtccacctt ggtcgcagtt | 1740 |
| cttattcccg agcccgagac cttcctgccc ttcgcgaatg ccattgctgg tgcctccgtc | 1800 |
| actgctggag atgttgaggg tttgaacaag ctgtgccaag atcccaaggt caagatcgcg | 1860 |
| gttctgaagg agttggagaa ggccggaaag gccggtgcga tgcgcggatt cgagttcgtg | 1920 |
| aagcgtgtcc acttgaccac ggatgcattc tcggtcgaca acggcatgat gacacctacc | 1980 |
| ttcaaggtcc gtcgcccaca gtagccgag catttcaggg agcaaatcac ggccatgtat | 2040 |
| aaggagatca atgcctcgac ccctgttgcc aagctgtag | 2079 |

<210> SEQ ID NO 39
<211> LENGTH: 2306
<212> TYPE: DNA
<213> ORGANISM: Mortierella alpina

<400> SEQUENCE: 39

| | |
|---|---|
| tgcttttctc ttcttcgtca ccctccttct tcccattcct ccggtcctcc tccgttccta | 60 |
| atcagtttct cagaccctgt ccattcctct ggcctccaca cacccccac tctcccttga | 120 |
| acaaatacct tatccagatc aaagacatgc cttccttcaa aaagtacaac ctcgacaagc | 180 |
| agagtgttga ggtccctggc actcggaagc ctggcgcttc aggccactac agacatgccg | 240 |
| cctacggcga tgctcttgtc accaacatcc gtgaggcccc tcatatcgaa actctttacg | 300 |
| acatgtggca gaactctgtg acaaagtatg cggcaatga cttttgggt caccgtccct | 360 |
| tcaacactgt tgcccagacc tatggtggct acagttggga gacgtaccgc cagattaacc | 420 |
| agcgcgttaa tgcgttcggc agcggtatca tgcacctgaa cgaggtgatc ctcggcaacc | 480 |
| gccagcttaa ccgctgggcg ttgggcatct ggtcccacgg tcgccctgag tggttcatta | 540 |
| cggagatgag ctgcaactgc tacaacctca tttctgttgc attgtacgac acccttggac | 600 |
| ctgatgcagt cgagtacatt gtcaaccacg ccgagattga gattgttgtc tcaagtgcca | 660 |

```
accatatcgc ctctttgctc gagaacgccg agaagctccc caagctcaag gccattgtca    720
gcatggatgc tcttcacgat accgtccccg tccccggcgc cacctctgcc gcacaggttc    780
ttcgtgcctg gggtgcacaa aagggcatca aggtctatga ctttaacgag attgagtccc    840
tcggtgccga gttccctcgc aagcacctgc ctcccaccgc tgatgaggtc gcctccatct    900
gctacacttc cggcaccacc ggtcagccta aggagccat gctcacccac agaaactttg      960
ttgctactgt tggtaccaac cgcgagggca tgcttctcac cgaggacgac gttttgatca   1020
gtttcttgcc cttggctcac attatgggac gcgtcattga cacttgctcg atgtacagcg   1080
gtggcaagat tggttacttc cgtggagata ttcttttgct tctcgaggac gttgctgagc   1140
tccgtcccac attcttccca gctgtgcctc gcctcttgaa ccgcatttat gccaagctcg   1200
ttgcctctac cattgaggcc cccggtttgg tcggtgcctt ggcccgtcgc ggtgtcgccg   1260
ccaagatggc caaccttgct gccggaaagg gtgtcaacca cgctctctgg gacagactgc   1320
tgttcaacaa ggtcaagatg gccctgggtg gtcgcgttca ggtcatcctg actggatctg   1380
cgcccattgc caaggaggtt ctcagcttct tgagaattgc tttcggatgc gtggttttgg   1440
agggatacgg ctccactgag ggcatggcta ccgccaccat cacaatggct gatgagtaca   1500
ttcctggtca cattggctgc cctcgtgctg gatgcgagct caagctggtg gatgtgcccg   1560
cgatgaacta cctctctacc gaccagcccct accccgtgg agagatctgg atccgtggtg   1620
acactgtttt caaaggatac ttcaaggacg agaagaacac tagtgagact atcgactctg   1680
aaggctggct cgctaccggt gatattggat tgtggataa gcgtggatgc tttacgatca   1740
ttgaccgcaa gaagaacatc ttcaagttgg cacaaggtga atacattgct cctgaaaaga   1800
ttgagaacgt cttgggcgca cgctgcaatc ttgtccagca gatctatgtt catggtgatt   1860
cgcttgagtc caccttggtc gcagttctta ttcccgagcc cgagaccttc ctgcccttcg   1920
cgaatgccat tgctggtgcc tccgtcactg ctggagatgt tgagggtttg aacaagctgt   1980
gccaagatcc caaggtcaag atcgcggttc tgaaggagtt ggagaaggcc ggaaaggccg   2040
gtgcgatgcg cggattcgag ttcgtgaagc gtgtccactt gaccacggat gcattctcgg   2100
tcgacaacgg catgatgaca cctaccttca aggtccgtcg cccacaagta gccgagcatt   2160
tcagggagca aatcacggcc atgtataagg agatcaatgc ctcgacccct gttgccaagc   2220
tgtagataga aaactctttg ccccttatta ccctttgaat agaaggtgac acgttgtttg   2280
attcacacaa aaaaaaaaaa aaaaaa                                        2306

<210> SEQ ID NO 40
<211> LENGTH: 2816
<212> TYPE: DNA
<213> ORGANISM: Mortierella alpina

<400> SEQUENCE: 40
atgccttcct tcaaaaagta caacctcgac aagcagagtg ttgaggtccc tggcactcgg     60
aagcctggcg cttcaggcaa gttggatagt ggctcatgag atccaactgt tgggccacgc    120
taccatgaaa ctagtcgcta atgcagattc tctattgcct ttcaccttct cacaggccac    180
tacagacatg ccgcctacgg cgatgctctt gtcaccaaca tccgtgaggc ccctcatatc    240
gaaactcttt acgacatgtg gcagaactgt aagttgattc ccgaggacct gggaaatctt    300
tactcggatc tgtctcacaa gaagactcac actctgctct ccacaattac cttgtaacct    360
tcagctgtga caaagtatgg cggcaatgac ttttgggtc accgtccctt caacactgtt     420
gcccagacct atggtggcta cagttgggag acgtaccgcc agattaacca gcgcgttaat    480
```

```
gcgttcggca gcggtatcat gcacctgaac gaggtgatcc tcggcaaccg ccagcttaac    540
cgctgggcgt tgggcatctg gtcccacggt cgccctgagt ggttcattac ggagatgagc    600
tgcaactgct acaacctcat ttctgttgca ttgtacgaca cccttggacc tgatgcagtc    660
gagtacattg tcaaccacgc cgagattgag attgttgtct caagtggtaa gtcgcttttt    720
ttttttttgct attggcgcct gcttgcttgc ctgcacgtga aaactataat ggtttctgat    780
ctccctttg tgtacctcct cctttcgatc aacttctttg taattttatt cccgggcatt     840
gactctatat gcagccaacc atatcgcctc tttgctcgag aacgccgaga agctccccaa    900
gctcaaggcc attgtcagca tggatgctct tcacgatacc gtccccgtcc ccggcgccac    960
ctctgccgca caggttcttc gtgcctgggg tgcacaaaag ggcatcaagg tctatgactt   1020
taacgagatt gagtccctcg gtgccgagtt ccctcgcaag cacctgcctc ccaccgctga   1080
tgaggtcgcc tccatctgct acacttccgg caccaccggt cagcctgtaa gtgtgttttc   1140
ccttcactga cgatgtcggc tgaggatgca ttttgctgat tgaaacttcc catctaacat   1200
cgcttgatct atagaaagga gccatgctca cccacagaaa ctttgttgct actgttggta   1260
ccaaccgcga gggcatgctt ctcaccgagg acgacgtttt gatcaggtat aactcatctt   1320
gaagctgatc aatgacacgc gatgtacaac gcgacgatgg agcgagatct acaatgcgga   1380
atggctcacc tccggtttac aattaccaca cttctagttt cttgcccttg gctcacatta   1440
tgggacgcgt cattgacact tgctcgatgt acagcggtgg caagattggt tacttccgtg   1500
gagatattct tttgcttctc gaggacgttg ctgagctccg tcccacattc ttcccagctg   1560
tgcctcgcct cttgaaccgc atttatgcca agctcgttgc ctctaccatt gaggcccccg   1620
gtttggtcgg tgccttggcc cgtcgcggtg tcgccgccaa gatggccaac cttgctgccg   1680
gaaagggtgt caaccacgct ctctgggaca gactgctgtt caacaaggtc aagatggccc   1740
tgggtggtcg cgttcaggtc atcctgactg gatctgcgcc cattgccaag gaggttctca   1800
gcttcttgag aattgctttc ggatgcgtgg ttttggaggg atacggctcc actgagggca   1860
tggctaccgc caccatcaca atggctgagt acgtgaacct agttatttta ttgaaatgtc   1920
gtggagcctg tcgactgtag catttcaatc taaccattag taatcttttc aaaaatagtg   1980
agtacattcc tggtcacatt ggctgccctc gtgctggatg cgagctcaag ctggtggatg   2040
tgcccgcgat gaactacctc tctaccgacc agccctaccc ccgtggagag atctggatcc   2100
gtggtgacac tgttttcaaa ggatacttca aggacgagaa gaacactagt gagactatcg   2160
actctgaagg ctggctcgct accggtgata ttggatttgt ggataagcgt ggatgcttta   2220
cgatcattga ccgcaagaag aacatcttca aggtatgagc aaaagtggg attgatctga    2280
tcgtttctct ctcgttttc ccgttaagga attccgctca tactaacgtt ctcgtcaatg    2340
gtttgcatgt attatagttg gcacaaggtg aatacattgc tcctgaaaag attgagaacg   2400
tcttgggcgc acgctgcaat cttgtccagc agatctatgt tcatggtgat tcgcttgagt   2460
ccaccttggt cgcagttctt attcccgagc ccgagacctt cctgcccttc gcgaatgcca   2520
ttgctggtgc ctccgtcact gctggagatg ttgagggttt gaacaagctg tgccaagatc   2580
ccaaggtcaa gatcgcggtt ctgaaggagt ggagaaggcc cggaaaggcc ggtgcgatgc   2640
gcggattcga gttcgtgaag cgtgtccact tgaccacgga tgcattctcg gtcgacaacg   2700
gcatgatgac acctaccttc aaggtccgtc gcccacaagt agccgagcat ttcagggagc   2760
aaatcacggc catgtataag gagatcaatg cctcgacccc tgttgccaag ctgtag        2816
```

<210> SEQ ID NO 41
<211> LENGTH: 1848
<212> TYPE: DNA
<213> ORGANISM: Mortierella alpina

<400> SEQUENCE: 41

| | | | | | |
|---|---|---|---|---|---|
| atggttgctc | tcccactcgt | cgcagcagct | gtcccagctg | ccatgtatgt | gagctcaaag | 60 |
| ctggcacttc | ctcgggatat | gaagttgatt | aagagcttga | tcggagccaa | gatgcctac | 120 |
| agtgccatgg | aaaagaacga | cgccctcaac | ctgacactcc | gcttcgacga | gtgctaccgc | 180 |
| aagtatcctg | accgtgaagc | cctggtcttt | gagggcaaat | cctattcatt | ccgtgatatt | 240 |
| cagcttgcct | ccaacaggtg | cggcaactgg | ttgctggcca | aagggatcaa | gcgaggagat | 300 |
| atcgtctcgc | ttttcatgtt | gaacaggcca | gagttcatct | tctgctggct | gggtctcaac | 360 |
| aagattggag | ccactggtgc | cttcatcaat | accaacctta | cgggcaaacc | cctgacacat | 420 |
| tccctccgga | cagccacgtc | gtcaatgttg | atcatggaca | cggagttgac | agacgcgatc | 480 |
| gccaactccc | tggatgagat | tcaggagatg | ggctattcaa | tttactctta | cggacccgaa | 540 |
| gccgtggact | tgctaccccc | gatggatatc | tcgcaggtcc | cagacaccga | tacacccgaa | 600 |
| cacctgcgcc | ggaacacgac | cgcggatgac | attgcgatgc | tcatctacac | ctctggaact | 660 |
| actggtcttc | ccaaggccgg | tcgtgtctct | catgcgcgtg | cctctatggg | acctcagttt | 720 |
| tggaaccgat | tctatcactt | cagtgagagc | gacagggtc | atctgtcctt | gcccttgtac | 780 |
| cacagtgctg | cgccatcatt | gggagtgatt | gcttgttgga | cctcgggagc | aaccttgatc | 840 |
| ctggcccgca | agttctccgc | gacacatttc | tgggaggatt | gccgcgtgaa | caacgcaact | 900 |
| gtgattcaat | acattggaga | aatttgcaga | tatctgctca | cacgccaga | atcacccctg | 960 |
| gacaaggcac | actcgatacg | actggcacat | ggtaatggaa | tgcgacccga | tgtctggact | 1020 |
| cgcttcagag | atcggttcgg | catcccgttg | attggcgagt | ggtatgcatc | gactgaggga | 1080 |
| actggagcct | tgtcgaatta | taacacaggc | ccaggcggcg | ctggagcgat | ggataccgc | 1140 |
| ggtacccttg | ccagagcatt | ggataaagga | ctcaggattg | cgagatttga | tgtccagaca | 1200 |
| gaggagttgg | ttcgggacaa | aaacggttat | tgcattgagt | gcaaacctgg | cgagcccgga | 1260 |
| gaattgctga | cgcttgttga | tgctaaagag | ccgaacaaag | acttcaaagg | ataccatcaa | 1320 |
| aaccaggcag | cgaccaacaa | aaagattgtc | aaagatgttt | tcaaagccgg | cgacatgtac | 1380 |
| ttccgtaccg | agatatcct | tcggcgcgat | agcgatgggt | acttttactt | tggcgaccgt | 1440 |
| gtgggcgata | cattccggtg | gaagtccgag | aatgtgtcta | cggccgaggt | gtctgaagtc | 1500 |
| ctctcgcagt | atccggactg | tatcgaagtc | aatgtgtatg | gagttcagat | cccagggcag | 1560 |
| gacggacgcg | ccgtatggc | agcgattgtg | tccaagagca | cgatggattg | ggagaaattt | 1620 |
| gcggcgtatg | cactcaagaa | cctgccgcgg | tattctgttc | cgatctttat | ccgcaagatg | 1680 |
| cccgagatgg | agatcacagg | gacgttcaag | cagcgcaaag | tcgagttggt | gaatgaggga | 1740 |
| atcgacccca | agacgattgc | caacgagatg | ctgtggttgg | acggacacca | ctataagccg | 1800 |
| ttcaaggcgg | ccgagcacca | gcgcgtcatc | agcggcaagg | ccaagcta | | 1848 |

<210> SEQ ID NO 42
<211> LENGTH: 616
<212> TYPE: PRT
<213> ORGANISM: Mortierella alpina

<400> SEQUENCE: 42

Met Val Ala Leu Pro Leu Val Ala Ala Ala Val Pro Ala Ala Met Tyr

-continued

```
1               5                   10                  15
Val Ser Ser Lys Leu Ala Leu Pro Arg Asp Met Lys Leu Ile Lys Ser
                20                  25                  30

Leu Ile Gly Ala Lys Met Ala Tyr Ser Ala Met Glu Lys Asn Asp Ala
                35                  40                  45

Leu Asn Leu Thr Leu Arg Phe Asp Glu Cys Tyr Arg Lys Tyr Pro Asp
                50                  55                  60

Arg Glu Ala Leu Val Phe Glu Gly Lys Ser Tyr Ser Phe Arg Asp Ile
65                  70                  75                  80

Gln Leu Ala Ser Asn Arg Cys Gly Asn Trp Leu Leu Ala Lys Gly Ile
                85                  90                  95

Lys Arg Gly Asp Ile Val Ser Leu Phe Met Leu Asn Arg Pro Glu Phe
                100                 105                 110

Ile Phe Cys Trp Leu Gly Leu Asn Lys Ile Gly Ala Thr Gly Ala Phe
                115                 120                 125

Ile Asn Thr Asn Leu Thr Gly Lys Pro Leu Thr His Ser Leu Arg Thr
                130                 135                 140

Ala Thr Ser Ser Met Leu Ile Met Asp Thr Glu Leu Thr Asp Ala Ile
145                 150                 155                 160

Ala Asn Ser Leu Asp Glu Ile Gln Glu Met Gly Tyr Ser Ile Tyr Ser
                165                 170                 175

Tyr Gly Pro Glu Ala Val Asp Phe Ala Thr Pro Met Asp Ile Ser Gln
                180                 185                 190

Val Pro Asp Thr Asp Thr Pro Glu His Leu Arg Arg Asn Thr Thr Ala
                195                 200                 205

Asp Asp Ile Ala Met Leu Ile Tyr Thr Ser Gly Thr Thr Gly Leu Pro
                210                 215                 220

Lys Ala Gly Arg Val Ser His Ala Arg Ala Ser Met Gly Pro Gln Phe
225                 230                 235                 240

Trp Asn Arg Phe Tyr His Phe Ser Glu Ser Asp Arg Val Tyr Leu Ser
                245                 250                 255

Leu Pro Leu Tyr His Ser Ala Gly Ala Ile Leu Gly Val Ile Ala Cys
                260                 265                 270

Trp Thr Ser Gly Ala Thr Leu Ile Leu Ala Arg Lys Phe Ser Ala Thr
                275                 280                 285

His Phe Trp Glu Asp Cys Arg Val Asn Asn Ala Thr Val Ile Gln Tyr
                290                 295                 300

Ile Gly Glu Ile Cys Arg Tyr Leu Leu Asn Thr Pro Glu Ser Pro Leu
305                 310                 315                 320

Asp Lys Ala His Ser Ile Arg Leu Ala His Gly Asn Gly Met Arg Pro
                325                 330                 335

Asp Val Trp Thr Arg Phe Arg Asp Arg Phe Gly Ile Pro Leu Ile Gly
                340                 345                 350

Glu Trp Tyr Ala Ser Thr Glu Gly Thr Gly Ala Leu Ser Asn Tyr Asn
                355                 360                 365

Thr Gly Pro Gly Gly Ala Gly Ala Ile Gly Tyr Arg Gly Thr Leu Ala
                370                 375                 380

Arg Ala Leu Asp Lys Gly Leu Arg Ile Ala Arg Phe Asp Val Gln Thr
385                 390                 395                 400

Glu Glu Leu Val Arg Asp Lys Asn Gly Tyr Cys Ile Glu Cys Lys Pro
                405                 410                 415

Gly Glu Pro Gly Glu Leu Leu Thr Leu Val Asp Ala Lys Glu Pro Asn
                420                 425                 430
```

```
Lys Asp Phe Lys Gly Tyr His Gln Asn Gln Ala Ala Thr Asn Lys Lys
        435                 440                 445

Ile Val Lys Asp Val Phe Lys Ala Gly Asp Met Tyr Phe Arg Thr Gly
    450                 455                 460

Asp Ile Leu Arg Arg Asp Ser Asp Gly Tyr Phe Tyr Phe Gly Asp Arg
465                 470                 475                 480

Val Gly Asp Thr Phe Arg Trp Lys Ser Glu Asn Val Ser Thr Ala Glu
                485                 490                 495

Val Ser Glu Val Leu Ser Gln Tyr Pro Asp Cys Ile Glu Val Asn Val
            500                 505                 510

Tyr Gly Val Gln Ile Pro Gly Gln Asp Gly Arg Ala Gly Met Ala Ala
            515                 520                 525

Ile Val Ser Lys Ser Thr Met Asp Trp Glu Lys Phe Ala Ala Tyr Ala
        530                 535                 540

Leu Lys Asn Leu Pro Arg Tyr Ser Val Pro Ile Phe Ile Arg Lys Met
545                 550                 555                 560

Pro Glu Met Glu Ile Thr Gly Thr Phe Lys Gln Arg Lys Val Glu Leu
                565                 570                 575

Val Asn Glu Gly Ile Asp Pro Lys Thr Ile Ala Asn Glu Met Leu Trp
            580                 585                 590

Leu Asp Gly His His Tyr Lys Pro Phe Lys Ala Ala Glu His Gln Arg
            595                 600                 605

Val Ile Ser Gly Lys Ala Lys Leu
            610                 615

<210> SEQ ID NO 43
<211> LENGTH: 1851
<212> TYPE: DNA
<213> ORGANISM: Mortierella alpina

<400> SEQUENCE: 43
atggttgctc tcccactcgt cgcagcagct gtcccagctg ccatgtatgt gagctcaaag      60
ctggcacttc ctcgggatat gaagttgatt aagagcttga tcggagccaa gatggcctac     120
agtgccatgg aaaagaacga cgccctcaac ctgacactcc gcttcgacga gtgctaccgc     180
aagtatcctg accgtgaagc cctggtcttt gagggcaaat cctattcatt ccgtgatatt     240
cagcttgcct ccaacaggtg cggcaactgg ttgctggcca aagggatcaa gcgaggagat     300
atcgtctcgc ttttcatgtt gaacaggcca gagttcatct tctgctggct gggtctcaac     360
aagattggag ccactggtgc cttcatcaat accaaccttg cgggcaaacc cctgacacat     420
tccctccgga cagccacgtc gtcaatgttg atcatggaca cggagttgac agacgcgatc     480
gccaactccc tggatgagat tcaggagatg ggctattcaa tttactctta cggacccgaa     540
gccgtggact tgctaccccc gatggatatc tcgcaggtcc agacaccga tacacccgaa      600 cacctgcgcc ggaacacgac cgcggatgac attgcgatgc tcatctacac ctctggaact     660
actggtcttc ccaaggccgg tcgtgtctct catgcgcgtg cctctatggg acctcagttt     720
tggaaccgat tctatcactt cagtgagagc gacagggtct atctgtcctt gcccttgtac     780
cacagtgctg gcgccatctt gggagtgatt gcttgttgga cctcgggagc aaccttgatc     840
ctggcccgca gttctccgc gacacatttc tgggaggatt gccgcgtgaa caacgcaact     900
gtgattcaat acattggaga aatttgcaga tatctgctca acacgccaga atcacccctg     960
gacaaggcac actcgatacg actggcacat ggtaatggaa tgcgacccga tgtctggact    1020
```

| | |
|---|---:|
| cgcttcagag atcggttcgg catcccgttg attggcgagt ggtatgcatc gactgaggga | 1080 |
| actggagcct tgtcgaatta taacacaggc ccaggcggcg ctggagcgat tggataccgc | 1140 |
| ggtacccttg ccagagcatt ggataaagga ctcaggattg cgagatttga tgtccagaca | 1200 |
| gaggagttgg ttcgggacaa aaacggttat tgcattgagt gcaaacctgg cgagcccgga | 1260 |
| gaattgctga cgcttgttga tgctaaagag ccgaacaaag acttcaaagg ataccatcaa | 1320 |
| aaccaggcag cgaccaacaa aaagattgtc aaagatgttt tcaaagccgg cgacatgtac | 1380 |
| ttccgtaccg gagatatcct tcggcgcgat agcgatgggt acttttactt tggcgaccgt | 1440 |
| gtgggcgata cattccggtg gaagtccgag aatgtgtcta cggccgaggt gtctgaagtc | 1500 |
| ctctcgcagt atccggactg tatcgaagtc aatgtgtatg gagttcagat cccagggcag | 1560 |
| gacggacgcg ccggtatggc agcgattgtg tccaagagca cgatggattg ggagaaattt | 1620 |
| gcggcgtatg cactcaagaa cctgccgcgg tattctgttc cgatctttat ccgcaagatg | 1680 |
| cccgagatgg agatcacagg gacgttcaag cagcgcaaag tcgagttggt gaatgaggga | 1740 |
| atcgacccca agacgattgc caacgagatg ctgtggttgg acggacacca ctataagccg | 1800 |
| ttcaaggcgg ccgagcacca gcgcgtcatc agcggcaagg ccaagctata g | 1851 |

<210> SEQ ID NO 44
<211> LENGTH: 2042
<212> TYPE: DNA
<213> ORGANISM: Mortierella alpina

<400> SEQUENCE: 44

| | |
|---|---:|
| tcgctatcta tcaccoctca ctccccactc cgcactctgc tcttcctttt tcctttctct | 60 |
| ctctcaccgt cgccactgtc tctactttct ttaccaccca cgcatcagtc acagcatggt | 120 |
| tgctctccca ctcgtcgcag cagctgtccc agctgccatg tatgtgagct caaagctggc | 180 |
| acttcctcgg gatatgaagt tgattaagag cttgatcgga gccaagatgg cctacagtgc | 240 |
| catggaaaag aacgacgccc tcaacctgac actccgcttc gacgagtgct accgcaagta | 300 |
| tcctgaccgt gaagccctgg tctttgaggg caaatcctat tcattccgtg atattcagct | 360 |
| tgcctccaac aggtgcggca actggttgct ggccaaaggg atcaagcgag agatatcgt | 420 |
| ctcgcttttc atgttgaaca ggccagagtt catcttctgc tggctgggtc tcaacaagat | 480 |
| tggagccact ggtgccttca tcaataccaa ccttacgggc aaaccoctga cacattccct | 540 |
| ccggacagcc acgtcgtcaa tgttgatcat ggacacggag ttgacagacg cgatcgccaa | 600 |
| ctccctggat gagattcagg agatgggcta ttcaatttac tcttacggac ccgaagccgt | 660 |
| ggactttgct accccgatgg atatctcgca ggtcccagac accgatacac ccgaacacct | 720 |
| gcgccggaac acgaccgcgg atgacattgc gatgctcatc tacacctctg aactactgg | 780 |
| tcttcccaag gccggtcgtg tctctcatgc gcgtgcctct atgggacctc agttttggaa | 840 |
| ccgattctat cacttcagtg agagcgacag ggtctatctg tccttgccct tgtaccacag | 900 |
| tgctggcgcc atcttgggag tgattgcttg ttggaccctcg ggagcaacct tgatcctggc | 960 |
| ccgcaagttc tccgcgacac atttctggga ggattgccgc gtgaacaacg caactgtgat | 1020 |
| tcaatacatt ggagaaattt gcagatatct gctcaacacg ccagaatcac ccctggacaa | 1080 |
| ggcacactcg atacgactgg cacatggtaa tggaatgcga cccgatgtct ggactcgctt | 1140 |
| cagagatcgg ttcggcatcc cgttgattgg cgagtggtat gcatcgactg agggaactgg | 1200 |
| agccttgtcg aattataaca caggcccagg cggcgctgga gcgattggat accgcggtac | 1260 |
| ccttgccaga gcattggata aaggactcag gattgcgaga tttgatgtcc agacagagga | 1320 |

```
gttggttcgg gacaaaaacg gttattgcat tgagtgcaaa cctggcgagc ccggagaatt   1380
gctgacgctt gttgatgcta aagagccgaa caaagacttc aaaggatacc atcaaaacca   1440
ggcagcgacc aacaaaaaga ttgtcaaaga tgttttcaaa gccggcgaca tgtacttccg   1500
taccggagat atccttcggc gcgatagcga tgggtacttt tactttggcg accgtgtggg   1560
cgatacattc cggtggaagt ccgagaatgt gtctacggcc gaggtgtctg aagtcctctc   1620
gcagtatccg gactgtatcg aagtcaatgt gtatggagtt cagatcccag ggcaggacgg   1680
acgcgccggt atggcagcga ttgtgtccaa gagcacgatg gattgggaga aatttgcggc   1740
gtatgcactc aagaacctgc cgcggtattc tgttccgatc tttatccgca agatgcccga   1800
gatggagatc acagggacgt tcaagcagcg caaagtcgag ttggtgaatg agggaatcga   1860
ccccaagacg attgccaacg agatgctgtg gttggacgga caccactata agccgttcaa   1920
ggcggccgag caccagcgcg tcatcagcgg caaggccaag ctatagtagg gcgcgtgcgc   1980
caatgcagta gcaatactat tccccgcttt gtccattaaa aaaaaaaaaa aaaaaaaaa    2040 aa                                                                 2042

<210> SEQ ID NO 45
<211> LENGTH: 2345
<212> TYPE: DNA
<213> ORGANISM: Mortierella alpina

<400> SEQUENCE: 45
atggttggtg agtaaacagc gatcgccctg ggtccaatcg actcatctgc taatctgatc     60
tcacacgtcc cttatcaatt cacaaaagaa aaaaagaga caagagagag aattactaac    120
attgctctct ccctcgtgtc gatgcagctc tcccactcgt cgcagcagct gtcccagctg    180
ccatgtatgt gagctcaaag ctggcacttc ctcgggatat gaagttgatt aagagcttga    240
tcggagccaa gatggcctac agtgccatgg aaaagaacga cgccctcaac ctgacactcc    300
gcttcgacga gtgctaccgc aagtatcctg accgtgaagc cctggtcttt gagggcaaat    360
cctattcatt ccgtgatatt cagcttggta agccattgtt acacggcact caccccacgc    420
ttcctgcttt cagagctcac gactgctcga accttcaatt ttttgtatcg atcgatcacc    480
gatcgatcat gcgcccacat tgcctagagc tatggcacac gcgctaatgc atgccttctt    540
gttatgaagc ctcaacaggt gcggcaact ggttgctggc caaagggatc aagcgaggag    600
atatcgtctc gcttttcatg ttgaacaggc cagagttcat cttctgctgg ctgggtctca    660
acaagattgg agccactggt gccttcatca ataccaacct tacgggcaaa cccctgacac    720
attccctccg gacagccacg tcgtcaatgt tgatcatgga cacggagttg acagacgcga    780
tcgccaactc cctggatgag attcaggaga tgggctattc aatttactct tacgacccg    840 aagccgtgga ctttgctacc ccgatggata tctcgcaggt cccagacacc gatacacccg    900
aacacctgcg ccggaacacg accgcggatg acattgcgat gctcatctac acctctggaa    960
ctactggtct tcccaaggcc ggtcgtgtct ctcatgcgcg tgcctctagt aagttgagag   1020
tcttcagcct tgacatacg tattttttga gcgtgctact aacagttctc gttgccgtta   1080
tctgcatatt tttagtggga cctcagtttt ggaaccgatt ctatcacttc agtgagagcg   1140
acagggtcta tctgtccttg cccttgtacc acagtgctgg cgccatcttg ggagtgattg   1200
cttgttggac ctcgggagca accttgatcc tggcccgcaa gttctccgcg acacatttct   1260
gggaggattg ccgcgtgaac aacgcaactg tgattcaata cattggagaa atttgcagat   1320
```

| | |
|---|---|
| atctgctcaa cacgccagaa tcaccectgg acaaggcaca ctcgatacga ctggcacatg | 1380 |
| gtaatggaat gcgacccgat gtctggactc gcttcagaga tcggttcggc atcccgttga | 1440 |
| ttggcgagtg gtatgcatcg actgagggaa ctggagcctt gtcgaattat aacacaggcc | 1500 |
| caggcggcgc tggagcgatt ggataccgcg gtacccttgc cagagcattg gataaaggac | 1560 |
| tcaggattgc gagatttgat gtccagacag aggagttggt tcgggacaaa aacggttatt | 1620 |
| gcattgaggt aaaacataag gcgcattgtt gaagtctaaa tcacttcaga tgctttgttc | 1680 |
| ggcatgctta ccaaacgcac cgaccatctt ttcactggtg cggcatataa tagtgcaaac | 1740 |
| ctggcgagcc cggagaattg ctgacgcttg ttgatgctaa agagccgaac aaagacttca | 1800 |
| aaggatacca tcaaaaccag gcagcgacca acaaaaagat tgtcaaagat gttttcaaag | 1860 |
| ccggcgacat gtacttccgt accggagata tccttcggcg cgatagcgat gggtactttt | 1920 |
| actttggcga ccgtgtgggc gatacattcc ggtggaagtc cgagaatgtg tctacggccg | 1980 |
| aggtgtctga gtcctctcg cagtatccgg actgtatcga agtcaatgtg tatggagttc | 2040 |
| agatcccagg gcaggacgga cgcgccggta tggcagcgat tgtgtccaag agcacgatgg | 2100 |
| attgggagaa atttgcggcg tatgcactca agaacctgcc gcggtattct gttccgatct | 2160 |
| ttatccgcaa gatgcccgag atggagatca cagggacgtt caagcagcgc aaagtcgagt | 2220 |
| tggtgaatga gggaatcgac cccaagacga ttgccaacga gatgctgtgg ttggacggac | 2280 |
| accactataa gccgttcaag gcggccgagc accagcgcgt catcagcggc aaggccaagc | 2340 |
| tatag | 2345 |

<210> SEQ ID NO 46
<211> LENGTH: 2073
<212> TYPE: DNA
<213> ORGANISM: Mortierella alpina

<400> SEQUENCE: 46

| | |
|---|---|
| atggaaacct tggttaacgg aaagtatgcg gtcgagtacg acgaggtcga tcacatctat | 60 |
| cgcaacgtca tggctacagg cgggctcctc gacaggccta tgcctccata ctacgacatc | 120 |
| aaggagcgca ccatggccca cctctttgag tatatggcca acacctacga agacaaagac | 180 |
| gccatgggct ggcgagacat tatcaaggtc cacaaggtcg agaagcaggc tgccaatcct | 240 |
| ggcgagaagc caaagacctg gatcacttat gagctctcgg actacaactg gatgtcgtac | 300 |
| cgccaagcca agaactatgc agatcgagtt ggcttgggca tcacacgcct tggagttgag | 360 |
| aagggagact ttgtcatgat ctttgctagc acatgtcccg aatggttcct gacagcgcat | 420 |
| ggatgcttct cgcagtcagt gactatcgtg acagcctacg actcgatgga cgagaagtcg | 480 |
| atccagtttta ttgttgacca gtcccagccc aaggccatct ttgctgatgc gcacacgctc | 540 |
| cctgtggtgt ccaaactcat gcagaagggc aacagtggtg tcaaggcagt catttacaca | 600 |
| ggccaagagt gggaagtgac cgatgcaatc aagaagatgg agcaagtaga aaaccgctca | 660 |
| tttgagctgg ttcatatcga cgaactcaag aagaccaagt cagcatctaa cggcgaacag | 720 |
| tctgccggaa aggggaagca gagatcatct gaggatgccg aaggcgctca ggacgagatc | 780 |
| gaggtcatat accctaaggc ggatgatctg gcctgtatta tgtataccte tgggtcgacg | 840 |
| ggtcagccca agggcgcgca attgacacat ggcaacttga tggcggccat tggaagtgct | 900 |
| gcggccatgg agggcgacca gctggacaag gaaacagaca ttgttatttc atatctgcca | 960 |
| ttggcccatg tcctcgagtt tgtcattttc cactttgtgg tatccatggg ctgccgtctt | 1020 |
| ggattcggac gagcacgcac tctgatggat gatgcagtcg ctcccaccgc aggaagtggc | 1080 |

```
aggtccaagg gccttggtga tctgaaggcg ctccagccaa cattgatggc tggtgtgcca    1140
acgatctggg agcgtatccg caagggcatc ctggccgagg tcaacaagca atccttccct    1200
atccgtacac tcttctttgc tgcactcaac accaagtggg ctatcgtcca ggctaccgga    1260
tctgagaact ttgtcaccaa gactattgac tcgttggtct ttagtaaggc taaggagctc    1320
gttggaggca agctgcgcct taccttgact ggaggggccg gaatcagtga tgagacgcac    1380
cggttcttga gcatggtaat gtgctacgtt atctcgggat atggtctcac tgaagtctgt    1440
ggtgttgccg ctgtcaccct gccacgtatg ggtcaccgtc tcaggaccgt tggaccaccc    1500
gcgcccagtc ttgagctgaa gttggtgaat gtgcccgaca ccgagtacac aggagacaat    1560
ggatcgggcg aaatctggtt ccgtggacct gcagtgatga agggatactt caaactcgag    1620
gaagagacca agaaggtgat gaccggggat ggttggttca agacaggcga cattggcacg    1680
atgaacccag acggcacact gtcaatcaag gacagggtca gaatctggtt caagctgtct    1740
catggagaat atgtcgccct ggagaaatgt gaagccgttt atcgcgattc caaggagatc    1800
aagagcattt gcatcgttgc ggacaatggg tgccctgtgt tgctggccgt tgtggaaccg    1860
agccacgcag gggcgtctga caaggagatt ttggatatcc tgaagagcca agccaaggcg    1920
gcgggcctct ccaagtccga gactgtgcaa ggcgttatca ttgatgattc ggactggatg    1980
acgaatgggt tcatgacctc gagcagcaag gtcaagagac gcgaggtccg caaggcacac    2040
aacaaggata ttgaggagat gtggaagaag ttc                                 2073

<210> SEQ ID NO 47
<211> LENGTH: 691
<212> TYPE: PRT
<213> ORGANISM: Mortierella alpina

<400> SEQUENCE: 47

Met Glu Thr Leu Val Asn Gly Lys Tyr Ala Val Glu Tyr Asp Glu Val
1               5                   10                  15

Asp His Ile Tyr Arg Asn Val Met Ala Thr Gly Gly Leu Leu Asp Arg
            20                  25                  30

Pro Met Pro Tyr Tyr Asp Ile Lys Glu Arg Thr Met Ala His Leu
        35                  40                  45

Phe Glu Tyr Met Ala Asn Thr Tyr Glu Asp Lys Asp Ala Met Gly Trp
    50                  55                  60

Arg Asp Ile Ile Lys Val His Lys Val Glu Lys Gln Ala Ala Asn Pro
65                  70                  75                  80

Gly Glu Lys Pro Lys Thr Trp Ile Thr Tyr Glu Leu Ser Asp Tyr Asn
                85                  90                  95

Trp Met Ser Tyr Arg Gln Ala Lys Asn Tyr Ala Asp Arg Val Gly Leu
            100                 105                 110

Gly Ile Thr Arg Leu Gly Val Glu Lys Gly Asp Phe Val Met Ile Phe
        115                 120                 125

Ala Ser Thr Cys Pro Glu Trp Phe Leu Thr Ala His Gly Cys Phe Ser
    130                 135                 140

Gln Ser Val Thr Ile Val Thr Ala Tyr Asp Ser Met Asp Glu Lys Ser
145                 150                 155                 160

Ile Gln Phe Ile Val Asp Gln Ser Gln Pro Lys Ala Ile Phe Ala Asp
                165                 170                 175

Ala His Thr Leu Pro Val Val Ser Lys Leu Met Gln Lys Gly Asn Ser
            180                 185                 190
```

-continued

```
Gly Val Lys Ala Val Ile Tyr Thr Gly Gln Glu Trp Glu Val Thr Asp
            195                 200                 205
Ala Ile Lys Lys Met Glu Gln Val Glu Asn Arg Ser Phe Glu Leu Val
210                 215                 220
His Ile Asp Glu Leu Lys Lys Thr Lys Ser Ala Ser Asn Gly Glu Gln
225                 230                 235                 240
Ser Ala Gly Lys Gly Lys Gln Arg Ser Ser Glu Asp Ala Glu Gly Ala
            245                 250                 255
Gln Asp Glu Ile Glu Val Ile Tyr Pro Lys Ala Asp Asp Leu Ala Cys
            260                 265                 270
Ile Met Tyr Thr Ser Gly Ser Thr Gly Gln Pro Lys Gly Ala Gln Leu
            275                 280                 285
Thr His Gly Asn Leu Met Ala Ala Ile Gly Ser Ala Ala Ala Met Glu
290                 295                 300
Gly Asp Gln Leu Asp Lys Glu Thr Asp Ile Val Ile Ser Tyr Leu Pro
305                 310                 315                 320
Leu Ala His Val Leu Glu Phe Val Ile Ser His Phe Val Val Ser Met
                325                 330                 335
Gly Cys Arg Leu Gly Phe Gly Arg Ala Arg Thr Leu Met Asp Asp Ala
            340                 345                 350
Val Ala Pro Thr Ala Gly Ser Gly Arg Ser Lys Gly Leu Gly Asp Leu
            355                 360                 365
Lys Ala Leu Gln Pro Thr Leu Met Ala Gly Val Pro Thr Ile Trp Glu
            370                 375                 380
Arg Ile Arg Lys Gly Ile Leu Ala Glu Val Asn Lys Gln Ser Phe Pro
385                 390                 395                 400
Ile Arg Thr Leu Phe Phe Ala Ala Leu Asn Thr Lys Trp Ala Ile Val
                405                 410                 415
Gln Ala Thr Gly Ser Glu Asn Phe Val Thr Lys Thr Ile Asp Ser Leu
            420                 425                 430
Val Phe Ser Lys Ala Lys Glu Leu Val Gly Gly Lys Leu Arg Leu Thr
            435                 440                 445
Leu Thr Gly Gly Ala Gly Ile Ser Asp Glu Thr His Arg Phe Leu Ser
450                 455                 460
Met Val Met Cys Tyr Val Ile Ser Gly Tyr Gly Leu Thr Glu Val Cys
465                 470                 475                 480
Gly Val Ala Ala Val Thr Leu Pro Arg Met Gly His Arg Leu Arg Thr
                485                 490                 495
Val Gly Pro Pro Ala Pro Ser Leu Glu Leu Lys Leu Val Asn Val Pro
            500                 505                 510
Asp Thr Glu Tyr Thr Gly Asp Asn Gly Ser Gly Glu Ile Trp Phe Arg
            515                 520                 525
Gly Pro Ala Val Met Lys Gly Tyr Phe Lys Leu Glu Glu Thr Lys
            530                 535                 540
Lys Val Met Thr Gly Asp Gly Trp Phe Lys Thr Gly Asp Ile Gly Thr
545                 550                 555                 560
Met Asn Pro Asp Gly Thr Leu Ser Ile Lys Asp Arg Val Lys Asn Leu
                565                 570                 575
Val Lys Leu Ser His Gly Glu Tyr Val Ala Leu Glu Lys Cys Glu Ala
            580                 585                 590
Val Tyr Arg Asp Ser Lys Glu Ile Lys Ser Ile Cys Ile Val Ala Asp
            595                 600                 605
Asn Gly Cys Pro Val Leu Leu Ala Val Val Glu Pro Ser His Ala Gly
```

```
                610              615              620
Ala Ser Asp Lys Glu Ile Leu Asp Ile Leu Lys Ser Gln Ala Lys Ala
625                 630                 635                 640

Ala Gly Leu Ser Lys Ser Glu Thr Val Gln Gly Val Ile Ile Asp Asp
                645                 650                 655

Ser Asp Trp Met Thr Asn Gly Phe Met Thr Ser Ser Lys Val Lys
            660                 665                 670

Arg Arg Glu Val Arg Lys Ala His Asn Lys Asp Ile Glu Glu Met Trp
        675                 680                 685

Lys Lys Phe
    690

<210> SEQ ID NO 48
<211> LENGTH: 2076
<212> TYPE: DNA
<213> ORGANISM: Mortierella alpina

<400> SEQUENCE: 48
atggaaacct tggttaacgg aaagtatgcg gtcgagtacg acgaggtcga tcacatctat      60
cgcaacgtca tggctacagg cgggctcctc gacaggccta tgcctccata ctacgacatc     120
aaggagcgca ccatggccca cctctttgag tatatggcca cacctacga agacaaagac      180 gccatgggct ggcgagacat tatcaaggtc acaaggtcg agaagcaggc tgccaatcct      240
ggcgagaagc caaagacctg gatcacttat gagctctcgg actacaactg gatgtcgtac     300
cgccaagcca gaactatgc agatcgagtt ggcttgggca tcacacgcct tggagttgag      360
aagggagact ttgtcatgat ctttgctagc acatgtcccg aatggttcct gacagcgcat     420
ggatgcttct cgcagtcagt gactatcgtg acagcctacg actcgatgga cgagaagtcg     480
atccagttta ttgttgacca gtcccagccc aaggccatct ttgctgatgc gcacacgctc     540
cctgtggtgt ccaaactcat gcagaagggc aacagtggtg tcaaggcagt catttacaca     600
ggccaagagt gggaagtgac cgatgcaatc aagaagatg agcaagtaga aaaccgctca      660
tttgagctgg ttcatatcga cgaactcaag aagaccaagt cagcatctaa cggcgaacag     720
tctgccggaa aggggaagca gagatcatct gaggatgccg aaggcgctca ggacgagatc     780
gaggtcatat accctaaggc ggatgatctg gcctgtatta tgtataccte tgggtcgacg     840 ggtcagccca gggcgcgca attgacacat ggcaacttga tggcggccat ggaagtgct      900 gcggccatgg agggcgacca gctggacaag gaaacagaca ttgttatttc atatctgcca     960
ttggcccatg tcctcgagtt tgtcatttcc cactttgtgg tatccatggg ctgccgtctt    1020
ggattcggac gagcacgcac tctgatggat gatgcagtcg ctcccaccgc aggaagtggc    1080
aggtccaagg gccttggtga tctgaaggcg ctccagccaa cattgatggc tggtgtgcca    1140
acgatctggg agcgtatccg caagggcatc ctggccgagg tcaacaagca atccttccct    1200
atccgtacac tcttctttgc tgcactcaac accaagtggg ctatcgtcca ggctaccgga    1260
tctgagaact tgtcaccaa gactattgac tcgttggtct ttagtaaggc taaggagctc     1320
gttggaggca agctgcgcct tacccttgact ggaggggccg gaatcagtga tgagacgcac    1380
cggttcttga gcatggtaat gtgctacgtt atctcgggat atggtctcac tgaagtctgt    1440
ggtgttgccg ctgtcaccct gccacgtatg ggtcaccgtc tcaggaccgt ggaccaccc    1500 gcgcccagtc ttgagctgaa gttggtgaat gtgcccgaca ccgagtacac aggagacaat    1560
ggatcgggcg aaatctggtt ccgtggacct gcagtgatga agggatactt caaactcgag    1620
```

```
gaagagacca agaaggtgat gaccggggat ggttggttca agacaggcga cattggcacg    1680
atgaacccag acggcacact gtcaatcaag gacagggtca agaatctggt caagctgtct    1740
catggagaat atgtcgccct ggagaaatgt gaagccgttt atcgcgattc aaggagatc     1800 aagagcattt gcatcgttgc ggacaatggg tgccctgtgt tgctggccgt tgtggaaccg    1860
agccacgcag gggcgtctga caaggagatt ttggatatcc tgaagagcca agccaaggcg    1920
gcgggcctct ccaagtccga gactgtgcaa ggcgttatca ttgatgattc ggactggatg    1980
acgaatgggt tcatgacctc gagcagcaag gtcaagagac gcgaggtccg caaggcacac    2040
aacaaggata ttgaggagat gtggaagaag ttctag                              2076
```

<210> SEQ ID NO 49
<211> LENGTH: 2076
<212> TYPE: DNA
<213> ORGANISM: Mortierella alpina

<400> SEQUENCE: 49

```
atggaaacct tggttaacgg aaagtatgcg gtcgagtacg acgaggtcga tcacatctat    60
cgcaacgtca tggctacagg cgggctcctc gacaggccta tgcctccata ctacgacatc    120
aaggagcgca ccatggccca cctctttgag tatatggcca cacctacga agacaaagac     180 gccatgggct ggcgagacat tatcaaggtc cacaaggtcg agaagcaggc tgccaatcct    240
ggcgagaagc caaagacctg gatcacttat gagctctcgg actacaactg gatgtcgtac    300
cgccaagcca gaactatgc agatcgagtt ggcttgggca tcacacgcct tggagttgag    360
aagggagact ttgtcatgat cttgctagc acatgtcccg aatggttcct gacagcgcat    420
ggatgcttct cgcagtcagt gactatcgtg acagcctacg actcgatgga cgagaagtcg    480
atccagttta ttgttgacca gtcccagccc aaggccatct tgctgatgc gcacacgctc    540 cctgtggtgt ccaaactcat gcagaagggc aacagtggtg tcaaggcagt catttacaca    600
ggccaagagt gggaagtgac cgatgcaatc aagaagatgg agcaagtaga aaaccgctca    660
tttgagctgg ttcatatcga cgaactcaag aagaccaagt cagcatctaa cggcgaacag    720
tctgccggaa aggggaagca gagatcatct gaggatgccg aaggcgctca ggacgagatc    780
gaggtcatat accctaaggc ggatgatctg gcctgtatta tgtataccctc tgggtcgacg    840 ggtcagccca gggcgcgca attgacacat ggcaacttga tggcggccat tggaagtgct    900
gcggccatgg agggcgacca gctggacaag gaaacagaca ttgttatttc atatctgcca    960
ttggcccatg tcctcgagtt tgtcatttcc cactttgtgg tatccatggg ctgccgtctt    1020
ggattcggac gagcacgcac tctgatggat gatgcagtcg ctcccaccgc aggaagtggc    1080
aggtccaagg gccttggtga tctgaaggcg ctccagccaa cattgatggc tggtgtgcca    1140
acgatctggg agcgtatccg caagggcatc ctggccgagg tcaacaagca atccttccct    1200
atccgtacac tcttctttgc tgcactcaac accaagtggg ctatcgtcca ggctaccgga    1260
tctgagaact ttgtcaccaa gactattgac tcgttggtct ttagtaaggc taaggagctc    1320
gttggaggca agctgcgcct taccttgact ggaggggccg gaatcagtga tgagacgcac    1380
cggttcttga gcatggtaat gtgctacgtt atctcgggat atggtctcac tgaagtctgt    1440
ggtgttgccg ctgtcaccct gccacgtatg ggtcaccgtc tcaggaccgt ggaccaccc    1500 gcgcccagtc ttgagctgaa gttggtgaat gtgcccgaca ccgagtacac aggagacaat    1560
ggatcgggcg aaatctggtt ccgtggacct gcagtgatga agggatactt caaactcgag    1620
gaagagacca agaaggtgat gaccggggat ggttggttca agacaggcga cattggcacg    1680
```

```
atgaacccag acggcacact gtcaatcaag gacagggtca agaatctggt caagctgtct    1740
catggagaat atgtcgccct ggagaaatgt gaagccgttt atcgcgattc caaggagatc    1800
aagagcattt gcatcgttgc ggacaatggg tgccctgtgt tgctggccgt tgtggaaccg    1860
agccacgcag gggcgtctga caaggagatt ttggatatcc tgaagagcca agccaaggcg    1920
gcgggcctct ccaagtccga gactgtgcaa ggcgttatca ttgatgattc ggactggatg    1980
acgaatgggt tcatgacctc gagcagcaag gtcaagagac gcgaggtccg caaggcacac    2040
aacaaggata ttgaggagat gtggaagaag ttctag                              2076
```

<210> SEQ ID NO 50
<211> LENGTH: 3236
<212> TYPE: DNA
<213> ORGANISM: Mortierella alpina

<400> SEQUENCE: 50

```
atggaaacct tggttaacgg aaagtatgcg gtcgagtacg acgaggtcga tcacatctat      60
cgcaacgtca tggctacagg cgggctcctc gacaggccta tgcctccata ctacgacatc     120
aaggagcgca ccatggccca cctctttgag tatatggcca acacctacga agacaaagac     180
gccatgggct ggcgagacat tatcaaggta ttgactgccc cggcctatca cttttttaccc    240 cacacgatcc tccctttttt ttctctccca ttcttctatc ctgaccgtat cgctatcgaa     300
cgagtcaacg agatcagttc ccacgcttac tttactccct cgtctgattc tgattatttt     360
ctctctctgc tcttcgtga tttgttcgca ggtccacaag gtcgagaagc aggctgccaa     420
tcctggcgag aagccaaaga cctggatcac ttatgagctc tcggactaca actggatgtc     480
gtaccgccaa gccaagaact atgcagatcg agttggcttg gcatcacac gccttggagt     540 tgagaaggga gactttgtca tgatctttgc tagcacatgg tataacctca tgcagacaac     600
tttcgcatcc atgacagcat cgcaagaaaa aaaaaagaga aggaaattat gataattcgg     660
gccaagcgac taaaacaccg ctatcgcacg ctttttttttt tttttcgct atcttgcatt     720 tcttatcgtt caaatagtcc cgaatggttc ctgacagcgc atggtaagct ttttcttttt     780
gcggatgatg atttcttctt atgacagcat gatgagattc aaccgggatt aggtgacggc     840
tgttgattgt gcaaaagggg ggccggacaa tttgaagaga cttggggagg tgtttgtgat     900
gacgacaaat ccaagattca acagaagact ggtgccaggg aagagtagag agggtgcctc     960
gttctttggc atatgaaagt ggattacgat atggctgagt taggagtcta attcatcgcg    1020
gaaaaagagt cgcgactgaa gtcccaagtc ggggactgta gaaagtattc cactcgtgtc    1080
tggtgaaatg aggaggactg ggttgggtt tggagtgccg acgagaaatc atggaatacg    1140
cttctcggtc ttcagtccac tgatcactca tggcgcaatt gactctacaa taataggatg    1200
cttctcgcag tcagtgacta tcgtgacagc ctacgactcg atggacgaga agtcgatcca    1260
gtttattgtt gaccagtccc agcccaaggc catctttgct gatgcgcaca cgctcccctgt   1320 ggtgtccaaa ctcatgcaga agggcaacag tggtgtcaag gcagtcattt acacaggcca    1380
agagtgggaa gtgaccgatg caatcaagaa gatggagcaa gtagaaaacc gctcatttga    1440
gctggttcat atcgacgaac tcaagaagac caagtcagca tctaacggcg aacagtctgc    1500
cggaaagggg aagcagagat catctgagga tgccgaaggc gctcaggacg agatcgaggt    1560 catatacccct aaggcggatg atctggcctg tattatgtat acctctgggt cgacgggtca    1620
gcccaagggc gcgcaattga cacatggcaa cttgatggcg ccattggaa gtgctgcggc    1680
```

```
catggagggc gaccagctgg acaaggaaac agacattgtt atttcatatc tgccattggc   1740
ccatgtcctc gagtttgtca tttcccactt tgtggtatcc atggtaagtc gaacatccct   1800
ttacatctgc atcccaaaat gcggctaaag tcaagttgtt gacctgaacg tttatattca   1860
tcttagggct gccgtcttgg attcggacga gcacgcactc tgatggatga tgcagtcgct   1920
cccaccgcag gaagtggcag gtccaagggc cttggtgatc tgaaggcgct ccagccaaca   1980
ttgatgggta tgattggcat gaagccagag actaatatga cgtagagtgg acaaaacct    2040 tattttgacg tattgcatat tgtgtcgatt ttcaaaaacg atagctggtg tgccaacgat   2100
ctgggagcgt atccgcaagg gcatcctggc cgaggtcaac aagcaatcct tccctatccg   2160
tacactcttc tttgctgcac tcaacaccaa gtgggctatc gtccaggcta ccggatctga   2220
gaactttgtc accaagacta ttgactcgtt ggtctttagt aaggctaagg agctcgttgg   2280
aggcaagctg cgccttacct tgactggagg ggccggaatc agtgatgaga cgcaccggtt   2340
cttgagcatg gtaatgtgct acgttatctc gggatatggt ctcactgaag tctgtggtgt   2400
tgccgctgtc accctgccac gtatgggtca ccgtctcagg accgttggac cacccgtaag   2460
tccgctcgca tatcttctcg cgatctgaat atgcgagctg ttttttttg tctttcaaaa    2520 gctaacactt tgcttttcg cgacaacagg cgcccagtct tgagctgaag ttggtgaatg    2580
tgcccgacac cgagtacaca ggagacaatg gatcgggcga aatctggttc cgtggacctg   2640
cagtgatgaa gggatacttc aaactcgagg aagagaccaa gaaggtgatg accggggatg   2700
gttggttcaa gacaggcgac attggcacga tgaacccaga cggcacactg tcaatcaagg   2760
acagggtcaa gaatctggtc aagctgtctc atggagaata tgtcgccctg gagaaatgtg   2820 aagccgtta tcgcgattcc aaggagatca agagcattg catcgttgcg gacaatgggt    2880
gccctgtgtt gctggccgtt gtggaaccga gccacgcagg ggtgagtgag acgcttttgg   2940
cctgacaagg tctcgttctt atgggaatgt ggatcattac tctatcacta cgagagagg    3000 ctgtattatt ctacttgcgt aacgtggcat aggcgtctga caaggagatt ttggatatcc   3060
tgaagagcca agccaaggcg gcgggcctct ccaagtccga gactgtgcaa ggcgttatca   3120
ttgatgattc ggactggatg acgaatgggt tcatgacctc gagcagcaag gtcaagagac   3180
gcgaggtccg caaggcacac aacaaggata ttgaggagat gtggaagaag ttctag       3236
```

<210> SEQ ID NO 51
<211> LENGTH: 2040
<212> TYPE: DNA
<213> ORGANISM: Mortierella alpina

<400> SEQUENCE: 51

```
atgccaaagt gctttaccgt caacgtcggc cccgaggacg tcaagggcga gactcgcatc     60
cgtcgctcca tccaggccgt cgacaaactc atggactcac cctcaagcga catcaagacc    120
ttgtacgatg tcatccagta ctctgccaag gtccgcccca acctcaacgc catcggctac    180
cgcaagattg tcaagatgat cgaagaggaa aaggagatcc caagatggt cagcggcgag    240 cctgtcaagg agaaaaagac gtggaaatac ttcaagctct ccggctacca ctatctgacc    300
tacaaggaca ccaaggccgt catcgacagc attggaagtg gcctgcgcaa gtggggtgtt   360
gagcccaagg agaggatcac cgtctttggt tccacaagtg ccaactggct gctggtcgct    420
catggtgcct tcacgcagtc catgaccatc gtcaccgtgt atgacacttt gggcgaggaa    480
ggattgctgc actcgatgaa cgaggccgag gtgggaacgg cctacacgaa cgctgatttg    540
atcaagacaa tgaccaacgt ttcaggacgc tgccccaccc tcaagaggat cgtctatgac    600
```

```
ggcgaagcca acgcagcaga cgtgatcgcc cttcagacgg cccatcctca ccttcagctt    660
atcactctgg aggagctgaa gcagctcggt gtggatcacc ctgtggagcc cactcctccc    720
accgccgagg attgctcctg catcatgtac acttctggat cgaccggaaa ccctaaggga    780
gtcatcctca ctcacggaaa cctcattgcc gccattggcg gagttaacaa gatgctggaa    840
aagtacattc gcgaaggcga tgtcttgctt gcctaccttc ccttggctca cgttctggaa    900
ttcatggttg agaacctctg tctcttctgg ggtgtaaccc ttggatatgg tactgtccgc    960
acgctgacgg atgcctctgt gcgtgagtgc cagggtgata tcaaggaatt gcggcctacg   1020
cttatgaccg gcgttccagc agtgtgggag accatccgca aggtgttcct cgcccaagta   1080
aaccagggtt cacctctggt tcaatccgtc ttcaacgcgg ctctgaacgc caaggcctgg   1140
tgcatggacc gcaaactagg cgctttgact ggaattttcg acactgtggt gttcaacaag   1200
gtccgtcagc aaactggagg tcgtcttcgc tacgcgctct cgggcggcgc gcctatctcc   1260
caggagaccc agcgcttctt gaccacagca ctgtgcccta tccttcaagc ctatggcatg   1320
actgagtcgt gcggcatgtg ctcgatcatg actccagagg cgttcaacta caaccgcgtc   1380
ggttcccctg ttccctgcac agaggtcaag ctcgtggatg tgcccgatgc aggatacttt   1440
tcgactgatt cgccccgccc tcgtggtgag atttggattc gcggaccctc catcacctct   1500
ggatacttca agaacgctga ggagacctcg gcagccatca cagaggaccg ctggctcaag   1560
actggagata ttggagagtg gcatgctgat ggcacactct cggtcattga tcgcaagaag   1620
aacttggtca agttgtcgca tggcgagtac attgctctag agaaacttga gtcggtgtac   1680
aagagcacgg cttactgcaa caacatctgc gtttatgccg attccatgca aaacaagcct   1740
gtggcgctga ttgttgcgag tgaaccccgc atcctcgagc tggccaaggc caagggcctg   1800
gagagccgcg acttttgcagt gctctgccac gataaggtga tcatcaaggc tgtcctcgac   1860
gcctgtctcg cgactgccaa aaaggctggc ctcaagcccg ccgagttgct gcagggtgtg   1920
tacctggagt ctgaggagtg gaccgctcaa ggcggtttgt tgactgctgc tcagaaattg   1980
aagcgcaagg aaatcaacca ggcttatgct gaccagatca gcagatcta tggctccaag   2040
```

<210> SEQ ID NO 52
<211> LENGTH: 680
<212> TYPE: PRT
<213> ORGANISM: Mortierella alpina

<400> SEQUENCE: 52

Met Pro Lys Cys Phe Thr Val Asn Val Gly Pro Glu Asp Val Lys Gly
1               5                   10                  15

Glu Thr Arg Ile Arg Arg Ser Ile Gln Ala Val Asp Lys Leu Met Asp
            20                  25                  30

Ser Pro Ser Ser Asp Ile Lys Thr Leu Tyr Asp Val Ile Gln Tyr Ser
        35                  40                  45

Ala Lys Val Arg Pro Asn Leu Asn Ala Ile Gly Tyr Arg Lys Ile Val
    50                  55                  60

Lys Met Ile Glu Glu Lys Glu Ile Thr Lys Met Val Ser Gly Glu
65                  70                  75                  80

Pro Val Lys Glu Lys Thr Trp Lys Tyr Phe Lys Leu Ser Gly Tyr
                85                  90                  95

His Tyr Leu Thr Tyr Lys Asp Thr Lys Ala Val Ile Asp Ser Ile Gly
            100                 105                 110

Ser Gly Leu Arg Lys Trp Gly Val Glu Pro Lys Glu Arg Ile Thr Val

```
            115                 120                 125
Phe Gly Ser Thr Ser Ala Asn Trp Leu Leu Val Ala His Gly Ala Phe
            130                 135                 140
Thr Gln Ser Met Thr Ile Val Thr Val Tyr Asp Thr Leu Gly Glu Glu
145                 150                 155                 160
Gly Leu Leu His Ser Met Asn Glu Ala Glu Val Gly Thr Ala Tyr Thr
                165                 170                 175
Asn Ala Asp Leu Ile Lys Thr Met Thr Asn Val Ser Gly Arg Cys Pro
                180                 185                 190
Thr Leu Lys Arg Ile Val Tyr Asp Gly Glu Ala Asn Ala Ala Asp Val
                195                 200                 205
Ile Ala Leu Gln Thr Ala His Pro His Leu Gln Leu Ile Thr Leu Glu
            210                 215                 220
Glu Leu Lys Gln Leu Gly Val Asp His Pro Val Glu Pro Thr Pro Pro
225                 230                 235                 240
Thr Ala Glu Asp Cys Ser Cys Ile Met Tyr Thr Ser Gly Ser Thr Gly
                245                 250                 255
Asn Pro Lys Gly Val Ile Leu Thr His Gly Asn Leu Ile Ala Ala Ile
                260                 265                 270
Gly Gly Val Asn Lys Met Leu Glu Lys Tyr Ile Arg Glu Gly Asp Val
                275                 280                 285
Leu Leu Ala Tyr Leu Pro Leu Ala His Val Leu Glu Phe Met Val Glu
            290                 295                 300
Asn Leu Cys Leu Phe Trp Gly Val Thr Leu Gly Tyr Gly Thr Val Arg
305                 310                 315                 320
Thr Leu Thr Asp Ala Ser Val Arg Glu Cys Gln Gly Asp Ile Lys Glu
                325                 330                 335
Leu Arg Pro Thr Leu Met Thr Gly Val Pro Ala Val Trp Glu Thr Ile
                340                 345                 350
Arg Lys Gly Val Leu Ala Gln Val Asn Gln Gly Ser Pro Leu Val Gln
                355                 360                 365
Ser Val Phe Asn Ala Ala Leu Asn Ala Lys Ala Trp Cys Met Asp Arg
            370                 375                 380
Lys Leu Gly Ala Leu Thr Gly Ile Phe Asp Thr Val Val Phe Asn Lys
385                 390                 395                 400
Val Arg Gln Gln Thr Gly Gly Arg Leu Arg Tyr Ala Leu Ser Gly Gly
                405                 410                 415
Ala Pro Ile Ser Gln Glu Thr Gln Arg Phe Leu Thr Thr Ala Leu Cys
                420                 425                 430
Pro Ile Leu Gln Ala Tyr Gly Met Thr Glu Ser Cys Gly Met Cys Ser
                435                 440                 445
Ile Met Thr Pro Glu Ala Phe Asn Tyr Asn Arg Val Gly Ser Pro Val
            450                 455                 460
Pro Cys Thr Glu Val Lys Leu Val Asp Val Pro Asp Ala Gly Tyr Phe
465                 470                 475                 480
Ser Thr Asp Ser Pro Arg Pro Arg Gly Glu Ile Trp Ile Arg Gly Pro
                485                 490                 495
Ser Ile Thr Ser Gly Tyr Phe Lys Asn Ala Glu Glu Thr Ser Ala Ala
                500                 505                 510
Ile Thr Glu Asp Arg Trp Leu Lys Thr Gly Asp Ile Gly Glu Trp His
                515                 520                 525
Ala Asp Gly Thr Leu Ser Val Ile Asp Arg Lys Lys Asn Leu Val Lys
            530                 535                 540
```

```
Leu Ser His Gly Glu Tyr Ile Ala Leu Glu Lys Leu Glu Ser Val Tyr
545                 550                 555                 560
Lys Ser Thr Ala Tyr Cys Asn Asn Ile Cys Val Tyr Ala Asp Ser Met
                565                 570                 575
Gln Asn Lys Pro Val Ala Leu Ile Val Ala Ser Glu Pro Arg Ile Leu
            580                 585                 590
Glu Leu Ala Lys Ala Lys Gly Leu Glu Ser Arg Asp Phe Ala Val Leu
        595                 600                 605
Cys His Asp Lys Val Ile Ile Lys Ala Val Leu Asp Ala Cys Leu Ala
    610                 615                 620
Thr Ala Lys Lys Ala Gly Leu Lys Pro Ala Glu Leu Leu Gln Gly Val
625                 630                 635                 640
Tyr Leu Glu Ser Glu Glu Trp Thr Ala Gln Gly Gly Leu Leu Thr Ala
                645                 650                 655
Ala Gln Lys Leu Lys Arg Lys Glu Ile Asn Gln Ala Tyr Ala Asp Gln
            660                 665                 670
Ile Lys Gln Ile Tyr Gly Ser Lys
        675                 680
```

<210> SEQ ID NO 53
<211> LENGTH: 2043
<212> TYPE: DNA
<213> ORGANISM: Mortierella alpina

<400> SEQUENCE: 53

| | | | | | |
|---|---|---|---|---|---|
| atgccaaagt | gctttaccgt | caacgtcggc | cccgaggacg | tcaagggcga | gactcgcatc | 60 |
| cgtcgctcca | tccaggccgt | cgacaaactc | atggactcac | cctcaagcga | catcaagacc | 120 |
| ttgtacgatg | tcatccagta | ctctgccaag | gtccgcccca | acctcaacgc | catcggctac | 180 |
| cgcaagattg | tcaagatgat | cgaagaggaa | aaggagatca | ccaagatggt | cagcggcgag | 240 |
| cctgtcaagg | agaaaaagac | gtggaaatac | ttcaagctct | ccggctacca | ctatctgacc | 300 |
| tacaaggaca | ccaaggccgt | catcgacagc | attggaagtg | gcctgcgcaa | gtgggtgtt | 360 |
| gagcccaagg | agaggatcac | cgtctttggt | tccacaagtg | ccaactggct | gctggtcgct | 420 |
| catggtgcct | tcacgcagtc | catgaccatc | gtcaccgtgt | atgacacttt | gggcgaggaa | 480 |
| ggattgctgc | actcgatgaa | cgaggccgag | gtgggaacgg | cctacacgaa | cgctgatttg | 540 |
| atcaagacaa | tgaccaacgt | ttcaggacgc | tgccccaccc | tcaagaggat | cgtctatgac | 600 |
| ggcgaagcca | acgcagcaga | cgtgatcgcc | cttcagacgg | cccatcctca | ccttcagctt | 660 |
| atcactctgg | aggagctgaa | gcagctcggt | gtggatcacc | ctgtggagcc | cactcctccc | 720 |
| accgccgagg | attgctcctg | catcatgtac | acttctggat | cgaccggaaa | ccctaaggga | 780 |
| gtcatcctca | ctcacggaaa | cctcattgcc | gccattggcg | gagttaacaa | gatgctggaa | 840 |
| aagtacattc | gcgaaggcga | tgtcttgctt | gcctaccttc | ccttggctca | cgttctggaa | 900 |
| ttcatggttg | agaacctctg | tctcttctgg | ggtgtaaccc | ttggatatgg | tactgtccgc | 960 |
| acgctgacgg | atgcctctgt | gcgtgagtgc | caggtgata | tcaaggaatt | gcggcctacg | 1020 |
| cttatgaccg | gcgttccagc | agtgtgggag | accatccgca | aggtgttct | cgcccaagta | 1080 |
| aaccagggtt | cacctctggt | tcaatccgtc | ttcaacgcgg | ctctgaacgc | caaggcctgg | 1140 |
| tgcatggacc | gcaaactagg | cgctttgact | ggaattttcg | acactgtggt | gttcaacaag | 1200 |
| gtccgtcaga | aaactggagg | tcgtcttcgc | tacgcgctct | cgggcggcgc | gcctatctcc | 1260 |
| caggagaccc | agcgcttctt | gaccacagca | ctgtgcccta | tccttcaagc | ctatggcatg | 1320 |

```
actgagtcgt gcggcatgtg ctcgatcatg actccagagg cgttcaacta caaccgcgtc    1380
ggttcccctg ttccctgcac agaggtcaag ctcgtggatg tgcccgatgc aggatacttt    1440
tcgactgatt cgccccgccc tcgtggtgag atttggattc gcggaccctc catcacctct    1500
ggatacttca agaacgctga ggagacctcg gcagccatca cagaggaccg ctggctcaag    1560
actggagata ttggagagtg gcatgctgat ggcacactct cggtcattga tcgcaagaag    1620
aacttggtca agttgtcgca tggcgagtac attgctctag agaaacttga gtcggtgtac    1680
aagagcacgg cttactgcaa caacatctgc gtttatgccg attccatgca aaacaagcct    1740
gtggcgctga ttgttgcgag tgaaccccgc atcctcgagc tggccaaggc caagggcctg    1800
gagagccgcg actttgcagt gctctgccac gataaggtga tcatcaaggc tgtcctcgac    1860
gcctgtctcg cgactgccaa aaaggctggc ctcaagcccg ccgagttgct gcagggtgtg    1920
tacctggagt ctgaggagtg gaccgctcaa ggcggtttgt tgactgctgc tcagaaattg    1980
aagcgcaagg aaatcaacca ggcttatgct gaccagatca agcagatcta tggctccaag    2040
taa                                                                  2043

<210> SEQ ID NO 54
<211> LENGTH: 2052
<212> TYPE: DNA
<213> ORGANISM: Mortierella alpina

<400> SEQUENCE: 54
catgccaaag tgctttaccg tcaacgtcgg ccccgaggac gtcaagggcg agactcgcat      60
ccgtcgctcc atccaggccg tcgacaaact catggactca ccctcaagcg acatcaagac     120
cttgtacgat gtcatccagt actctgccaa ggtccgcccc aacctcaacg ccatcggcta     180
ccgcaagatt gtcaagatga tcgaagagga aaaggagatc accaagatgg tcagcggcga     240
gcctgtcaag gagaaaaaga cgtggaaata cttcaagctc tccggctacc actatctgac     300
ctacaaggac accaaggccg tcatcgacag cattggaagt ggcctgcgca gtggggtgt     360 tgagcccaag gagaggatca ccgtcttggg ttccacaagt gccaactggc tgctggtcgc     420
tcatggtgcc ttcacgcagt ccatgaccat cgtcaccgtg tatgacactt tgggcgagga     480
aggattgctg cactcgatga acgaggccga ggtgggaacg gcctacacga acgctgattt     540
gatcaagaca atgaccaacg tttcaggacg ctgccccacc ctcaagagga tcgtctatga     600
cggcgaagcc aacgcagcag acgtgatcgc ccttcagacg gcccatcctc accttcagct     660
tatcactctg gaggagctga agcagctcgg tgtggatcac cctgtggagc ccactcctcc     720
caccgccgag gattgctcct gcatcatgta cacttctgga tcgaccggaa accctaaggg     780
agtcatcctc actcacggaa acctcattgc cgccattggc ggagttaaca agatgctgga     840
aaagtacatt cgcgaaggcg atgtcttgct tgcctacctt cccttggctc acgttctgga     900
attcatggtt gagaacctct gtctcttctg gggtgtaacc cttggatatg gtactgtccg     960
cacgctgacg gatgcctctg tgcgtgagtg ccagggtgat atcaaggaat gcggcctac    1020 gcttatgacc ggcgttccag cagtgtggga gaccatccgc aaaggtgttc tcgcccaagt    1080
aaaccagggt tcacctctgg ttcaatccgt cttcaacgcg gctctgaacg ccaaggcctg    1140
gtgcatggac cgcaaactag gcgctttgac tggaattttc gacactgtgg tgttcaacaa    1200
ggtccgtcag caaactggag gtcgtcttcg ctacgcgctc tcgggcggcg cgcctatctc    1260
ccaggagacc cagcgcttct tgaccacagc actgtgccct atccttcaag cctatggcat    1320
```

```
gactgagtcg tgcggcatgt gctcgatcat gactccagag gcgttcaact acaaccgcgt    1380
cggttcccct gttccctgca cagaggtcaa gctcgtggat gtgcccgatg caggatactt    1440
ttcgactgat tcgccccgcc ctcgtggtga gatttggatt cgcggaccct ccatcacctc    1500
tggatacttc aagaacgctg aggagacctc ggcagccatc acagaggacc gctggctcaa    1560
gactggagat attggagagt ggcatgctga tggcacactc tcggtcattg atcgcaagaa    1620
gaacttggtc aagttgtcgc atggcgagta cattgctcta gagaaacttg agtcggtgta    1680
caagagcacg gcttactgca caacatctg cgtttatgcc gattccatgc aaaacaagcc    1740
tgtggcgctg attgttgcga gtgaaccccg catcctcgag ctggccaagg ccaagggcct    1800
ggagagccgc gactttgcag tgctctgcca cgataaggtg atcatcaagg ctgtcctcga    1860
cgcctgtctc gcgactgcca aaaaggctgg cctcaagccc gccgagttgc tgcagggtgt    1920
gtacctggag tctgaggagt ggaccgctca aggcggtttg ttgactgctg ctcagaaatt    1980
gaagcgcaag gaaatcaacc aggcttatgc tgaccagatc aagcagatct atggctccaa    2040
gtaaaaatga ac                                                        2052

<210> SEQ ID NO 55
<211> LENGTH: 2569
<212> TYPE: DNA
<213> ORGANISM: Mortierella alpina
<220> FEATURE:
<221> NAME/KEY: modified_base
<222> LOCATION: (557)..(767)
<223> OTHER INFORMATION: n is a, c, g, or t

<400> SEQUENCE: 55
atgccaaagt gctttaccgt caacgtcggc cccgaggacg tcaagggcga gactcgcatc      60
cgtcgctcca tccaggccgt cgacaaactc atggactcac cctcaagcga catcaagacc     120
ttgtacgatg tcatccagta ctctgccaag gtccgcccca acctcaacgc catcggctac     180
cgcaagattg tcaagatgat cgaagaggaa aaggagatca ccaagatggt cagcggcgag     240
cctgtcaagg agaaaaagac gtggaaatac ttcaagctct ccggctacca ctatctgacc     300
tacaaggaca ccaaggccgt catcgacagc attggaagtg gcctgcgcaa gtggggtgtt     360
gagcccaagg agaggatcac cgtctttggt tccacaaggt aatgtgtagc gccacgaaaa     420
tacgatcatt gcagcgtgaa gggtgggaag aattaggggg gaaatgacat cgataacagg     480
aacgaaaaaa aaaaaaaaca agacgaagtc ggagatcctc gctattggcg tttaagcacc     540
gccagcgttc ttttttnnnn nnnnnnnnn nnnnnnnnnn nnnnnnnnnn nnnnnnnnnn     600
nnnnnnnnnn nnnnnnnnnn nnnnnnnnnn nnnnnnnnnn nnnnnnnnnn nnnnnnnnnn     660
nnnnnnnnnn nnnnnnnnnn nnnnnnnnnn nnnnnnnnnn nnnnnnnnnn nnnnnnnnnn     720
nnnnnnnnnn nnnnnnnnnn nnnnnnnnnn nnnnnnnnnn nnnnnnctt gttaaccaaa     780 ggctgacccg tacctcgttt gcttgacttg acacgtatag tgccaactgg ctgctggtcg     840
ctcatggtgc cttcacgcag tccatgacca tcgtcaccgt gtatgacact ttgggcgagg     900
aaggattgct gcactcgatg aacgaggccg aggtgggaac ggcctacacg aacgctgatt     960
tgatcaagac aatgaccaac gtttcaggac gctgccccac cctcaagagg atcgtctatg    1020
acggcgaagc caacgcagca gacgtgatcg cccttcagac ggcccatcct caccttcagc    1080
ttatcactct ggaggagctg aagcagctcg gtgtggatca ccctgtggag cccactcctc    1140
ccaccgccga ggattgctcc tgcatcatgt acacttctgg atcgaccgga aaccctaagg    1200
gagtcatcct cactcacgga aacctcattg ccgccagtag gtgtttctct cactctcttt    1260
```

```
aaccctctct ctttcacttg caaatatgct gggaatctct acttacctga atgttactgt    1320
tcttcgggtt atcaacctag ttggcggagt taacaagatg ctggaaaagt acattcgcga    1380
aggcgatgtc ttgcttgcct accttccctt ggctcacgtt ctggaattca tggttgagaa    1440
cctctgtctc ttctggggtg taaccettgg atatggtact gtccgcacgc tgacggatgc    1500
ctctgtgcgt gagtgccagg gtgatatcaa ggaattgcgg cctacgctta tgaccggcgt    1560
tccagcagtg tgggagacca tccgcaaagg tgttctcgcc caagtaaacc agggttcacc    1620
tctggttcaa tccgtcttca acgcggctct gaacgccaag gcctggtgca tggaccgcaa    1680
actaggcgct ttgactggaa ttttcgacac tgtggtgttc aacaaggtcc gtcagcaaac    1740
tggaggtcgt cttcgctacg cgctctcggg cggcgcgcct atctcccagg agacccagcg    1800
cttcttgacc acagcactgt gccctatcct tcaagcctat ggcatgactg agtcgtgcgg    1860
catgtgctcg atcatgactc cagaggcgtt caactacaac cgcgtcggtt cccctgttcc    1920
ctgcacagag gtcaagctcg tggatgtgcc cgatgcagga tacttttcga ctgattcgcc    1980
ccgccctcgt ggtgagattt ggattcgcgg accctccatc acctctggat acttcaagaa    2040
cgctgaggag acctcggcag ccatcacaga ggaccgctgg ctcaagactg agatattgg    2100 agagtggcat gctgatggca cactctcggt cattgatcgc aagaagaact tggtcaagtt    2160
gtcgcatggc gagtacattg ctctagagaa acttgagtcg gtgtacaaga gcacggctta    2220
ctgcaacaac atctgcgttt atgccgattc catgcaaaac aagcctgtgg cgctgattgt    2280
tgcgagtgaa ccccgcatcc tcgagctggc caaggcaaag ggcctggaga ccgcgactt    2340 tgcagtgctc tgccacgata aggtgatcat caaggctgtc ctcgacgcct gtctcgcgac    2400
tgccaaaaag gctggcctca gcccgccga gttgctgcag ggtgtgtacc tggagtctga    2460
ggagtggacc gctcaaggcg gtttgttgac tgctgctcag aaattgaagc gcaaggaaat    2520
caaccaggct tatgctgacc agatcaagca gatctatggc tccaagtaa               2569
```

<210> SEQ ID NO 56
<211> LENGTH: 2040
<212> TYPE: DNA
<213> ORGANISM: Mortierella alpina

<400> SEQUENCE: 56

```
atgacaaagt gcctcaccgt cgaagtcgga cccgccgacg tccagggcga gacccgcatc     60
cgccgctccg tcctctctgc aaagcgcctc atgtcctcgc cctcggatga catcaagacc    120
ctctacgacg tcttcaacca ctccgtcacc gtccgcccca acttcaacgc gatcggatac    180
cgcaaggtcg tcaagattgt cgaggaagaa aaggaggtcg tcaaggttgt caacggcgag    240
gaagtcaagg aaaagaagac ctggaagttc ttcaagatgt ccggctacca ctggctcacc    300
tacaaggatg cgaagcaggt cgtcgacagc atcggatgcg tcttcgcaa gtttggcgtc    360 gagcccaagg acaagctgac cgttttcggt gccacaagtg ccaactggct cctgcttgcc    420
cacggtgctt tcacccagtc catcaccatt gttaccgcct acgacaccct gggcgaggac    480
ggtcttttgc actctatgaa cgaggccgag gtgccaccg cttacacaaa cgccgacttg    540
ctcaacacta tcaagaacgt tgccggcaaa tgccccaccc tgaagaagat catctacgac    600
ggcgatgcca agcccgcaga tgtcattgcc ctccaggagg ccatcctca cctccagctc    660 atccccctcg aggagctgaa gcagctcgga gtggacaacc ctgtcgcccc aaccctcct    720 gctgccaagg actactgctg catcatgtac acttcgggat cgactggcaa ccccaaggga    780
```

-continued

```
gtgttgctga cccatggaaa cctcgttgct gccatcggag gtgtgaacaa gatgctgaca      840
aagtacgttc acgagggaga cgtcttgctc gcgtacttgc ctcttgctca cgttctcgag      900
ttcctggtcg aaaacgtctg tctcttctgg ggtgtgactc ttggctacgg taccgtccgc      960
acattgactg atgcctcagt ccgtgagtgc cagggtgata tcaaggagtt gcgccctaca     1020
ttgatgaccg tgttcctgc tgtgtgggag acgattcgta agggagtgtt ggctcaggtt     1080
tcccagggct cacctcttgt tcaaaagatc ttccatgctg ctttgaacgc caaggcctgg     1140
tgcctggacc gcaagttggg tgcgttgact ggaatcttcg atactgtcgt cttcaacaag     1200
gtcaagcagc agacaggagg acgtcttcgc ttcgcccttt cgggaggtgc acccatctct     1260
caggagaccc agcgcttctt gacgacagct ttgtgcccta cctccaggg ctacggtatg     1320 acagagtctt gcggcatgtg cgccattttg acccccgatg tcttcaacta cagccgtgtc     1380
ggatccccag ttccttgcac ggaggtcaag ttggtcgatg tgcccgatgc aggataccac     1440
tcaacggact gcctctcccc cgtggtgag gtctgcattc gtggaccctc catcactgct     1500
ggatacttca agaaccccga ggagacctcc gccacattga ctgctgatcg ctggctcaag     1560
actggagata tcggagagtg gcaccccgac ggcactatct cgatcattga ccgcaagaag     1620
aacttggtca agctgtcaca cggagagtac attgctttgg agaagcttga gtctgtctac     1680
aagagcacag cctactgcaa caacatttgc gtgtatgccg actcgatgca gaacaagccc     1740
gttgccatta ttgttgccag cgaacccccgc atcctcgagt tggccaaggc caagggcatt     1800
gagagccgcg actttgctgc tctctgccac gacaaggtta tcatcaaggc tgtccacgat     1860
gcctgcctcg ccactgccaa gcgtgctgga ctcaagcccg ctgagatgct tcagggagtg     1920
tacttggagt cagaagaatg gacggcccag gctggcatgt tgactgccgc tcagaagctc     1980
aagcgcaagg agatcaacca ggcctatgtc tcacagatca gcagcttta tggaacggcc     2040
```

<210> SEQ ID NO 57
<211> LENGTH: 680
<212> TYPE: PRT
<213> ORGANISM: Mortierella alpina

<400> SEQUENCE: 57

Met Thr Lys Cys Leu Thr Val Glu Val Gly Pro Ala Asp Val Gln Gly
1               5                   10                  15

Glu Thr Arg Ile Arg Arg Ser Val Leu Ser Ala Lys Arg Leu Met Ser
            20                  25                  30

Ser Pro Ser Asp Asp Ile Lys Thr Leu Tyr Asp Val Phe Asn His Ser
        35                  40                  45

Val Thr Val Arg Pro Asn Leu Asn Ala Ile Gly Tyr Arg Lys Val Val
    50                  55                  60

Lys Ile Val Glu Glu Lys Glu Val Val Lys Val Asn Gly Glu
65                  70                  75                  80

Glu Val Lys Glu Lys Lys Thr Trp Lys Phe Phe Lys Met Ser Gly Tyr
                85                  90                  95

His Trp Leu Thr Tyr Lys Asp Ala Lys Gln Val Val Asp Ser Ile Gly
            100                 105                 110

Cys Gly Leu Arg Lys Phe Gly Val Glu Pro Lys Asp Lys Leu Thr Val
        115                 120                 125

Phe Gly Ala Thr Ser Ala Asn Trp Leu Leu Leu Ala His Gly Ala Phe
    130                 135                 140

Thr Gln Ser Ile Thr Ile Val Thr Ala Tyr Asp Thr Leu Gly Glu Asp
145                 150                 155                 160

```
Gly Leu Leu His Ser Met Asn Glu Ala Glu Val Ala Thr Ala Tyr Thr
                165                 170                 175

Asn Ala Asp Leu Leu Asn Thr Ile Lys Asn Val Ala Gly Lys Cys Pro
            180                 185                 190

Thr Leu Lys Lys Ile Ile Tyr Asp Gly Asp Ala Lys Pro Ala Asp Val
        195                 200                 205

Ile Ala Leu Gln Glu Ala His Pro His Leu Gln Leu Ile Thr Leu Glu
    210                 215                 220

Glu Leu Lys Gln Leu Gly Val Asp Asn Pro Val Ala Pro Thr Pro Pro
225                 230                 235                 240

Ala Ala Lys Asp Tyr Cys Cys Ile Met Tyr Thr Ser Gly Ser Thr Gly
                245                 250                 255

Asn Pro Lys Gly Val Leu Leu Thr His Gly Asn Leu Val Ala Ala Ile
            260                 265                 270

Gly Gly Val Asn Lys Met Leu Thr Lys Tyr Val His Glu Gly Asp Val
        275                 280                 285

Leu Leu Ala Tyr Leu Pro Leu Ala His Val Leu Glu Phe Leu Val Glu
    290                 295                 300

Asn Val Cys Leu Phe Trp Gly Val Thr Leu Gly Tyr Gly Thr Val Arg
305                 310                 315                 320

Thr Leu Thr Asp Ala Ser Val Arg Glu Cys Gln Gly Asp Ile Lys Glu
                325                 330                 335

Leu Arg Pro Thr Leu Met Thr Gly Val Pro Ala Val Trp Glu Thr Ile
            340                 345                 350

Arg Lys Gly Val Leu Ala Gln Val Ser Gln Gly Ser Pro Leu Val Gln
        355                 360                 365

Lys Ile Phe His Ala Ala Leu Asn Ala Lys Ala Trp Cys Leu Asp Arg
    370                 375                 380

Lys Leu Gly Ala Leu Thr Gly Ile Phe Asp Thr Val Val Phe Asn Lys
385                 390                 395                 400

Val Lys Gln Gln Thr Gly Gly Arg Leu Arg Phe Ala Leu Ser Gly Gly
                405                 410                 415

Ala Pro Ile Ser Gln Glu Thr Gln Arg Phe Leu Thr Thr Ala Leu Cys
            420                 425                 430

Pro Ile Leu Gln Gly Tyr Gly Met Thr Glu Ser Cys Gly Met Cys Ala
        435                 440                 445

Ile Leu Thr Pro Asp Val Phe Asn Tyr Ser Arg Val Gly Ser Pro Val
    450                 455                 460

Pro Cys Thr Glu Val Lys Leu Val Asp Val Pro Asp Ala Gly Tyr His
465                 470                 475                 480

Ser Thr Asp Leu Pro Leu Pro Arg Gly Glu Val Cys Ile Arg Gly Pro
                485                 490                 495

Ser Ile Thr Ala Gly Tyr Phe Lys Asn Pro Glu Glu Thr Ser Ala Thr
            500                 505                 510

Leu Thr Ala Asp Arg Trp Leu Lys Thr Gly Asp Ile Gly Glu Trp His
        515                 520                 525

Pro Asp Gly Thr Ile Ser Ile Ile Asp Arg Lys Lys Asn Leu Val Lys
    530                 535                 540

Leu Ser His Gly Glu Tyr Ile Ala Leu Glu Lys Leu Glu Ser Val Tyr
545                 550                 555                 560

Lys Ser Thr Ala Tyr Cys Asn Asn Ile Cys Val Tyr Ala Asp Ser Met
                565                 570                 575
```

```
Gln Asn Lys Pro Val Ala Ile Ile Val Ala Ser Glu Pro Arg Ile Leu
            580                 585                 590
Glu Leu Ala Lys Ala Lys Gly Ile Glu Ser Arg Asp Phe Ala Ala Leu
        595                 600                 605
Cys His Asp Lys Val Ile Ile Lys Ala Val His Asp Ala Cys Leu Ala
    610                 615                 620
Thr Ala Lys Arg Ala Gly Leu Lys Pro Ala Glu Met Leu Gln Gly Val
625                 630                 635                 640
Tyr Leu Glu Ser Glu Glu Trp Thr Ala Gln Ala Gly Met Leu Thr Ala
                645                 650                 655
Ala Gln Lys Leu Lys Arg Lys Glu Ile Asn Gln Ala Tyr Val Ser Gln
            660                 665                 670
Ile Lys Gln Leu Tyr Gly Thr Ala
            675                 680

<210> SEQ ID NO 58
<211> LENGTH: 2043
<212> TYPE: DNA
<213> ORGANISM: Mortierella alpina

<400> SEQUENCE: 58
atgacaaagt gcctcaccgt cgaagtcgga cccgccgacg tccagggcga cccgcatc       60 cgccgctccg tcctctctgc aaagcgcctc atgtcctcgc cctcggatga catcaagacc    120
ctctacgacg tcttcaacca ctccgtcacc gtccgcccca acctcaacgc gatcggatac    180
cgcaaggtcg tcaagattgt cgaggaagaa aaggaggtcg tcaaggttgt caacggcgag    240
gaagtcaagg aaaagaagac ctggaagttc ttcaagatgt ccggctacca ctggctcacc    300
tacaaggatg cgaagcaggt cgtcgacagc atcggatgcg gtcttcgcaa gtttggcgtc    360
gagcccaagg acaagctgac cgttttcggt gccacaagtg ccaactggct cctgcttgcc    420
cacggtgctt tcacccagtc catcaccatt gttaccgcct acgacaccct gggcgaggac    480
ggtcttttgc actctatgaa cgaggccgag gtggccaccg cttacacaaa cgccgacttg    540
ctcaacacta tcaagaacgt tgccggcaaa tgccccaccc tgaagaagat catctacgac    600
ggcgatgcca agcccgcaga tgtcattgcc ctccaggagg cccatcctca cctccagctc    660
atcaccctcg aggagctgaa gcagctcgga gtggacaacc tgtcgcccc  aaccctcct    720 gctgccaagg actactgctg catcatgtac acttcgggat cgactggcaa ccccaaggga    780
gtgttgctga cccatggaaa cctcgttgct gccatcggag tgtgaacaa  gatgctgaca    840 aagtacgttc acgagggaga cgtcttgctc gcgtacttgc ctcttgctca cgttctcgag    900
ttcctggtcg aaaacgtctg tctcttctgg ggtgtgactc ttggctacgg taccgtccgc    960
acattgactg atgcctcagt ccgtgagtgc agggtgata  tcaaggagtt cgcccctaca   1020
ttgatgaccg tgttcctgc  tgtgtgggag acgattcgta agggagtgtt ggctcaggtt   1080
tcccagggct cacctcttgt tcaaaagatc ttccatgctg ctttgaacgc caaggcctgg   1140
tgcctggacc gcaagttggg tgcgttgact ggaatcttcg atactgtcgt cttcaacaag   1200
gtcaagcagc agacaggagg acgtcttcgc ttcgcccttt cgggaggtgc acccatctct   1260
caggagaccc agcgcttctt gacgacagct ttgtgcccta cctccaggg  ctacggtatg   1320 acagagtctt gcggcatgtg cgccattttg accccgatg  tcttcaacta cagccgtgtc   1380
ggatccccag ttccttgcac ggaggtcaag ttggtcgatg tgcccgatgc aggataccac   1440
tcaacggact tgcctctccc ccgtggtgag gtctgcattg gtggaccctc catcactgct   1500
```

| | |
|---|---|
| ggatacttca agaaccccga ggagacctcc gccacattga ctgctgatcg ctggctcaag | 1560 |
| actggagata tcggagagtg caccccgac ggcactatct cgatcattga ccgcaagaag | 1620 |
| aacttggtca agctgtcaca cggagagtac attgctttgg agaagcttga gtctgtctac | 1680 |
| aagagcacag cctactgcaa caacatttgc gtgtatgccg actcgatgca gaacaagccc | 1740 |
| gttgccatta ttgttgccag cgaaccccgc atcctcgagt tggccaaggc caagggcatt | 1800 |
| gagagccgcg actttgctgc tctctgccac gacaaggtta tcatcaaggc tgtccacgat | 1860 |
| gcctgcctcg ccactgccaa gcgtgctgga ctcaagcccg ctgagatgct tcagggagtg | 1920 |
| tacttggagt cagaagaatg gacggcccag gctggcatgt tgactgccgc tcagaagctc | 1980 |
| aagcgcaagg agatcaacca ggcctatgtc tcacagatca gcagctttta tggaacggcc | 2040 |
| taa | 2043 |

<210> SEQ ID NO 59
<211> LENGTH: 2414
<212> TYPE: DNA
<213> ORGANISM: Mortierella alpina

<400> SEQUENCE: 59

| | |
|---|---|
| cctttatccc cgcaccgcca tctctcgccg ccaccatctc gcattccttt caatccacac | 60 |
| tcccacctgt gccccctgct tttcacgtcc cgctctcatc ccgccttctc ctttcatcac | 120 |
| cccaattcaa catgacaaag tgcctcaccg tcgaagtcgg accgccgac gtccagggcg | 180 |
| agacccgcat ccgccgctcc gtcctctctg caaagcgcct catgtcctcg ccctcggatg | 240 |
| acatcaagac cctctacgac gtcttcaacc actccgtcac cgtccgcccc aacctcaacg | 300 |
| cgatcggata ccgcaaggtc gtcaagattg tcgaggaaga aaaggaggtc gtcaaggttg | 360 |
| tcaacggcga ggaagtcaag gaaaagaaga cctggaagtt cttcaagatg tccggctacc | 420 |
| actggctcac ctacaaggat gcgaagcagg tcgtcgacag catcggatgc ggtcttcgca | 480 |
| agtttggcgt cgagcccaag gacaagctga ccgttttcgg tgccacaagt gccaactggc | 540 |
| tcctgcttgc ccacggtgct ttcacccagt ccatcaccat tgttaccgcc tacgacaccc | 600 |
| tgggcgagga cggtcttttg cactctatga cgaggccga ggtggccacc gcttacacaa | 660 |
| acgccgactt gctcaacact atcaagaacg ttgccggcaa atgccccacc ctgaagaaga | 720 |
| tcatctacga cggcgatgcc aagcccgcag atgtcattgc cctccaggag gcccatcctc | 780 |
| acctccagct catcaccctc gaggagctga agcagctcgg agtggacaac cctgtcgccc | 840 |
| caaccctcc tgctgccaag gactactgct gcatcatgta cacttcggga tcgactggca | 900 |
| accccaaggg agtgttgctg acccatggaa acctcgttgc tgccatcgga ggtgtgaaca | 960 |
| agatgctgac aaagtacgtt cacgagggag acgtcttgct cgcgtacttg cctcttgctc | 1020 |
| acgttctcga gttcctggtc gaaaacgtct gtctcttctg gggtgtgact cttggctacg | 1080 |
| gtaccgtccg cacattgact gatgcctcag tccgtgagtg ccagggtgat atcaaggagt | 1140 |
| gcgccctac attgatgacc ggtgttcctg ctgtgtggga cgattcgt aagggagtgt | 1200 |
| tggctcaggt ttcccagggc tcacctcttg ttcaaaagat cttccatgct gctttgaacg | 1260 |
| ccaaggcctg gtgcctggac cgcaagttgg gtgcgttgac tggaatcttc gatactgtcg | 1320 |
| tcttcaacaa ggtcaagcag cagacaggag gacgtcttcg cttcgcccttt cgggaggtg | 1380 |
| cacccatctc tcaggagacc cagcgcttct tgacgacagc tttgtgccct atcctccagg | 1440 |
| gctacgtat gacagagtct tgcggcatgt gcgccatttt gaccccgat gtcttcaact | 1500 |
| acagccgtgt cggatcccca gttccttgca cggaggtcaa gttggtcgat gtgcccgatg | 1560 |

```
caggatacca ctcaacggac ttgcctctcc cccgtggtga ggtctgcatt cgtggaccct    1620
ccatcactgc tggatacttc aagaaccccg aggagacctc cgccacattg actgctgatc    1680
gctggctcaa gactggagat atcggagagt ggcaccccga cggcactatc tcgatcattg    1740
accgcaagaa gaacttggtc aagctgtcac acggagagta cattgctttg gagaagcttg    1800
agtctgtcta caagagcaca gcctactgca acaacatttg cgtgtatgcc gactcgatgc    1860
agaacaagcc cgttgccatt attgttgcca gcgaaccccg catcctcgag ttggccaagg    1920
ccaagggcat tgagagccgc gactttgctg ctctctgcca cgacaaggtt atcatcaagg    1980
ctgtccacga tgcctgcctc gccactgcca agcgtgctgg actcaagccc gctgagatgc    2040
ttcagggagt gtacttggag tcagaagaat ggacggccca ggctggcatg ttgactgccg    2100
ctcagaagct caagcgcaag gagatcaacc aggcctatgt ctcacagatc aagcagcttt    2160
atggaacggc ctaagtcgct gaaaggtgtg cctttgtccg tctcttcaac cccacaagtc    2220
ctatgtataa tgacccgcgc ggccctcctt taatcctata cccacccttt tttacacgtt    2280
aaagaagcca cattttggt tcttttttt ctctcgcaca cactacacac tccccatcca    2340
ttccctccaa acaggatggt tgtctgcaaa taaattgacg aatttctct tgaaaaaaaa    2400 aaaaaaaaaa aaaa                                                      2414

<210> SEQ ID NO 60
<211> LENGTH: 2537
<212> TYPE: DNA
<213> ORGANISM: Mortierella alpina

<400> SEQUENCE: 60
atgacaaagt gcctcaccgt cgaagtcgga cccgccgacg tccagggcga gacccgcatc      60
cgccgctccg tcctctctgc aaagcgcctc atgtcctcgc cctcggatga catcaagacc     120
ctctacgacg tcttcaacca ctccgtcacc gtccgcccca acctcaacgc gatcggatac     180
cgcaaggtcg tcaagattgt cgaggaagaa aaggaggtcg tcaaggttgt caacggcgag     240
gaagtcaagg aaaagaagac ctggaagttc ttcaagatgt ccggctacca ctggctcacc     300
tacaaggatg cgaagcaggt cgtcgacagc atcggatgcg gtcttcgcaa gtttggcgtc     360
gagcccaagg acaagctgac cgttttcggt gccacaaggt aagaaagagg cataacaaga     420
aaatgcaaga gaggcaaaaa aaatggcttg acgtgagagc ataagggaac caacagacag     480
gtgtttgtgt gggttgcgga tagtgggtga gcatgcttcg ttatcgaatg tgggagaaga     540
gagcggacgc gaatatggct ctcgtctctg gcgggatgcg agtggccaag tgtgggatac     600
atatcctcgc ggtggggtgt ccgggtcggc ccttgaatct tgttgaagca tgataatgtg     660
aatgtggacc gcaatcacgc tcagattatg cgtagcaagc gtgttgctag tctacatcat     720
gctcacacgt attcacattt attcattttc actctatctc gctcttagtg ccaactggct     780
cctgcttgcc cacggtgctt tcacccagtc catcaccatt gttaccgcct acgacaccct     840
gggcgaggac ggtcttttgc actctatgaa cgaggccgag gtggccaccg cttacacaaa     900
cgccgacttg ctcaacacta tcaagaacgt tgccggcaaa tgccccaccc tgaagaagat     960
catctacgac ggcgatgcca agcccgcaga tgtcattgcc ctccaggagg cccatcctca    1020
cctccagctc atcaccctcg aggagctgaa gcagctcgga gtggacaacc ctgtcgcccc    1080 aaccctcct gctgccaagg actactgctg catcatgtac acttcgggat cgactggcaa    1140
ccccaaggga gtgttgctga cccatggaaa cctcgttgct gccagtacgt atctttctcg    1200
```

```
tcatgatcgt cctcccgcat ttccactgcg cttgttacca tttgatggga aatgtattta   1260
acccgaacca cacattttt cttttctca cacttgccac gtcactagtc ggaggtgtga    1320
acaagatgct gacaaagtac gttcacgagg gagacgtctt gctcgcgtac ttgcctcttg   1380
ctcacgttct cgagttcctg gtcgaaaacg tctgtctctt ctggggtgtg actcttggct   1440
acggtaccgt ccgcacattg actgatgcct cagtccgtga gtgccagggt gatatcaagg   1500
agttgcgccc tacattgatg accggtgttc ctgctgtgtg ggagacgatt cgtaagggag   1560
tgttggctca ggtttcccag ggctcacctc ttgttcaaaa gatcttccat gctgctttga   1620
acgccaaggc ctggtgcctg gaccgcaagt tgggtgcgtt gactggaatc ttcgatactg   1680
tcgtcttcaa caaggtcaag cagcagacag gaggacgtct tcgcttcgcc ctttcgggag   1740
gtgcacccat ctctcaggag acccagcgct tcttgacgac agctttgtgc cctatcctcc   1800
agggctacgg tatgacagag tcttgcggca tgtgcgccat tttgacccc gatgtcttca    1860 actacagccg tgtcggatcc ccagttcctt gcacggaggt caagttggtc gatgtgcccg   1920
atgcaggata ccactcaacg gacttgcctc tcccccgtgg tgaggtctgc attcgtggac   1980
cctccatcac tgctggatac ttcaagaacc ccgaggagac ctccgccaca ttgactgctg   2040
atcgctggct caagactgga gatatcggag agtggcaccc cgacggcact atctcgatca   2100
ttgaccgcaa gaagaacttg gtcaagctgt cacacggaga gtacattgct ttggagaagc   2160
ttgagtctgt ctacaagagc acagcctact gcaacaacat ttgcgtgtat gccgactcga   2220
tgcagaacaa gcccgttgcc attattgttg ccagcgaacc ccgcatcctc gagttggcca   2280
aggccaaggg cattgagagc cgcgactttg ctgctctctg ccacgacaag gttatcatca   2340
aggctgtcca cgatgcctgc ctcgccactg ccaagcgtgc tggactcaag cccgctgaga   2400
tgcttcaggg agtgtacttg gagtcagaag aatggacggc ccaggctggc atgttgactg   2460
ccgctcagaa gctcaagcgc aaggagatca ccaggccta tgtctcacag atcaagcagc   2520
tttatggaac ggcctaa                                                 2537

<210> SEQ ID NO 61
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gtcggctcca agcttgcaat cc                                              22

<210> SEQ ID NO 62
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
ggacagctcc agcactgtgg taaag                                           25

<210> SEQ ID NO 63
<211> LENGTH: 24
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 63
gaccacggga ttccccaagg ctgc                                          24

<210> SEQ ID NO 64
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
cttggtcgcg cttgttcctg gccac                                         25

<210> SEQ ID NO 65
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
tacagctttg ttgctgtccc catc                                          24

<210> SEQ ID NO 66
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
gatgatgggt gtgcttgcaa agatc                                         25

<210> SEQ ID NO 67
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
aacccaaagc tgcgccaggc tgtcc                                         25

<210> SEQ ID NO 68
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
ttacagcttg gattcctttt gatgg                                         25

<210> SEQ ID NO 69
<211> LENGTH: 22
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 69
gtcgtgcccg atgcggagac gc                                           22

<210> SEQ ID NO 70
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
tcagtggatc ccgttataca tcag                                         24

<210> SEQ ID NO 71
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
gcgtccccct ctatgataca ttg                                          23

<210> SEQ ID NO 72
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
gtgggatgca ggacggcaac atcg                                         24

<210> SEQ ID NO 73
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
ggatgccgaa caacagcgcg tgg                                          23

<210> SEQ ID NO 74
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
gcaccctcct cagaaacagc cctc                                         24

<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 75
cagtcgagta cattgtcaac cacg                                          24

<210> SEQ ID NO 76
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
gcggttcaag aggcgaggca cagc                                          24

<210> SEQ ID NO 77
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
gttcatcttc tgctggctgg gtctc                                         25

<210> SEQ ID NO 78
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
gttgcgttgt tcacgcggca atcc                                          24

<210> SEQ ID NO 79
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
atggaaacct tggttaacgg aaag                                          24

<210> SEQ ID NO 80
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
tcagcaaaga tggccttggg ctgg                                          24

<210> SEQ ID NO 81
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
```
gtcaagggcg agactcgcat cc                                              22

<210> SEQ ID NO 82
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
cggtgacgat ggtcatggac tgc                                             23

<210> SEQ ID NO 83
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
gcgagacccg catccgccgc tcc                                             23

<210> SEQ ID NO 84
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
gaccgtcctc gcccagggtg tcg                                             23

<210> SEQ ID NO 85
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
ggatccatgc cttccttcaa aaagtacaac c                                    31

<210> SEQ ID NO 86
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
cccgggcaaa gagttttcta tctacagctt                                      30

<210> SEQ ID NO 87
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87

```
gaattcatgg ttgctctccc actcg                                          25
```

<210> SEQ ID NO 88
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88

```
ggatccctac tatagcttgg ccttgcc                                        27
```

<210> SEQ ID NO 89
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89

```
ggatccatgt atgtcggctc caagcttgc                                      29
```

<210> SEQ ID NO 90
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90

```
gtcgactcaa agcctggctt tgccgctgac g                                   31
```

<210> SEQ ID NO 91
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91

```
ggatccatgg aaaccttggt taacggaaag                                     30
```

<210> SEQ ID NO 92
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92

```
ggtacctaga acttcttcca catctcctc                                      29
```

<210> SEQ ID NO 93
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93

```
gagctcatgc caaagtgctt taccgtcaac g                                   31
```

<210> SEQ ID NO 94
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
ggatccttac ttggagccat agatctgctt g                                    31

<210> SEQ ID NO 95
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
tctagaatgg cacctcccaa cactattg                                        28

<210> SEQ ID NO 96
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
aagcttttac ttcttgaaaa agaccacgtc                                      30

<210> SEQ ID NO 97
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
tctagaatgg ctgctgctcc cagtgtgag                                       29

<210> SEQ ID NO 98
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
aagcttttac tgtgccttgc ccatcttgg                                       29

<210> SEQ ID NO 99
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
tctagaatgg agtcgattgc gcaattcc                                        28

<210> SEQ ID NO 100
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
gagctcttac tgcaacttcc ttgccttctc                                30

<210> SEQ ID NO 101
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
tctagaatgg gtgcggacac aggaaaaacc                                30

<210> SEQ ID NO 102
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
aagcttttac tcttccttgg gacgaagacc                                30

<210> SEQ ID NO 103
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
gaattcatga caaagtgcct caccgtcg                                  28

<210> SEQ ID NO 104
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
cccgggactt aggccgttcc ataaagctg                                 29

<210> SEQ ID NO 105
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
aattcataag aatgcggccg ctaaactatt ctagactagg tcgacggcgc gcca     54

```
<210> SEQ ID NO 106
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
agcttggcgc gccgtcgacc tagtctagaa tagtttagcg gccgcattct tatg        54

<210> SEQ ID NO 107
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
agcggccgca tagggagat cgaacc                                         26

<210> SEQ ID NO 108
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
agaattcggc gcgccatgca cgggtccttc tca                                33

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
gtcgaccatg acaagtttgc                                               20

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
gtcgactgga agacgagcac g                                             21

<210> SEQ ID NO 111
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
ggcaaacttg tcatgaagcg aaagagagat tatgaaaaca agc                     43

<210> SEQ ID NO 112
```

```
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
cactcccttt tcttaattgt tgagagagtg ttgggtgaga gt                           42

<210> SEQ ID NO 113
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
taagaaaagg gagtgaatcg cataggg                                           27

<210> SEQ ID NO 114
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
catgacaagt ttgccaagat gcg                                               23

<210> SEQ ID NO 115
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
attgttgaga gagtgttggg tgagagtg                                          28

<210> SEQ ID NO 116
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
cactctctca acaatatgga aaccttggtt aacggaaagt                             40

<210> SEQ ID NO 117
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
cactcccttt tcttactaga acttcttcca catctcctca atatc                       45

<210> SEQ ID NO 118
<211> LENGTH: 41
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
cactcccttt tcttattact tggagccata gatctgcttg a                      41

<210> SEQ ID NO 119
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
cactctctca acaatatgcc aaagtgcttt accgtcaac                         39

<210> SEQ ID NO 120
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
gtcccgaatg gttcct                                                  16

<210> SEQ ID NO 121
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
agcggttttc tacttgc                                                 17

<210> SEQ ID NO 122
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
aactacaacc gcgtcg                                                  16

<210> SEQ ID NO 123
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
cggcataaac gcagat                                                  16

<210> SEQ ID NO 124
<211> LENGTH: 700
<212> TYPE: PRT
```

<213> ORGANISM: Saccharomyces cerevisiae

<400> SEQUENCE: 124

```
Met Val Gln Tyr Thr Val Pro Val Gly Lys Ala Ala Asn Glu His
1               5                   10                  15

Glu Thr Ala Pro Arg Arg Asn Tyr Gln Cys Arg Glu Lys Pro Leu Val
            20                  25                  30

Arg Pro Pro Asn Thr Lys Cys Ser Thr Val Tyr Glu Phe Val Leu Glu
        35                  40                  45

Cys Phe Gln Lys Asn Lys Asn Ser Asn Ala Met Gly Trp Arg Asp Val
    50                  55                  60

Lys Glu Ile His Glu Ser Lys Ser Val Met Lys Lys Val Asp Gly
65                  70                  75                  80

Lys Glu Thr Ser Val Glu Lys Lys Trp Met Tyr Tyr Glu Leu Ser His
                85                  90                  95

Tyr His Tyr Asn Ser Phe Asp Gln Leu Thr Asp Ile Met His Glu Ile
            100                 105                 110

Gly Arg Gly Leu Val Lys Ile Gly Leu Lys Pro Asn Asp Asp Lys
        115                 120                 125

Leu His Leu Tyr Ala Ala Thr Ser His Lys Trp Met Lys Met Phe Leu
    130                 135                 140

Gly Ala Gln Ser Gln Gly Ile Pro Val Val Thr Ala Tyr Asp Thr Leu
145                 150                 155                 160

Gly Glu Lys Gly Leu Ile His Ser Leu Val Gln Thr Gly Ser Lys Ala
                165                 170                 175

Ile Phe Thr Asp Asn Ser Leu Leu Pro Ser Leu Ile Lys Pro Val Gln
            180                 185                 190

Ala Ala Gln Asp Val Lys Tyr Ile Ile His Phe Asp Ser Ile Ser Ser
        195                 200                 205

Glu Asp Arg Arg Gln Ser Gly Lys Ile Tyr Gln Ser Ala His Asp Ala
    210                 215                 220

Ile Asn Arg Ile Lys Glu Val Arg Pro Asp Ile Lys Thr Phe Ser Phe
225                 230                 235                 240

Asp Asp Ile Leu Lys Leu Gly Lys Glu Ser Cys Asn Glu Ile Asp Val
                245                 250                 255

His Pro Pro Gly Lys Asp Asp Leu Cys Cys Ile Met Tyr Thr Ser Gly
            260                 265                 270

Ser Thr Gly Glu Pro Lys Gly Val Leu Lys His Ser Asn Val Val
        275                 280                 285

Ala Gly Val Gly Gly Ala Ser Leu Asn Val Leu Lys Phe Val Gly Asn
    290                 295                 300

Thr Asp Arg Val Ile Cys Phe Leu Pro Leu Ala His Ile Phe Glu Leu
305                 310                 315                 320

Val Phe Glu Leu Leu Ser Phe Tyr Trp Gly Ala Cys Ile Gly Tyr Ala
                325                 330                 335

Thr Val Lys Thr Leu Thr Ser Ser Val Arg Asn Cys Gln Gly Asp
            340                 345                 350

Leu Gln Glu Phe Lys Pro Thr Ile Met Val Gly Val Ala Ala Val Trp
        355                 360                 365

Glu Thr Val Arg Lys Gly Ile Leu Asn Gln Ile Asp Asn Leu Pro Phe
    370                 375                 380

Leu Thr Lys Ile Phe Trp Thr Ala Tyr Asn Thr Lys Leu Asn Met
385                 390                 395                 400
```

```
Gln Arg Leu His Ile Pro Gly Gly Ala Leu Gly Asn Leu Val Phe
            405                 410                 415

Lys Lys Ile Arg Thr Ala Thr Gly Gly Gln Leu Arg Tyr Leu Leu Asn
        420                 425                 430

Gly Gly Ser Pro Ile Ser Arg Asp Ala Gln Glu Phe Ile Thr Asn Leu
            435                 440                 445

Ile Cys Pro Met Leu Ile Gly Tyr Gly Leu Thr Glu Thr Cys Ala Ser
        450                 455                 460

Thr Thr Ile Leu Asp Pro Ala Asn Phe Glu Leu Gly Val Ala Gly Asp
465                 470                 475                 480

Leu Thr Gly Cys Val Thr Val Lys Leu Val Asp Val Glu Glu Leu Gly
            485                 490                 495

Tyr Phe Ala Lys Asn Asn Gln Gly Glu Val Trp Ile Thr Gly Ala Asn
        500                 505                 510

Val Thr Pro Glu Tyr Tyr Lys Asn Glu Glu Thr Ser Gln Ala Leu
            515                 520                 525

Thr Ser Asp Gly Trp Phe Lys Thr Gly Asp Ile Gly Glu Trp Glu Ala
    530                 535                 540

Asn Gly His Leu Lys Ile Ile Asp Arg Lys Lys Asn Leu Val Lys Thr
545                 550                 555                 560

Met Asn Gly Glu Tyr Ile Ala Leu Glu Lys Leu Glu Ser Val Tyr Arg
            565                 570                 575

Ser Asn Glu Tyr Val Ala Asn Ile Cys Val Tyr Ala Asp Gln Ser Lys
        580                 585                 590

Thr Lys Pro Val Gly Ile Val Pro Asn His Ala Pro Leu Thr Lys
            595                 600                 605

Leu Ala Lys Lys Leu Gly Ile Met Glu Gln Lys Asp Ser Ser Ile Asn
610                 615                 620

Ile Glu Asn Tyr Leu Glu Asp Ala Lys Leu Ile Lys Ala Val Tyr Ser
625                 630                 635                 640

Asp Leu Leu Lys Thr Gly Lys Asp Gln Gly Leu Val Gly Ile Glu Leu
            645                 650                 655

Leu Ala Gly Ile Val Phe Phe Asp Gly Glu Trp Thr Pro Gln Asn Gly
        660                 665                 670

Phe Val Thr Ser Ala Gln Lys Leu Lys Arg Lys Asp Ile Leu Asn Ala
    675                 680                 685

Val Lys Asp Lys Val Asp Ala Val Tyr Ser Ser Ser
        690                 695                 700

<210> SEQ ID NO 125
<211> LENGTH: 744
<212> TYPE: PRT
<213> ORGANISM: Saccharomyces cerevisiae

<400> SEQUENCE: 125

Met Ala Ala Pro Asp Tyr Ala Leu Thr Asp Leu Ile Glu Ser Asp Pro
1               5                   10                  15

Arg Phe Glu Ser Leu Lys Thr Arg Leu Ala Gly Tyr Thr Lys Gly Ser
            20                  25                  30

Asp Glu Tyr Ile Glu Glu Leu Tyr Ser Gln Leu Pro Leu Thr Ser Tyr
        35                  40                  45

Pro Arg Tyr Lys Thr Phe Leu Lys Lys Gln Ala Val Ala Ile Ser Asn
    50                  55                  60

Pro Asp Asn Glu Ala Gly Phe Ser Ser Ile Tyr Arg Ser Ser Leu Ser
65                  70                  75                  80
```

```
            Ser Glu Asn Leu Val Ser Cys Val Asp Lys Asn Leu Arg Thr Ala Tyr
                            85                  90                  95

Asp His Phe Met Phe Ser Ala Arg Arg Trp Pro Gln Arg Asp Cys Leu
                        100                 105                 110

Gly Ser Arg Pro Ile Asp Lys Ala Thr Gly Thr Trp Glu Glu Thr Phe
                        115                 120                 125

Arg Phe Glu Ser Tyr Ser Thr Val Ser Lys Arg Cys His Asn Ile Gly
                    130                 135                 140

Ser Gly Ile Leu Ser Leu Val Asn Thr Lys Lys Arg Pro Leu Glu
            145                 150                 155                 160

Ala Asn Asp Phe Val Val Ala Ile Leu Ser His Asn Asn Pro Glu Trp
                            165                 170                 175

Ile Leu Thr Asp Leu Ala Cys Gln Ala Tyr Ser Leu Thr Asn Thr Ala
                        180                 185                 190

Leu Tyr Glu Thr Leu Gly Pro Asn Thr Ser Glu Tyr Ile Leu Asn Leu
                        195                 200                 205

Thr Glu Ala Pro Ile Leu Ile Phe Ala Lys Ser Asn Met Tyr His Val
                    210                 215                 220

Leu Lys Met Val Pro Asp Met Lys Phe Val Asn Thr Leu Val Cys Met
            225                 230                 235                 240

Asp Glu Leu Thr His Asp Glu Leu Arg Met Leu Asn Glu Ser Leu Leu
                            245                 250                 255

Pro Val Lys Cys Asn Ser Leu Asn Glu Lys Ile Thr Phe Phe Ser Leu
                        260                 265                 270

Glu Gln Val Glu Gln Val Gly Cys Phe Asn Lys Ile Pro Ala Ile Pro
                    275                 280                 285

Pro Thr Pro Asp Ser Leu Tyr Thr Ile Ser Phe Thr Ser Gly Thr Thr
                    290                 295                 300

Gly Leu Pro Lys Gly Val Glu Met Ser His Arg Asn Ile Ala Ser Gly
            305                 310                 315                 320

Ile Ala Phe Ala Phe Ser Thr Phe Arg Ile Pro Pro Asp Lys Arg Asn
                            325                 330                 335

Gln Gln Leu Tyr Asp Met Cys Phe Leu Pro Leu Ala His Ile Phe Glu
                        340                 345                 350

Arg Met Val Ile Ala Tyr Asp Leu Ala Ile Gly Phe Gly Ile Gly Phe
                        355                 360                 365

Leu His Lys Pro Asp Pro Thr Val Leu Val Glu Asp Leu Lys Ile Leu
                    370                 375                 380

Lys Pro Tyr Ala Val Ala Leu Val Pro Arg Ile Leu Thr Arg Phe Glu
            385                 390                 395                 400

Ala Gly Ile Lys Asn Ala Leu Asp Lys Ser Thr Val Gln Arg Asn Val
                            405                 410                 415

Ala Asn Thr Ile Leu Asp Ser Lys Ser Ala Arg Phe Thr Ala Arg Gly
                        420                 425                 430

Gly Pro Asp Lys Ser Ile Met Asn Phe Leu Val Tyr His Arg Val Leu
                        435                 440                 445

Ile Asp Lys Ile Arg Asp Ser Leu Gly Leu Ser Asn Asn Ser Phe Ile
                    450                 455                 460

Ile Thr Gly Ser Ala Pro Ile Ser Lys Asp Thr Leu Leu Phe Leu Arg
            465                 470                 475                 480

Ser Ala Leu Asp Ile Gly Ile Arg Gln Gly Tyr Gly Leu Thr Glu Thr
                            485                 490                 495
```

```
Phe Ala Gly Val Cys Leu Ser Glu Pro Phe Lys Asp Val Gly Ser
            500                 505                 510

Cys Gly Ala Ile Gly Ile Ser Ala Glu Cys Arg Leu Lys Ser Val Pro
        515                 520                 525

Glu Met Gly Tyr His Ala Asp Lys Asp Leu Lys Gly Glu Leu Gln Ile
        530                 535                 540

Arg Gly Pro Gln Val Phe Glu Arg Tyr Phe Lys Asn Pro Asn Glu Thr
545                 550                 555                 560

Ser Lys Ala Val Asp Gln Asp Gly Trp Phe Ser Thr Gly Asp Val Ala
                565                 570                 575

Phe Ile Asp Gly Lys Gly Arg Ile Ser Val Ile Asp Arg Val Lys Asn
            580                 585                 590

Phe Phe Lys Leu Ala His Gly Glu Tyr Ile Ala Pro Glu Lys Ile Glu
        595                 600                 605

Asn Ile Tyr Leu Ser Ser Cys Pro Tyr Ile Thr Gln Ile Phe Val Phe
        610                 615                 620

Gly Asp Pro Leu Lys Thr Phe Leu Val Gly Ile Val Gly Val Asp Val
625                 630                 635                 640

Asp Ala Ala Gln Pro Ile Leu Ala Ala Lys His Pro Glu Val Lys Thr
                645                 650                 655

Trp Thr Lys Glu Val Leu Val Glu Asn Leu Asn Arg Asn Lys Lys Leu
            660                 665                 670

Arg Lys Glu Phe Leu Asn Lys Ile Asn Lys Cys Thr Asp Gly Leu Gln
        675                 680                 685

Gly Phe Glu Lys Leu His Asn Ile Lys Val Gly Leu Glu Pro Leu Thr
        690                 695                 700

Leu Glu Asp Asp Val Val Thr Pro Thr Phe Lys Ile Lys Arg Ala Lys
705                 710                 715                 720

Ala Ser Lys Phe Phe Lys Asp Thr Leu Asp Gln Leu Tyr Ala Glu Gly
                725                 730                 735

Ser Leu Val Lys Thr Glu Lys Leu
            740

<210> SEQ ID NO 126
<211> LENGTH: 694
<212> TYPE: PRT
<213> ORGANISM: Saccharomyces cerevisiae

<400> SEQUENCE: 126

Met Ser Glu Gln His Ser Val Ala Val Gly Lys Ala Ala Asn Glu His
1               5                   10                  15

Glu Thr Ala Pro Arg Arg Asn Val Arg Val Lys Lys Arg Pro Leu Ile
            20                  25                  30

Arg Pro Leu Asn Ser Ser Ala Ser Thr Leu Tyr Glu Phe Ala Leu Glu
        35                  40                  45

Cys Phe Asn Lys Gly Gly Lys Arg Asp Gly Met Ala Trp Arg Asp Val
        50                  55                  60

Ile Glu Ile His Glu Thr Lys Lys Thr Ile Val Arg Lys Val Asp Gly
65                  70                  75                  80

Lys Asp Lys Ser Ile Glu Lys Thr Trp Leu Tyr Glu Met Ser Pro
                85                  90                  95

Tyr Lys Met Met Thr Tyr Gln Glu Leu Ile Trp Val Met His Asp Met
                100                 105                 110

Gly Arg Gly Leu Ala Lys Ile Gly Ile Lys Pro Asn Gly Glu His Lys
        115                 120                 125
```

```
Phe His Ile Phe Ala Ser Thr Ser His Lys Trp Met Lys Ile Phe Leu
        130                 135                 140
Gly Cys Ile Ser Gln Gly Ile Pro Val Val Thr Ala Tyr Asp Thr Leu
145                 150                 155                 160
Gly Glu Ser Gly Leu Ile His Ser Met Val Glu Thr Glu Ser Ala Ala
                165                 170                 175
Ile Phe Thr Asp Asn Gln Leu Leu Ala Lys Met Ile Val Pro Leu Gln
                180                 185                 190
Ser Ala Lys Asp Ile Lys Phe Leu Ile His Asn Glu Pro Ile Asp Pro
        195                 200                 205
Asn Asp Arg Arg Gln Asn Gly Lys Leu Tyr Lys Ala Ala Lys Asp Ala
210                 215                 220
Ile Asn Lys Ile Arg Glu Val Arg Pro Asp Ile Lys Ile Tyr Ser Phe
225                 230                 235                 240
Glu Glu Val Val Lys Ile Gly Lys Lys Ser Lys Asp Glu Val Lys Leu
                245                 250                 255
His Pro Pro Glu Pro Lys Asp Leu Ala Cys Ile Met Tyr Thr Ser Gly
                260                 265                 270
Ser Ile Ser Ala Pro Lys Gly Val Val Leu Thr His Tyr Asn Ile Val
        275                 280                 285
Ser Gly Ile Ala Gly Val Gly His Asn Val Phe Gly Trp Ile Gly Ser
290                 295                 300
Thr Asp Arg Val Leu Ser Phe Leu Pro Leu Ala His Ile Phe Glu Leu
305                 310                 315                 320
Val Phe Glu Phe Glu Ala Phe Tyr Trp Asn Gly Ile Leu Gly Tyr Gly
                325                 330                 335
Ser Val Lys Thr Leu Thr Asn Thr Ser Thr Arg Asn Cys Lys Gly Asp
                340                 345                 350
Leu Val Glu Phe Lys Pro Thr Ile Met Ile Gly Val Ala Ala Val Trp
        355                 360                 365
Glu Thr Val Arg Lys Ala Ile Leu Glu Lys Ile Ser Asp Leu Thr Pro
370                 375                 380
Val Leu Gln Lys Ile Phe Trp Ser Ala Tyr Ser Met Lys Glu Lys Ser
385                 390                 395                 400
Val Pro Cys Thr Gly Phe Leu Ser Arg Met Val Phe Lys Lys Val Arg
                405                 410                 415
Gln Ala Thr Gly Gly His Leu Lys Tyr Ile Met Asn Gly Gly Ser Ala
                420                 425                 430
Ile Ser Ile Asp Ala Gln Lys Phe Phe Ser Ile Val Leu Cys Pro Met
        435                 440                 445
Ile Ile Gly Tyr Gly Leu Thr Glu Thr Val Ala Asn Ala Cys Val Leu
450                 455                 460
Glu Pro Asp His Phe Glu Tyr Gly Ile Val Gly Asp Leu Val Gly Ser
465                 470                 475                 480
Val Thr Ala Lys Leu Val Asp Val Lys Asp Leu Gly Tyr Tyr Ala Lys
                485                 490                 495
Asn Asn Gln Gly Glu Leu Leu Leu Lys Gly Ala Pro Val Cys Ser Glu
                500                 505                 510
Tyr Tyr Lys Asn Pro Ile Glu Thr Ala Val Ser Phe Thr Tyr Asp Gly
        515                 520                 525
Trp Phe Arg Thr Gly Asp Ile Val Glu Trp Thr Pro Lys Gly Gln Leu
530                 535                 540
```

```
Lys Ile Ile Asp Arg Arg Lys Asn Leu Val Lys Thr Leu Asn Gly Glu
545                 550                 555                 560

Tyr Ile Ala Leu Glu Lys Leu Glu Ser Val Tyr Arg Ser Asn Ser Tyr
                565                 570                 575

Val Lys Asn Ile Cys Val Tyr Ala Asp Glu Ser Arg Val Lys Pro Val
            580                 585                 590

Gly Ile Val Val Pro Asn Pro Gly Pro Leu Ser Lys Phe Ala Val Lys
        595                 600                 605

Leu Arg Ile Met Lys Lys Gly Glu Asp Ile Glu Asn Tyr Ile His Asp
    610                 615                 620

Lys Ala Leu Arg Asn Ala Val Phe Lys Glu Met Ile Ala Thr Ala Lys
625                 630                 635                 640

Ser Gln Gly Leu Val Gly Ile Glu Leu Leu Cys Gly Ile Val Phe Phe
                645                 650                 655

Asp Glu Glu Trp Thr Pro Glu Asn Gly Phe Val Thr Ser Ala Gln Lys
            660                 665                 670

Leu Lys Arg Arg Glu Ile Leu Ala Ala Val Lys Ser Gly Val Glu Arg
        675                 680                 685

Val Tyr Lys Glu Asn Ser
    690

<210> SEQ ID NO 127
<211> LENGTH: 694
<212> TYPE: PRT
<213> ORGANISM: Saccharomyces cerevisiae

<400> SEQUENCE: 127

Met Thr Glu Gln Tyr Ser Val Ala Val Gly Glu Ala Ala Asn Glu His
1               5                   10                  15

Glu Thr Ala Pro Arg Arg Asn Ile Arg Val Lys Asp Gln Pro Leu Ile
            20                  25                  30

Arg Pro Ile Asn Ser Ser Ala Ser Thr Leu Tyr Glu Phe Ala Leu Glu
        35                  40                  45

Cys Phe Thr Lys Gly Gly Lys Arg Asp Gly Met Ala Trp Arg Asp Ile
    50                  55                  60

Ile Asp Ile His Glu Thr Lys Lys Thr Ile Val Lys Arg Val Asp Gly
65                  70                  75                  80

Lys Asp Lys Pro Ile Glu Lys Thr Trp Leu Tyr Tyr Glu Leu Thr Pro
                85                  90                  95

Tyr Ile Thr Met Thr Tyr Glu Glu Met Ile Cys Val Met His Asp Ile
            100                 105                 110

Gly Arg Gly Leu Ile Lys Ile Gly Val Lys Pro Asn Gly Glu Asn Lys
        115                 120                 125

Phe His Ile Phe Ala Ser Thr Ser His Lys Trp Met Lys Thr Phe Leu
    130                 135                 140

Gly Cys Met Ser Gln Gly Ile Pro Val Val Thr Ala Tyr Asp Thr Leu
145                 150                 155                 160

Gly Glu Ser Gly Leu Ile His Ser Met Val Glu Thr Asp Ser Val Ala
                165                 170                 175

Ile Phe Thr Asp Asn Gln Leu Leu Ser Lys Leu Ala Val Pro Leu Lys
            180                 185                 190

Thr Ala Lys Asn Val Lys Phe Val Ile His Asn Glu Pro Ile Asp Pro
        195                 200                 205

Ser Asp Lys Arg Gln Asn Gly Lys Leu Tyr Lys Ala Ala Lys Asp Ala
    210                 215                 220
```

-continued

```
Val Asp Lys Ile Lys Glu Val Arg Pro Asp Ile Lys Ile Tyr Ser Phe
225                 230                 235                 240

Asp Glu Ile Ile Glu Ile Gly Lys Lys Ala Lys Asp Glu Val Glu Leu
            245                 250                 255

His Phe Pro Lys Pro Glu Asp Pro Ala Cys Ile Met Tyr Thr Ser Gly
        260                 265                 270

Ser Thr Gly Thr Pro Lys Gly Val Val Leu Thr His Tyr Asn Ile Val
    275                 280                 285

Ala Gly Ile Gly Gly Val Gly His Asn Val Ile Gly Trp Ile Gly Pro
290                 295                 300

Thr Asp Arg Ile Ile Ala Phe Leu Pro Leu Ala His Ile Phe Glu Leu
305                 310                 315                 320

Thr Phe Glu Phe Glu Ala Phe Tyr Trp Asn Gly Ile Leu Gly Tyr Ala
                325                 330                 335

Asn Val Lys Thr Leu Thr Pro Thr Ser Thr Arg Asn Cys Gln Gly Asp
            340                 345                 350

Leu Met Glu Phe Lys Pro Thr Val Met Val Gly Val Ala Ala Val Trp
        355                 360                 365

Glu Thr Val Arg Lys Gly Ile Leu Ala Lys Ile Asn Glu Leu Pro Gly
    370                 375                 380

Trp Ser Gln Thr Leu Phe Trp Thr Val Tyr Ala Leu Lys Glu Arg Asn
385                 390                 395                 400

Ile Pro Cys Ser Gly Leu Leu Ser Gly Leu Ile Phe Lys Arg Ile Arg
                405                 410                 415

Glu Ala Thr Gly Gly Asn Leu Arg Phe Ile Leu Asn Gly Gly Ser Ala
            420                 425                 430

Ile Ser Ile Asp Ala Gln Lys Phe Leu Ser Asn Leu Leu Cys Pro Met
        435                 440                 445

Leu Ile Gly Tyr Gly Leu Thr Glu Gly Val Ala Asn Ala Cys Val Leu
    450                 455                 460

Glu Pro Glu His Phe Asp Tyr Gly Ile Ala Gly Asp Leu Val Gly Thr
465                 470                 475                 480

Ile Thr Ala Lys Leu Val Asp Val Glu Asp Leu Gly Tyr Phe Ala Lys
                485                 490                 495

Asn Asn Gln Gly Glu Leu Leu Phe Lys Gly Ala Pro Ile Cys Ser Glu
            500                 505                 510

Tyr Tyr Lys Asn Pro Glu Glu Thr Ala Ala Ala Phe Thr Asp Asp Gly
        515                 520                 525

Trp Phe Arg Thr Gly Asp Ile Ala Glu Trp Thr Pro Lys Gly Gln Val
    530                 535                 540

Lys Ile Ile Asp Arg Lys Lys Asn Leu Val Lys Thr Leu Asn Gly Glu
545                 550                 555                 560

Tyr Ile Ala Leu Glu Lys Leu Glu Ser Ile Tyr Arg Ser Asn Pro Tyr
                565                 570                 575

Val Gln Asn Ile Cys Val Tyr Ala Asp Glu Asn Lys Val Lys Pro Val
            580                 585                 590

Gly Ile Val Val Pro Asn Leu Gly His Leu Ser Lys Leu Ala Ile Glu
        595                 600                 605

Leu Gly Ile Met Val Pro Gly Glu Asp Val Glu Ser Tyr Ile His Glu
    610                 615                 620

Lys Lys Leu Gln Asp Ala Val Cys Lys Asp Met Leu Ser Thr Ala Lys
625                 630                 635                 640
```

```
Ser Gln Gly Leu Asn Gly Ile Glu Leu Leu Cys Gly Ile Val Phe Phe
                645                 650                 655

Glu Glu Glu Trp Thr Pro Glu Asn Gly Leu Val Thr Ser Ala Gln Lys
            660                 665                 670

Leu Lys Arg Arg Asp Ile Leu Ala Ala Val Lys Pro Asp Val Glu Arg
            675                 680                 685

Val Tyr Lys Glu Asn Thr
        690

<210> SEQ ID NO 128
<211> LENGTH: 669
<212> TYPE: PRT
<213> ORGANISM: Saccharomyces cerevisiae

<400> SEQUENCE: 128

Met Ser Pro Ile Gln Val Val Phe Ala Leu Ser Arg Ile Phe Leu
1               5                   10                  15

Leu Leu Phe Arg Leu Ile Lys Leu Ile Ile Thr Pro Ile Gln Lys Ser
            20                  25                  30

Leu Gly Tyr Leu Phe Gly Asn Tyr Phe Asp Glu Leu Asp Arg Lys Tyr
        35                  40                  45

Arg Tyr Lys Glu Asp Trp Tyr Ile Ile Pro Tyr Phe Leu Lys Ser Val
    50                  55                  60

Phe Cys Tyr Ile Ile Asp Val Arg Arg His Arg Phe Gln Asn Trp Tyr
65                  70                  75                  80

Leu Phe Ile Lys Gln Val Gln Gln Asn Gly Asp His Leu Ala Ile Ser
                85                  90                  95

Tyr Thr Arg Pro Met Ala Glu Lys Gly Glu Phe Gln Leu Glu Thr Phe
            100                 105                 110

Thr Tyr Ile Glu Thr Tyr Asn Ile Val Leu Arg Leu Ser His Ile Leu
        115                 120                 125

His Phe Asp Tyr Asn Val Gln Ala Gly Asp Tyr Val Ala Ile Asp Cys
    130                 135                 140

Thr Asn Lys Pro Leu Phe Val Phe Leu Trp Leu Ser Leu Trp Asn Ile
145                 150                 155                 160

Gly Ala Ile Pro Ala Phe Leu Asn Tyr Asn Thr Lys Gly Thr Pro Leu
                165                 170                 175

Val His Ser Leu Lys Ile Ser Asn Ile Thr Gln Val Phe Ile Asp Pro
            180                 185                 190

Asp Ala Ser Asn Pro Ile Arg Glu Ser Glu Glu Ile Lys Asn Ala
        195                 200                 205

Leu Pro Asp Val Lys Leu Asn Tyr Leu Glu Glu Gln Asp Leu Met His
    210                 215                 220

Glu Leu Leu Asn Ser Gln Ser Pro Glu Phe Leu Gln Gln Asp Asn Val
225                 230                 235                 240

Arg Thr Pro Leu Gly Leu Thr Asp Phe Lys Pro Ser Met Leu Ile Tyr
                245                 250                 255

Thr Ser Gly Thr Thr Gly Leu Pro Lys Ser Ala Ile Met Ser Trp Arg
            260                 265                 270

Lys Ser Ser Val Gly Cys Gln Val Phe Gly His Val Leu His Met Thr
        275                 280                 285

Asn Glu Ser Thr Val Phe Thr Ala Met Pro Leu Phe His Ser Thr Ala
    290                 295                 300

Ala Leu Leu Gly Ala Cys Ala Ile Leu Ser His Gly Gly Cys Leu Ala
305                 310                 315                 320
```

```
Leu Ser His Lys Phe Ser Ala Ser Thr Phe Trp Lys Gln Val Tyr Leu
            325                 330                 335

Thr Gly Ala Thr His Ile Gln Tyr Val Gly Glu Val Cys Arg Tyr Leu
            340                 345                 350

Leu His Thr Pro Ile Ser Lys Tyr Glu Lys Met His Lys Val Lys Val
            355                 360                 365

Ala Tyr Gly Asn Gly Leu Arg Pro Asp Ile Trp Gln Asp Phe Arg Lys
370                 375                 380

Arg Phe Asn Ile Glu Val Ile Gly Glu Phe Tyr Ala Ala Thr Glu Ala
385                 390                 395                 400

Pro Phe Ala Thr Thr Thr Phe Gln Lys Gly Asp Phe Gly Ile Gly Ala
            405                 410                 415

Cys Arg Asn Tyr Gly Thr Ile Ile Gln Trp Phe Leu Ser Phe Gln Gln
            420                 425                 430

Thr Leu Val Arg Met Asp Pro Asn Asp Ser Val Ile Tyr Arg Asn
            435                 440                 445

Ser Lys Gly Phe Cys Glu Val Ala Pro Val Gly Glu Pro Gly Glu Met
            450                 455                 460

Leu Met Arg Ile Phe Phe Pro Lys Lys Pro Glu Thr Ser Phe Gln Gly
465                 470                 475                 480

Tyr Leu Gly Asn Ala Lys Glu Thr Lys Ser Lys Val Val Arg Asp Val
            485                 490                 495

Phe Arg Arg Gly Asp Ala Trp Tyr Arg Cys Gly Asp Leu Leu Lys Ala
            500                 505                 510

Asp Glu Tyr Gly Leu Trp Tyr Phe Leu Asp Arg Met Gly Asp Thr Phe
            515                 520                 525

Arg Trp Lys Ser Glu Asn Val Ser Thr Thr Val Glu Asp Gln Leu
            530                 535                 540

Thr Ala Ser Asn Lys Glu Gln Tyr Ala Gln Val Leu Val Gly Ile
545                 550                 555                 560

Lys Val Pro Lys Tyr Glu Gly Arg Ala Gly Phe Ala Val Ile Lys Leu
            565                 570                 575

Thr Asp Asn Ser Leu Asp Ile Thr Ala Lys Thr Lys Leu Leu Asn Asp
            580                 585                 590

Ser Leu Ser Arg Leu Asn Leu Pro Ser Tyr Ala Met Pro Leu Phe Val
            595                 600                 605

Lys Phe Val Asp Glu Ile Lys Met Thr Asp Asn His Lys Ile Leu Lys
            610                 615                 620

Lys Val Tyr Arg Glu Gln Lys Leu Pro Lys Gly Leu Asp Gly Asn Asp
625                 630                 635                 640

Thr Ile Phe Trp Leu Lys Asn Tyr Lys Arg Tyr Glu Val Leu Thr Ala
            645                 650                 655

Ala Asp Trp Glu Ala Ile Asp Ala Gln Thr Ile Lys Leu
            660                 665

<210> SEQ ID NO 129
<211> LENGTH: 543
<212> TYPE: PRT
<213> ORGANISM: Saccharomyces cerevisiae

<400> SEQUENCE: 129

Met Thr Ser Ala Ala Thr Val Thr Ala Ser Phe Asn Asp Thr Phe Ser
1               5                   10                  15

Val Ser Asp Asn Val Ala Val Ile Val Pro Glu Thr Asp Thr Gln Val
```

-continued

```
                20                  25                  30
Thr Tyr Arg Asp Leu Ser His Met Val Gly His Phe Gln Thr Met Phe
             35                  40                  45
Thr Asn Pro Asn Ser Pro Leu Tyr Gly Ala Val Phe Arg Gln Asp Thr
 50                  55                  60
Val Ala Ile Ser Met Arg Asn Gly Leu Glu Phe Ile Val Ala Phe Leu
 65                  70                  75                  80
Gly Ala Thr Met Asp Ala Lys Ile Gly Ala Pro Leu Asn Pro Asn Tyr
                 85                  90                  95
Lys Glu Lys Glu Phe Asn Phe Tyr Leu Asn Asp Leu Lys Ser Lys Ala
                100                 105                 110
Ile Cys Val Pro Lys Gly Thr Thr Lys Leu Gln Ser Ser Glu Ile Leu
            115                 120                 125
Lys Ser Ala Ser Thr Phe Gly Cys Phe Ile Val Glu Leu Ala Phe Asp
            130                 135                 140
Ala Thr Arg Phe Arg Val Glu Tyr Asp Ile Tyr Ser Pro Glu Asp Asn
145                 150                 155                 160
Tyr Lys Arg Val Ile Tyr Arg Ser Leu Asn Asn Ala Lys Phe Val Asn
                165                 170                 175
Thr Asn Pro Val Lys Phe Pro Gly Phe Ala Arg Ser Ser Asp Val Ala
            180                 185                 190
Leu Ile Leu His Thr Ser Gly Thr Thr Ser Thr Pro Lys Thr Val Pro
            195                 200                 205
Leu Leu His Leu Asn Ile Val Arg Ser Thr Leu Asn Ile Ala Asn Thr
            210                 215                 220
Tyr Lys Leu Thr Pro Leu Asp Arg Ser Tyr Val Val Met Pro Leu Phe
225                 230                 235                 240
His Val His Gly Leu Ile Gly Val Leu Leu Ser Thr Phe Arg Thr Gln
                245                 250                 255
Gly Ser Val Val Val Pro Asp Gly Phe His Pro Lys Leu Phe Trp Asp
            260                 265                 270
Gln Phe Val Lys Tyr Asn Cys Asn Trp Phe Ser Cys Val Pro Thr Ile
            275                 280                 285
Ser Met Ile Met Leu Asn Met Pro Lys Pro Asn Pro Phe Pro His Ile
            290                 295                 300
Arg Phe Ile Arg Ser Cys Ser Ser Ala Leu Ala Pro Ala Thr Phe His
305                 310                 315                 320
Lys Leu Glu Lys Glu Phe Asn Ala Pro Val Leu Glu Ala Tyr Ala Met
                325                 330                 335
Thr Glu Ala Ser His Gln Met Thr Ser Asn Asn Leu Pro Pro Gly Lys
            340                 345                 350
Arg Lys Pro Gly Thr Val Gly Gln Pro Gln Gly Val Thr Val Val Ile
            355                 360                 365
Leu Asp Asp Asn Asp Asn Val Leu Pro Pro Gly Lys Val Gly Glu Val
            370                 375                 380
Ser Ile Arg Gly Glu Asn Val Thr Leu Gly Tyr Ala Asn Asn Pro Lys
385                 390                 395                 400
Ala Asn Lys Glu Asn Phe Thr Lys Arg Glu Asn Tyr Phe Arg Thr Gly
                405                 410                 415
Asp Gln Gly Tyr Phe Asp Pro Glu Gly Phe Leu Val Leu Thr Gly Arg
            420                 425                 430
Ile Lys Glu Leu Ile Asn Arg Gly Gly Glu Lys Ile Ser Pro Ile Glu
            435                 440                 445
```

```
Leu Asp Gly Ile Met Leu Ser His Pro Lys Ile Asp Glu Ala Val Ala
        450                 455                 460

Phe Gly Val Pro Asp Asp Met Tyr Gly Gln Val Gln Ala Ala Ile
465                 470                 475                 480

Val Leu Lys Lys Gly Glu Lys Met Thr Tyr Glu Glu Leu Val Asn Phe
                485                 490                 495

Leu Lys Lys His Leu Ala Ser Phe Lys Ile Pro Thr Lys Val Tyr Phe
            500                 505                 510

Val Asp Lys Leu Pro Lys Thr Ala Thr Gly Lys Ile Gln Arg Arg Val
        515                 520                 525

Ile Ala Glu Thr Phe Ala Lys Ser Ser Arg Asn Lys Ser Lys Leu
    530                 535                 540

<210> SEQ ID NO 130
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130 ttttttttt ttttttttt ttttttttt                                      30

<210> SEQ ID NO 131
<211> LENGTH: 2066
<212> TYPE: DNA
<213> ORGANISM: Mortierella alpina

<400> SEQUENCE: 131
gctctttttt gttctgttct ttgccacccc actctgctgt gcctctccac tcccctgcc      60 cgtcgaacgt tcttctgtca ctttgcacag cagtatctcc tctgatctcg cttgrttata    120
ttccctctaa tctcgtttgg ttatattccc tctgatctcg ctcggttata ttcttcagat    180
atggatgctg tccctgcagt tgctgctgcg ccatccccg cagccatgta tgtcggctcc     240
aagcttgcaa tccccgtga tgtcaagtta gctaaaggcc tagtcagtgc caagctaggt    300
tacaggtcct acgagaagaa cgactcgatc aatatctctt atcgttttga agagacctgt    360
aagaagcacc ctcatcgcga agctttggtg tttgaaggca aatcgtacac cttccaggac    420
atccagcgag aatcgaatag ggtgggacac tggctgttgt ccaaaggcgt caagcgagga    480
gagatcgtgt cgctcttcat gcaaaataag ccagagtttc tcttcttctg gcttggactc    540
aacaagatcg gcgctacggg agcattcatc aacacgaacc tctcgggcaa acctctgacg    600
cactcattgc gtaccgcgac agcatccatt ctgattatgg atgcggaact gccgacgccc    660
atttatagtg tcctcgatga agtccttgag atgggatatc agatatattc ctacggagga    720
tcccagcaac acgcctttgc tacacaagtt gaactttctc aaatctcgga tgcggccttg    780
cccaagagtc tgcgaaggaa aaccactgca atgatattg ccatgttgat ttacacctcc    840
ggaacgacgg gtttgcccaa agctggacgg ttctcccatg ctcgagccaa cgttgccgca    900
cttttctgga cgtctttcta ccacttcagc gaaaaagacc gcctgtacat cgccttgcct    960 cttttaccaca gtgctggagc tgtccttgga atatgtgtgg cctgggtcac cggtgctacg   1020
gtggtcctgg cgcgcaagtt ttcaactact tccttctggg acgaatgcag ggccaacaag   1080
gtcaccgtga tccagtatat tggagaaatc tgccgatact tactgaatgc tcctccttct   1140
cccttggaca agacacacac gatccgaatg gcgcatggca acggcatgcg tccggatgta   1200
```

```
tggaacagat tcagagatcg tttcggcatc cctttgatcg agaatggta tgcaagcact    1260 gagggcaccg gaatcttgac aaactataac acaggaccca atggcgctgg tgcgatagga    1320
tacagaggct ccttggccag aactgtcgat aagggtctga agattgcgaa gttcgacatc    1380
caaaccgagg aacttattcg tgacaaaaat ggtcgatgca ttgagtgtgt cgcagatgag    1440
cccggcgagc tcttgacaat gattgattca agtgatccca ctcgcgcttt ccaagggtac    1500
cataaaaatg caggtgcaaa ctccaagaaa gtcgtccagg atgcattcag tgttggcgac    1560
caatactttc gtactggtga catccttcgt cgcgacgctg atggctattt ctattttggc    1620
gatcgtgttg gagatacttt ccgctggaaa tctgaaaacg tgtcaactgc ggaggtttct    1680
gaggtgctct cagcataccc ggactgcatc gaggtcaacg tttatggcgt tcaagtccct    1740
ggacacgacg ccgcgcagg catggctgcc attgtctcca aggacaccat gaactgggat    1800
agtttcgcca gtttgcact caaaaatctg ccgaagtact ctgtgccgat tttcatccgc    1860
aaggtcccag agatggagat tacgggaacg ttcaagcaac gaaaggttga actggtgaac    1920
gagggcatgg acccgagcaa gatcaaagac gaaatgctgt ggttggatgg gcactcctac    1980
cggcccttca agaggcgga gcatactaga gtcgtcagcg gcaaagccag gctttgacga    2040
ataaaattat ttcgttttgt ccgttg                                         2066

<210> SEQ ID NO 132
<211> LENGTH: 2135
<212> TYPE: DNA
<213> ORGANISM: Mortierella alpina

<400> SEQUENCE: 132
atccgcccat ccgctctctt gccactgatc tcaaagcgtg atccaaaggt cattcttagg      60
cagcactcac gcagctactt agaactctac ccacatatcc cttattgata caatggctcc     120
cgtcgctgca ctcgccgccg ctctggcggc aggatactat ctcaatggca agtaccaaat     180
cactaaggac ttggcgcttg ttcgcgttgg tctccatgca cgcaaaagac ttgaggcctt     240
ggtcgagaat cgggactgca gtctttacaa caggttcgag gaacaatgcc agatccggcc     300
tttctctgtt gcccttgttt ttgagaacac gtcttacacc tggagagact ggagctggc     360 gtccaacagg atggcccatt ggtttgttgc tcaaggaatc caaaaaaaag gagcgtgtgg    420
cgatgatgat gcataactcg cctctgttca ttatcacctg gctggcaatg ctcaagatca    480
tggttgtacc tgcttttatc aataaccaga ttgcaggacc tgttctggtt cattctctta    540
aagtggccga cgccaagttt ctcttgttcg attacgagtt ggcacctgtc atccaaaagt    600
cgctcaatga gatcaaggac atgggttaca atctctacac tgtcacaccc aaggatcaag    660
ttctaggtca acttttacgcc aatctgcccg aggctgctcg tcaggtgttg gatgaggctc    720
cttcattctt tggttatgtc gaatggcaga acctcagtac cgaaggtttc tcgaacgaga    780
gtcgtcagga ggtggtgatc tccgaccccg cagccttgat ttacaccagc gggaccacgg    840
gattccccaa ggctgctatc atggaccatg acgttgcaa cttggcttcg atctcttatg    900
gcactctatg cggcatcaaa ccagagaaca aggtttacat cacattgccg ctctatcatt    960
ctgctggagc catcattggt ctgggccaga gcttcaccag cggatgcacc attgtgctgg   1020
cgcgaaagtt ctccgtgaca aagttttggc gtgattgcgt tgagtacgac gtaactcatt   1080
ttcagtacat tggcgaactc tgccgctacc ttctaaatgc ccccgaaagt ccactggaca   1140
aaaggcataa ggttcggatg gcgtttggca acggaatgcg cccggatgtt tgggcaaagt   1200
```

| | |
|---|---|
| ttcaggaacg attcaatatc cccattattg ttgagtacta cgccatgagc gaaggaacat | 1260 |
| cgtcgctttt gaatgtggcc aggaacaagc gcgaccaagg tgcggtggga ttccgtggcc | 1320 |
| ccgtcgtgag ggccttgacg cctcccgttc aactggtcaa ggtggacttt gacacggagg | 1380 |
| agctgatccg cgataagaag acgggacttt gcgtcctatg ccagcctggt gagattggag | 1440 |
| aactggtcac gctagccgac aacaagacga ctggcgcacg ctatgctggg tatttcaatc | 1500 |
| agccagaggt ttcgaaggca aggctggtcc agaacgtggt agtgaaggac gacatctact | 1560 |
| tccggacggg tgacctcttg tactccaagg accagtactg gtactttgct gatcgcgcag | 1620 |
| gagacacgta ccggtggaaa ggagagaacg tgtcgacagc cgagattgca gacactatcg | 1680 |
| gccgtgttga gggcgtggct agttgtactg tttatggcgt atcggtcccg ggcatggatg | 1740 |
| gacgcgcggg catggctgct ttggtgctca agaactcgat tgtgcagatg gcaggtggaa | 1800 |
| gccaggcaaa gttccatgtg gatgaggctg cgctgaacgc gttttttgcgt gacttgagca | 1860 |
| aggatgtggt caaaaaactg ccggcgtatg cgattcctcg gttcttgcgc attgcagagc | 1920 |
| aggaactgga gacgacgggc acgttcaaga acaagaaggt ggagctgaag aaggaagggt | 1980 |
| tcgacctcgg taaggtcaag gagcggctgt actggtggac acccaagggt gaatatgccc | 2040 |
| cttttggcgt ggcggagaac gagcagatcc tcgcaggacg cgctcgtctt tgagcgatgt | 2100 |
| ttgtcaatga agtcatcggc atcatcatca tcatc | 2135 |

<210> SEQ ID NO 133
<211> LENGTH: 1753
<212> TYPE: DNA
<213> ORGANISM: Mortierella alpina

<400> SEQUENCE: 133

| | |
|---|---|
| gcctactttg cgctcgcctc atcgacccaa aggcagcaat ggaaacggat gctcttacca | 60 |
| tcgctttgac catcgccatc gccatcgtgc tggctttggt caaattcaac gaaaaagagc | 120 |
| ctgacctgca tccgctcctg ctcgggcagc aatcgtctgt cacgcccatt cggaacgagg | 180 |
| gcgagtccgt tatccataga tccaaaacgg tgccacacgg gacactgctg acgaagcgcc | 240 |
| cgagcgagaa aatcaagact ctgcacgatg tctggcagac tggagcagct gtcaacccag | 300 |
| ccggccgatc gttgatgttt atgctgcaga accagtttgc gtttatcgag gccacgtatg | 360 |
| agcaagtcaa taggaggatt ggcggcttcg gaacaggttt cgtgaaggca acagggctaa | 420 |
| agcccaagac ggacacacca gtaggaatct ttatgcccta ctctcaagaa tcgttcgttg | 480 |
| cccagcaggc attctatcga tacagctttg ttgctgtccc catccatgat ctgaggaaca | 540 |
| acgacctctt ggtggaggta gtagaccaga ccaagctcaa ggccatcata gtctcacaaa | 600 |
| aggtgctccc gttattgctg caatctctga aggagtgtcc aaccatcaag acaatcatca | 660 |
| tggcaggaat ctacatctca caggagcagc tggaaatggc agcacagcat ggagtaaagc | 720 |
| tgctcaaatt cgcggcagtg gaatatgagg atcctcgac tctgatggag cctgttcagc | 780 |
| ctgatccgga ggatgttgcc atgatcaact ataacacaaa gtcgtcttcg ctctcgaaag | 840 |
| gcgtcatgct tacccatgcc aacctgatcg cggcgatgac tgccttcacg gagtcacttc | 900 |
| cggcaaaaaa gcgtttctcc agcaaagatc gtcttctctc tcattttttcc aatggagatg | 960 |
| tcatctctgt cttcatgtcg agcgccatca tcctgatggg aggttctttg gtctttccat | 1020 |
| ctggtttgat gaagaacgtt ttgcatgatt cccaagcttc tgcaccaacg atctttgcaa | 1080 |
| gcacacccat catcctggaa aagattcacg aagcacttca gttgacgtat ggccaaggct | 1140 |
| ccatgttcag gcgcggcttt gctgccaaat tggccatact tcaagctgga cgaatcacta | 1200 |

```
caacaagcct atgggacttg attggactgg gcgaggtccg cagcaaactt ggtggaaagg    1260
ttcgaatggt tgtaacaaca catcctacca aacctgagac gctggattat atcagagccg    1320
cgatgggcat ccatgtcatt accacttacg gcaggacaga gacgtcgggc attgtgacag    1380
cccgcaacat gctggattat gccaacgcac ctcatttagg accaccagtg ggttgcaacg    1440
aggttaagct tgtggacgat gttgcagctg gctttacaag tgcagacgag cccaacccac    1500
gaggcgagat cctatccga ggccccaatg tgatgaaagg ttattacaag aagccgggtg     1560
ccacttcaac ggctatcgat gaggaagggt ggttccattc aggagagctg gcacattcc     1620 actccaacgg cactttagac gtgttgggca agaagaagaa gacgaagtct gcagttggat    1680
caccgtcatg aaaggagatg ctgcatgtgc tacagaatat aaaaagggag aagatacgtt    1740
cggtaaccac atc                                                      1753

<210> SEQ ID NO 134
<211> LENGTH: 2309
<212> TYPE: DNA
<213> ORGANISM: Mortierella alpina

<400> SEQUENCE: 134
cacacgctca cgttcgctct cacccgaccc actccccact ctcgctctca ttctctccct     60
tgtccttccc ttgtcccttt caaggtctaa cagcatcaac atcagcatca gcatcaagct    120
tctcattcct ccctcgtcta aatctctgaa agagttcgct ttgcaattca gcaatgtccc    180
tcgaccagaa cgcccagtcc gttgagctcc caggcacccg gcaaccaggc cagacaggca    240
tctatcgccg caaaggcttc gagaatgccc ttctcgccgt cccacccagc agaccgcaca    300
tcaagaccat ctacgatgcc ttccagcacg gactgaagct taatcccaac ggagctgccc    360
tgggcagccg agtgtacgac ccggtgacgg acacctttgg aggctatgtc tggcagacgt    420
atgcacaggt gaacgaccgc atcactcgct tcggcagtgg attggtcaaa attcataagg    480
acgtccatgg tcttgccacc gtgggccaga agtggtctct cggaatctgg gccatcaacc    540
gacccgagtg gaccatcgcg tccgaggctt gctcggccta caacctggtc tccgtgggtc    600
tttacgatac tttgggaccc gaggctgtga cttatggcat taatcacgct gagtgctcta    660
ttgtcgtaac aagtgtggat catatcgcga cgctgctgaa cgaatcttcc aagatgcctg    720
ggctcaaaat catcatcagc atggatgacc tcgatactgg gagagcaggc ccaggactgg    780
ctcccaccgg caccatcctc aggacttacg ctcaggacaa aggggtacta ctttatgatt    840
ggtctgaggt tgaagccgtc ggtattcagc atggacgaaa gcatacgcca caacctcct    900 ccgacgcata tacgatctgc tataccagcg ggacaacagg cttgccaaaa ggtgccattt    960
tgacccatgg aaacttgatc gcccttttgg cctccagtga tgtggccaca ccagtgctgg    1020
ctgacgattg cctcatcagt ttcttgcccc tgcctcacgt cttggtcgg gtcatggagc     1080 tcttcgcgat ggccgcagga ggaaagattg gctacagcac gggagatcct ttgcgtctct    1140
tggaggacgt ctcgcaccta aagccctcca tcttccccgc tgtgcccaga ctgctgaacc    1200
gcgtgtatgc caaggtgtat gcggcaactg ttggagcgcc tggactcaca ggggcactgg    1260
cgcgacgagg attggccacc aagctcacca atttgagaga gggcaaaggt ttccaccacc    1320
cattgtggga ccgaatcctc ttctcaaagg tcaagcaagc gctcggcggc aatgtgagac    1380
tgatgttgac tgcctccgct cccatctcgg ccgagatctt ggaattcgtc cgtgtcgctt    1440
tctgctgcga ggtcgtggag gcatatggac agactgaggg cggtggagcg gccacaaaca    1500
```

| | |
|---|---|
| ccgtgattgg cgagaccgag gctggacacg tcggtcctcc tcaagcttgt tgcgagatca | 1560 |
| aactggtgga tgtacccgag ctgaactact ttgcgaccga taaaccattc cctcgtggtg | 1620 |
| agatttgtgt ccgtggaccc ggtgtcattc ctggttatct caaggatgag gccaagacca | 1680 |
| aggagaccat tgatgaggag ggctggctgc actcgggcga tatcgccatc atgagtggca | 1740 |
| aaggcaccgt taccatcatt gacaggaaga gaacgtgtt caagctgagc caaggagaat | 1800 |
| acatcgcggc agagaacatt gaagggcgtt cctctccaa ggttccattc atccaacaaa | 1860 |
| ttctggtgca cggcgactcg accgagagct gtttggtggc catcttgatc ccagagcctg | 1920 |
| aggccttcat cccctttgtg aacaaagtgc tcgagaacgt caatcttcaa cctgagatc | 1980 |
| ttgcagccta caggaagatc gttaacaacc caaagctgcg ccaggctgtc ctcaaagagc | 2040 |
| tgatcaaggc tggcaaggat gctggattga aggctttga gattccaaag gcgatcctcc | 2100 |
| tcgaatctga ggcattcacg gtcgaaaacg acaagatgac cccgactttc aagatcaaaa | 2160 |
| gacaccctgt cgtccaggct taccgcgagc aactgcagc cctctacaac gaaatccatc | 2220 |
| aaaaggaatc caagctgtaa aaagaaaccc ttagaacctg cggtgctcgc agcaattaaa | 2280 |
| aaaaaagag agatattact ctcacagct | 2309 |

<210> SEQ ID NO 135
<211> LENGTH: 2196
<212> TYPE: DNA
<213> ORGANISM: Mortierella alpina

<400> SEQUENCE: 135

| | |
|---|---|
| tttttttttt tttctttct ctccaaccct ttcacccca cgcctcggct cgtactcaag | 60 |
| cctcacgtcc acactctcgt cctctagcct gctgcattca cgattcacat tcctcctcga | 120 |
| ctccagcatc gctactccct cgtgctactt tcaccatgac cacccaattg tactccatcg | 180 |
| aagtggcagg cagcccagag attccgggcg agggcaaacc tcggcgcagc gttctcagcc | 240 |
| cagacaaact cgtccagagc tatcagtctt tcaaggcga cggctccatc accactctat | 300 |
| atgagaactt tttggagggc atccagcgct cagagggagg agagtttctc ggacaccgcc | 360 |
| ccatcgtcga taatgtagct cagccgtacg aatggctaag ctacacgcgc gttcaggaac | 420 |
| gtgtcgccaa cttttggcgct ggtctcatcc agctgggcct gaaagtcgac tcgaactttg | 480 |
| gcatctttc catcaacagg cccgaatgga caatgagtga gctggcaggc tacatgtaca | 540 |
| actttacatc tgtgccgctt tacgacactc tgggcgtctc ggccatcgaa tacatcgtta | 600 |
| atcagaccga gatggagacc atcatcgcgt cggctgataa agcctcgatc ctgttaaaca | 660 |
| tgaaatcaac tctgccgaca ctcaagaaca ttgtcgttat gggctcgctc gaagacgcgc | 720 |
| tcgttgtcga gggtagggaa atggatatcc acatcgttgc gtggagtgac gtcgaacgcg | 780 |
| atggcttcaa caacccgcg ccagccaacc ctccaacacc ggacgacgtc gccaccatct | 840 |
| gctacacgtc aggaacaacc gggacaccaa agggcgcaat cctgacccac aaaaactttg | 900 |
| tggctggcct tgcctcgttc catatgatgg caaagcacca aaagttttc atccctctcga | 960 |
| gcgttgacac tcacatatct tacctgcccc tggcacatgt gttcgagcgt ttgtctcagg | 1020 |
| ctgttatgat ttctggcgca gctcggattg ggtattacca aggagacact ttgaagctac | 1080 |
| tcgatgatgt ggcgatcttg cagcccacca tctttgtgtc cgttccacga ctctttaaca | 1140 |
| ggatttacga caaggttcta gcaggtgtga agccaagggg cggtctcgca gctttcttat | 1200 |
| tcaaccgcgc ttttgaaacc aagaaggcta atttgaaacg cggtatcctg gagcacgcca | 1260 |
| tctgggatcg actggtattt ggtgcaattc gtgcgcgact cggtggcaaa gttaagcata | 1320 |

```
ttgtctcagg atcagccct atagccccgg acgtcatgga tttccttcgc atttgcttca    1380
gtgccgacgt ttatgaaggg tatggacaga cggagcaggc tgctggtttg tgtatgagct    1440
acagaggtga cttgacctcg ggtcaagtgg accccctca gctgtgcgtc gaagtgaagc    1500
tcagagacgt tccggacatg cactacacaa gccaggacaa gcctcgccct cgcgggggaga  1560
tcatgcttcg aggccattca gttttcaaag gctattacaa ggctccaaag caaacagagg   1620
agacactgga cgcacaggga tgggcaagca ctggagacgt tggtgaatgg gacgagcgtg   1680
gccgcttggt ggtgatcgac cgtgtcaaaa acattttcaa gttggctcaa ggcgaataca   1740
ttgcacctga aaagatcgaa gccgtcctgg ccaaacacta ccttgtcgcc caggtctttg   1800
tctacggaga ctccttccaa gcgacattgg tgggagttgt cgtgcccgat gcggagacgc   1860
taaagccttg ggccgatgac catggccttg gaggcaagag ctatgaagaa ctatgcgctc   1920
atcccgctgt caaagaaact ttgctgaagg agctcaaaga gtttggtcgt gaaaatgatc   1980
tgaagggctt tgagatattg aagaacattc atgtaacggc ggagcaattc tcaattgaga   2040
atgatctttt gacacccaca ttcaagctga agagacacac cgcgaaagag aagtacatcg   2100
ccgagattga gctgatgtat aacgggatcc actgaaagag tctagccaaa gcagatcttt   2160
ttattactgt cgttaaaaaa actactcgta accatc                              2196

<210> SEQ ID NO 136
<211> LENGTH: 2113
<212> TYPE: DNA
<213> ORGANISM: Mortierella alpina

<400> SEQUENCE: 136
tttcctcacc ttccctccgc tgccctctgc tgcacactcc tctggcttat accatccacc     60
cctctagccc cgccacttcg ccgccaacct catccgactc acaccgcaat ggctactcaa    120
atgtactcgg tggtcgtccc caacagcccc gacattcccg cgcaaggcaa gccccgccgt   180
agtgtgcttt gtccagacaa gctcctggag aactacccct cagtgaaagc aggctcaacg   240
atcacgaccc tgtacgagaa cttccaagaa ggtgttctcc gttcaggcgg cgcccatttt   300
ttgggccatc gtcccattgt gaatggccag cctcaggctt acaagtggca gtcgtatgtc   360
gatgtcagca agcgtgttac gcacttcggc gctggcctgg ctcatctcgg cttgtctcca   420
aagcaaaact ttggaatttt ctctatcaac cggcctgagt ggaccatgag tgagcttgct   480
ggctatatgc acaactacac cagcgtcccc ctctatgata cattgggagt cgccgcgatc   540
gagtatatcg ttaaccagac tgagatgcag atcatcattg cttcgtccga caaagcttct   600
atcatcctcc acatgaaatc agcacttcca accgttcaga cgattgtcgt catggggggaa   660
tttactgacg ctctcgtcgc agagggtaag gagctcaaca tcaacattgt atcctggacc   720
gatgtcgaaa agagcggtct tgagcggcct gtcgaagccg tgcaccccac agccgaggat   780
atcgctacca tctgttacac atctggaacc actggaacgc caaaaggtgc tatcttgacc   840
cacaagaact tgttgccac tatcgcttca ttccacatga tggcaaagca tggcaggttc   900
ttcattccct cgcctgccga cacacatgta tcctacctgc ccttgcccca cgtcttgag    960
cgcctttgcc aggctgttat gatctcgggc gctgcgcgta ttggttacta ccaaggagat   1020
acgctgaagc tgctggacga tgttgccgtc ctgcatccca ccatttttgc ctccgtccct   1080
cgtctctta accgtatcta cgacaaggtg cttgctggcg tcaaggccaa gggtggtatc   1140
gccgccttct tgtttaaccg cgcatataat tccaagaagg ccaacttgcg aaagggcgta   1200
```

```
cttgagcatc cgctctggga caagctggtc tttggagcga ttcgcgcgcg cttgggtggc     1260
aaggttaagc acatcgtgtc aggatctgcc cccatctctc ctgatgtgat ggatttcctc     1320
cgcatctgct tcagcgctga tgtgtatgag ggatatggcc agacggaaca ggcagccgga     1380
ttaagtatga gctatcgcgg tgatttgact ccaggacagg ttggcccacc tcaactgtgc     1440
acagaggtca agttgaagga catccctagt atgaactata gcagcgcgga caagcctttc     1500
ccccgtggag aaatcatgct tcgcggaaac tctgtgttca agggctatta caaagcacca     1560
aagcagactg aagaaacatt ggatgctgac ggttggtcca gtaccggaga cgttggacag     1620
tgggatgccc aaggccgtct ggtggtcatt gatcgcgtca agaacatctt caagttggcg     1680
caaggagaat atattgcgcc tgaaaagatc gaggctgtcc tcgccaagca cttcctcgtt     1740
gcccagattt ttgtctatgg gcactcgctc caggccacca ttgtcgcggt ggttgtccct     1800
gatgctgaga cgctcaagtt gtgggctaaa gaaaacaagc tgggtgacaa gtcttacgag     1860
gagctgtgcg ctctccctca gcttcgcaca cccctccaaa aggagttggc tacttttggc     1920
aaagaatcgg atctgaaggg ctttgagatt cctaagaaca ttcatgttat ctccgagcag     1980
ttttcaattg agaacgatct tttgacccccc accttcaagc tgaagagaca tgctgccaaa     2040
gagaagtata acgccgaaat cgaccgcatg tatgcagaaa tcgcttaata taataatgg      2100 ttgtactcaa tat                                                       2113

<210> SEQ ID NO 137
<211> LENGTH: 2087
<212> TYPE: DNA
<213> ORGANISM: Mortierella alpina

<400> SEQUENCE: 137
ggcacgaggc tctactctcc attgcccact cactcattgc ccctctgtcc atcaccggca       60
ttgctcgttc gcgccttccg ccactccact cttctttca ttccttcttt acaacggcca      120 tctcccctc gctctgcgct ctcccatcc acgctaacaa tgcacattct gaatgccaca       180
agaccattct ccaggctgtc tccaaccgta aggagacctt ggctaggact cggccagacg      240
cgcccttatg ctatcgcgca gaccgaggcc agtcctaggc tgtcatatgt ccgaggcacc      300
accgtcggca cccagctatg cgaggatccc atcggtgcgt actgggacag ggtcgtcaat      360
cgtcacggtg accgctcgg acttgtcgtc aagcacgagc aggacctgca ctggaccttc      420
cgtcagtttg gcgggcaggt tgatagcctc tgccgtgggc tctatgagtc tggcttgcga      480
aagggtgatc gactcgctgt ctggatgccg aacaacagcg cgtgggccac gctccagtat      540
gctactgcca agtctggcat cattctggta actctcaacc ctgcgtaccg gaggcaagag      600
ctactgcaga cattgtcttt ggtcgagtgc aagtcattgg tctatgtgcc aagtctaaag      660
acttcgaatt atagcgagat gttgctcgac ctcctaccag aactccagta ccagtcgcca      720
aatcagctct tgaccgagaa gctaccctca cttcgtcaag tcatcgtgtt tgacaatggc      780
tcgcaagtcc cagagacagc aaaattgaag ggattgacaa agtatcagga tttgttgatc      840
aagaatccct cgaccgctgt cgacggagct cttgaaaagg aacggctcgc tatcgacaac      900
agggatatca tcaatctcca gtttactagc ggaactacag gccttcccaa gggcgtctcg      960
ctgtcgcatc gaaacatctt gaataacggc attcatattg gagataacat gcgactgacg     1020
gaaaaggatt tgctttgctg cccggtcccg ctcttcact gctttggact ggtgctggca     1080
agcttggctg caatgaccca tggcgcagga attatttacc cttcgcagtc cttgatgct      1140 gaggccacac tgagggctgt ttctgaggag ggtgctacag cgctgcatgg cgtgccgact     1200
```

```
atgctgttgg aagagatgaa ccaccccaac tttgcaaagt acaacctttc gacacttcgg    1260
acaggaattg cagctggatc ccctgtgccc attgaggtca tgaagaacgt gcagacaaag    1320
atgaacctga aggagctgac tatctgttac ggcatgaccg agacctcgcc cgtgtccttc    1380
atgacactca caacggatga attacgggat cgatgtgaga ctgttggacg aattatgcca    1440
catctcgagg ccaaagtcgt caaccctgag acgggagaga ctttgccagt gaattcatca    1500
ggagagttgt gcacgcgcgg gtatgctgtg atggagggtg gttactggcg atcccaggag    1560
cagacagatg cagtggtgga caaggatggc tggatgcaca ctggcgacac tgccgtgctc    1620
gatgaccgtg gcttttgcag gatcgacgga cgcatcaagg acatggtgat ccgaggaggc    1680
gaaaaaatcc atcctgtaga ggtcgagaac tgtctctttg agatggacgg cgtcaagaac    1740
gtgtctgtga ttggcgttcc cgacaagcgg tatggcgagc aggtgtgtgc gtggatctcg    1800
accaaggacg ggaagacggt cagtctggag gcagtgcaaa agttctgtga gggcaagatt    1860
gcgcactaca aggtgccgcg gtatgtggtt gtggtggagt ccaatgagtt cccgactacc    1920
ccctcgggca agatccaaaa gaatgtgatg cgcgagctga ccaaggcgaa gctgcagctg    1980
ccttgatggt actaggatat ggagccgacg aaagtaataa aggcgtatgc tggcatggcg    2040
caagatctga gccctgcggt gaggtgcatt cagtgacgcc attagaa                  2087
```

<210> SEQ ID NO 138
<211> LENGTH: 2288
<212> TYPE: DNA
<213> ORGANISM: Mortierella alpina

<400> SEQUENCE: 138

```
tgctttctc ttcttcgtca ccctcctct tcccattcct ccggtcctcc tccgttccta      60
atcagtttct cagaccctgt ccattcctct ggcctccaca cacacccac tctcccttga    120 acaaatacct tatccagatc aaagacatgc cttccttcaa aaagtacaac ctcgacaagc    180
agagtgttga ggtccctggc actcggaagc ctggcgcttc aggccactac agacatgccg    240
cctacggcga tgctcttgtc accaacatcc gtgaggcccc tcatatcgaa actctttacg    300
acatgtggca gaactctgtg acaaagtatg gcggcaatga cttttttgggt caccgtcccct   360 tcaacactgt tgcccagacc tatggtggct acagttggga gacgtaccgc cagattaacc    420
agcgcgttaa tgcgttcggc agcggtatca tgcacctgaa cgaggtgatc ctcggcaacc    480
gccagcttaa ccgctgggcg ttgggcatct ggtcccacgg tcgccctgag tggttcatta    540
cggagatgag ctgcaactgc tacaacctca tttctgttgc attgtacgac acccttggac    600
ctgatgcagt cgagtacatt gtcaaccacg ccgagattga gattgttgtc tcaagtgcca    660
accatatcgc ctctttgctc gagaacgccg agaagctccc caagctcaag gccattgtca    720
gcatggatgc tcttcacgat accgtccccg tccccggcgc cacctctgcc gcacaggttc    780
ttcgtgcctg gggtgcacaa aagggcatca aggtctatga ctttaacgag attgagtccc    840
tcggtgccga gttccctcgc aagcacctgc ctcccaccgc tgatgaggtc gcctccatct    900
gctacacttc cggcaccacc ggtcagccta aaggagccat gctcacccac agaaactttg    960
ttgctactgt tggtaccaac cgcgagggca tgcttctcac cgaggacgac gttttgatca   1020
gtttcttgcc cttggctcac attatgggac gcgtcattga cacttgctcg atgtacagcg   1080
gtggcaagat tggttacttc cgtggagata ttcttttgct tctcgaggac gttgctgagc   1140
tccgtcccac attcttccca gctgtgcctc gcctcttgaa ccgcatttat gccaagctcg   1200
```

| | |
|---|---|
| ttgcctctac cattgaggcc cccggtttgg tcggtgcctt ggcccgtcgc ggtgtcgccg | 1260 |
| ccaagatggc caaccttgct gccggaaagg gtgtcaacca cgctctctgg gacagactgc | 1320 |
| tgttcaacaa ggtcaagatg gccctgggtg gtcgcgttca ggtcatcctg actggatctg | 1380 |
| cgcccattgc caaggaggtt ctcagcttct tgagaattgc tttcggatgc gtggttttgg | 1440 |
| agggatacgg ctccactgag ggcatggcta ccgccaccat cacaatggct gatgagtaca | 1500 |
| ttcctggtca cattggctgc cctcgtgctg atgcgagct caagctggtg gatgtgcccg | 1560 |
| cgatgaacta cctctctacc gaccagccct accccgtgg agagatctgg atccgtggtg | 1620 |
| acactgtttt caaaggatac ttcaaggacg agaagaacac tagtgagact atcgactctg | 1680 |
| aaggctggct cgctaccggt gatattggat tgtggataa gcgtggatgc tttacgatca | 1740 |
| ttgaccgcaa gaagaacatc ttcaagttgg cacaaggtga atacattgct cctgaaaaga | 1800 |
| ttgagaacgt cttgggcgca cgctgcaatc ttgtccagca gatctatgtt catggtgatt | 1860 |
| cgcttgagtc caccttggtc gcagttctta ttcccgagcc cgagaccttc ctgcccttcg | 1920 |
| cgaatgccat tgctggtgcc tccgtcactg ctggagatgt tgagggtttg aacaagctgt | 1980 |
| gccaagatcc caaggtcaag atcgcggttc tgaaggagtt ggagaaggcc ggaaaggccg | 2040 |
| gtgcgatgcg cggattcgag ttcgtgaagc gtgtccactt gaccacggat gcattctcgg | 2100 |
| tcgacaacgg catgatgaca cctaccttca aggtccgtcg cccacaagta gccgagcatt | 2160 |
| tcagggagca aatcacggcc atgtataagg agatcaatgc ctcgacccct gttgccaagc | 2220 |
| tgtagataga aaactctttg ccccttatta cccctttgaat agaaggtgac acgttgtttg | 2280 |
| attcacac | 2288 |

<210> SEQ ID NO 139
<211> LENGTH: 2017
<212> TYPE: DNA
<213> ORGANISM: Mortierella alpina

<400> SEQUENCE: 139

| | |
|---|---|
| tcgctatcta tcaccctca ctcccactc cgcactctgc tcttcctttt tcctttctct | 60 |
| ctctcaccgt cgccactgtc tctactttct ttaccaccca cgcatcagtc acagcatggt | 120 |
| tgctctccca ctcgtcgcag cagctgtccc agctgccatg tatgtgagct caaagctggc | 180 |
| acttcctcgg gatatgaagt tgattaagag cttgatcgga gccaagatgg cctacagtgc | 240 |
| catggaaaag aacgacgccc tcaacctgac actccgcttc gacgagtgct accgcaagta | 300 |
| tcctgaccgt gaagccctgg tctttgaggg caaatcctat tcattccgtg atattcagct | 360 |
| tgcctccaac aggtgcggca actggttgct ggccaaaggg atcaagcgag gagatatcgt | 420 |
| ctcgcttttc atgttgaaca ggccagagtt catcttctgc tggctgggtc tcaacaagat | 480 |
| tggagccact ggtgccttca tcaataccaa ccttacgggc aaacccctga cacattccct | 540 |
| ccggacagcc acgtcgtcaa tgttgatcat ggacacggag ttgacagacg cgatcgccaa | 600 |
| ctccctggat gagattcagg agatgggcta ttcaatttac tcttacggac ccgaagccgt | 660 |
| ggactttgct accccgatgg atatctcgca ggtcccagac accgatacac ccgaacacct | 720 |
| gcgccggaac acgaccgcgg atgacattgc gatgctcatc tacacctctg aactactgg | 780 |
| tcttcccaag gccggtcgtg tctctcatgc gcgtgcctct atgggacctc agttttggaa | 840 |
| ccgattctat cacttcagtg agagcgacag ggtctatctg tccttgccct tgtaccacag | 900 |
| tgctggcgcc atcttgggag tgattgcttg ttggacctcg ggagcaacct tgatcctggc | 960 |
| ccgcaagttc tccgcgacac atttctggga ggattgccgc gtgaacaacg caactgtgat | 1020 |

```
tcaatacatt ggagaaattt gcagatatct gctcaacacg ccagaatcac ccctggacaa      1080
ggcacactcg atacgactgg cacatggtaa tggaatgcga cccgatgtct ggactcgctt      1140
cagagatcgg ttcggcatcc cgttgattgg cgagtggtat gcatcgactg agggaactgg      1200
agccttgtcg aattataaca caggcccagg cggcgctgga gcgattggat accgcggtac      1260
ccttgccaga gcattggata aaggactcag gattgcgaga tttgatgtcc agacagagga      1320
gttggttcgg gacaaaaacg gttattgcat tgagtgcaaa cctggcgagc cggagaatt       1380 gctgacgctt gttgatgcta aagagccgaa caaagacttc aaaggatacc atcaaaacca      1440
ggcagcgacc aacaaaaaga ttgtcaaaga tgttttcaaa gccggcgaca tgtacttccg       1500
taccggagat atccttcggc gcgatagcga tgggtacttt tactttggcg accgtgtggg      1560
cgatacattc cggtggaagt ccgagaatgt gtctacggcc gaggtgtctg aagtcctctc      1620
gcagtatccg gactgtatcg aagtcaatgt gtatggagtt cagatcccag gcaggacgg       1680 acgcgccggt atggcagcga ttgtgtccaa gagcacgatg gattgggaga aatttgcggc      1740
gtatgcactc aagaacctgc cgcggtattc tgttccgatc tttatccgca agatgcccga      1800
gatggagatc acagggacgt tcaagcagcg caaagtcgag ttggtgaatg agggaatcga      1860
ccccaagacg attgccaacg agatgctgtg gttggacgga caccactata agccgttcaa      1920
ggcggccgag caccagcgcg tcatcagcgg caaggccaag ctatagtagg gcgcgtgcgc      1980
caatgcagta gcaatactat tccccgcttt gtccatt                               2017

<210> SEQ ID NO 140
<211> LENGTH: 2170
<212> TYPE: DNA
<213> ORGANISM: Mortierella alpina

<400> SEQUENCE: 140
ttcacgcact accttctttt ttcacccatc cagcagtaaa gacaacatgg aaaccttggt        60
taacggaaag tatgcggtcg agtacgacga ggtcgatcac atctatcgca acgtcatggc       120
tacaggcggg ctcctcgaca ggcctatgcc tccatactac gacatcaagg agcgcaccat       180
ggcccacctc tttgagtata tggccaacac ctacgaagac aaagacgcca tgggctggcg       240
agacattatc aaggtccaca aggtcgagaa gcaggctgcc aatcctggcg agaagccaaa       300
gacctggatc acttatgagc tctcggacta caactggatg tcgtaccgcc aagccaagaa       360
ctatgcagat cgagttggct tgggcatcac acgccttgga gttgagaagg gagacttttgt      420 catgatcttt gctagcacat gtcccgaatg gttcctgaca gcgcatggat gcttctcgca       480
gtcagtgact atcgtgacag cctacgactc gatggacgag aagtcgatcc agtttattgt       540
tgaccagtcc cagcccaagg ccatctttgc tgatgcgcac acgctccctg tggtgtccaa       600
actcatgcag aagggcaaca gtggtgtcaa ggcagtcatt tacacaggcc aagagtggga       660
agtgaccgat gcaatcaaga agatggagca agtagaaaac cgctcatttg agctggttca       720
tatcgacgaa ctcaagaaga ccaagtcagc atctaacggc gaacagtctg ccggaaaggg       780
gaagcagaga tcatctgagg atgccgaagg cgctcaggac gagatcgagg tcatatacc        840 taaggcggat gatctggcct gtattatgta tacctctggg tcgacgggtc agcccaaggg       900
cgcgcaattg acacatggca acttgatggc ggccattgga agtgctgcgg ccatggaggg       960
cgaccagctg gacaaggaaa cagacattgt tatttcatat ctgccattgg cccatgtcct      1020
cgagtttgtc atttcccact tgtgggtatc catgggctgc cgtcttggat tcggacgagc      1080
```

-continued

| | |
|---|---|
| acgcactctg atggatgatg cagtcgctcc caccgcagga agtggcaggt ccaagggcct | 1140 |
| tggtgatctg aaggcgctcc agccaacatt gatggctggt gtgccaacga tctgggagcg | 1200 |
| tatccgcaag ggcatcctgg ccgaggtcaa caagcaatcc ttccctatcc gtacactctt | 1260 |
| ctttgctgca ctcaacacca agtgggctat cgtccaggct accggatctg agaactttgt | 1320 |
| caccaagact attgactcgt tggtctttag taaggctaag gagctcgttg gaggcaagct | 1380 |
| gcgccttacc ttgactggag gggccggaat cagtgatgag acgcaccggt tcttgagcat | 1440 |
| ggtaatgtgc tacgttatct cgggatatgg tctcactgaa gtctgtggtg ttgccgctgt | 1500 |
| caccctgcca cgtatgggtc accgtctcag gaccgttgga ccacccgcgc ccagtcttga | 1560 |
| gctgaagttg gtgaatgtgc ccgacaccga gtacacagga gacaatggat cgggcgaaat | 1620 |
| ctggttccgt ggacctgcag tgatgaaggg atacttcaaa ctcgaggaag agaccaagaa | 1680 |
| ggtgatgacc ggggatggtt ggttcaagac aggcgacatt ggcacgatga acccagacgg | 1740 |
| cacactgtca atcaaggaca gggtcaagaa tctggtcaag ctgtctcatg gagaatatgt | 1800 |
| cgccctggag aaatgtgaag ccgttatcg cgattccaag gagatcaaga gcatttgcat | 1860 |
| cgttgcggac aatgggtgcc ctgtgttgct ggccgttgtg gaaccgagcc acgcaggggc | 1920 |
| gtctgacaag gagattttgg atatcctgaa gagccaagcc aaggcggcgg gcctctccaa | 1980 |
| gtccgagact gtgcaaggcg ttatcattga tgattcggac tggatgacga atgggttcat | 2040 |
| gacctcgagc agcaaggtca agagacgcga ggtccgcaag gcacacaaca aggatattga | 2100 |
| ggagatgtgg aagaagttct agagaagcgt gggaagggca tgaaataaac atacgcaatg | 2160 |
| gatttattgg | 2170 |

<210> SEQ ID NO 141
<211> LENGTH: 2392
<212> TYPE: DNA
<213> ORGANISM: Mortierella alpina

<400> SEQUENCE: 141

| | |
|---|---|
| cctttatccc cgcaccgcca tctctcgccg ccaccatctc gcattccttt caatccacac | 60 |
| tcccacctgt gccccctgct tttcacgtcc cgctctcatc ccgccttctc ctttcatcac | 120 |
| cccaattcaa catgacaaag tgcctcaccg tcgaagtcgg acccgccgac gtccagggcg | 180 |
| agacccgcat ccgccgctcc gtcctctctg caaagcgcct catgtcctcg ccctcggatg | 240 |
| acatcaagac cctctacgac gtcttcaacc actccgtcac cgtccgcccc aacctcaacg | 300 |
| cgatcggata ccgcaaggtc gtcaagattg tcgaggaaga aaaggaggtc gtcaaggttg | 360 |
| tcaacggcga ggaagtcaag gaaaagaaga cctggaagtt cttcaagatg tccggctacc | 420 |
| actggctcac ctacaaggat gcgaagcagg tcgtcgacag catcggatgc ggtcttcgca | 480 |
| agtttggcgt cgagcccaag gacaagctga ccgttttcgg tgccacaagt gccaactggc | 540 |
| tcctgcttgc ccacggtgct ttcacccagt ccatcaccat tgttaccgcc tacgacaccc | 600 |
| tgggcgagga cggtcttttg cactctatga acgaggccga ggtggccacc gcttacacaa | 660 |
| acgccgactt gctcaacact atcaagaacg ttgccggcaa atgccccacc ctgaagaaga | 720 |
| tcatctacga cggcgatgcc aagcccgcag atgtcattgc cctccaggag gcccatcctc | 780 |
| acctccagct catcaccctc gaggagctga agcagctcgg agtggacaac cctgtcgccc | 840 |
| caaccccctcc tgctgccaag gactactgct gcatcatgta cacttcggga tcgactggca | 900 |
| accccaaggg agtgttgctg acccatgaa acctcgttgc tgccatcgga ggtgtgaaca | 960 |
| agatgctgac aaagtacgtt cacgagggag acgtcttgct cgcgtacttg cctcttgctc | 1020 |

```
acgttctcga gttcctggtc gaaaacgtct gtctcttctg gggtgtgact cttggctacg    1080
gtaccgtccg cacattgact gatgcctcag tccgtgagtg ccagggtgat atcaaggagt    1140
tgcgccctac attgatgacc ggtgttcctg ctgtgtggga gacgattcgt aagggagtgt    1200
tggctcaggt ttcccagggc tcacctcttg ttcaaaagat cttccatgct gctttgaacg    1260
ccaaggcctg gtgcctggac cgcaagttgg gtgcgttgac tggaatcttc gatactgtcg    1320
tcttcaacaa ggtcaagcag cagacaggag gacgtcttcg cttcgccctt tcggaggtg    1380
cacccatctc tcaggagacc cagcgcttct tgacgacagc tttgtgccct atcctccagg    1440
gctacggtat gacagagtct tgcggcatgt gcgccatttt gacccccgat gtcttcaact    1500
acagccgtgt cggatcccca gttccttgca cggaggtcaa gttggtcgat gtgcccgatg    1560
caggatacca ctcaacggac ttgcctctcc ccgtggtga ggtctgcatt cgtggaccct     1620
ccatcactgc tggatacttc aagaaccccg aggagacctc cgccacattg actgctgatc    1680
gctggctcaa gactggagat atcggagagt ggcaccccga cggcactatc tcgatcattg    1740
accgcaagaa gaacttggtc aagctgtcac acggagagta cattgctttg gagaagcttg    1800
agtctgtcta caagagcaca gcctactgca caacatttg cgtgtatgcc gactcgatgc     1860
agaacaagcc cgttgccatt attgttgcca gcgaaccccg catcctcgag ttggccaagg    1920
ccaagggcat tgagagccgc gactttgctg ctctctgcca cgacaaggtt atcatcaagg    1980
ctgtccacga tgcctgcctc gccactgcca agcgtgctgg actcaagccc gctgagatgc    2040
ttcagggagt gtacttggag tcagaagaat ggacggccca ggctggcatg ttgactgccg    2100
ctcagaagct caagcgcaag gagatcaacc aggcctatgt ctcacagatc aagcagcttt    2160
atggaacggc ctaagtcgct gaaaggtgtg cctttgtccg tctcttcaac cccacaagtc    2220
ctatgtataa tgacccgcgc ggccctcctt taatcctata cccaccttt tttacacgtt     2280
aaagaagcca catttttggt tcttttttt ctctcgcaca cactacacac tccccatcca     2340
ttccctccaa acaggatggt tgtctgcaaa taaattgacg aatttctct tg              2392
```

<210> SEQ ID NO 142
<211> LENGTH: 627
<212> TYPE: PRT
<213> ORGANISM: Mortierella alpina

<400> SEQUENCE: 142

```
Met Asp Ala Val Pro Ala Val Ala Ala Ala Ile Pro Ala Ala Met
1               5                  10                  15

Tyr Val Gly Ser Lys Leu Ala Ile Pro Arg Asp Val Lys Leu Ala Lys
            20                  25                  30

Gly Leu Val Ser Ala Lys Leu Gly Tyr Arg Ser Tyr Glu Lys Asn Asp
        35                  40                  45

Ser Ile Asn Ile Ser Tyr Arg Phe Glu Glu Thr Cys Lys Lys His Pro
    50                  55                  60

His Arg Glu Ala Leu Val Phe Glu Gly Lys Ser Tyr Thr Phe Gln Asp
65                  70                  75                  80

Ile Gln Arg Glu Ser Asn Arg Val Gly His Trp Leu Leu Ser Lys Gly
                85                  90                  95

Val Lys Arg Gly Glu Ile Val Ser Leu Phe Met Gln Asn Lys Pro Glu
            100                 105                 110

Phe Leu Phe Phe Trp Leu Gly Leu Asn Lys Ile Gly Ala Thr Gly Ala
        115                 120                 125
```

-continued

```
Phe Ile Asn Thr Asn Leu Ser Gly Lys Pro Leu Thr His Ser Leu Arg
130                 135                 140

Thr Ala Thr Ala Ser Ile Leu Ile Met Asp Ala Glu Leu Pro Thr Pro
145                 150                 155                 160

Ile Tyr Ser Val Leu Asp Glu Val Leu Glu Met Gly Tyr Gln Ile Tyr
                165                 170                 175

Ser Tyr Gly Gly Ser Gln Gln His Ala Phe Ala Thr Gln Val Glu Leu
            180                 185                 190

Ser Gln Ile Ser Asp Ala Ala Leu Pro Lys Ser Leu Arg Arg Lys Thr
        195                 200                 205

Thr Ala Asn Asp Ile Ala Met Leu Ile Tyr Thr Ser Gly Thr Thr Gly
210                 215                 220

Leu Pro Lys Ala Gly Arg Phe Ser His Ala Arg Ala Asn Val Ala Ala
225                 230                 235                 240

Leu Phe Trp Thr Ser Phe Tyr His Phe Ser Glu Lys Asp Arg Leu Tyr
                245                 250                 255

Ile Ala Leu Pro Leu Tyr His Ser Ala Gly Ala Val Leu Gly Ile Cys
            260                 265                 270

Val Ala Trp Val Thr Gly Ala Thr Val Val Leu Ala Arg Lys Phe Ser
        275                 280                 285

Thr Thr Ser Phe Trp Asp Glu Cys Arg Ala Asn Lys Val Thr Val Ile
290                 295                 300

Gln Tyr Ile Gly Glu Ile Cys Arg Tyr Leu Leu Asn Ala Pro Pro Ser
305                 310                 315                 320

Pro Leu Asp Lys Thr His Thr Ile Arg Met Ala His Gly Asn Gly Met
                325                 330                 335

Arg Pro Asp Val Trp Asn Arg Phe Arg Asp Arg Phe Gly Ile Pro Leu
            340                 345                 350

Ile Gly Glu Trp Tyr Ala Ser Thr Glu Gly Thr Gly Ile Leu Thr Asn
        355                 360                 365

Tyr Asn Thr Gly Pro Asn Gly Ala Gly Ala Ile Gly Tyr Arg Gly Ser
370                 375                 380

Leu Ala Arg Thr Val Asp Lys Gly Leu Lys Ile Ala Lys Phe Asp Ile
385                 390                 395                 400

Gln Thr Glu Glu Leu Ile Arg Asp Lys Asn Gly Arg Cys Ile Glu Cys
                405                 410                 415

Val Ala Asp Glu Pro Gly Glu Leu Leu Thr Met Ile Asp Ser Ser Asp
            420                 425                 430

Pro Thr Arg Ala Phe Gln Gly Tyr His Lys Asn Ala Gly Ala Asn Ser
        435                 440                 445

Lys Lys Val Val Gln Asp Ala Phe Ser Val Gly Asp Gln Tyr Phe Arg
450                 455                 460

Thr Gly Asp Ile Leu Arg Arg Asp Ala Asp Gly Tyr Phe Tyr Phe Gly
465                 470                 475                 480

Asp Arg Val Gly Asp Thr Phe Arg Trp Lys Ser Glu Asn Val Ser Thr
                485                 490                 495

Ala Glu Val Ser Glu Val Leu Ser Ala Tyr Pro Asp Cys Ile Glu Val
            500                 505                 510

Asn Val Tyr Gly Val Gln Val Pro Gly His Asp Gly Arg Ala Gly Met
        515                 520                 525

Ala Ala Ile Val Ser Lys Asp Thr Met Asn Trp Asp Ser Phe Ala Lys
530                 535                 540

Phe Ala Leu Lys Asn Leu Pro Lys Tyr Ser Val Pro Ile Phe Ile Arg
```

-continued

```
545                 550                 555                 560

Lys Val Pro Glu Met Glu Ile Thr Gly Thr Phe Lys Gln Arg Lys Val
            565                     570                 575

Glu Leu Val Asn Glu Gly Met Asp Pro Ser Lys Ile Lys Asp Glu Met
            580                 585                 590

Leu Trp Leu Asp Gly His Ser Tyr Arg Pro Phe Lys Glu Ala Glu His
        595                 600                 605

Thr Arg Val Val Ser Gly Lys Ala Arg Leu Arg Ile Lys Leu Phe Arg
    610                 615                 620

Phe Val Arg
625
```